(12) United States Patent
Ahmed et al.

(10) Patent No.: US 9,598,491 B2
(45) Date of Patent: Mar. 21, 2017

(54) METHODS FOR THE TREATMENT OF INFECTIONS AND TUMORS

(75) Inventors: Rafi Ahmed, Atlanta, GA (US); Rama Amara, Decatur, GA (US); Vijayakumar Velu, Tucker, GA (US); Kehmia Titanji, Atlanta, GA (US); Gordon Freeman, Brookline, MA (US)

(73) Assignees: Emory University, Atlanta, GA (US); Dana-Farber Cancer Institute, Inc., Boston, MA (US)

(*) Notice: Subject to any disclaimer, the term of this patent is extended or adjusted under 35 U.S.C. 154(b) by 963 days.

(21) Appl. No.: 12/626,848

(22) Filed: Nov. 27, 2009

(65) Prior Publication Data

US 2010/0151492 A1 Jun. 17, 2010

Related U.S. Application Data

(60) Provisional application No. 61/118,570, filed on Nov. 28, 2008.

(51) Int. Cl.
| | | |
|---|---|---|
| *C12Q 1/02* | (2006.01) | |
| *C07K 16/28* | (2006.01) | |
| *A61K 31/7105* | (2006.01) | |
| *A61K 39/39* | (2006.01) | |
| *A61K 39/395* | (2006.01) | |
| *G01N 33/50* | (2006.01) | |
| *G01N 33/569* | (2006.01) | |
| *A61K 39/00* | (2006.01) | |

(52) U.S. Cl.
CPC ...... *C07K 16/2803* (2013.01); *A61K 31/7105* (2013.01); *A61K 39/39* (2013.01); *A61K 39/39541* (2013.01); *C07K 16/2818* (2013.01); *C07K 16/2827* (2013.01); *G01N 33/5052* (2013.01); *G01N 33/56966* (2013.01); *A61K 2039/505* (2013.01); *A61K 2039/507* (2013.01); *A61K 2039/55516* (2013.01); *C07K 2317/24* (2013.01); *C07K 2317/74* (2013.01); *C07K 2317/76* (2013.01); *G01N 2333/52* (2013.01)

(58) Field of Classification Search
None
See application file for complete search history.

(56) References Cited

U.S. PATENT DOCUMENTS

| | | |
|---|---|---|
| 5,698,520 A | 12/1997 | Honjo et al. |
| 5,858,358 A | 1/1999 | June et al. |
| 5,939,281 A | 8/1999 | Lehmann et al. |
| 6,103,479 A | 8/2000 | Taylor |
| 6,232,445 B1 | 5/2001 | Rhode et al. |
| 6,235,488 B1 | 5/2001 | Tom-Moy et al. |
| 6,329,209 B1 | 12/2001 | Wagner et al. |
| 6,355,479 B1 | 3/2002 | Webb et al. |
| 6,610,542 B1 | 8/2003 | Bell et al. |
| 6,803,192 B1 | 10/2004 | Chen |
| 6,808,710 B1 | 10/2004 | Wood et al. |
| 6,913,747 B1 | 7/2005 | Co et al. |
| 6,936,704 B1 | 8/2005 | Freeman et al. |
| 6,984,720 B1 | 1/2006 | Korman et al. |
| 7,041,474 B2 | 5/2006 | Kingsbury |
| 7,101,550 B2 | 9/2006 | Wood et al. |
| 7,105,328 B2 | 9/2006 | Wood et al. |
| 7,195,798 B2 | 3/2007 | Wung et al. |
| 7,238,360 B2 | 7/2007 | Shirwan |
| 7,385,036 B2 | 6/2008 | Kingsbury |
| 7,432,059 B2 | 10/2008 | Freeman et al. |
| 2002/0095024 A1 | 7/2002 | Mikesell et al. |
| 2002/0099022 A1 | 7/2002 | Killam |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0160000 A1 | 10/2002 | Wood et al. |
| 2002/0164600 A1 | 11/2002 | Freeman et al. |

(Continued)

FOREIGN PATENT DOCUMENTS

| | | |
|---|---|---|
| EP | 0 670 369 A2 | 9/1995 |
| EP | 1 074 617 A2 | 2/2001 |

(Continued)

OTHER PUBLICATIONS

Nishimura et al. (International Immunology, 1998, vol. 10, p. 1563-1572 in IDS Apr. 8, 2011).*
Moir et al. (Journal of Experimental Medicine, 2008, vol. 205, p. 1797-1805).*
Agata et al., "Expression of the PD-1 antigen on the surface of stimulated mouse T and B lymphocytes," *Int. Immunol.*, 8(5):765-772 (1996).
Ahmed et al. "Immune Therapy of a Persistent and Disseminated Viral Infection," Journal of Virolgoy 61(12):3920-3929 (1987).
Ansari et al., "The Programmed Death-1 (PD-1) Pathway Regulates Autoimmune Diabetes in Nonobese Diabetic (NOD) Mice," *J. Exp. Med.*, 198(1):63-69 (2003).
Barber et al., "Restoring function in exhausted CD8 T cells during chronic viral infection," *Nature*, 439(9):682-687 (2006).

(Continued)

*Primary Examiner* — Agnieszka Boesen
(74) *Attorney, Agent, or Firm* — Klarquist Sparkman, LLP

(57) ABSTRACT

PD-1 antagonists are disclosed that can be used to reduce the expression or activity of PD-1 in a subject. An immune response specific to an infectious agent or to tumor cells can be enhanced using these PD-1 antagonists in conjunction with an antigen from the infectious agent or tumor. Thus, subjects with infections, such as persistent infections can be treated using PD-1 antagonists. In addition, subjects with tumors can be treated using the PD-1 antagonists. In several examples, subjects can be treated by transplanting a therapeutically effective amount of activated T cells that recognize an antigen of interest and by administering a therapeutically effective amount of a PD-1 antagonist. Methods are also disclosed for determining the efficacy of a PD-1 antagonist in a subject administered the PD-1 antagonist. In some embodiments, these methods include measuring proliferation of memory B cells in a sample from a subject administered the PD-1 antagonist.

40 Claims, 43 Drawing Sheets

(56) References Cited

U.S. PATENT DOCUMENTS

| | | |
|---|---|---|
| 2003/0027998 A1 | 2/2003 | Holtzman et al. |
| 2003/0039653 A1 | 2/2003 | Chen et al. |
| 2003/0044768 A1 | 3/2003 | Wood et al. |
| 2003/0064380 A1 | 4/2003 | Rao et al. |
| 2003/0118592 A1 | 6/2003 | Ledbetter et al. |
| 2003/0133939 A1 | 7/2003 | Ledbetter et al. |
| 2003/0147896 A1 | 8/2003 | Solanki |
| 2003/0161827 A1 | 8/2003 | Celnicker et al. |
| 2003/0166531 A1 | 9/2003 | Madrenas et al. |
| 2003/0180292 A1 | 9/2003 | Hanna et al. |
| 2003/0180309 A1 | 9/2003 | Baum et al. |
| 2003/0224520 A1 | 12/2003 | June et al. |
| 2003/0232323 A1 | 12/2003 | Feeman et al. |
| 2004/0101519 A1 | 5/2004 | June et al. |
| 2004/0110290 A1 | 6/2004 | June et al. |
| 2004/0137577 A1 | 7/2004 | Coyle et al. |
| 2004/0156858 A1 | 8/2004 | Franzusoff et al. |
| 2004/0180047 A1 | 9/2004 | Chen et al. |
| 2004/0248205 A1 | 12/2004 | Stern et al. |
| 2005/0136049 A1 | 6/2005 | Ledbetter et al. |
| 2005/0208496 A1 | 9/2005 | Ohtani et al. |
| 2006/0003452 A1 | 1/2006 | Humeau et al. |
| 2006/0034810 A1 | 2/2006 | Riley et al. |
| 2006/0034826 A1 | 2/2006 | Carreno |
| 2006/0052295 A1 | 3/2006 | Terman |
| 2006/0083744 A1 | 4/2006 | Chen et al. |
| 2006/0110383 A1 | 5/2006 | Honjo et al. |
| 2006/0110755 A1 | 5/2006 | Duke et al. |
| 2006/0165665 A1 | 7/2006 | Min et al. |
| 2006/0205034 A1 | 9/2006 | Fraser et al. |
| 2006/0269526 A1 | 11/2006 | Galipeau et al. |
| 2006/0276422 A1 | 12/2006 | Usman et al. |
| 2007/0036783 A1 | 2/2007 | Humeau et al. |
| 2007/0122378 A1 | 5/2007 | Freeman et al. |
| 2007/0172504 A1 | 7/2007 | Shirwan et al. |
| 2007/0172947 A1 | 7/2007 | Shirwan |
| 2007/0184473 A1 | 8/2007 | Shirwan et al. |
| 2007/0243584 A1 | 10/2007 | West |
| 2008/0069831 A1 | 3/2008 | Duke et al. |
| 2008/0069833 A1 | 3/2008 | Franzusoff et al. |
| 2008/0107671 A1 | 5/2008 | Duke et al. |
| 2008/0118511 A1 | 5/2008 | Freeman et al. |
| 2009/0055944 A1 | 2/2009 | Korman et al. |
| 2009/0217401 A1 | 8/2009 | Korman et al. |
| 2010/0040614 A1 | 2/2010 | Ahmed et al. |
| 2012/0251537 A1 | 10/2012 | Ahmed et al. |
| 2014/0178370 A1 | 6/2014 | Freeman et al. |
| 2015/0239972 A1 | 8/2015 | Ahmed et al. |

FOREIGN PATENT DOCUMENTS

| | | |
|---|---|---|
| EP | 1 537 878 A1 | 6/2005 |
| EP | 1 997 887 | 9/2013 |
| JP | 2006-340714 | 12/2006 |
| JP | 2007-089496 | 4/2007 |
| WO | WO 95/03408 | 2/1995 |
| WO | WO 97/46256 | 12/1997 |
| WO | WO 00/32231 | 6/2000 |
| WO | WO 00/55375 | 9/2000 |
| WO | WO 00/61612 | 10/2000 |
| WO | WO 01/14556 A1 | 3/2001 |
| WO | WO 01/14557 A1 | 3/2001 |
| WO | WO 01/21631 A2 | 3/2001 |
| WO | WO 01/34629 A1 | 5/2001 |
| WO | WO 01/39722 A2 | 6/2001 |
| WO | WO 01/68134 A3 | 9/2001 |
| WO | WO 01/77137 A1 | 10/2001 |
| WO | WO 01/83750 A2 | 11/2001 |
| WO | WO 01/94413 A2 | 12/2001 |
| WO | WO 02/00692 A2 | 1/2002 |
| WO | WO 02/00730 A2 | 1/2002 |
| WO | WO 02/08279 A2 | 1/2002 |
| WO | WO 02/068647 A2 | 9/2002 |
| WO | WO 02/072631 A2 | 9/2002 |
| WO | WO 02/077208 A1 | 10/2002 |
| WO | WO 02/078731 A2 | 10/2002 |
| WO | WO 02/079474 A2 | 10/2002 |
| WO | WO 02/079499 A1 | 10/2002 |
| WO | WO 02/086083 A2 | 10/2002 |
| WO | WO 02/092792 A2 | 11/2002 |
| WO | WO 02/092793 A1 | 11/2002 |
| WO | WO 03/006632 A2 | 1/2003 |
| WO | WO 03/042402 A2 | 5/2003 |
| WO | WO 03/083069 A2 | 10/2003 |
| WO | WO 03/086459 | 10/2003 |
| WO | WO 03/104456 A1 | 12/2003 |
| WO | WO 2004/000221 A2 | 12/2003 |
| WO | WO 2004/004771 A1 | 1/2004 |
| WO | WO 2004/037321 A2 | 5/2004 |
| WO | WO 2004/056875 A1 | 7/2004 |
| WO | WO 2004/094458 A2 | 11/2004 |
| WO | WO 2005/035779 | 4/2005 |
| WO | WO 2005/042556 A1 | 5/2005 |
| WO | WO 2005/044835 A1 | 5/2005 |
| WO | WO 2005/046712 A1 | 5/2005 |
| WO | WO 2005/047288 A1 | 5/2005 |
| WO | WO 2005/042769 A1 | 12/2005 |
| WO | WO 2006/007539 A1 | 1/2006 |
| WO | WO 2006/042237 A2 | 4/2006 |
| WO | WO 2006/121168 A1 | 11/2006 |
| WO | WO 2006/133396 A2 | 12/2006 |
| WO | WO 2007/005874 A2 | 1/2007 |
| WO | WO 2007/016340 | 2/2007 |
| WO | WO 2007/030523 | 3/2007 |
| WO | WO 2007/067681 A2 | 6/2007 |
| WO | WO 2007/067682 A2 | 6/2007 |
| WO | WO 2007/067683 A2 | 6/2007 |
| WO | WO 2007/082144 A2 | 7/2007 |
| WO | WO 2007/082154 A2 | 7/2007 |
| WO | WO 2007/084865 A2 | 7/2007 |
| WO | WO 2007/100098 A1 | 9/2007 |
| WO | WO 2007/121364 A2 | 10/2007 |
| WO | WO 2007/124361 A2 | 11/2007 |
| WO | WO 2008/034076 A2 | 3/2008 |
| WO | WO 2008/078673 | 7/2008 |
| WO | WO 2008/083174 A3 | 7/2008 |
| WO | WO 2008/085562 A2 | 7/2008 |
| WO | WO 2008/091643 A2 | 7/2008 |
| WO | WO 2008/092153 A2 | 7/2008 |

OTHER PUBLICATIONS

Bendayan "Possibilities of False Immunocytochemical Results Generated by the Use of Monoclonal Antibodies: The Example of the Anti-proinsulin Antibody," *J. Histochem. Cytochem.*, 43(9):881-886 (1995).

Blank et al., "Interaction of PD-L1 on tumor cells with PD-1 on tumor-specific T cells as a mechanism of immune evasion: implications for tumor immunotherapy," *Cancer Immunol Immunother.* 54:307-314 (2005).

Bordignon et al., "Cell Therapy: Achievements and Perspectives," *Haematologica*, 84:1110-1149 (1999).

Borkner et al., "RNA Interface Targeting Programmed Death Receptor-1 Improves Immune Functions of Tumor-specific T cells," *Cancer Immunology Immunotherapy*, 59:1173-1183 (2010).

Branch, "A good antisense molecule is hard to find," *TIBS*, 23(2):45-50 (1998).

Britten et al., "The use of HLA-A* 0201-transfected K562 as standard antigen-presenting cells for CD8+ T lymphocytes in INF-γ ELISPOT assays," *J. Immunol. Meth.*, 259:95-110 (2002).

Brown et al., "Blockade of Programmed Death-1 Ligands on Dendritic Cells Enhances T Cell Activiation and Cytokine Production," *J. Immunol.*, 170:1257-1266 (2003).

Cai, et al., "PD-1 ligands, negative regulators for activation of naïve, memory, and recently activated human CD4+ T cells," *Cellular Immunology*, 230:89-98 (2004).

Coyle et al., "The expanding B7 superfamily: Increasing complexity in costimulatory signals regulating T cell function," *Nat. Immunol.*, 2(3):203-209 (2001).

Curiel et al., "Blockade of B7-H1 Improves Myeloid Dendritic Cell-Mediated Antitumor Immunity," *Nature Medicine* 9(5):562-567 (2003).

(56) References Cited

OTHER PUBLICATIONS

Day et al., "PD-1 expression on HIV-specific T cells is associated with T-cell exhaustion and disease progression," *Nature*, 443(21):350-354 (2006).
Dong et al., "B7-H1, a third member of the B7 family, co-stimulates T-cell proliferation and interleukin-10 secretion," *Nat. Med.*, 5(12):1365-1369 (1999).
Ellis et al., "Interactions of CD80 and CD86 with CD28 and CTLA4," *J. Immunol.*, 156:2700-2709 (1996).
Fanger et al., "Type I (CD64) and Type II (CD32) Fcγ Receptor-Mediated Phagocytosis by Human Blood Dendritic Cells," *J. Immunol.* 157:541-548 (1996).
Freeman et al., "Engagement of the PD-1 Immunoinhibitory Receptor by a Novel B7 Family Member Leads to Negative Regulation of Lymphocyte Activation," *Journal of Experimental Medicine* 192(7):1027-1034 (2000).
Freeman et al., "The B7-homologue, PD-L, is the ligand of the PD-1 Immunoinhibitory Receptor," *FASEB J.*, 14(6):A1170, Abstract 153.34 (2000).
Gajewski et al., "Immune Suppression in the Tumor Microenvironment," *Journal of Immunotherapy*, 29:233-240 (2006).
Giorgi et al., "Elevated Levels of $CD38^+$ $CD8^+$ T Cells in HIV Infection Add to the Prognostic Value of Low $CD4^+$ T Cell Levels: Results of 6 Years of Follow-Up," *Journal of Acquired Immune Deficiency Syndromes*, 6:904-912 (1993).
Greenfield et al., "CD28/B7 Costimulation: A Review," *Crit. Rev. Immunol.*, 18:389-418 (1998).
Greenwald et al., "Negative co-receptors on lymphocytes," *Curr. Opin. Immunol.*, 14:391-396 (2002).
Ha et al., "Enhancing therapeutic vaccination by blocking PD-1-mediated inhibitory signals during chronic infection," *The Journal of Experimental Medicine*, 205(3):543-555 (2008).
He et al., "Blockade of B7-H1 with sPD-1 Improves Immunity Against Murine Hepatocarcinoma," *Anticancer Res.*, 25:3309-13 (2005).
Henry et al., "Structure and evolution of the extended B7 family," *Immunol. Today*, 20(6):285-288 (1999).
Hirano et al., "Blockade of B7-H1 and PD-1 by Monoclonal Antibodies Potentiates Cancer Therapeutic Immunity," *Cancer Research*, 65(3):1089-1096 (2005).
Huang, Z., "Structural chemistry and therapeutic intervention of protein-protein interactions in immune response, human immunodeficiency virus entry, and apoptosis," *Pharmacol. Ther.*, 86:201-215 (2000).
International Search Report for PCT Application No. PCT/US2006/022423, 11 pages (Jun. 18, 2007).
International Search report for PCT Application No. PCT/US2007/088851; 8 pages (Sep. 24, 2008).
International Search Report from PCT Application No. PCT/US2009/066023, 6 pages (Aug. 2, 2010).
Ishida et al., "Induced expression of PD-1, a novel member of the immunoglobulin gene superfamily, upon programmed cell death," *EMBO J.*, 11(11):3887-3895 (1992).
Iwai et al., "Involvement of PD-L1 on tumor cells in the escape from host immune system and tumor immunotherapy by PD-L1 blockade," *PNAS*, 99(19):12293-12297 (2002).
Kanai et al., "Blockade of B7-H1 Suppresses the Development of Chronic Intestinal Inflammation," *J. Immunol.*, 171:4156-4163 (2003).
Keir et al., "Tissue Expression of PD-L1 Mediates Peripheral T Cell Tolerance," *The Journal of Experimental Medicine*, 203(4):883-895 (2006).
Keir et al., "PD-1 Regulates Self-Reactive CD8 T Cell Responses to Antigen in Lymph Nodes and Tissues," *The Journal of Immunology*, 179:5064-5070 (2007).
Klenerman et al., "Of Mice and Men: Cytotoxic T Cells and AIDS Pathogenesis," *AIDS Reader*, 9(7):474-480 (1999).
Knutson et al., "Adoptive T-Cell Therapy for the Treatment of Solid Tumours," *Expert Opin. Biol. Ther.* 2(1):55-66 (2002).
Koga et al., "Blockade of the Interaction Between PD-1 and PD-L1 Accelerates Graft Arterial Disease in Cardiac Allografts," *Arterioscler. Thromb. Vasc. Biol.*, 24:2057-2062 (2004).
Krummel et al., "CTLA-4 Engagement Inhibits IL-2 Accumulation and Cell Cycle Progression upon Activation of Resting T Cells," *J. Exp. Med.*, 183:2533-2540 (1996).
Latchman et al., "PD-L2 is a second ligand for PD-1 and inhibits T cell activation," *Nat. Immunol.*, 2(3):261-268 (2001).
Le Blanc et al., "HLA expression and immunologic properties of differentiated and undifferentiated mesenchymal stem cells," *Exp. Hematol.*, 31:890-896 (2003).
Liang et al., "The right place at the right time: novel B7 family members regulate effector T cell responses," *Curr. Opin. Immunol.*, 14:384-390 (2002).
Liu et al., "$CD8^+$ T Cells Can Block Herpes Simplex Virus Type 1 (HSV-1) Reactivation from Latency in Sensory Neurons," *Journal of Experimental Medicine*, 191(9):1459-1466 (2000).
Liu et al., "B7DC/PDL2 Promotes Tumor Immunity by a PD-1-independent Mechanism," *Journal of Experimental Medicine*, 197(12):1721-1730 (2003).
Machuca et al., "Human Immunodeficiency Virus Type 2 Infection in Spain," *Intervirology*, 42:37-42 (1999).
Metzler et al., "Solution structure of human CTLA-4 and delineation of a CD80/CD86 binding site conserved in CD28," *Nat. Struct. Biol.*, 4(7):527-531 (1997).
Morgan et al., "Cancer Regression in Patients After Transfer of Genetically Engineered Lymphocytes," *Science* 314:126-129 (2006).
Musey et al. "Cytotoxic-T-Cell Responses, Viral Load, and Disease Progression in Early Human Immunodeficiency Virus Type 1 Infection" *The New England Journal of Medicine*, 337(18):1267-1274 (1997).
Nishimura et al., "Developmentally regulated expression of the PD-1 protein on the surface of double-negative ($CD4^-$ $CD8^-$) thymocytes," *Int. Immunol.*, 8(5):773-780 (1996).
Nishimura et al., "Immunological studies on PD-1-deficient mice: implication of PD-1 as a negative regulator for B cell responses," *Inter. Immunol.*, 10(10):1563-1572 (1998).
Nishimura et al., "Development of Lupus-like Autoimmune Diseases by Disruption of the PD-1 Gene Encoding an ITIM Motif-Carrying Immunoreceptor," *Immunity*, 11:141-151 (1999).
Nishimura et al., "Autoimmune Dilated Cardiomyopathy in PD-1 Receptor-Deficient Mice," *Science*, 291:319-322 (2001).
Ohigashi et al., "Clinical Significance of Programmed Death-1 Ligand-1 and Programmed Death-1 Ligand-2 Expression in Human Esophageal Cancer," *Clin Cancer Res.*, 11(8):2947-2953 (2005).
Ozkaynak et al., "Programmed Death-1 Targeting Can Promote Allograft Survival," *J. Immunol.*, 169:6546-6553 (2002).
Pascale et al., "Immunological Markers of Disease Progression in Patients Infected with the Human Immunodeficiency Virus," *Clinical and Diagnostic Laboratory Immunology* 4(4):474-477 (1997).
Petrovas et al., "PD-1 is a regulator of virus-specific $CD8^+$ T cell survival in HIV infection," *JEM*, 203(10):2281-2292 (2006).
Pilon-Thomas et al., "Blockade of Programmed Death Ligand 1 Enhances the Therapeutic Efficacy of Combination Immunotherapy Against Melanoma," *The Journal of Immunology*, 184:3442-3449 (2010).
Riddell and Greenberg, "Principles for adoptive T Cell therapy of human viral diseases," *Annual Review of Immunology*, 13:545-586 (1995).
Riley and June, "The road to recovery: translating PD-1 biology into clinical benefit," *Trends in Immunology*, 28(2):48-50 (2006).
Salama et al., "Critical Role of the Programmed Death-1 (PD-1) Pathway in Regulation of Experimental Autoimmune Encephalomyelitis," *J. Exp. Med.*, 198(1):71-78 (2003).
Saunders et al., "PD-L2:PD-1 involvement in T cell proliferation, cytokine production, and integrin-mediated adhesion," *Eur. J. Immunol.*, 35:3561-3569 (2005).
Sedy et al., "B and T lymphocyte attenuator regulates T cell activation through interaction with herpesvirus entry mediator," *Nat. Immunol.*, 6(1)90-98 (2005).
Sharpe et al., "The B7-CD28 Superfamily," *Nat. Rev. Immunol.*, 1(2):116-126 (2002).

(56) References Cited

OTHER PUBLICATIONS

Shin et al., "Cooperative B7-1/2 (CD80/CD86) and B7-DC Costimulation of CD4+ T Cells Independent of the PD-1 Receptor," *J. Exp. Med.*, 198(1):31-38 (2003).
Shinohara et al., "Structure and Chromosomal Localization of the Human PD-1 Gene (PDCD1)," *Genomics*, 23:704-706 (1994).
Strome et al., "B7-H1 Blockade Augments Adoptive T-Cell Immunotherapy for Squamous Cell Carcinoma," *Cancer Research*, 63:6501-6505 (2003).
Subudhi et al., "Local expression of B7-H1 promotes organ-specific autoimmunity and transplant rejection," *J. Clin. Invest.*, 113(5):694-700 (2004).
Trabattoni et al., "B7-H1 is up-regulated in HIV infection and is a novel surrogate marker of disease progression," *Blood*, 101(7):2514-2520 (2003).
Trautmann et al., "Upregulation of PD-1 expression on HIV-specific CD8+ T cells leads to reversible immune dysfunction," *Nature Medicine*, 12 (10):1198-1202 (2006).
Tseng et al., "B7-DC, A New Dendritic Cell Molecule with Potent Costimulatory Properties for T Cells," *J. Exp. Med.*, 193(7):839-845 (2001).
Tsushima et al., Preferential contribution of B7-H1 to programmed death-1-mediated regulation of hapten-specific allergic inflammatory responses, *Eur. J. Immunol.*, 33:2773-2782 (2003).
Velu et al., "Enhancing SIV-specific immunity in vivo by PD-1 blockade," *Nature*, 458(7235):206-210 (2009).
Walter et al., "Reconstruction of Cellular Immunity Against Cytomegalovirus in Recipients of Allogeneic Bone Marrow by Transfer of T-Cell Clones from the Donor," The New England Journal of Medicine 333:1038-1044 (1995).
Walunas et al., "CTLA-4 Ligation Blocks CD28-dependent T Cell Activation," *J. Exp. Med.*, 183:2541-2550 (1996).
Wang et al., "Molecular Modeling and Functional Mapping of B7-H1 and B7-DC Uncouple Costimulatory Function from PD-1 Interaction," *J. Exp. Med.*, 197(9):1083-1091 (2003).
Webster et al., "Targeting Molecular and Cellular Inhibiting Mechanisms for Improvement of Antitumor Memory Response Reactivated by Tumor Cell Vaccine," *Journal of Immunology* 179(5):2860-2869 (2007).
Wherry et al. "Lineage Relationship and Protective Immunity of Memory CD8 T Cell Subsets," *Nature Immunology*, 4:225-234 (2003).
Yao and Chen, "Reviving Exhausted T Lymphocytes During Chronic Virus Infection by B7-H1 Blockade," *Trends in Molecular Medicine*, 12(6):244-246 (2006).
Yee et al., "Adoptive T cell therapy using antigen-specific CD8+ T cell clones for the treatment of patients with metastatic melanoma: In vivo persistence, migration, and antitumor effect of transferred T cells," PNAS, 99(25):16168-16173 (2002).
Yee et al., "Adoptive T-Cell Therapy of Cancer," *Hematology/Oncology Clinics of North America*, 20(3):711-733 (2006).
Yershov and Ospelnikova, "The Current Arsenal of Antiherpetic Medications," *Infections and Antimicrobial Therapy*, 3(4) (2001), in Russian with English language translation.
NCBI GenBank Acc No. AF329193 "*Homo sapiens* butyrophilin precursor B7-DC mRNA, complete cds" (Apr. 10, 2001).
NCBI GenBank Acc No. AF142780 "Mus musculus butyrophilin-like protein (Btdc) mRNA, complete cds," (Apr. 12, 2001).
NCBI GenBank Acc No. AF344424 "*Homo sapiens* PD-1-ligand 2 protein (PDL2) mRNA, complete cds," (Apr. 8, 2002).
NCBI GenPept Acc. No. AAH07485 "Golga4 protein" (Feb. 13, 2004).
NCBI GenPept Acc. No. AAH14818 "NADH dehydrogenase (ubiquinone) flavoprotein 1" (Dec. 2, 2006).
NCBI GenBank Acc No. AK001872 "*Homo sapiens* cDNA FLJ11010 fis, clone PLACE1003145" (Jan. 9, 2008).
NCBI GenPept Acc No. Q9BQ51 "Butyrophilin precursor B7-DC (PD-1-lingand 2 protein)" (Feb. 9, 2008).
NCBI GenPept Acc. No. Q9WUL5 "Butyrophilin-like protein" (Oct. 14, 2008).
NCBI GenBank Acc No. AL162253 "Human DNA sequence from clone RP11-574F11 on chromosome 9 Contains the gene for B7-H1 protein (PD-L1), the gene for programmed death ligand 2 (PDL2) (PDCD1L2) and a novel gene, complete sequence" (Jan. 13, 2009).
Ohshima et al., "The World Health Organization classification of malignant lymphoma: Incidence and clinical prognosis in HTLV-1-endemic area of Fukuoka," *Pathology International* 52:1-12 (Jan. 2002).
Ottensmeier, "The classification of lymphomas and leukemias," *Chemico-Biological Interactions* 135-136:653-664 (Jun. 1, 2001).
Browne et al., "The B-Cell Transcription Factors BSAO, Oct. 2, and BOB.1 and the Pan-B-Cell Markers CD20, CD22, and CD79a Are Useful in the Differential Diagnosis of Classic Hodgkin Lymphoma," *Am. J. Clin. Pathol.* 120:767-777 (2003).
Planz et al., "A critical role for neutralizing-antibody-producing B cells, CD4+ T cells, and interferons in persistent and acute infections of mice with lymphocytic choriomeningitis virus: Implications for adoptive immunotherapy of virus carriers," *Proc. Natl. Acad. Sci. USA* 94:6874-6879 (Jun. 1997).
Wilson and Brooks, "Translating insights from persistent LCMV infection into anti-HIV immunity," *Immunol Res.* 48(1-3):3-13 (Dec. 2010).
He et al. "Blocking programmed death-1 ligand-PD-1 interactions by local gene therapy results in enhancement of antitumor effect of secondary lymphoid tissue chemokine," *J. Immunol.* 173(8):4919-4928 (Aug. 16, 2004).
Leung and Suh "The CD28-B7 Family in Anti-Tumor Immunity: Emerging Concepts in Cancer Immunotherapy," *Immune Network* 14(6):265-276 (Dec. 2014).
Saudemont et al., "In a model of tumor dormancy, long-term persistent leukemic cells have increased B7-H1 and B7.1 expression and resist CTL-mediated lysis," *Blood* 104(7):2124-2133 (Oct. 1, 2004).
Vereecque et al., "Cytosine Arabinoside Induces Costimulatory Molecule Expression in Acute Myeloid Leukemia Cells," *Leukemia* 18:1223-1230 (2004).
Yamazaki et al., "Expression of Programmed Death 1 Ligands by Murine T Cells and APC," *Journal of Immunology* 169:5538-5545 (2002).
Yang et al., "Intratumoral CD4+CD25+ Regulatory T-Cell-Mediated Suppression of Infiltrating CD4+ T Cells in B-cell Non-Hodgkin Lynphoma," Blood 107(9):3639-3646 (May 1, 2006).
Akpek et al., "A clinician's guide to the updated Real/Who classification of non-Hodgkin's lymphoma: part I (indolent lymphomas)," *Turkish Journal of Cancer* 30(1):5-14 (2000).
Ansell et al., "PD-1 blockade with nivolumab in relapsed or refractory Hodgkin's Lymphoma," *New Engl. J. Med.*, pp. 1-9 (Dec. 6, 2014).
*Annual Review of Immunity* 171-177 (2004) (in Japanese).
Barber et al., "PD-L1 Blockade Restores Function to CD8 T cells during Chronic Viral Infection," Experimental Biology/IUPS 2005: Meeting Abstracts *FASEB Journal* 19(4):Supple., p. A893(#551.1) (dated Mar. 4, 2005).
Blank et al., "PD-L1/B7H-1 inhibits the effector phase of tumor rejection by T cell receptor (TCR) transgenic CD8+ T cells," *Cancer Research* 1140-1145 (Feb. 1, 2004).
Blank et al., "Blockade of PD-L1 (B7-H1) Augments Human Tumor-specific T Cell Responses in Vitro," *International Journal of Cancer* 119:317-327 (2006).
Desrosiers, "Prospects for an AIDS Vaccine," *Nature Med* 10(3):221-223 (2004).
Dorfman et al., "Programmed death-1 (PD-1) is a marker of germinal center-associated T Cells and angioimmunoblastic T-Cell lymphoma," *Am. J. Surg. Pathol.* 30:802-810 (2006).
EMBL Acc No. AF142780 "Mus musculus butyrophilin-like protein (Btdc) mRNA, complete cds," (Apr. 12, 2001).
EMBL Acc No. AF329193 "*Homo sapiens* butyrophilin precursor B7-DC mRNA, complete cds" (Apr. 10, 2001).
EMBL Acc No. AF344424 "*Homo sapiens* PD-1-ligand 2 protein (PDL2) mRNA, complete cds," (Apr. 8, 2002).
EMBL Acc No. AK001872 "*Homo sapiens* cDNA FLJ11010 fis, clone PLACE1003145" (Jan. 9, 2008).

(56) References Cited

OTHER PUBLICATIONS

EMBL Acc No. AL162253 "Human DNA sequence from clone RP11-574F11 on chromosome 9 Contains the gene for B7-H1 protein (PD-L1), the gene for programmed death ligand 2 (PDL2) (PDCD1L2) and a novel gene, complete sequence" (Jan. 13, 2009).
Freeman et al., "Reinvigorating exhausted HIV-specific T cells via PD-1-PD-1 ligand blockade," JEM 203(10):2223-2227 (Oct. 2, 2006).
GENESEQ Acc. No. AAH07485 "Golga4 protein" (Feb. 13, 2004).
GENESEQ Acc. No. AAH14818 "NADH dehydrogenase (ubiquinone) flavoprotein 1" (Dec. 2, 2006).
Ghiotto et al., "PD-L1 and PD-L2 differ in their molecular mechanisms of interaction with PD-1," International Immunology 22(8):651-660 (Jun. 29, 2010).
Habicht et al., "Striking dichotomy of PD-L1 and PD-L2 pathways in regulating alloreactive CD4$^+$ and CD8$^+$ T cells in vivo," T Am. J. Transplan. 7:2683-2692 (2007).
Hargreaves et al., "Selective depletion of activated T cells: the CD40L-specific antibody experience," Trends in Molecular Medicine 10(3):130-135 (Mar. 20004).
Haynes and Montefiori, "Aiming to induce broadly reactive neutralizing antibody responses with HIV-1 vaccine candidates," Expert Rev Vaccines 5(3):347-363 (2006).
Haynes and Shattock, "Critical Issued in Mucosal Immunity for HIV-1 Vaccine Development," J. Allergy Clin. Immunol. 122:3-9 (2008).
Hillinger et al., "Impaired cell-mediated immunity in Hodgkin's disease mediated by suppresser lymphocytes and monocytes," Journal of Clinical Investigation 61(6):1620-1627 (Jun. 1978).
"Hodgkin's lymphoma" Merck Manual 18th edition [online], Internet URL: <http://merckmanual.jp/mmpej/print/sec11/ch143/ch143b.html> (webpage in English).
Houghton and Abrignani, "Prospects for a vaccine against the hepatitis C virus," Nature 436(18):961-966 (2005).
Iwai and Honjo, "Cancer cell immune escape mechanisms through PD-1/PD-L1 signals," Genetic Medicine 7(1):109-111 (2003) (in Japanese, with English Language Translation).
Iwai et al., "PD-1 inhibits antiviral immunity at the effector phase in the liver," Journal of Experimental Medicine 198(1):39-50 (Jul. 7, 2003).
Iwai et al., "PD-1 blockade inhibits hematogenous spread of poorly immunogenic tumor cells by enhanced recruitment of effector T cells," Int. Immunol. 17(2):133-144 (2004).
Klenerman and Zinkernagel, "What can we learn about human immunodeficiency virus infection from a study of lymphocytic choriomeningitis virus?" Immunological Reviews 159:5-16 (1997).
Klenerman and Zinkernagel, "Clinical Investigation of Mice and Men: Cytotoxic T Cells and AIDS pathogenesis," The AIDS Reader 9(7):474-480 (1999).
Kozlov and Chernykh, "Current Problems in Cancer Immunotherapy," Bulletin SB Rams 2(112):13-19 (2004) (in Russian with English language translation).
Lambert et al., "Safety and immunogenicity of HIV recombinant envelope vaccines in HIV-infected infants and children," Journal of Acquired Immune Deficiency Syndromes & Human Retrovirology 19(5):451-461 (1998).

Leiberman et al., "Safety of Autologous, Ex Vivo-Expanded Human Immunodeficiency Virus (HIV)-Specific Cytotoxic T-Lymphocyte Infusion in HIV-Infected Patients," Blood 90:2196-2206 (1997).
Letvin, "Progress Toward an HIV vaccine," Annu. Rev. 56:213-233 (2005).
Levy et al., "Impaired lymphocyte function in untreated Hodgkin's disease," The New England Journal of Medicine 290:181-186 (Jan. 24, 1974).
Loke and Allison, "PD-L1 and PD-L2 are differentially regulated by Th1 and Th2 cells," PNAS 100(9):5336-5341 (Apr. 29, 2003).
Marshall et al., "Immunosuppressive regulatory T cells are abundant in the reactive lymphocytes of Hodgkin lymphoma," Blood 103(5): 1755-1762 (Mar. 1, 2004).
Martins et al., "CTLA-4 Blockage Increases Resistance to Infection with the Intracellular Protozoan Trypanosoma cruzi," Journal of Immunology 172:4893-4901 (2004).
Mueller et al., "PD-L1 has distinct functions in hematopoietic and nonhematopoietic cells in regulating T cell responses during chronic infection in mice," Journal of Clinical Investigation 120(7):2508-2515 (Jul. 2010).
English language translation of Notice of Reasons for Rejection from related Japanese Patent Application No. 2014-136588, 6 pages (mailed Mar. 28, 2016).
Okazaki and Honjo, "The PD-1-PD-L pathway in immunological tolerance," Trends in Immunology 27(4):195-201 (Apr. 2006).
Poppema and van den Berg, "Interaction between host T cells and Reed-Sternberg cells in Hodgkin lymphomas," Cancer Biology 10:345-350 (2000).
*Records of the plenary session and academic meetings of Japanese Society for Immunology* 34:228 (2004) (in Japanese).
*Records of the plenary session and academic meetings of Japanese Society for Immunology* 34:270 (2004) (in Japanese).
Rosenwald et al., "Molecular diagnosis of primary mediastinal B cell lymphoma identifies a clinically favorable subgroup of diffuse large B cell lymphoma related to Hodgkin lymphoma," Journal of Experimental Medicine 198(6):851-862 (Sep. 15, 2003).
Song et al., "Enhancement of vaccine-induced primary and memory CD8(+) T-cell response by soluble PD-1," J. Immunother. 34: 297-306 (2011) (abstract).
Sotrel and Dal Canto, "HIV-1 and its causal relationship to immunosuppression and nervous system disease in AIDS: A review," Human Pathology 31: 1274-1298 (2000).
Swissprot Acc No. Q9BQ51 "Butyrophilin precursor B7-DC (PD-1-lingand 2 protein)" (Feb. 9, 2008).
Swissprot Acc. No. Q9WUL5 "Butyrophilin-like protein" (Oct. 14, 2008).
Wang et al., "T Lymphocyte Co-Signaling Pathways of the B7-CD28 Family," Cellular & Molecular Immunology 1(1):37-42 (2004).
Wei et al., "Strength of PD-1 signaling differentially affects T-cell effector functions," Proceedings of the National Academy of Sciences, vol. 110, No. 27, published online Apr. 22, 2013, pp. E2480-E2489.
Fuller et al., "Immunotherapy of chronic hepatitis C virus infection with antibodies against programed cell death-1 (PD-1)," PNAS 110(37:15001-15006 (Sep. 10, 2013).
Urbani et al., "PD-1expression in acute hepatitis C virus (HCV) infection is associated with HCV-specific CD8 exhaustion," Journal of Virology 80(22):11398-11403 (Nov. 2006).

* cited by examiner

A

B

C

D

A

B

C

D

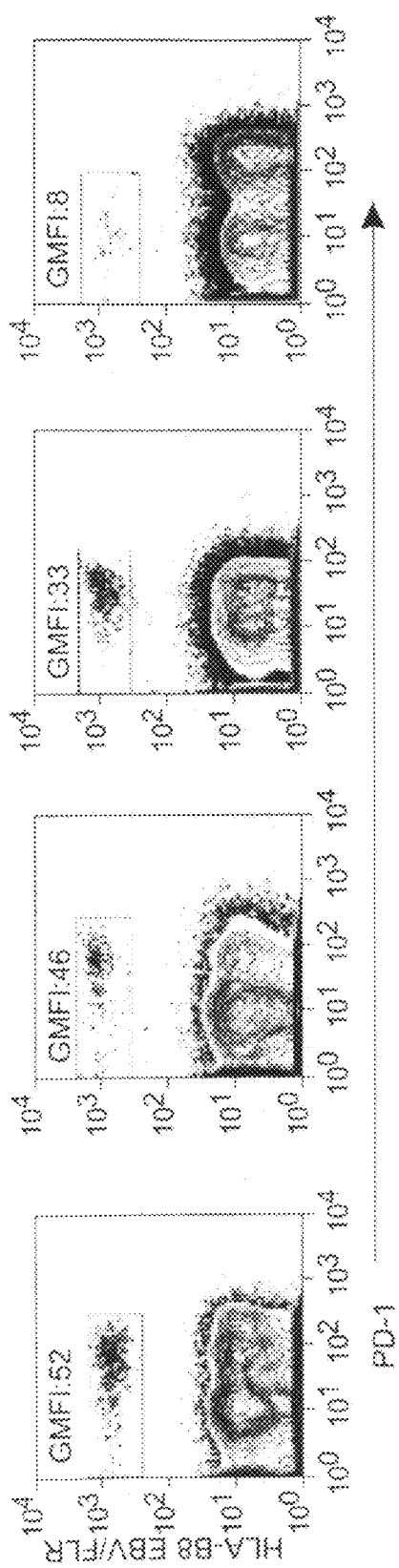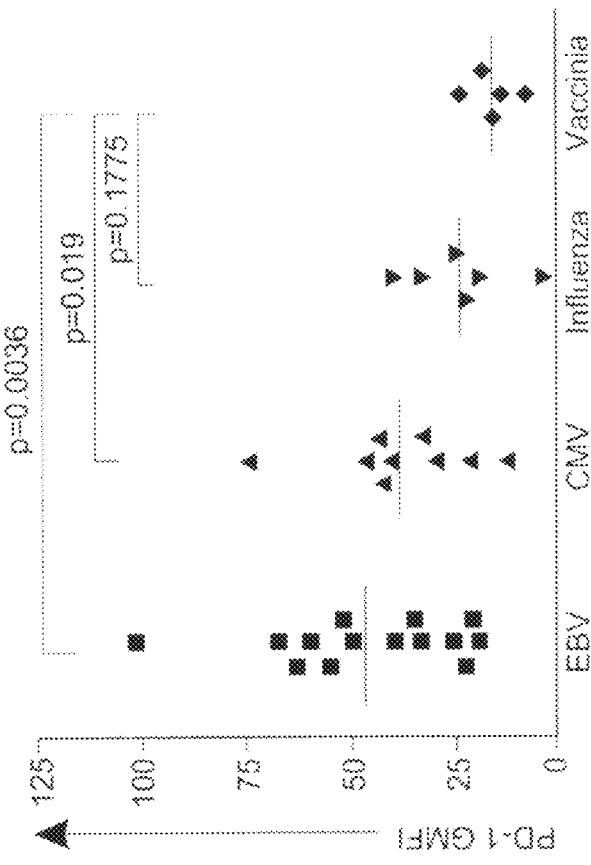
FIG. 21A
FIG. 21B

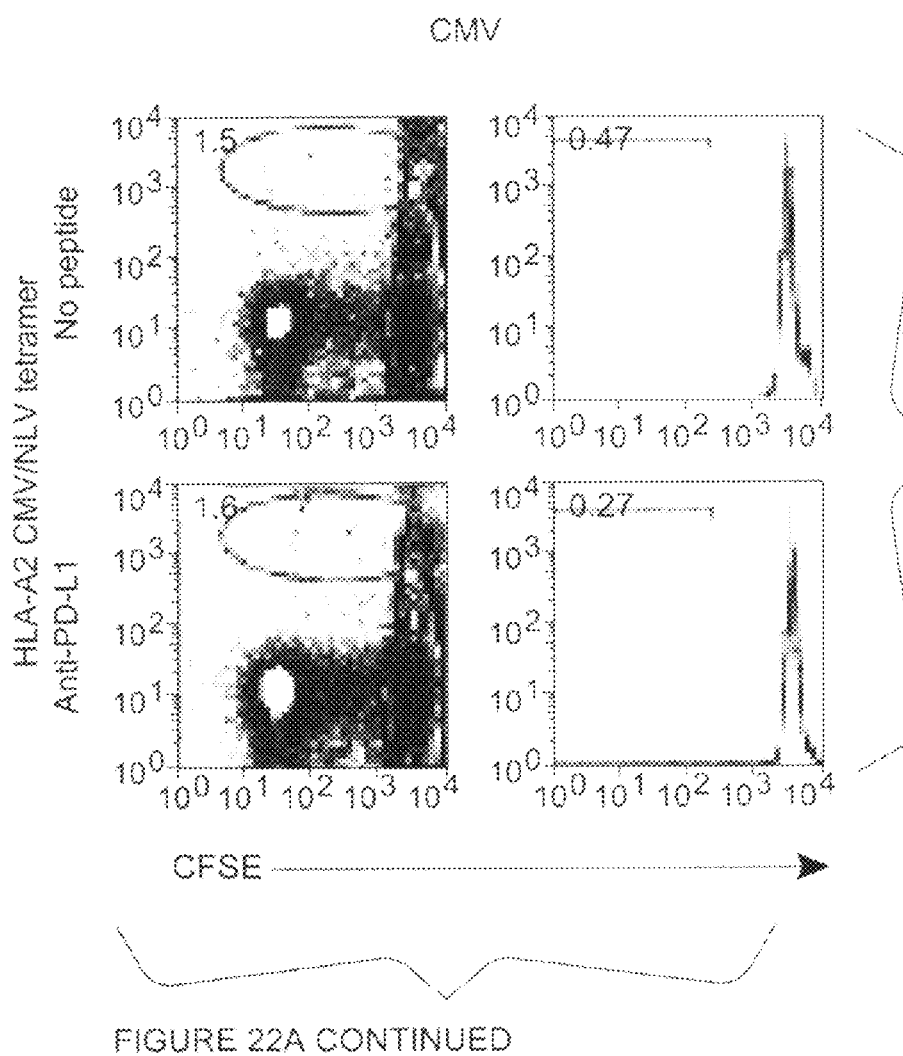

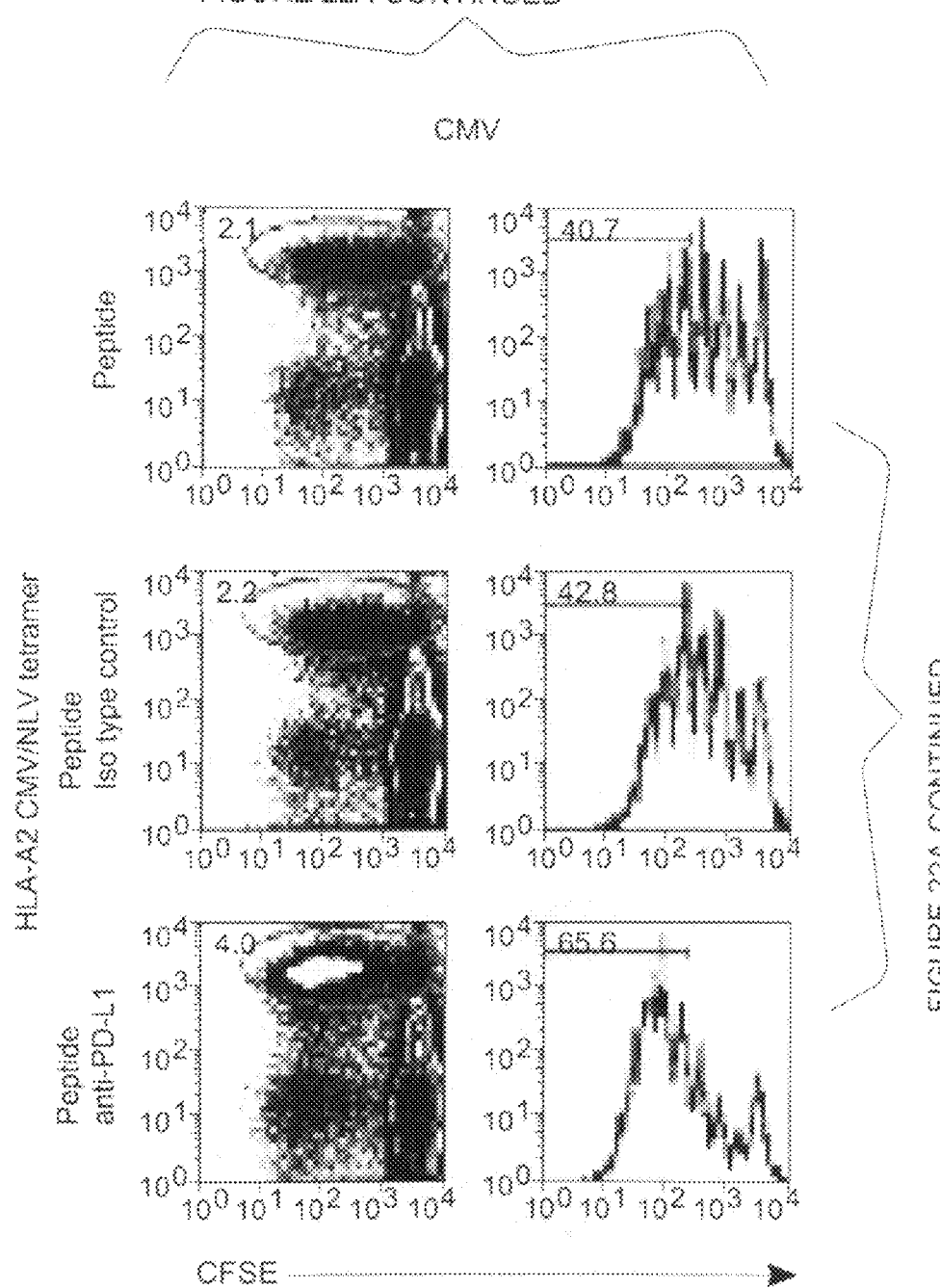

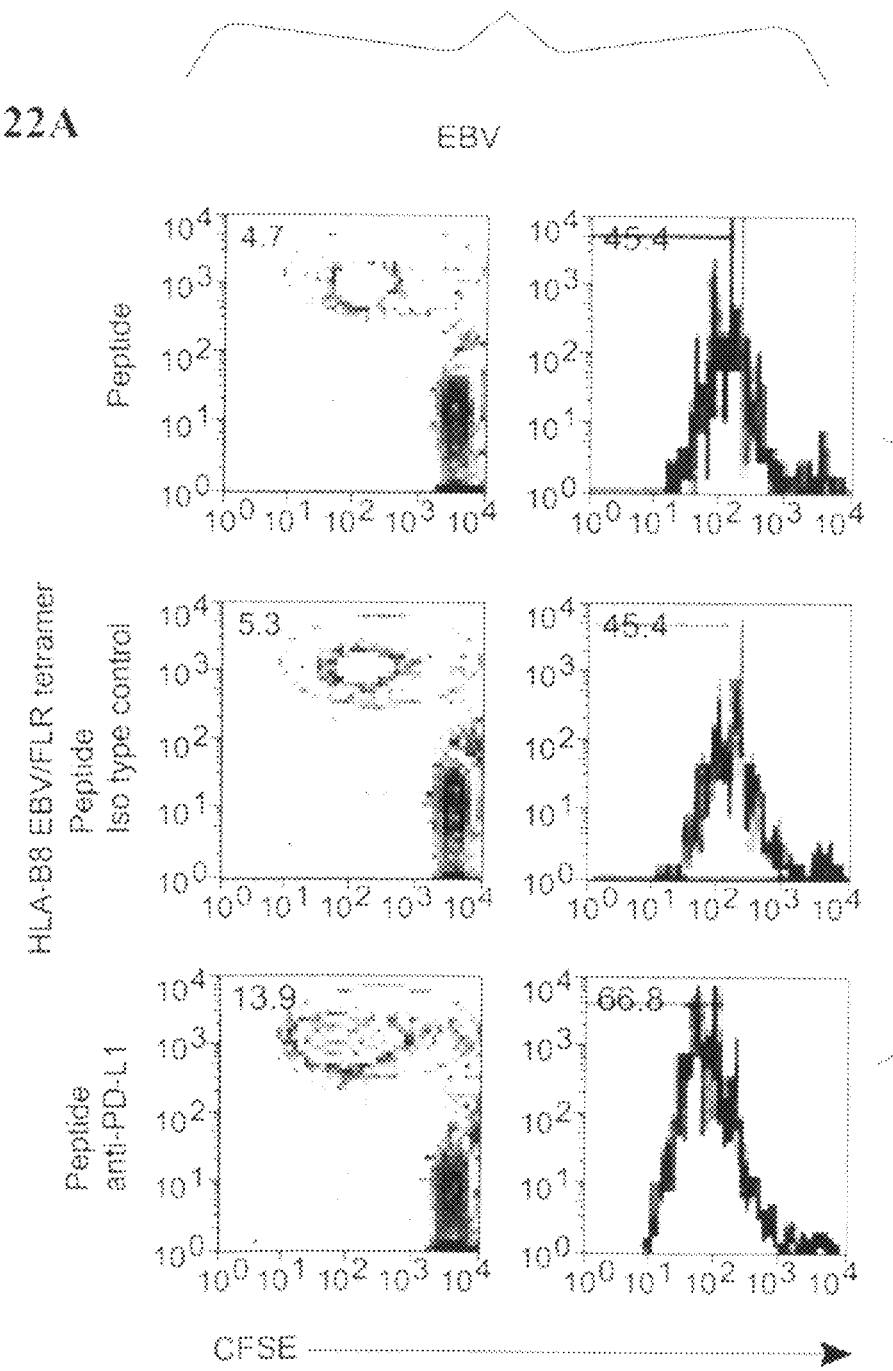

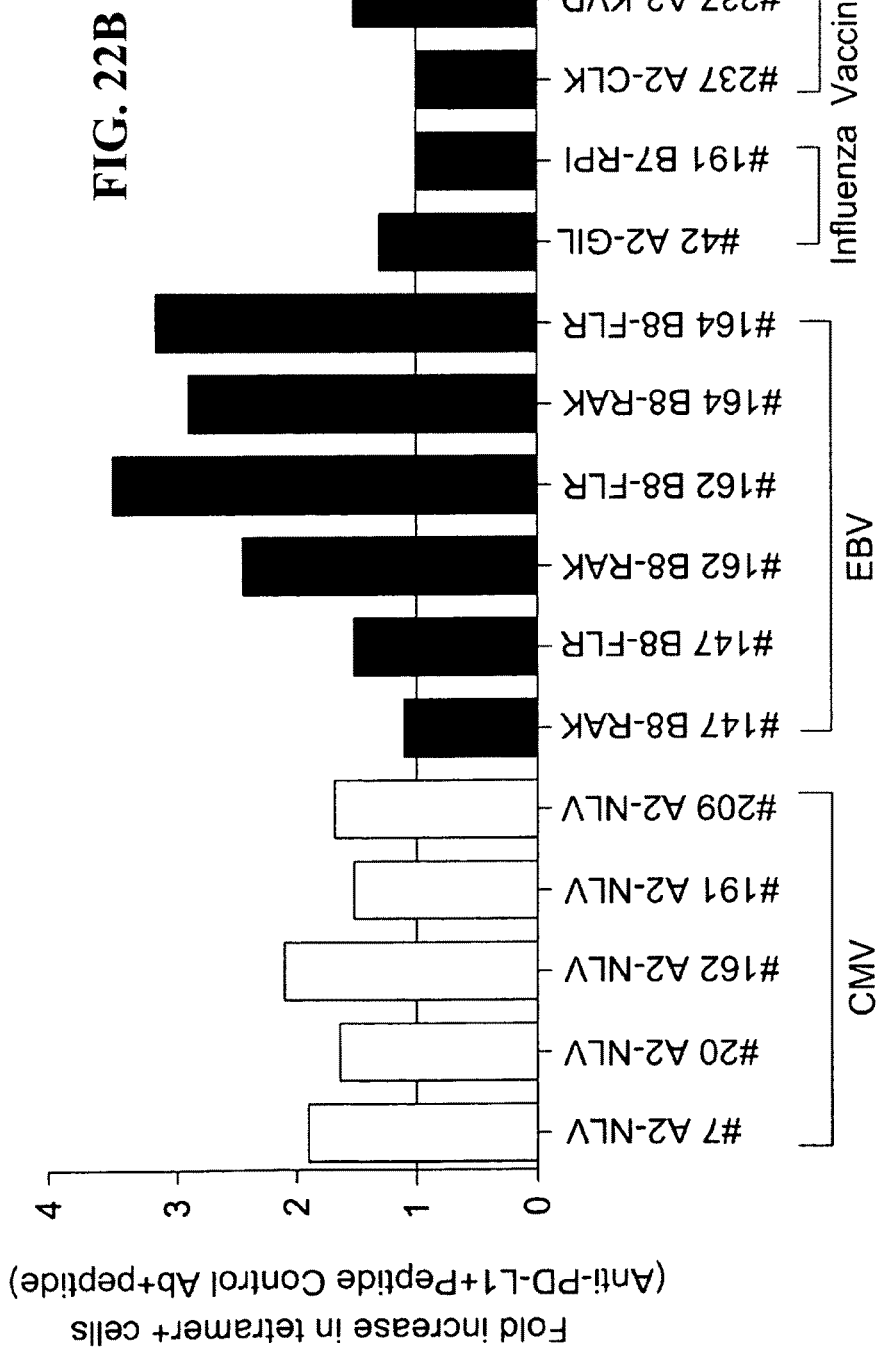

METHODS FOR THE TREATMENT OF INFECTIONS AND TUMORS

PRIORITY CLAIM

This application claims the benefit of U.S. Provisional Patent Application No. 61/118,570 filed Nov. 28, 2008, which is incorporated by reference herein in its entirety.

RELATED APPLICATIONS

The disclosed subject matter is also related to the subject matter of PCT Application No. PCT/US2007/088851, filed Dec. 26, 2007, U.S. Provisional Application No. 60/688,872, filed Jun. 8, 2005, U.S. Utility application Ser. No. 11/449,919, filed Jun. 8, 2006, and PCT Application No. PCT/US2006/22423, Jun. 8, 2006. This application is also related to U.S. Provisional Application No. 60/877,518, filed Dec. 27, 2006. These prior applications are incorporated herein by reference in their entirety.

STATEMENT OF GOVERNMENT SUPPORT

This invention was made with U.S. government support under NIH grants RO1 AI057029, R01 AI071852 and RO1 AI074417. The government has certain rights in the invention.

FIELD

This application relates to the use of antagonists, specifically to the use of PD-1 antagonists for the treatment of persistent infections and tumors, and to methods for determining an effective dose of a PD-1 antagonist.

BACKGROUND

Immunosuppression of a host immune response plays a role in persistent infection and tumor immunosuppression. Persistent infections are infections in which the virus is not cleared but remains in specific cells of infected individuals. Persistent infections often involve stages of both silent and productive infection without rapidly killing or even producing excessive damage of the host cells. There are three types of persistent virus-host interaction: latent, chronic and slow infection. Latent infection is characterized by the lack of demonstrable infectious virus between episodes of recurrent disease. Chronic infection is characterized by the continued presence of infectious virus following the primary infection and can include chronic or recurrent disease. Slow infection is characterized by a prolonged incubation period followed by progressive disease. Unlike latent and chronic infections, slow infection may not begin with an acute period of viral multiplication. During persistent infections, the viral genome can be either stably integrated into the cellular DNA or maintained episomally. Persistent infection occurs with viruses such as human T-Cell leukemia viruses, Epstein-Barr virus, cytomegalovirus, herpesviruses, varicella-zoster virus, measles, papovaviruses, xenotropic murine leukemia virus-related virus (XMRV), prions, hepatitis viruses, adenoviruses, parvoviruses and papillomaviruses.

The mechanisms by which persistent infections are maintained can involve modulation of virus and cellular gene expression and modification of the host immune response. Reactivation of a latent infection may be triggered by various stimuli, including changes in cell physiology, superinfection by another virus, and physical stress or trauma. Host immunosuppression is often associated with reactivation of a number of persistent virus infections.

Many studies show defective immune responses in patients diagnosed with cancer. A number of tumor antigens have been identified that are associated with specific cancers. Many tumor antigens have been defined in terms of multiple solid tumors: MAGE 1, 2, & 3, defined by immunity; MART-1/Melan-A, gp100, carcinoembryonic antigen (CEA), HER-2, mucins (i.e., MUC-1), prostate-specific antigen (PSA), and prostatic acid phosphatase (PAP). In addition, viral proteins such as hepatitis B (HBV), Epstein-Barr (EBV), and human papilloma (HPV) have been shown to be important in the development of hepatocellular carcinoma, lymphoma, and cervical cancer, respectively. However, due to the immunosuppression of patients diagnosed with cancer, the innate immune system of these patients often fails to respond to the tumor antigens.

Both passive and active immunotherapy has been proposed to be of use in the treatment of tumors. Passive immunity supplies a component of the immune response, such as antibodies or cytotoxic T cells to the subject of interest. Active immunotherapy utilizes a therapeutic agent, such as a cytokine, antibody or chemical compound to activate an endogenous immune response, where the immune system is primed to recognize the tumor as foreign. The induction of both passive and active immunity have been successful in the treatment of specific types of cancer.

In general, a need exists to provide safe and effective therapeutic methods and to establish safe dosing of agents to treat disease, for example, autoimmune diseases, inflammatory disorders, allergies, transplant rejection, cancer, immune deficiency, viral infections and other immune system-related disorders. There also remains a need for methods for determining if a particular dose of a therapeutic agent, such as a PD-1 antagonist, is effectively treating a subject.

SUMMARY

PD-1 antagonists reduce the expression and/or activity of PD-1. Subjects with infections, such as persistent infections can be treated using PD-1 antagonists. Subject with tumors can also be treated using PD-1 antagonists. Additionally, subjects can be treated by transplanting a therapeutically effective amount of activated T cells that recognize an antigen of interest in conjunction with a therapeutically effective amount of a PD-1 antagonist.

An immune response can be measured in the mammalian recipient. In some embodiments the method of treatment disclosed herein includes measuring B cells. In some embodiments, the methods include measuring the proliferation of memory B cells in a sample from the subject.

In some embodiments, methods are disclosed for determining the efficacy of a PD-1 antagonist in a subject administered the PD-1 antagonist. These methods include measuring proliferation of memory B cells in a sample from a subject administered the PD-1 antagonist, wherein an increase in proliferation of memory B cells from the sample as compared to a control indicates that the PD-1 antagonist is efficacious for treating the subject.

Methods for determining the dose of a PD-1 antagonist that is useful to treat a subject are also disclosed herein. These methods include administering to the subject a first dose of a PD-1 antagonist, and determining the proliferation of memory B cells in a first sample from the subject. An increase in the proliferation of memory B cells from the first sample as compared to a control indicates that the first dose of the PD-1 antagonist is of use treating the subject. An absence of a significant alteration in the proliferation of memory B cells as compared to the control indicates that the first dose of the PD-1 antagonist is not sufficient to treat the subject.

The foregoing and other features and advantages will become more apparent from the following detailed description of several embodiments, which proceeds with reference to the accompanying figures.

BRIEF DESCRIPTION OF THE FIGURES

FIG. 9A is a schematic diagram of an experimental protocol. LCMV clone-13 (CL-13)-infected mice were vaccinated with wild-type vaccinia virus (VV/WT) or LCMV GP33-41 epitope-expressing vaccinia virus (VV/GP33) at 4 (week) post-infection. At the same time, the mice were treated 5 times every three days with or without anti-PD-L1. FIG. 9B is a series of images of a flow cytometry experiment showing the frequency of GP33- and GP276-specific CD8-T cells in PBMC at 1-wk post-therapy. The number represents frequency of tetramer-positive cells per CD8-T cells. Data are representative of three experiments. FIGS. 9C-9D are graphs of the frequency of GP33- and GP276-specific CD8-T cells (FIG. 9C) and viral titers (FIG. 9D) in the blood post-therapy. Changes in the numbers of tetramer-positive CD8-T cells and the viral titers were monitored in the blood by tetramer staining and plaque assay, respectively, at the indicated time points. The numbers of tetramer-positive CD8-T cells and viral titers are shown for individual (upper four panels) and multiple (lower panel) mice following infection with VV/WT or VV/GP33 (straight line) and treatment with anti-PD-L1 (shade region). Dashed lines represent virus detection limit. Results are pooled from three experiments.

FIG. 10A is a series of images of a flow cytometry experiment showing the frequency of GP33-specific CD8-T cells in different tissues at 4-wk post-therapy. The number represents frequency of GP33 tetramer-positive cells per CD8-T cells. Data are representative of two experiments. FIG. 10B is a graph of GP33-specific CD8 T-cell numbers in different tissues at 4-wk post-therapy. FIG. 10C is a set of bar graphs of viral titers in the indicated tissues at 2 (filled)- and 4 (blank)-wk post-therapy. Dashed lines represent virus detection limit. n=6 mice per group. Results are pooled from two experiments. FIG. 10D is a digital image of immunostaining of spleen with aLCMV antigens (red) at 2-wk post-therapy. Magnification, ×20.

FIG. 11A is a series of images of a flow cytometry experiment showing IFN-γ production and degranulation by splenocytes of the vaccinated mice at 4-wk post-therapy. Splenocytes were stimulated with the indicated peptides in the presence of αCD107a/b antibodies and then co-stained for IFN-γ. The shown plots are gated on CD8-T cells and are the representative of two independent experiments. FIG. 11B is a graph showing the percentage of IFN-γ$^+$CD107$^+$ cells per CD8-T cells specific for each of LCMV peptides from FIG. 11A are summarized for multiple mice (n=6 for each response). Results are pooled from two experiments. FIG. 11C is a set of plots showing TNF-α production from CD8-T cells capable of producing IFN-γ in the vaccinated mice. After stimulation of splenocytes with GP33-41 or GP276-286 peptide, IFN-γ-producing CD8-T cells were gated and then plotted by IFN-γ (x-axis) versus TNF-α (y-axis). The upper and lower numbers on plots indicate frequency of TNF-α$^+$ cells among IFN-γ$^+$ cells and mean fluorescent intensity (MFI) of IFN-γ$^+$ cells, respectively. The data are representative of two independent experiments. FIG. 11D is a graph showing the percentage of TNF-α$^+$ cells per IFN-γ$^+$ cells for GP33-41 or GP276-286 peptide from FIG. 11C are summarized for multiple mice (n=6 for each response).

FIG. 12A is a set of plots showing the phenotype of GP33 tetramer-specific CD8-T cells in PBMC at the indicated times post-therapy. Histograms were gated on GP33$^+$CD8-T cells. Frequency of population expressing high-level of CD27 or CD127 is indicated by percent on plots. The numbers on histograms of Granzyme B represent MFI of expression. The data are representative of three independent experiments. FIG. 12B is a set of plots showing phenotypic changes of GP33 tetramer-specific CD8-T cells in different tissues at 4-wk post-therapy. Histograms were gated on GP33$^+$CD8-T cells. Frequency of population expressing high-level of CD127 or PD-1 is indicated by percent on plots. The numbers on histograms of Granzyme B and Bcl-2 represent MFI of expression. The data are representative of two independent experiments.

FIG. 13A is a schematic diagram of the protocol. Mice were depleted of CD4 T cells and then infected with LCMV clone-13. Some mice were vaccinated with wild-type vaccinia virus (VV/WT) or LCMV GP33-41 epitope-expressing vaccinia virus (VV/GP33) at 7-wk post-infection. At the same time, the mice were treated 5 times every three days with αPD-L1 or its isotype. Two weeks after initial treatment of antibodies, mice were sacrificed for analysis. FIG. 13B is a series of images of a flow cytometry experiment and a bar graph showing the frequency of GP33-specific CD8-T cells in the indicated tissues at 4-weeks post-therapy. The number represents frequency of GP33 tetramer-positive cells per CD8-T cells. Frequency of GP33-specific cells per CD8 T-cells in different tissues at 2-weeks post-therapy is also summarized. FIG. 13C is a series of images of a flow cytometry experiment showing the results from experiments wherein splenocytes stimulated with GP33 peptide in the presence of αCD107a/b antibodies and then co-stained for IFN-γ. The shown plots are gated on CD8-T cells. The percentage of IFN-γ$^+$CD107$^+$ cells per CD8-T cells specific for GP33 peptide are summarized for multiple mice. FIG. 13D is a bar graph of the percentage of IFN-γ$^+$ cells after stimulation with GP33 peptide per cells positive for Db-restricted GP33-41 tetramer are summarized for multiple mice. FIG. 13E is a bar graph of viral titers in the indicated tissues at 2-wk post-therapy. All plots are representative of two experiments and all summarized results are pooled from two experiments (n=6 mice per group).

FIG. 14A is a set of representative flow cytometry plots from specific time-points gated on CD8+ T cells. FIG. 14B are graphs showing the kinetics of Db GP33-specific CD8 T cell expansion in peripheral blood from two independent experiments (n=4 animals per group)

FIG. 15A is a set of representative flow plots are shown for the expression of IFNγ assessed by intracellular cytokine staining following 5 hours of stimulation with defined CD8 epitopes or no peptide controls. FIGS. 15B and 15D are representative plots are shown for the dual expression of TNFα or 107ab and IFNγ (quadrant stats are percentage of CD8 gate). FIGS. 15C and 15E are graphs of the percentage of IFNγ producing cells also producing TNFα or 107ab (n=3 animals per group)

FIG. 16A is a graph of total number of splenic ASC, summary of results from three independent experiments. FIG. 16B is a set of plots showing an increase in antibody secreting cells (ASC) in the spleen can be measured by the marker CD138. Showing one representative plot, ASC are CD138+ and B220 low/intermediate (gated on lymphocytes).

FIG. 19A is a plot of flow cytometric analysis of CD4 T cells and B cells shows elevated Ki-67 levels following αPD-L1 treatment. Results are gated on either CD4 or B cells as listed above each column. FIG. 19B is a set of plots showing an increased frequency of B cells expressing PNA and high levels of FAS, which indicate enhanced germinal center activity in mice treated with αPD-L1. Plots are one representative graph summarizing the results of two separate experiments.

FIG. 20A is a series of images of a flow cytometry experiment showing co-expression of PD-1 and various phenotypic markers among CD8+/CD3+ lymphocytes in blood. FIG. 20B is a set of plots of the percentage of various CD8+/CD3+ and (D) CD4+/CD3+ T cell subsets that express PD-1. Horizontal bars indicate mean percentage of PD-1 on T cells that are positive (hollow circles) and negative (solid triangles) for the indicated marker. FIG. 20C is a set of plots representing the phenotypic data of PD-1 expressing CD4+ T cells from one subject.

FIG. 21A-B are plots and graphs demonstrating that PD-1 is more highly expressed among CD8 T cells specific for chronic infections. FIG. 21A is a series of images of a flow cytometry experiment showing representative PD-1 staining of Ebstein Bar Virus (EBV), Cylomegalovirus (CMV), influenza and vaccinia virus-specific CD8 T cells. Geometric mean fluorescence intensity (GMFI) of PD-1 expression among tetramer+ cells is indicated. FIG. 21B is a plot showing a summary of PD-1 GMFI on EBV, CMV, influenza and vaccinia virus-specific CD8 T cells from healthy volunteers (n=35).

FIG. 22A-C are plots and graphs demonstrating that anti-PD-L1 blockade increases in vitro proliferation of CD8 T cells specific for chronic infections. FIG. 22A is a series of images of a flow cytometry experiment showing lymphocytes that were labeled with CFSE, then cultured for 6 days under the indicated conditions. The images show representative staining from EBV and CMV positive subjects. FIG. 22B is a bar graph of EBV, CMV, influenza and vaccinia virus antigen-specific responses following blockade with anti-PD-L1 blocking antibody. The bars indicate fold increase of tetramer+ cells in the presence of peptide plus anti-PD-L1 blocking antibody compared to peptide alone. FIG. 22C is a line graph showing the relationship between the fold-increase in tetramer+ cells following anti-PD-L1 antibody blockade and PD-1 expression (prior to culture).

FIG. 23B is a comparison of PD-1 expression on CD8+ T cells from healthy donors (CD8 Healthy), HCV infected patients (CD8 HCV) and on CD8+ HCV specific T cells (HCV tet+). FIG. 23C is a graph of PD-1 expression on CD8+ T cells specific for influenza virus (Flu tet+) from HCV infected (HCV+) and healthy donors (Healthy) compared with PD-1 expression on CD8+ T cells specific for HCV (HCV tet+). An unpaired t test was used to compare differences in expression of PD-1 within the same patient on total CD8+ T cells versus HCV specific CD8+ T cells.

FIG. 24A is representative plots from five patients with chronic HCV infection showing the expression of PD-1 on total CD8+ T cells from the peripheral blood versus the liver. Numbers in bold within the plots identify the frequency of cells with PD-1 expression among total CD8+ T cells in the lymphocyte gate. Plots are on a logarithmic scale. FIG. 24B is a comparison of PD-1 expression on CD8+ T cells from peripheral blood versus liver in HCV chronically infected patients. A paired t test was used to compare the difference in PD-1 expression within the same patients. FIG. 24C is a comparison of PD-1 expression on the CD8+ Effector Memory ($T_{EM}$) cells from peripheral blood versus the liver. Memory subsets were identified by differential expression of CD62L and CD45RA. Bold numbers in the top plots represent the frequency of cells in each quadrant. Cells were gated on CD8+ lymphocytes. The $T_{EM}$ subset was gated (boxes) and the expression of PD-1 is shown in the histogram plots below. The dotted line shows PD-1 expression on naïve CD8+ T cells (used as the negative population). The numbers in the histogram plots represent the frequency of cells expressing PD-1. Comparison of the frequency of PD-1 expression on CD8+ $T_{EM}$ cells for ten patients with chronic HCV infection is summarized below the histogram plots. A paired t test was used to compare the difference in PD-1 expression on CD8+ $T_{EM}$ from the peripheral blood versus the liver within the same patient. FIG. 24D are representative plots from two patients with chronic HCV infection showing the difference in CD127 expression on total CD8+ T cells from the peripheral blood versus the liver. Numbers in bold identify the frequency of CD127 expression on total CD8+ T cells. Cells were gated on CD8+ lymphocytes. Plots are on a logarithmic scale. A summary of the comparison of CD127 expression on total CD8+ T cells in the peripheral blood versus the liver is shown below the FACS plots. A paired t test was used for statistical analysis.

FIG. 27A is a plot showing PD-1 expression on total CD8 T cells from a normal macaque. FIG. 27B is a plot showing PD-1 expression on total and SIV gag-specific CD8 T cells in a SIV239 infected macaque. Analysis was done on PBMC at 12 weeks following SIV-infection. FIG. 27C is a graph providing a summary of PD-1 positive cells on total and SIV-specific CD8 T cells from normal and SIV-infected macaques. Data for SIV-infected macaques represent at 12 weeks following infection. FIG. 27D (last panel) is a graph providing a summary of mean fluorescence intensity (MFI) of PD-1 expression on total and SIV-specific CD8 T cells from normal and SIV-infected macaques.

FIG. 28A is a representative FACS plots. Numbers on the graph represent the frequency of tetramer positive cells as a percent of total CD8 T cells. FIG. 28B is a graph providing a summary of data from six macaques. Analyses were performed using cells obtained at 12 weeks following infection. Fold increase was calculated as a ratio of the frequency of tetramer positive cells in P11C stimulated cultures and unstimulated cells.

FIG. 30a is a representative FACS plots for macaque RRk10. FIGS. 30b and 30c are FACS plots showing the magnitude and phenotype of Gag-CM9-tetramer-positive CD8 T cells in blood (FIG. 30b) and gut (colorectal mucosal tissue) (FIG. 30c). Representative FACS plots are shown on the left and summary for all Mamu A*01-positive animals is shown on the right. Numbers on the FACS plots represent the frequency of tetramer-positive cells as a percent of total CD8 T cells. Arrows and vertical lines indicate anti-PD-1 antibody or control antibody treatment.

FIG. 31a shows the frequency of Gag-specific cytokine-secreting CD8 T cells as a percentage of total CD8 T cells. Representative FACS plots are shown on the left and summary for the group is shown on the right. Arrows and vertical lines indicate anti-PD-1 antibody or control antibody treatment. Lines represent anti-PD-1-antibody-treated macaques and red lines represent control-antibody-treated macaques. FIG. 31b shows cytokine co-expression subsets expressed as a percentage of total cytokine-positive cells. Mean percentages for each group are shown.

FIG. 32a shows expression of PD-1 on memory ($CD20^+CD27^+CD21^-$) and naïve ($CD20^+CD27^-CD21^+$) B cells in blood after SW infection and before in vivo PD-1 blockade. FIG. 32b shows titres of anti-SW Env-binding antibody in serum after blockade.

FIG. 33d shows the fold reduction in plasma viral load between day 0 and day 28 (early chronic study) or day 0 and day 21 (late chronic study). FIG. 33e shows the survival of SW-infected macaques after PD-1 blockade.

SEQUENCE LISTING

Figure 1:
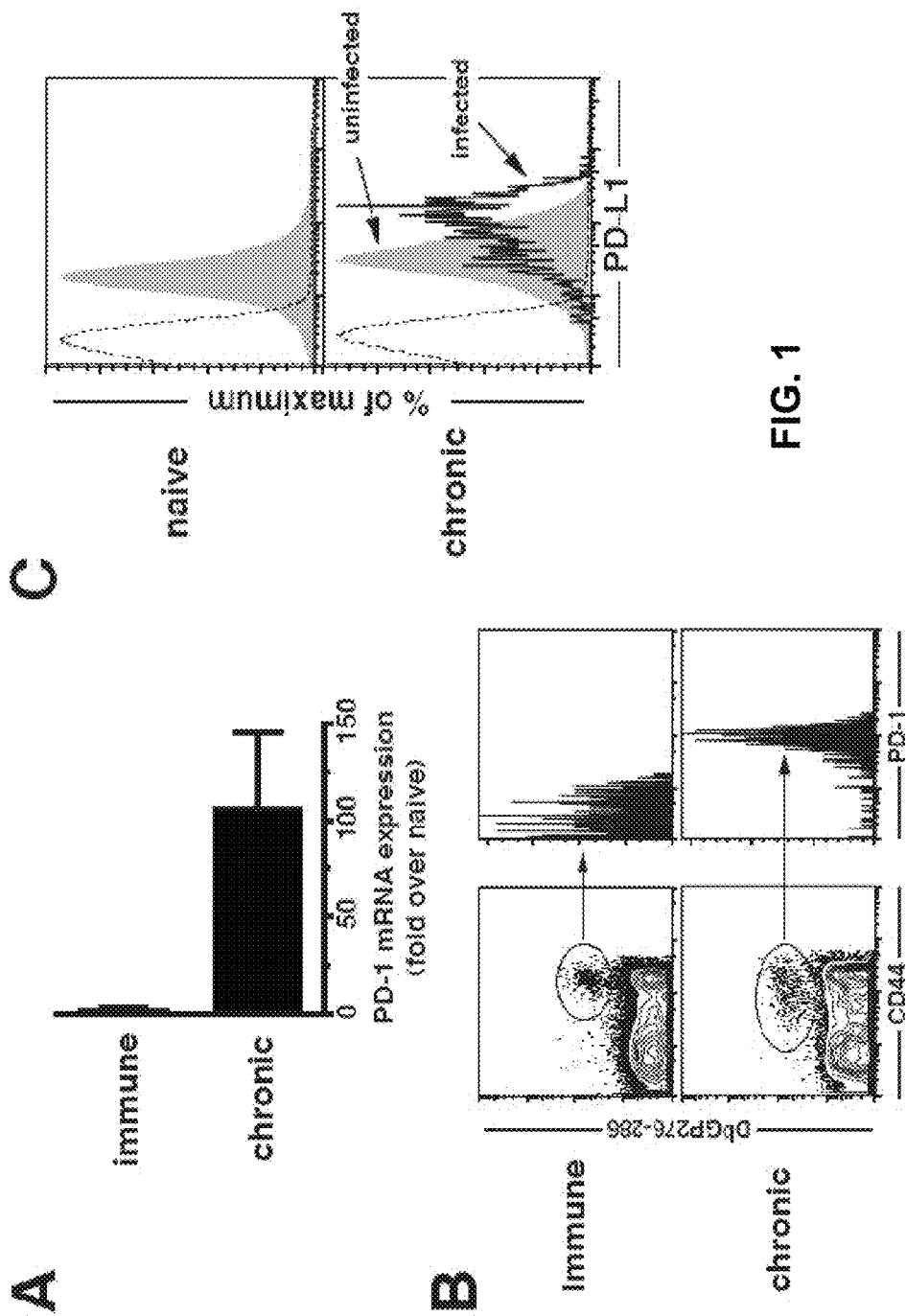
FIG. 1A is a bar graph showing the levels of PD-1 mRNA in $D^bGP33$-41 and/or $D^bGP276$-286 specific T cells from naïve transgenic mice, lymphocytic choriomeningitis virus (LCMV) Armstrong immune (approximately 30 days post-infection) infected mice, or CD4-depleted LCMV-Cl-13 infected mice (approximately 30 days post-infection), as measured by gene array analysis.
FIG. 1B is a series of images of a flow cytometry experiment showing PD-1 surface expression on CD8+ tetramer+ T cells in LCMV Armstrong immune and CD4 depleted LCMV-Cl-13 infected mice approximately 60 days post-infection. Anergic CD8+ T cells express high levels of PD-1 polypeptide on the cell surface approximately 60 days after chronic infection with LCMV-Cl-13 virus (labeled "chronic"), but virus-specific CD8+ T cells do not express PD-1 polypeptide after clearance of an acute LCMV Armstrong infection (labeled "immune").
FIG. 1C is a series of images of a flow cytometry experiment demonstrating the presence of PD-L1 on splenocytes from chronically infected and uninfected mice. It demonstrates that PD-L1 expression is the highest on the splenocytes that are infected by the virus.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is an exemplary amino acid sequence of human PD-1.

SEQ ID NO: 2 is an exemplary amino acid sequence of mouse PD-1.

SEQ ID NO: 3 is an exemplary amino acid sequence of human PD-L1.

SEQ ID NO: 4 is an exemplary amino acid sequence of human PD-L2.

SEQ ID NOs: 5-12 are exemplary amino acid sequences of human framework regions.

SEQ ID NOs: 13-35 are exemplary amino acid sequences of antigenic peptides.

SEQ ID NOs: 36-43 are the amino acid sequences of major histocompatibility peptides.

SEQ ID NO: 44 and SEQ ID NO: 45 are the amino acid sequence of T cell epitopes.

SEQ ID NO: 46 is an exemplary amino acid sequence of a variant human PD-L2.

SEQ ID NOs: 47-52 are exemplary amino acid sequences of antigenic peptides.

SEQ ID NOs: 53-56 are the nucleic acid sequences of primers.

DETAILED DESCRIPTION

This disclosure relates to the use of PD-1 antagonists for the induction of an immune response, such as to a tumor or a persistent viral infection. This disclosure also relates to methods for determining the dose of a PD-1 antagonist that is effective for treating a subject.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Altering: A statistically significant change in a parameter as compared to a control value for that parameter. In one example, an "increase" is a statistically significant elevation in a parameter, such as the number or proliferation of memory B cells, as compared to a control. Suitable statistical analyses are well known in the art, and include, but are not limited to, Student's T test and ANOVA assays. In some examples, this is a p value ≤0.05. In other examples, a significant alteration, such as an increase or a decrease is a change that is two standard deviations from the mean or greater. An "absence of a significant alteration" means that a change in a value did not achieve statistical significance, using the appropriate statistical test. In some examples, this is a p value >0.05. In other examples, an "absence of a significant alteration" is an increase or a decrease that is less than two standard deviations from the mean. In some embodiments, an "increase" or "elevation," such as in the proliferation of memory B cells, is about a 20%, 30%, 40% 50%, 60%, 70%, 80%, 90% or a 2-fold, 3-fold, 4-fold or 5-fold increase. In one example, a "decrease" or "reduction" is a statistically significant decline in a parameter, such as the number or proliferation of memory B cells, as compared to a control. Suitable statistical analyses are well known in the art, and include, but are not limited to, Student's T test and ANOVA assays. In some embodiments, a "decrease," such as in the proliferation of memory B cells, is about a 20%, 30%, 40% 50%, 60%, 70%, 80%, 90% or a 2-fold, 3-fold, 4-fold or 5-fold decrease.

Antisense, Sense, and Antigene: DNA has two antiparallel strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, an RNA transcript will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target. An antisense RNA (asRNA) is a molecule of RNA complementary to a sense (encoding) nucleic acid molecule.

Amplification: When used in reference to a nucleic acid, this refers to techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antibody: A polypeptide ligand comprising at least a light chain or heavy chain immunoglobulin variable region which specifically recognizes and binds an epitope (e.g., an antigen, such as a tumor or viral antigen or a fragment thereof). This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (e.g., humanized murine antibodies), heteroconjugate antibodies (e.g., bispecific antibodies). See also, *Pierce Catalog and Handbook,* 1994-1995 (Pierce Chemical Co., Rockford, Ill.); Kuby, J., *Immunology,* 3$^{rd}$ Ed., W.H. Freeman & Co., New York, 1997.

Typically, an immunoglobulin has a heavy and light chain. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs has been defined (see, Kabat et al., *Sequences of Proteins of Immunological Interest,* U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (e.g., see U.S. Pat. No. 5,585, 089).

A "neutralizing antibody" is an antibody that interferes with any of the biological activities of a polypeptide, such as a PD-1 polypeptide. For example, a neutralizing antibody can interfere with the ability of a PD-1 polypeptide to reduce an immune response such as the cytotoxicity of T cells. In several examples, the neutralizing antibody can reduce the ability of a PD-1 polypeptide to reduce an immune response by about 50%, about 70%, about 90% or more. Any standard assay to measure immune responses, including those described herein, may be used to assess potentially neutralizing antibodies.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen, a uterine specific antigen, and/or a testes specific antigen. A tissue specific antigen may be expressed by more than one tissue, such as, but not limited to, an antigen that is expressed in more than one reproductive tissue, such as in both prostate and uterine tissue. A disease-specific antigen is expressed coincidentally with a disease process. Specific non-limiting examples of a disease-specific antigen are an antigen whose expression correlates with, or is predictive of, tumor formation. A disease-specific antigen can be an antigen recognized by T cells or B cells.

Antigen-presenting cell (APC): A cell that can present antigen bound to MHC class I or class II molecules to T cells. APCs include, but are not limited to, monocytes, macrophages, dendritic cells, B cells, T cells and Langerhans cells. A T cell that can present antigen to other T cells (including CD4+ and/or CD8+ T cells) is an antigen presenting T cell (T-APC).

B Cells: A subset of lymphocytes, that is, white blood cells (leukocytes). Mature B cells differentiate into plasma cells, which produces antibodies, and memory B cells. A "B cell progenitor" is a cell that can develop into a mature B cell. B cell progenitors include stem cells, early pro-B cells, late pro-B cells, large pre-B cells, small pre-B cells, and immature B cells and transitional B cells. Generally, early pro-B cells (that express, for example, CD43 or B220) undergo immunoglobulin heavy chain rearrangement to become late pro B and pre B cells, and further undergo immunoglobulin light chain rearrangement to become an immature B cells. Immature B cells include T1 and T2 B cells. For example, in mice, immature B cells include T1 B cells that are AA41$^{hi}$CD23$^{hi}$ cells. Another example of a mouse immature B cell is a T2 B that is an AA41$^{hi}$CD23$^{hi}$ cell. In humans, immature B cells (for example, immature peripheral transitional B cells) include CD38$^{hi}$, IgD$^+$, CD10$^+$, CD24$^{hi}$, CD44$^{lo}$, CD23$^{lo}$ and CD1$^{lo}$ cells. Thus, immature B cells include B220 (CD45R) expressing cells wherein the light and the heavy chain immunoglobulin genes are rearranged. In one embodiment, immature B cells express CD45R, class II, IgM, CD19 and CD40. Immature B cells do not exhibit surrogate light chain expression, but do express Ig αβ and RAG Immature B cells can develop into mature B cells, which can produce immunoglobulins (e.g., IgA, IgG or IgM). Mature B cells have acquired surface IgM and IgD, are capable of responding to antigen, and express characteristic markers such as CD21 and CD23 (CD23$^{hi}$CD21$^{hi}$ cells). B cells can be activated by agents such as lipopolysaccharide (LPS) or IL-4 and antibodies to IgM. Common biological sources of B cells and B cell progenitors include bone marrow, peripheral blood, spleen and lymph nodes.

B cells that encounter antigen for the first time are known as "naïve" B cells; the cells have IgM and IgD on their cell surfaces. After a B cell progenitor (e.g., a pre-committed small lymphocyte) is stimulated by an antigen, it differentiates into a blast cell, which differentiates into an immature plasma cell that can differentiate into either a mature plasma cell or a memory B cell. A mature plasma cell secretes immunoglobulins in response to a specific antigen. A memory B cell is a B cell that undergoes isotype switching and somatic hypermutation that is generally found during a secondary immune response (a subsequent antigen exposure following a primary exposure) but can also be detected during a primary antigen response. The development of memory B cells takes place in germinal centers (GC) of lymphoid follicles where antigen-driven lymphocytes undergo somatic hypermutation and affinity selection, presumably under the influence of helper T cells. Memory B cells generally express CD27. Typically, memory B cells also express high affinity antigen specific immunoglobulin (B cell receptor) on their cell surface. Thus, memory B cells can be CD20$^+$CD27$^+$, and include CD20$^{int}$/CD21$^+$/CD27$^+$ (resting memory), CD20$^{hi}$/CD21$^-$/CD27$^+$ (activated memory). CD20$^{hi}$/CD21$^-$/CD27$^-$ cells are distinct "unconventional or tissue memory" B cells.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1\times10^{-8}$ M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$M.

Binding or stable binding (oligonucleotide): An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target: oligonucleotide complex. Binding between a target and an oligonucleotide can be detected by any procedure known to one skilled in the art, including both functional and physical binding assays. For instance, binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Cancer or Tumor: A malignant neoplasm that has undergone characteristic anaplasia with loss of differentiation, increase rate of growth, invasion of surrounding tissue, and is capable of metastasis. A reproductive cancer is a cancer that has its primary origin in a reproductive tissue, such as in the uterus, testes, ovary, prostate, fallopian tube, or penis. For example, prostate cancer is a malignant neoplasm that arises in or from prostate tissue, and uterine cancer is a malignant neoplasm that arises in or from uterine tissue, and testicular cancer is a malignant neoplasm that arises in the testes. Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived.

CD28 (Cluster of Differentiation 28): One of the molecules expressed on T cells that provide co-stimulatory signals, which are required for T cell activation. CD28 is the receptor for B7.1 (CD80) and B7.2 (CD86). When activated by Toll-like receptor ligands, the B7.1 expression is upregulated in antigen presenting cells (APCs). The B7.2 expression on antigen presenting cells is constitutive. CD28 is the only B7 receptor constitutively expressed on naïve T cells.

Chemotherapy; chemotherapeutic agents: As used herein, any chemical agent with therapeutic usefulness in the treatment of diseases characterized by abnormal cell growth. Such diseases include tumors, neoplasms and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The immunogenic polypeptides disclosed herein can be used in conjunction with additional chemotherapeutic agents.

CD28: A cell surface antigen is known also as T90/44 antigen or Tp44 that is expressed on T cells. CD28 is a receptor for co-stimulatory proteins acting on T-cells. The natural ligand of CD28 is a 44-54 kDa glycoprotein, called B7-1 or CD80. There is a related molecule, B7-2. B7-1 is expressed on activated B cells and other antigen-presenting cells. It is expressed by macrophages, keratinocytes, T-cells, B-cells, peripheral blood dendritic and Langerhans cells. B7-2 is found on blood dendritic and Langerhans cells, B-cells, macrophages, Kupffer cells, activated monocytes and various natural killer cell clones. Binding of B7 to CD28 on T-cells delivers a costimulatory signal that triggers T-cell proliferation.

Control level (immune parameter): A baseline level of an immune parameter. In some embodiments, and control level is the level of a component of the immune system, such as memory B cells or proliferating memory B cells, in the absence of a therapeutic agent. A control level can be measured in a sample from a subject that has not been treated with an agent of interest, or a sample from a subject that has been treated with a control agent. The control level can also be a standard value, such as a value determined from an average of a large number of samples over time. The control level can also be measured in a sample from a subject treated with the specific dose of a therapeutic agent, wherein that dose is not administered to the subject at the time the subject is currently under evaluation. The control can be from the subject under evaluation, or can be from a different subject.

Control level (polypeptide or nucleic acid): The level of a molecule, such as a polypeptide or nucleic acid, normally found in nature under a certain condition and/or in a specific genetic background. In certain embodiments, a control level of a molecule can be measured in a cell or specimen that has not been subjected, either directly or indirectly, to a treatment. In some examples, a control level can be the level in a cell not contacted with the agent, such as a PD-1 antagonist. In additional examples, a control level can be the level in a subject not administered the PD-1 antagonist.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule.

Detecting or detection (cell or biomolecule): Refers to quantitatively or qualitatively determining the presence of a biomolecule or specific cell type, such as a memory B cell, under investigation. For example, quantitatively or qualitatively determining the presence of memory B cells in a sample from a subject, or detecting proliferating memory B cells. Generally, detection of a biological molecule, such as a protein, nucleic acid, or detecting a specific cell type or cell proliferation, requires performing a biological assay and not simple observation. For example, assays that utilize antibodies or nucleic acid probes (which can both be labeled), or can be used to detect proteins or cells, respectively. Diagnosing or diagnosis of the efficacy of treatment with a PD-1 antagonist involves detecting a significant change in a cell or biomolecule, such as the proliferation of memory B cells.

Encode: A polynucleotide is said to encode a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Expression: The process by which a gene's coded information is converted into the structures present and operating in the cell. Expressed genes include those that are transcribed into mRNA and then translated into protein and those that are transcribed into RNA but not translated into protein (for example, siRNA, transfer RNA and ribosomal RNA). Thus, expression of a target sequence, such as a gene or a promoter region of a gene, can result in the expression of an mRNA, a protein, or both. The expression of the target sequence can be inhibited or enhanced (decreased or increased).

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals, elements for the maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Heterologous: Originating from separate genetic sources or species. Generally, an antibody that specifically binds to a protein of interest will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies, or the proliferation of memory B cells. A B cell response can be a memory B cell response or a plasma B cell response. An example of a plasma B cell response is the production of antibody. An example of a response of a memory B cell is proliferation of memory B cells.

"Unresponsiveness" with regard to immune cells includes refractivity of immune cells to stimulation, such as stimulation via an activating receptor or a cytokine. Unresponsiveness can occur, for example, because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased.

For example, anergy in T cells (as opposed to unresponsiveness) is characterized by lack of cytokine production (such as IL-2). T cell anergy occurs when T cells are exposed to antigen and receive a first signal (a T cell receptor or CD-3 mediated signal) in the absence of a second signal (a costimulatory signal). Under these conditions, re-exposure of the cells to the same antigen (even if exposure occurs in the presence of a costimulatory molecule) results in failure to produce cytokines and, thus, failure to proliferate. Anergic T cells can, however, mount responses to unrelated antigens and can proliferate if cultured with cytokines (such as IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. Science 257:1134, 1992). Anergic antigen specific T cells may have a reduction of at least 10%, 20%, 30%, 40%, 50%, 60%, 70%, 80%, 90%, 95%, or even 100% in cytotoxic activity relative a corresponding control antigen specific T cell.

Immunogenic peptide: A peptide which comprises an allele-specific motif or other sequence such that the peptide will bind an MHC molecule and induce a cytotoxic T lymphocyte ("CTL") response, or a B cell response (e.g. antibody production or memory B cell proliferation) specific to the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein.

Immunogenic composition: A composition comprising an immunogenic polypeptide or a nucleic acid encoding the immunogenic polypeptide that induces a measurable CTL response against cells expressing the polypeptide, or induces a measurable B cell response (such as production of antibodies that specifically bind the polypeptide or proliferation of memory B cells) against the polypeptide. For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant, a PD-1 antagonist, a costimulatory molecule, or a nucleic acid encoding a costimulatory molecule. A polypeptide, or nucleic acid encoding the polypeptide, can be readily tested for its ability to induce a CTL by art-recognized assays.

Immunologically reactive conditions (in vitro): Includes "conditions sufficient to form an immune complex" which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols (such as ELISA or radioimmunoassay), FACS or those conditions encountered in vivo. See Harlow & Lane, Antibodies, *A Laboratory Manual*, Cold Spring Harbor Publications, New York (1988), for a description of immunoassay formats and conditions. The immunologically reactive conditions employed in the methods disclosed herein are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0'C and below 50° C. Osmolarity is within the range that is supportive of cell viability and proliferation.

Inhibiting or treating a disease: Inhibiting a disease, such as tumor growth or a persistent infection, refers to inhibiting the full development of a disease or lessening the physiological effects of the disease process. In several examples, inhibiting or treating a disease refers to lessening symptoms of a tumor or an infection with a pathogen. For example, cancer treatment can prevent the development of paraneoplastic syndrome in a person who is known to have a cancer, or lessening a sign or symptom of the tumor. In another embodiment, treatment of an infection can refer to inhibiting development or lessening a symptom of the infection. "Treatment" refers to a therapeutic intervention that ameliorates a sign or symptom of a disease or pathological condition related to the disease. Therapeutic vaccination refers to administration of an agent to a subject already infected with a pathogen. The subject can be asymptomatic, so that the treatment prevents the development of a symptom. The therapeutic vaccine can also reduce the severity of one or more existing symptoms, or reduce pathogen load.

Infectious disease: Any disease caused by an infectious agent. Examples of infectious pathogens include, but are not limited to: viruses, bacteria, mycoplasma and fungi. In a particular example, it is a disease caused by at least one type of infectious pathogen. In another example, it is a disease caused by at least two different types of infectious pathogens. Infectious diseases can affect any body system, be acute (short-acting) or chronic/persistent (long-acting), occur with or without fever, strike any age group, and overlap each other.

Viral diseases commonly occur after immunosupression due to re-activation of viruses already present in the recipient. Particular examples of persistent viral infections include, but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); and hepatitis A, B or C.

Additional examples of infectious virus include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of fungal infections include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans.*

Examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and

*Actinomyces israelli.* Other infectious organisms (such as protists) include: *Plasmodium falciparum* and *Toxoplasma gondii.*

A "persistent infection" is an infection in which the infectious agent (such as a virus, mycoplasma, bacterium, parasite, or fungus) is not cleared or eliminated from the infected host, even after the induction of an immune response. Persistent infections can be chronic infections, latent infections, or slow infections. Latent infection is characterized by the lack of demonstrable infectious virus between episodes of recurrent disease. Chronic infection is characterized by the continued presence of infectious virus following the primary infection and can include chronic or recurrent disease. Slow infection is characterized by a prolonged incubation period followed by progressive disease. Unlike latent and chronic infections, slow infection may not begin with an acute period of viral multiplication. While acute infections are relatively brief (lasting a few days to a few weeks) and resolved from the body by the immune system, persistent infections can last for example, for months, years, or even a lifetime. These infections may also recur frequently over a long period of time, involving stages of silent and productive infection without cell killing or even producing excessive damage to the host cells. Persistent infections often involve stages of both silent and productive infection without rapidly killing or even producing excessive damage of the host cells. During persistent viral infections, the viral genome can be either stably integrated into the cellular DNA or maintained episomally. Persistent infection occurs with viruses such as human T-Cell leukemia viruses, Epstein-Barr virus, cytomegalovirus, herpesviruses, varicella-zoster virus, measles, papovaviruses, prions, hepatitis viruses, adenoviruses, parvoviruses and papillomaviruses.

The causative infectious agents may also be detected in the host (such as inside specific cells of infected individuals) even after the immune response has resolved, using standard techniques. Mammals are diagnosed as having a persistent infection according to any standard method known in the art and described, for example, in U.S. Pat. Nos. 6,368,832, 6,579,854, and 6,808,710 and U.S. Patent Application Publication Nos. 20040137577, 20030232323, 20030166531, 20030064380, 20030044768, 20030039653, 20020164600, 20020160000, 20020110836, 20020107363, and 20020106730, all of which are hereby incorporated by reference.

"Alleviating a symptom of a persistent infection" is ameliorating any condition or symptom associated with the persistent infection. Alternatively, alleviating a symptom of a persistent infection can involve reducing the infectious microbial (such as viral, bacterial, fungal or parasitic) load in the subject relative to such load in an untreated control. As compared with an equivalent untreated control, such reduction or degree of prevention is at least 5%, 10%, 20%, 40%, 50%, 60%, 80%, 90%, 95%, or 100% as measured by any standard technique. Desirably, the persistent infection is completely cleared as detected by any standard method known in the art, in which case the persistent infection is considered to have been treated. A patient who is being treated for a persistent infection is one who a medical practitioner has diagnosed as having such a condition. Diagnosis may be by any suitable means. Diagnosis and monitoring may involve, for example, detecting the level of microbial load in a biological sample (for example, a tissue biopsy, blood test, or urine test), detecting the level of a surrogate marker of the microbial infection in a biological sample, detecting symptoms associated with persistent infections, or detecting immune cells involved in the immune response typical of persistent infections (for example, detection of antigen specific T cells that are anergic and/or functionally impaired). A patient in whom the development of a persistent infection is being prevented may or may not have received such a diagnosis. One in the art will understand that these patients may have been subjected to the same standard tests as described above or may have been identified, without examination, as one at high risk due to the presence of one or more risk factors (such as family history or exposure to infectious agent).

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

A "purified antibody" is at least 60%, by weight free from proteins and naturally occurring organic molecules with which it is naturally associated. In some examples the preparation is at least about 75%, at least about 80%, at least about 90%, at least about 95%, or at least about 99%, by weight of antibody, such as a PD-1, PD-L1, or PD-L2 specific antibody. A purified antibody can be obtained, for example, by affinity chromatography using recombinantly-produced protein or conserved motif peptides and standard techniques.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Lymphocytes: A type of white blood cell that is involved in the immune defenses of the body. There are two main types of lymphocytes: B cells and T cells.

Major Histocompatibility Complex (MHC): A generic designation meant to encompass the histocompatibility antigen systems described in different species, including the human leukocyte antigens ("HLA").

Mammal: This term includes both human and non-human mammals. Similarly, the term "subject" includes both human and veterinary subjects.

Mean Fluorescence Intensity (flow cytometry): Flow cytometry is concerned with the measurement of the light intensity of a cell or particle, whether it be scattered laser light or fluorescence emitted by a fluorochrome. Light is detected by a photomultiplier tube (PMT) which converts it via an amplifier to a voltage that is proportional to the original fluorescence intensity and the voltage on the PMT. These voltages, which are a continuous distribution, are converted to a discrete distribution by an Analog to Digital converter (ADC) which places each signal into a specific channel depending on the level of fluorescence. The greater the resolution of the ADC, the closer this reflects the continuous distribution.

Flow cytometric data can be displayed using either a linear or a logarithmic scale. The use of a logarithmic scale is indicated in most biological situations where distributions are skewed to the right. In this case the effect is to normalize the distribution—it is said to be Log Normal and the data has been log-transformed. Linear signals come through a linear amplifier but the logarithmic transformation may be achieved either by a logarithmic amplifier or by the use of Look Up Tables (LUT). Most ADCs in analytical cytometers are 10-bit, i.e., they divide data into 2e10 or 1024 channels, although there is a growing trend to use 12- or 14-bit ADCs to give greater resolution of data.

Data from a single data channel (scatter or fluorescence) is displayed as a histogram in which the x axis is divided into 1024 channels (for a 10-bit ADC). If the data is in a linear scale, the channel number and the linear value for that channel will be easily obtained. On a logarithmic scale, the x axis is still divided into 1024 channels but is displayed as a 4-log decade scale (in general 4 log decades are used).

To quantify flow cytometric data the measures of the distribution of a population are utilized. Generally, the measures of central tendency are the mean and the median. The mean is the 'average' and can be either arithmetic or geometric. The arithmetic mean is calculated as Sigma(x)/n, and the geometric mean as n root(a1×a2×a3 . . . an). In general, with log-amplified data the geometric mean is used as it takes into account the weighting of the data distribution, and the arithmetic mean is used for linear data or data displayed on a linear scale. The median is the central value, i.e., the 50th percentile, where half the values are above and half below. A cell with "high" expression and "low" expression can be determined relatively depending on the fluorescence of the entire population; these parameters are readily visualized on plots of flow cytometric data.

Neoplasm: An abnormal cellular proliferation, which includes benign and malignant tumors, as well as other proliferative disorders.

Neutralizing antibody: An antibody which reduces the infectious titer of an infectious agent by binding to a specific antigen on the infectious agent. In some examples the infectious agent is a virus, bacteria or fungus.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition or a cell to achieve a desired biological effect in a subject being treated. For instance, this can be the amount of a PD-1 antagonist necessary to induce an immune response, inhibit tumor growth, induce memory B cell proliferation, or to measurably alter outward symptoms of a tumor or persistent infection. When administered to a subject, a dosage will generally be used that will achieve target tissue concentrations (for example, in lymphocytes) that has been shown to achieve an in vitro effect.

In particular examples, a therapeutically effective amount is an amount of an agent, such as PD-1 antagonist, effective to induce the proliferation of memory B cells. In another particular example, a therapeutically effective amount is an amount of a PD-1 antagonist that alters a sign or a symptom of a disorder in a subject, such as a disorder that can be improved by increasing a memory B cell response and/or a T cell response.

An effective amount of an agent such as a PD-1 antagonist can be administered in a single dose, or in several doses, for example daily, during a course of treatment. However, the effective amount of a PD-1 antagonist will be dependent on the subject being treated, the severity and type of the condition being treated, and the manner of administration. The methods disclosed herein have equal application in medical and veterinary settings. Therefore, the general term "subject being treated" is understood to include all organisms (e.g., humans, apes, dogs, cats, horses, and cows) that require an increase in the desired biological effect, such as an enhanced immune response.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). A polypeptide can be between 3 and 30 amino acids in length. In one embodiment, a polypeptide is from about 7 to about 25 amino acids in length. In yet another embodiment, a polypeptide is from about 8 to about 10 amino acids in length. In yet another embodiment, a peptide is about 9 amino acids in length. With regard to polypeptides, "comprises" indicates that additional amino acid sequence or other molecules can be included in the molecule, "consists essentially of" indicates that additional amino acid sequences are not included in the molecule, but that other agents (such as labels or chemical compounds) can be included, and "consists of" indicates that additional amino acid sequences and additional agents are not included in the molecule.

Proliferation: The division of a cell to produce progeny, which can be measured in a number of ways known in the art. This includes, but is not limited to, assays that count the total number of cells, assays that count the number of cells of a specific cell type, KI-67 assays, thymidine incorporation, and bromodeoxyuridine assays.

Programmed Death (PD)-1: A protein that forms a complex with PD-L1 or PD-L2 protein and is involved in an immune response, such as the co-stimulation of T cells. Generally, PD-1 protein are substantially identical to the naturally occurring (wild type) PD-1 (see, for example, Ishida et al. EMBO J. 11:3887-3895, 1992, Shinohara et al. Genomics 23:704-706, 1994; and U.S. Pat. No. 5,698,520, all incorporated by reference herein in their entirety). In several examples, PD-1 signaling reduces, for example, CD8+ T cell cytoxicity by reducing T cell proliferation, cytokine production, or viral clearance. Thus, a PD-1 polypeptide can reduce CD8+ T cell cytotoxic activity by at least 5%, 10%, 20%, 30%, 40%, 50%, 60%, 70%, 80%, 90%, or more than 100% below control levels as measured by any standard method.

As used herein, the term "activity" with respect to a PD-1 polypeptide or protein includes any activity which is inherent to the naturally occurring PD-1 protein, such as the ability to modulate an inhibitory signal in an activated immune cell, such as by engaging a natural ligand on an antigen presenting cell. Such modulation of an inhibitory signal in an immune cell results in modulation of proliferation and/or survival of an immune cell and/or cytokine secretion by an immune cell. PD-1 protein can also modulate a costimulatory signal by competing with a costimulatory receptor for binding of a B7 molecule. Thus, the term "PD-1 activity" includes the ability of a PD-1 polypeptide or protein to bind its natural ligand(s), the ability to modulate immune cell costimulatory or inhibitory signals, and the ability to modulate the immune response.

"Reduce the expression or activity of PD-1" refers to a decrease in the level or biological activity of PD-1 relative to the level or biological activity of PD-1 protein in a control, such as an untreated subject or sample. In specific examples, the level or activity is reduced by at least 10%, 20%, 30%, 40%, 50%, 60%, 70%, 80%, 90%, 100%, or even greater than 100%, relative to an untreated control. For example, the biological activity of PD-1 protein is reduced if binding of PD-1 protein to PD-L1, PD-L2, or both is reduced, thereby resulting in a reduction in PD-1 signaling and therefore resulting in an increase in CD8+ T cell cytotoxicity.

A "PD-1 gene" is a nucleic acid that encodes a PD-1 protein. A "PD-1 fusion gene" is a PD-1 coding region operably linked to a second, heterologous nucleic acid sequence. A PD-1 fusion gene can include a PD-1 promoter, or can include a heterologous promoter. In some embodiments, the second, heterologous nucleic acid sequence is a reporter gene, that is, a gene whose expression may be assayed; reporter genes include, without limitation, those encoding glucuronidase (GUS), luciferase, chloramphenicol transacetylase (CAT), green fluorescent protein (GFP), alkaline phosphatase, and .beta.-galactosidase.

Sample (Biological sample): Includes biological samples containing fluids, tissues, cells, and subcomponents thereof, such as DNA, RNA, and proteins. For example, common samples in the context of the present invention include bone marrow, spleen, lymph node, blood, e.g., peripheral blood (but can also include any other source from which B cells or B cell progenitors can be isolated, including: urine, saliva, tissue biopsy, surgical specimens, fine needle aspirates, autopsy material, and the like).

Specific binding agent: An agent that binds substantially only to a defined target. Thus a PD-1 specific binding agent is an agent that binds substantially to a PD-1 polypeptide and not unrelated polypeptides. In one embodiment, the specific binding agent is a monoclonal or polyclonal antibody that specifically binds the PD-1, PD-L1 OR PD-L2 polypeptide.

The term "specifically binds" refers, with respect to an antigen such as PD-1, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. Specific binding results in a much stronger association between the antibody (or other ligand) and cells bearing the antigen than between the antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the PD-1 polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8+ T cell is a cytotoxic T lymphocyte. In another embodiment, a CD8+ cell is a suppressor T cell. A T cell is "activated" when it can respond to a specific antigen of interest presented on an antigen presenting cells.

Transduced/Transfected: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more nucleic acids encoding a selectable marker and other genetic elements known in the art. Vectors include plasmid vectors, including plasmids for expression in gram negative and gram positive bacterial cells. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

PD-1 Antagonists

The methods disclosed herein involve the use of inhibitors of the PD-1 pathway (PD-1 antagonists). PD-1 molecules are members of the immunoglobulin gene superfamily. The human PD-1 has an extracellular region containing an immunoglobulin superfamily domain, a transmembrane domain, and an intracellular region including an immunoreceptor tyrosine-based inhibitory motif (ITIM) ((Ishida et al., EMBO J. 11:3887, 1992; Shinohara et al., Genomics 23:704, 1994; U.S. Pat. No. 5,698,520). These features also define a larger family of molecules, called the immunoinhibitory receptors, which also includes gp49B, PIR-B, and the killer inhibitory receptors (KIRs) (Vivier and Daeron (1997) Immunol. Today 18:286). Without being bound by theory, it is believed that the tyrosyl phosphorylated ITIM motif of these receptors interacts with the S112-domain containing phosphatase, which leads to inhibitory signals. A subset of these immuno-inhibitory receptors bind to major histocompatibility complex (MHC) molecules, such as the KIRs, and CTLA4 binds to B7-1 and B7-2.

In humans, PD-1 is a 50-55 kDa type I transmembrane receptor that was originally identified in a T cell line undergoing activation-induced apoptosis. PD-1 is expressed on T cells, B cells, and macrophages. The ligands for PD-1 are the B7 family members PD-ligand 1 (PD-L1, also known as B7-H1) and PD-L2 (also known as B7-DC).

In vivo, PD-1 is expressed on activated T cells, B cells, and monocytes. Experimental data implicates the interactions of PD-1 with its ligands in downregulation of central and peripheral immune responses. In particular, proliferation in wild-type T cells but not in PD-1-deficient T cells is inhibited in the presence of PD-L1. Additionally, PD-1-deficient mice exhibit an autoimmune phenotype.

An exemplary amino acid sequence of human PD-1 is set forth below (see also Ishida et al., EMBO J. 11:3887, 1992; Shinohara et al. Genomics 23:704, 1994; U.S. Pat. No. 5,698,520):

```
                                              (SEQ ID NO: 1)
mqipqapwpv vwavlqlgwr pgwfldspdr pwnpptffpa llvvtegdna tftcsfsnts esfvlnwyrm spsnqtdkla afpedrsqpg qdcrfrvtql pngrdfhmsv vrarrndsgt ylcgaislap kaqikeslra elrvterrae vptahpspsp rpagqfqtlv vgvvggllgs lvllvwvlav icsraargti garrtgqplk edpsavpvfs vdygeldfqw rektpeppvp cvpeqteyat ivfpsgmgts sparrgsadg prsaqplrpe dghcswpl
```

An exemplary amino acid sequence of mouse PD-1 is set forth below:

```
                                              (SEQ ID NO: 2)
mwvrqvpwsf twavlqlswq sgwllevpng pwrsltfypa wltvsegana tftcslsnws edlmlnwnrl spsnqtekqa afcnglsqpv qdarfqiiql pnrhdfhmni ldtrrndsgi ylcgaislhp kakieespga elvvterile tstrypspsp kpegrfqgmv igimsalvgi pvllllawal avfcstsmse argagskddt lkeepsaapv psvayeeldf qgrektpelp tacvhteyat ivfteglgas amgrrgsadg lqgprpprhe dghcswpl
```

Additional amino acid sequences are disclosed in U.S. Pat. No. 6,808,710 and U.S. Patent Application Publication Nos. 2004/0137577, 2003/0232323, 2003/0166531, 2003/0064380, 2003/0044768, 2003/0039653, 2002/0164600, 2002/0160000, 2002/0110836, 2002/0107363, and 2002/0106730, which are incorporated herein by reference. PD-1 is a member of the immunoglobulin (Ig) superfamily that contains a single Ig V-like domain in its extracellular region. The PD-1 cytoplasmic domain contains two tyrosines, with the most membrane-proximal tyrosine (VAYEEL (see amino acids 223-228 of SEQ ID NO: 2) in mouse PD-1) located within an ITIM (immuno-receptor tyrosine-based inhibitory motif). The presence of an ITIM on PD-1 indicates that this molecule functions to attenuate antigen receptor signaling by recruitment of cytoplasmic phosphatases. Human and murine PD-1 proteins share about 60% amino acid identity with conservation of four potential N-glycosylation sites, and residues that define the Ig-V domain. The ITIM in the cytoplasmic region and the ITIM-like motif surrounding the carboxy-terminal tyrosine (TEYATI (see amino acids 166-181 of SEQ ID NO: 2) in human and mouse, respectively) are also conserved between human and murine orthologues.

PD-1 is a member of the CD28/CTLA-4 family of molecules based on its ability to bind to PD-L1. In vivo, like CTLA4, PD-1 is rapidly induced on the surface of T-cells in response to anti-CD3 (Agata et al. Int. Immunol. 8:765, 1996). In contrast to CTLA4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773).

T cell anergy is concomitant with an induction in PD-1 expression. It is disclosed herein that T-cell cytoxicity can be increased by contacting a T-cell with an agent that reduces the expression or activity of PD-1. More specifically, it is disclosed herein that an agent that reduces the expression or activity of PD-1 can be used to increase an immune response, such as to a viral antigen or a tumor antigen.

Without being bound by theory, reduction of PD-1 expression or activity results in an increase in cytotoxic T cell activity, increasing the specific immune response to the infectious agent. In order for T cells to respond to foreign proteins, two signals must be provided by antigen-presenting cells (APCs) to resting T lymphocytes. The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional. Costimulation is neither antigen-specific, nor MHC-restricted and is provided by one or more distinct cell surface polypeptides expressed by APCs. If T cells are only stimulated through the T cell receptor, without receiving an additional costimulatory signal, they become nonresponsive, anergic, or die, resulting in downmodulation of the immune response.

The CD80 (B7-1) and CD86 (B7-2) proteins, expressed on APCs, are critical costimulatory polypeptides. While B7-2 plays a predominant role during primary immune responses, B7-1 is upregulated later in the course of an immune response to prolong primary T cell responses or costimulating secondary T cell responses. B7 polypeptides are capable of providing costimulatory or inhibitory signals to immune cells to promote or inhibit immune cell responses. For example, when bound to a costimulatory receptor, PD-L1 (B7-4) induces costimulation of immune cells or inhibits immune cell costimulation when present in a soluble form. When bound to an inhibitory receptor, PD-L1 molecules can transmit an inhibitory signal to an immune cell. Exemplary B7 family members include B7-1, B7-2, B7-3 (recognized by the antibody BB-1), B7h (PD-L1), and B7-4 and soluble fragments or derivatives thereof. B7 family members bind to one or more receptors on an immune cell, such as CTLA4, CD28, ICOS, PD-1 and/or other receptors, and, depending on the receptor, have the ability to transmit an inhibitory signal or a costimulatory signal to an immune cell.

CD28 is a receptor that is constitutively expressed on resting T cells. After signaling through the T cell receptor, ligation of CD28 and transduction of a costimulatory signal induces T cells to proliferate and secrete IL-2. CTLA4 (CD152), a receptor homologous to CD28, is absent on resting T cells but its expression is induced following T cell activation. CTLA4 plays a role in negative regulation of T cell responses. ICOS, a polypeptide related to CD28 and CTLA4, is involved in IL-10 production. PD-1, the receptor to which PD-L1 and PD-L2 bind, is also rapidly induced on the surface of T-cells. PD-1 is also expressed on the surface of B-cells (in response to anti-IgM) and on a subset of thymocytes and myeloid cells.

Engagement of PD-1 (for example by crosslinking or by aggregation), leads to the transmission of an inhibitory signal in an immune cell, resulting in a reduction of immune responses concomitant with an increase in immune cell anergy. PD-1 family members bind to one or more receptors, such as PD-L1 and PD-L2 on antigen presenting cells. PD-L1 and PD-L2, both of which are human PD-1 ligand polypeptides, are members of the B7 family of polypeptides (see above). Each PD-1 ligand contains a signal sequence, an IgV domain, an IgC domain, a transmembrane domain, and a short cytoplasmic tail. In vivo, these ligands have been shown to be expressed in placenta, spleen, lymph nodes, thymus, and heart. PD-L2 is also expressed in the pancreas, lung, and liver, while PD-L1 is expressed in fetal liver, activated T-cells and endothelial cells. Expression of both PD-1 ligands are upregulated on activated monocytes and dendritic cells.

An exemplary amino acid sequence for PD-L1 (GENBANK® Accession No. AAG18508, as available Oct. 4, 2000) is set forth below:

```
                                                (SEQ ID NO: 3)
    mrifavfifm tywhllnaft vtvpkdlyvv eygsnmtiec kfpvekqldl aalivyweme dkniiqfvhg eedlkvqhss yrqrarllkd qlslgnaalq itdvklqdag vyrcmisygg adykritvkv napynkinqr ilvvdpvtse heltcqaegy pkaeviwtss dhqvlsgktt ttnskreekl fnvtstlrin tttneifyct frrldpeenh taelvipelp lahppnerth ivilgaillc lgvaltfifr lrkgrmmdvk kcgiqdtnsk kqsdthleet
```

An exemplary PD-L2 precursor amino acid sequence (GENBANK® Accession No. AAK15370, as available Apr. 8, 2002) is set forth below:

```
                                                (SEQ ID NO: 4)
    mifllllmlsl elqlhqiaal ftvtvpkely iiehgsnvtl ecnfdtgshv nlgaitaslq kvendtsphr eratlleeql plgkasfhip qvqvrdegqy qciiiygvaw dykyltlkvk asyrkinthi lkvpetdeve ltcqatgypl aevswpnvsv pantshsrtp eglyqvtsvl rlkpppgrnf scvfwnthvr eltlasidlq sqmeprthpt wllhifipsc iiafifiatv ialrkqlcqk lysskdttkr pvtttkrevn sai
```

An exemplary variant PD-L2 precursor amino acid sequence (GENBANK® Accession No. Q9BQ51, as available Dec. 12, 2006) is set forth below:

```
                                          (SEQ ID NO: 46)
miflllmlsl elqlhqiaal ftvtvpkely iiehgsnvtl ecnfdtgshv nlgaitaslq kvendtsphr eratlleeql plgkasfhip qvqvrdegqy qciiiygvaw dykyltlkvk asyrkinthi lkvpetdeve ltcqatgypl aevswpnvsv pantshsrtp eglyqvtsvl rlkpppgrnf scvfwnthvr eltlasidlq sqmeprthpt wllhifipfc iiafifiatv ialrkqlcqk lysskdttkr pvtttkrevn sai
```

PD-1 antagonists include agents that reduce the expression or activity of a PD ligand 1 (PD-L1) or a PD ligand 2 (PD-L2) or reduces the interaction between PD-1 and PD-L1 or the interaction between PD-1 and PD-L2. Exemplary compounds include antibodies (such as an anti-PD-1 antibody, an anti-PD-L1 antibody, and an anti-PD-L2 antibody), RNAi molecules (such as anti-PD-1 RNAi molecules, anti-PD-L1 RNAi, and an anti-PD-L2 RNAi), antisense molecules (such as an anti-PD-1 antisense RNA, an anti-PD-L1 antisense RNA, and an anti-PD-L2 antisense RNA), dominant negative proteins (such as a dominant negative PD-1 protein, a dominant negative PD-L1 protein, and a dominant negative PD-L2 protein), and small molecule inhibitors.

An antagonist of PD-1 is any agent having the ability to reduce the expression or the activity of PD-1 in a cell. PD-1 expression or activity is reduced by at least about 10%, 20%, 30%, 40%, 50%, 60%, 70%, 80%, 90%, or 100% compared to such expression or activity in a control. Exemplary reductions in activity are at least about 50%, at least about 60%, at least about 70%, at least about 80%, at least about 90%, at least about 95%, or a complete absence of detectable activity. In one example, the control is a cell that has not been treated with the PD-1 antagonist. In another example, the control is a standard value, or a cell contacted with an agent, such as a carrier, known not to affect PD-1 activity. PD-1 expression or activity can be determined by any standard method in the art, including those described herein. Optionally, the PD-1 antagonist inhibits or reduces binding of PD-1 to PD-L1, PD-L2, or both.

A. Antibodies

Antibodies that specifically bind PD-1, PD-L1 or PD-L2 (or a combination thereof) are of use in the methods disclosed herein. Antibodies include monoclonal antibodies, humanized antibodies, deimmunized antibodies, and immunoglobulin (Ig) fusion proteins. Polyclonal anti-PD-1, anti-PDL1 or PD-L2 antibodies can be prepared by one of skill in the art, such as by immunizing a suitable subject (such as a veterinary subject) with a PD-1 ligand or PD-1 immunogen. The anti-PD-1, anti-PD-L1 or anti-PD-L2 antibody titer in the immunized subject can be monitored over time by standard techniques, such as with an enzyme linked immunosorbent assay (ELISA) using immobilized a PD-1 ligand or PD-1 polypeptide.

In one example, the antibody molecules that specifically bind PD-1, PD-L1 or PD-L2 (or combinations thereof) can be isolated from the mammal (such as from serum) and further purified by techniques known to one of skill in the art. For example, antibodies can be purified using protein A chromatography to isolate IgG antibodies.

Antibody-producing cells can be obtained from the subject and used to prepare monoclonal antibodies by standard techniques (see Kohler and Milstein Nature 256:495 49, 1995; Brown et al., J. Immunol. 127:539 46, 1981; Cole et al., Monoclonal Antibodies and Cancer Therapy, Alan R. Liss, Inc., pp. 77 96, 1985; Gefter, M. L. et al. (1977) Somatic Cell Genet. 3:231 36; Kenneth, R. H. in Monoclonal Antibodies: A New Dimension In Biological Analyses. Plenum Publishing Corp., New York, N.Y. (1980); Kozbor et al. Immunol. Today 4:72, 1983; Lerner, E. A. (1981) Yale J. Biol. Med. 54:387 402; Yeh et al., Proc. Natl. Acad. Sci. 76:2927 31, 1976). In one example, an immortal cell line (typically a myeloma) is fused to lymphocytes (typically splenocytes) from a mammal immunized with PD-1, PD-L1 or PD-L2, and the culture supernatants of the resulting hybridoma cells are screened to identify a hybridoma producing a monoclonal antibody that specifically binds to the polypeptide of interest.

In one embodiment, to produce a hybridoma, an immortal cell line (such as a myeloma cell line) is derived from the same mammalian species as the lymphocytes. For example, murine hybridomas can be made by fusing lymphocytes from a mouse immunized with a PD-1, PD-L1 or PD-L2 peptide with an immortalized mouse cell line. In one example, a mouse myeloma cell line is utilized that is sensitive to culture medium containing hypoxanthine, aminopterin and thymidine ("HAT medium"). Any of a number of myeloma cell lines can be used as a fusion partner according to standard techniques, including, for example, P3-NS1/1-Ag4-1, P3-x63-Ag8.653 or Sp2/O-Ag14 myeloma lines, which are available from the American Type Culture Collection (ATCC), Rockville, Md. HAT-sensitive mouse myeloma cells can be fused to mouse splenocytes using polyethylene glycol ("PEG"). Hybridoma cells resulting from the fusion are then selected using HAT medium, which kills unfused (and unproductively fused) myeloma cells. Hybridoma cells producing a monoclonal antibody of interest can be detected, for example, by screening the hybridoma culture supernatants for the production antibodies that bind a PD-1, PD-L1 or PD-L2 molecule, such as by using an immunological assay (such as an enzyme-linked immunosorbant assay (ELISA) or radioimmunoassay (RIA).

As an alternative to preparing monoclonal antibody-secreting hybridomas, a monoclonal antibody that specifically binds PD-1, PD-L1 or PD-L2 can be identified and isolated by screening a recombinant combinatorial immunoglobulin library (such as an antibody phage display library) with PD-1, PD-L1 or PD-L2 to isolate immunoglobulin library members that specifically bind the polypeptide. Kits for generating and screening phage display libraries are commercially available (such as, but not limited to, Pharmacia and Stratagene). Examples of methods and reagents particularly amenable for use in generating and screening antibody display library can be found in, for example, U.S. Pat. No. 5,223,409; PCT Publication No. WO 90/02809; PCT Publication No. WO 91/17271; PCT Publication No. WO 92/18619; PCT Publication WO 92/20791; PCT Publication No. WO 92/15679; PCT Publication No. WO 92/01047; PCT Publication WO 93/01288; PCT Publication No. WO 92/09690; Barbas et al., Proc. Natl. Acad. Sci. USA 88:7978 7982, 1991; Hoogenboom et al., Nucleic Acids Res. 19:4133 4137, 1991.

The amino acid sequence of antibodies that bind PD-1 are disclosed, for example, in U.S. Patent Publication No. 2006/0210567, which is incorporated herein by reference. Antibodies that bind PD-1 are also disclosed in U.S. Patent Publication No. 2006/0034826, which is also incorporated herein by reference. In several examples, the antibody specifically binds PD-1 or a PD-1 or PD-2 ligand with an affinity constant of at least $10^7$ $M^{-1}$, such as at least $10^8$ $M^{-1}$ at least $5\times10^8$ $M^{-1}$ or at least $10^9$ $M^{-1}$.

In one example the sequence of the specificity determining regions of each CDR is determined. Residues are outside the SDR (non-ligand contacting sites) are substituted. For example, in any of the CDR sequences, at most one, two or three amino acids can be substituted. The production of chimeric antibodies, which include a framework region from one antibody and the CDRs from a different antibody, is well known in the art. For example, humanized antibodies can be routinely produced. The antibody or antibody fragment can be a humanized immunoglobulin having complementarity determining regions (CDRs) from a donor monoclonal antibody that binds PD-1, PD-L1 or PD-L2, and immunoglobulin and heavy and light chain variable region frameworks from human acceptor immunoglobulin heavy and light chain frameworks. Generally, the humanized immunoglobulin specifically binds to PD-1, PD-L1 or PD-L2 with an affinity constant of at least $10^7$ $M^{-1}$, such as at least $10^8$ $M^{-1}$ at least $5\times10^8$ $M^{-1}$ or at least $10^9 M^{-1}$.

Humanized monoclonal antibodies can be produced by transferring donor complementarity determining regions (CDRs) from heavy and light variable chains of the donor mouse immunoglobulin (such PD-1, PD-L1 or PD-L2) into a human variable domain, and then substituting human residues in the framework regions when required to retain affinity. The use of antibody components derived from humanized monoclonal antibodies obviates potential problems associated with the immunogenicity of the constant regions of the donor antibody. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993. The antibody may be of any isotype, but in several embodiments the antibody is an IgG, including but not limited to, $IgG_1$, $IgG_2$, $IgG_3$ and $IgG_4$.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in humanized antibody framework regions, are known in the art (see, for example, in U.S. Pat. No. 5,585,089, which is incorporated herein by reference).

Exemplary human antibodies are LEN and 21/28 CL. The sequences of the heavy and light chain frameworks are known in the art. Exemplary light chain frameworks of human MAb LEN have the following sequences:

```
FR1:
DIVMTQS PDSLAVSLGERATINC          (SEQ ID NO: 5)

FR2:
WYQQKPGQPPLLIY                    (SEQ ID NO: 6)
```

```
FR3:
GVPDRPFGSGSGTDFTLTISSLQAEDVAVYYC  (SEQ ID NO: 7)

FR4:
FGQGQTKLEIK                       (SEQ ID NO: 8)
```

Exemplary heavy chain frameworks of human MAb 21/28' CL have the following sequences:

```
FR1:
QVQLVQSGAEVKKPQASVKVSCKASQYTFT    (SEQ ID NO: 9)

FR2:
WVRQAPGQRLEWMG                    (SEQ ID NO: 10)

FR3:
RVTITRDTSASTAYMELSSLRSEDTAVYYCAR  (SEQ ID NO: 11)

FR4:
WGQGTLVTVSS.                      (SEQ ID NO: 12)
```

Antibodies, such as murine monoclonal antibodies, chimeric antibodies, and humanized antibodies, include full length molecules as well as fragments thereof, such as Fab, $F(ab')_2$, and Fv which include a heavy chain and light chain variable region and are capable of binding specific epitope determinants. These antibody fragments retain some ability to selectively bind with their antigen or receptor. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). In several examples, the variable region includes the variable region of the light chain and the variable region of the heavy chain expressed as individual polypeptides. Fv antibodies are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are known in the art (see Whitlow et al., Methods: a Companion to Methods in Enzymology, Vol. 2, page 97, 1991; Bird et al., Science 242:423, 1988; U.S. Pat. No. 4,946,778; Pack et al., Bio/Technology 11:1271, 1993; and Sandhu, supra).

Antibody fragments can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., Arch. Biochem. Biophys. 89:230, 1960; Porter, Biochem. J. 73:119, 1959; Edelman et al., Methods in Enzymology, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, one of skill in the art can readily review the amino acid sequence of an antibody of interest, locate one or more of the amino acids in the brief table above, identify a conservative substitution, and produce the conservative variant using well-known molecular techniques.

Effector molecules, such as therapeutic, diagnostic, or detection moieties can be linked to an antibody that specifically binds PD-1, PD-L1 or PD-L2, using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

Nucleic acid sequences encoding the antibodies can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68:109-151, 1979; the diethylphosphoramidite method of Beaucage et al., Tetra. Lett. 22:1859-1862, 1981; the solid phase phosphoramidite triester method described by Beaucage & Caruthers, Tetra. Letts. 22(20):1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding an antibody that specifically binds PD-1, PD-L1 or PD-L2 can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody of use is prepared by inserting the cDNA which encodes a variable region from an antibody that specifically binds PD-1, PD-L1 or PD-L2 into a vector which comprises the cDNA encoding an effector molecule (EM). The insertion is made so that the variable region and the EM are read in frame so that one continuous polypeptide is produced. Thus, the encoded polypeptide contains a functional Fv region and a functional EM region. In one embodiment, cDNA encoding a detectable marker (such as an enzyme) is ligated to a scFv so that the marker is located at the carboxyl terminus of the scFv. In another example, a detectable marker is located at the amino terminus of the scFv. In a further example, cDNA encoding a detectable marker is ligated to a heavy chain variable region of an antibody that specifically binds PD-1, PD-L1 or PD-L2, so that the marker is located at the carboxyl terminus of the heavy chain variable region. The heavy chain-variable region can subsequently be ligated to a light chain variable region of the antibody that specifically binds PD-1, PD-L1 or PD-L2 using disulfide bonds. In a yet another example, cDNA encoding a marker is ligated to a light chain variable region of an antibody that binds PD-1, PD-L1 or PD-L2, so that the marker is located at the carboxyl terminus of the light chain variable region. The light chain-variable region can subsequently be ligated to a heavy chain variable region of the antibody that specifically binds PD-1, PD-L1 or PD-L2 using disulfide bonds.

Once the nucleic acids encoding the antibody or functional fragment thereof are isolated and cloned, the protein can be expressed in a recombinantly engineered cell such as bacteria, plant, yeast, insect and mammalian cells. One or more DNA sequences encoding the antibody or functional fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the antibody or functional fragment thereof can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody or functional fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody of functional fragment thereof and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the recombinant antibodies can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

In addition to recombinant methods, the antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis, 2nd ed.*, Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicycylohexylcarbodimide) are well known in the art.

B. Inhibitory Nucleic Acids

Inhibitory nucleic acids that decrease the expression and/or activity of PD-1, PD-L1 or PD-L2 can also be used in the methods disclosed herein. One embodiment is a small inhibitory RNA (siRNA) for interference or inhibition of expression of a target gene. Nucleic acid sequences encoding PD-1, PD-L1 and PD-L2 are disclosed in GENBANK® Accession Nos. NM_005018, AF344424, NP_079515, and NP_054862.

Generally, siRNAs are generated by the cleavage of relatively long double-stranded RNA molecules by Dicer or DCL enzymes (Zamore, *Science*, 296:1265-1269, 2002; Bernstein et al., *Nature*, 409:363-366, 2001). In animals and plants, siRNAs are assembled into RISC and guide the sequence specific ribonucleolytic activity of RISC, thereby resulting in the cleavage of mRNAs or other RNA target molecules in the cytoplasm. In the nucleus, siRNAs also guide heterochromatin-associated histone and DNA methylation, resulting in transcriptional silencing of individual genes or large chromatin domains. PD-1 siRNAs are commercially available, such as from Santa Cruz Biotechnology, Inc.

The present disclosure provides RNA suitable for interference or inhibition of expression of a target gene, which RNA includes double stranded RNA of about 15 to about 40 nucleotides containing a 0 to 5-nucleotide 3' and/or 5' overhang on each strand. The sequence of the RNA is substantially identical to a portion of an mRNA or transcript of a target gene, such as PD-1, PD-L1 or PD-L2) for which interference or inhibition of expression is desired. For purposes of this disclosure, a sequence of the RNA "substantially identical" to a specific portion of the mRNA or transcript of the target gene for which interference or inhibition of expression is desired differs by no more than about 30 percent, and in some embodiments no more than about 10 percent, from the specific portion of the mRNA or transcript of the target gene. In particular embodiments, the sequence of the RNA is exactly identical to a specific portion of the mRNA or transcript of the target gene.

Thus, siRNAs disclosed herein include double-stranded RNA of about 15 to about 40 nucleotides in length and a 3' or 5' overhang having a length of 0 to 5-nucleotides on each strand, wherein the sequence of the double stranded RNA is substantially identical to (see above) a portion of a mRNA or transcript of a nucleic acid encoding PD-1, PD-L1 or PD-L2. In particular examples, the double stranded RNA contains about 19 to about 25 nucleotides, for instance 20, 21, or 22 nucleotides substantially identical to a nucleic acid encoding PD-1, PD-L1 or PD-L2. In additional examples, the double stranded RNA contains about 19 to about 25 nucleotides 100% identical to a nucleic acid encoding PD-1, PD-L1 or PD-L2. It should be not that in this context "about" refers to integer amounts only. In one example, "about" 20 nucleotides refers to a nucleotide of 19 to 21 nucleotides in length.

Regarding the overhang on the double-stranded RNA, the length of the overhang is independent between the two strands, in that the length of one overhang is not dependent on the length of the overhang on other strand. In specific examples, the length of the 3' or 5' overhang is O-nucleotide on at least one strand, and in some cases it is O-nucleotide on both strands (thus, a blunt dsRNA). In other examples, the length of the 3' or 5' overhang is 1-nucleotide to 5-nucleotides on at least one strand. More particularly, in some examples the length of the 3' or 5' overhang is 2-nucleotides on at least one strand, or 2-nucleotides on both strands. In particular examples, the dsRNA molecule has 3' overhangs of 2-nucleotides on both strands.

Thus, in one particular provided RNA embodiment, the double-stranded RNA contains 20, 21, or 22 nucleotides, and the length of the 3' overhang is 2-nucleotides on both strands. In embodiments of the RNAs provided herein, the double-stranded RNA contains about 40-60% adenine+uracil (AU) and about 60-40% guanine+cytosine (GC). More particularly, in specific examples the double-stranded RNA contains about 50% AU and about 50% GC.

Also described herein are RNAs that further include at least one modified ribonucleotide, for instance in the sense strand of the double-stranded RNA. In particular examples, the modified ribonucleotide is in the 3' overhang of at least one strand, or more particularly in the 3' overhang of the sense strand. It is particularly contemplated that examples of modified ribonucleotides include ribonucleotides that include a detectable label (for instance, a fluorophore, such as rhodamine or FITC), a thiophosphate nucleotide analog, a deoxynucleotide (considered modified because the base molecule is ribonucleic acid), a 2'-fluorouracil, a 2'-aminouracil, a 2'-aminocytidine, a 4-thiouracil, a 5-bromouracil, a 5-iodouracil, a 5-(3-aminoallyl)-uracil, an inosine, or a 2'O-Me-nucleotide analog.

Antisense and ribozyme molecules for PD-1, PD-L1 and PD-L2 are also of use in the method disclosed herein. Antisense nucleic acids are DNA or RNA molecules that are complementary to at least a portion of a specific mRNA molecule (Weintraub, *Scientific American* 262:40, 1990). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into the target cell producing PD-1, PD-L1 or PD-L2. The use of antisense methods to inhibit the in vitro translation of genes is well known in the art (see, for example, Marcus-Sakura, *Anal. Biochem.* 172:289, 1988).

An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid molecule can be chemically synthesized using naturally occurring nucleotides or variously modified nucleotides designed to increase the biological stability of the molecules or to increase the physical stability of the duplex formed between the antisense and sense nucleic acids, such as phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridin-e, 5-carboxymethylaminomethyluracil, dihydrouracil, beta-D-galactosylqueosine, inosine, amongst others.

Use of an oligonucleotide to stall transcription is known as the triplex strategy since the bloomer winds around double-helical DNA, forming a three-strand helix. Therefore, these triplex compounds can be designed to recognize a unique site on a chosen gene (Maher, et al., *Antisense Res. and Dev.* 1(3):227, 1991; Helene, C., *Anticancer Drug Design* 6(6):569), 1991. This type of inhibitory oligonucleotide is also of use in the methods disclosed herein.

Ribozymes, which are RNA molecules possessing the ability to specifically cleave other single-stranded RNA in a manner analogous to DNA restriction endonucleases, are also of use. Through the modification of nucleotide sequences which encode these RNAs, it is possible to engineer molecules that recognize specific nucleotide sequences in an RNA molecule and cleave it (Cech, *J. Amer. Med. Assn.* 260:3030, 1988). A major advantage of this approach is that, because they are sequence-specific, only mRNAs with particular sequences are inactivated.

There are two basic types of ribozymes namely, tetrahymena-type (Hasselhoff, *Nature* 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

Various delivery systems are known and can be used to administer the siRNAs and other inhibitory nucleic acid molecules as therapeutics. Such systems include, for example, encapsulation in liposomes, microparticles, microcapsules, nanoparticles, recombinant cells capable of expressing the therapeutic molecule(s) (see, e.g., Wu et al., *J. Biol. Chem.* 262, 4429, 1987), construction of a therapeutic nucleic acid as part of a retroviral or other vector, and the like.

C. Small Molecule Inhibitors

PD-1 antagonists include molecules that are identified from large libraries of both natural product or synthetic (or semi-synthetic) extracts or chemical libraries according to methods known in the art. The screening methods that detect decreases in PD-1 activity (such as detecting cell death) are useful for identifying compounds from a variety of sources for activity. The initial screens may be performed using a diverse library of compounds, a variety of other compounds and compound libraries. Thus, molecules that bind PD-1, PD-L1 or PD-L2, molecules that inhibit the expression of PD-1, PD-L1 and/or PD-L2, and molecules that inhibit the activity of PD-1, PD-L1 and/or PD-L2 can be identified. These small molecules can be identified from combinatorial libraries, natural product libraries, or other small molecule libraries. In addition, PD-1 antagonist can be identified as compounds from commercial sources, as well as commercially available analogs of identified inhibitors.

The precise source of test extracts or compounds is not critical to the identification of PD-1 antagonists. Accordingly, PD-1 antagonists can be identified from virtually any number of chemical extracts or compounds. Examples of such extracts or compounds that can be PD-1 antagonists include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). PD-1 antagonists can be identified from synthetic compound libraries that are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). PD-1 antagonists can be identified from a rare chemical library, such as the library that is available from Aldrich (Milwaukee, Wis.). PD-1 antagonists can be identified in libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, such as less than about 750 or less than about 350 daltons can be utilized in the methods disclosed herein. Exemplary classes include heterocycles, peptides, saccharides, steroids, and the like. The compounds may be modified to enhance efficacy, stability, pharmaceutical compatibility, and the like. In several embodiments, compounds of use has a Kd for PD-1, PD-L1 or PD-L2 of less than 1 nM, less than 10 nm, less than 1 μM, less than 10 μM, or less than 1 mM.

D. PD-1 Peptide Variants as Antagonists

In one embodiment, variants of a PD-1 protein which function as an antagonist can be identified by screening combinatorial libraries of mutants, such as point mutants or truncation mutants, of a PD-1 protein to identify proteins with antagonist activity. In one example, the antagonist is a soluble PD-1 protein.

Thus, a library of PD-1 variants can be generated by combinatorial mutagenesis at the nucleic acid level and is encoded by a variegated gene library. A library of PD-1 variants can be produced by, for example, by enzymatically ligating a mixture of synthetic oligonucleotides into gene sequences such that a degenerate set of potential PD-1 sequences is expressible as individual polypeptides, or alternatively, as a set of larger fusion proteins (such as for phage display) containing the set of PD-1 sequences.

There are a variety of methods which can be used to produce libraries of potential PD-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PD-1 antagonist sequences. Methods for synthesizing degenerate oligonucleotides are known in the art (see, for example, Narang, et al., Tetrahedron 39:3, 1983; Itakura et al. Annu. Rev. Biochem. 53:323, 1984; Itakura et al. Science 198:1056, 1984).

In addition, libraries of fragments of a PD-1 protein coding sequence can be used to generate a population of PD-1 fragments for screening and subsequent selection of variants of a PD-1 antagonist. In one embodiment, a library of coding sequence fragments can be generated by treating a double stranded PCR fragment of a PD-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of PD-1.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PD-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM) can be used in combination with the screening assays to identify PD-1 antagonists (Arkin and Youvan, Proc. Natl. Acad. Sci. USA 89:78117815, 1992; Delagrave et al., Protein Eng. 6(3):327 331, 1993).

In one embodiment, cell based assays can be exploited to analyze a library of PD-1 variants. For example, a library of expression vectors can be transfected into a cell line which ordinarily synthesizes and secretes PD-1. The transfected cells are then cultured such that PD-1 and a particular PD-1 variant are secreted. The effect of expression of the mutant on PD-1 activity in cell supernatants can be detected, such as by any of a functional assay. Plasmid DNA can then be recovered from the cells wherein endogenous PD-1 activity is inhibited, and the individual clones further characterized.

Peptidomimetics can also be used as PD-1 antagonists. Peptide analogs are commonly used in the pharmaceutical industry as non-peptide drugs with properties analogous to those of the template peptide. These types of non-peptide compounds and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (for example, polypeptide that has a PD-1 biological activity), but has one or more peptide linkages optionally replaced by a —$CH_2NH$—, —$CH_2S$—, —$CH_2$—$CH_2$—, —CH.=.CH— (cis and trans), —COCH$_2$—, —CH(OH)CH$_2$—, and —CH$_2$SO— linkages. These peptide linkages can be replaced by methods known in the art (see, for example, Morley, Trends Pharm. Sci. pp. 463 468, 1980; Hudson et al. Int. J. Pept. Prot. Res. 14:177 185, 1979; Spatola, Life Sci. 38:1243 1249, 1986; Holladay, et al. Tetrahedron Lett. 24:44014404, 1983). Peptide mimetics can be procured economically, be stable, and can have increased half-life or absorption. Labeling of peptidomimetics usually involves covalent attachment of one or more labels, directly or through a spacer (such as by an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization of peptidomimetics should not substantially interfere with the desired biological or pharmacological activity of the peptidomimetic.

A dominant negative protein or a nucleic acid encoding a dominant negative protein that interferes with the biological activity of PD-1 (i.e. binding of PD-1 to PD-L1, PD-L2, or both) can also be used in the methods disclosed herein. A dominant negative protein is any amino acid molecule having a sequence that has at least 50%, 70%, 80%, 90%, 95%, or even 99% sequence identity to at least 10, 20, 35, 50, 100, or more than 150 amino acids of the wild type protein to which the dominant negative protein corresponds. For example, a dominant-negative PD-L1 has mutation such that it binds PD-1 more tightly than native (wild-type) PD-1 but does not activate any cellular signaling through PD-1.

The dominant negative protein may be administered as an expression vector. The expression vector may be a non-viral vector or a viral vector (e.g., retrovirus, recombinant adeno-associated virus, or a recombinant adenoviral vector). Alternatively, the dominant negative protein may be directly administered as a recombinant protein systemically or to the infected area using, for example, microinjection techniques.

Polypeptide antagonists can be produced in prokaryotic or eukaryotic host cells by expression of polynucleotides encoding the amino acid sequence, frequently as part of a larger polypeptide (a fusion protein, such as with ras or an enzyme). Alternatively, such peptides can be synthesized by chemical methods. Methods for expression of heterologous proteins in recombinant hosts, chemical synthesis of polypeptides, and in vitro translation are well known in the art (see Maniatis et al. Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Kaiser et al., Science 243:187, 1989; Merrifield, Science 232:342, 1986; Kent, Annu. Rev. Biochem. 57:957, 1988).

Peptides can be produced, such as by direct chemical synthesis, and used as antagonists of a PD-1 interaction with a ligand. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (for example, acetylation) or alkylation (for example, methylation) and carboxy-terminal-modifications such as amidation, as well as other terminal modifications, including cyclization, can be incorporated into various embodiments. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others.

Method of Treatment

Administration of a PD-1 Antagonist to a Subject

Methods are provided herein to treat a variety of infections and cancers. In these methods, the infection or cancer is treated, prevented or a symptom is alleviated by administering to a subject a therapeutically effective amount of a PD-1 antagonist. The subject can be any mammal such as human, a primate, mouse, rat, dog, cat, cow, horse, and pig. In several examples, the subject is a primate, such as a human. In additional examples, the subject is a murine subject, such as a mouse. In some embodiments, the method includes measuring memory B cell proliferation in a sample from the subject (see below). In some examples, the methods also include measuring naïve B cells in a sample from the subject. In additional examples, the methods include measure T cells that express CD28 (CD28+) cells.

In several embodiments, the subject is at risk of developing infection. A subject at risk of developing infection is a subject that does not yet have the infection, but can be infected by the infectious agent of interest. In additional examples, the subject has an infection, such as a persistent infection, for example a chronic infection. A subject with a persistent infection, such as a chronic infection, can be identified by standard methods suitable by one of skill in the art, such as a physician.

In several examples, the subject has a persistent infection with a bacteria virus, fungus, or parasite. Generally, persistent infections, in contrast to acute infections are not effectively cleared by the induction of a host immune response. The infectious agent and the immune response reach equilibrium such that the infected subject remains infectious over a long period of time without necessarily expressing symptoms. Persistent infections include for example, latent, chronic and slow infections. Persistent infection occurs with viruses such as human T-Cell leukemia viruses, Epstein-Barr virus, cytomegalovirus, herpesviruses, varicella-zoster virus, measles, papovaviruses, prions, hepatitis viruses, adenoviruses, XMRV, polyoma JC virus, parvoviruses and papillomaviruses.

In a chronic infection, the infectious agent can be detected in the body at all times. However, the signs and symptoms of the disease may be present or absent for an extended period of time. Examples of chronic infection include hepatitis B (caused by heptatitis B virus (HBV)) and hepatitis C (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus K, polyomavirus JC, XMRV, measles virus, rubella virus, human immunodeficiency virus (HIV), human T cell leukemia virus I, and human T cell leukemia virus II. Parasitic persistent infections may arise as a result of infection by *Leishmania, Toxoplasma, Trypanosoma, Plasmodium, Schistosoma*, and *Encephalitozoon*.

In a latent infection, the infectious agent (such as a virus) is seemingly inactive and dormant such that the subject does always exhibit signs or symptoms. In a latent viral infection, the virus remains in equilibrium with the host for long periods of time before symptoms again appear; however, the actual viruses cannot be detected until reactivation of the disease occurs. Examples of latent infections include infections caused by herpes simplex virus (HSV)-1 (fever blisters), HSV-2 (genital herpes), and varicella zoster virus VZV (chickenpox-shingles).

In a slow infection, the infectious agents gradually increase in number over a very long period of time during which no significant signs or symptoms are observed. Examples of slow infections include AIDS (caused by HIV-1 and HIV-2), lentiviruses that cause tumors in animals, and prions.

In addition, persistent infections often arise as late complications of acute infections. For example, subacute sclerosing panencephalitis (SSPE) can occur following an acute measles infection or regressive encephalitis can occur as a result of a rubella infection.

In one non-limiting example, a subject may be diagnosed as having a persistent Chlamydial infection following the detection of Chlamydial species in a biological sample from this individual using PCR analysis. Mammals need not have not been diagnosed with a persistent infection to be treated according to this disclosure. Microbial agents capable of establishing a persistent infection include viruses (such as papilloma virus, hepatitis virus, human immune deficiency virus, and herpes virus), bacteria (such as *Escherichia coli* and *Chlamydia* spp.), parasites, (such as *Leishmania* spp., *Schistosoma* spp., *Trypanosoma* spp., *Toxoplasma* spp.) and fungi.

In addition to the compound that reduces PD-1 expression or activity, the subject being treated may also be administered a vaccine. In one example, the vaccine can include an adjuvant. In another example, the vaccine can include a prime booster immunization. The vaccine can be a heat-killed vaccine, an attenuated vaccine, or a subunit vaccine. A subject already infected with a pathogen can be treated with a therapeutic vaccine, such as a PD-1 antagonist and an antigen. The subject can be asymptomatic, so that the treatment prevents the development of a symptom. The therapeutic vaccine can also reduce the severity of one or more existing symptoms, or reduce pathogen load.

In several examples of treatment methods, the subject is administered a therapeutically effective amount of a PD-1 antagonist in conjunction with a viral antigen. Non-limiting examples of suitable viral antigens include: influenza HA, NA, M, NP and NS antigens; HIV p24, pol, gp41 and gp120; Metapneumovirus (hMNV) F and G proteins; Hepatitis C virus (HCV) E1, E2 and core proteins; Dengue virus (DEN1-4) E1, E2 and core proteins; Human Papilloma Virus L1 protein; Epstein Barr Virus gp220/350 and EBNA-3A peptide; Cytomegalovirus (CMV) gB glycoprotein, gH glycoprotein, pp 65, IE1 (exon 4) and pp 150; Varicella Zoster virus (VZV) IE62 peptide and glycoprotein E epitopes; Herpes Simplex Virus Glycoprotein D epitopes, polyoma JC virus polypeptides, XMRV polypeptides, among many others. The antigenic polypeptides can correspond to polypeptides of naturally occurring animal or human viral isolates, or can be engineered to incorporate one or more amino acid substitutions as compared to a natural (pathogenic or non-pathogenic) isolate. Exemplary antigens are listed below:

TABLE 1

Exemplary antiens of interest (target antigens)

| | Exemplary Antigen Sequences from the Antigens of interest | SEQ ID NO: |
|---|---|---|
| Viral Antigens | | |
| BK | TLYKKMEQDVKVAHQ | 13 |
| | GNLPLMRKAYLRKCK | 14 |
| | TFSRMKYNICMGKCI | 15 |
| JC | SITEVECFL | 16 |
| Epstein-Barr (EBV) | QPRAPIRPI | 17 |
| cytomegalovirus (CMV) | NLVPMVATV | 18 |
| HPV | YMLDLQPET(T) | 19 |
| Influenza A | GILGFVFTL | 20 |
| Fungal Antigen | | |
| Blastomyces dermatitidis | CELDNSHEDYNWNLWFKWCSGHGR | 47 |
| | TGHGKHFYDCDWDPSHGDYSWYLW | 48 |
| | DPSHGDYSWYLWDYLCGNGHHPYD | 49 |
| | DYLCGNGHHPYDCELDNSHEDYSW | 50 |
| | DPYNCDWDPYHEKYDWDLWNKWCN | 51 |
| | KYDWDLWNKWCNKDPYNCDWDPYH | 52 |

In additional embodiments, the subject has a tumor. The method includes administering to the subject a therapeutically effective amount of a PD-1 antagonist, thereby treating the tumor. In several examples, a therapeutically effective amount of a tumor antigen, or a nucleotide encoding the tumor antigen, is also administered to the subject. The PD-1 antagonist and the tumor antigen, or nucleotide encoding the tumor antigen, can be administered simultaneously or sequentially.

Administration of the PD-1 antagonist results in a decrease in size, prevalence, or metastatic potential of a tumor in a subject. Assessment of cancer is made using standard clinical protocols. Efficacy is determined in association with any known method for diagnosing or treating the particular tumor.

Tumors (also called "cancers") include solid tumors and leukemias. Exemplary tumors include those listed in table 2 (along with known tumor antigens associated with these cancers).

TABLE 2

Exemplary tumors and their tumor antigens

| Tumor | Tumor Antigens |
|---|---|
| Acute myelogenous leukemia | Wilms tumor 1 (WT1), preferentially expressed antigen of melanoma (PRAME), PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | New York esophageous 1 (NY-Eso1) |
| Malignant melanoma | MAGE, MART, Tyrosinase, PRAME, GP100 |
| Breast cancer | WT1, herceptin |
| Lung cancer | WT1 |
| Prostate cancer | Prostate-specific antigen (PSA) |
| Colon cancer | Carcinoembryonic antigen (CEA) |
| Renal cell carcinoma (RCC) | Fibroblast growth factor 5 (FGF-5) |

TABLE 3

Exemplary tumor antigens of interest include those listed below

Table 3: Tumor Antigens and their derivative peptides

| | | |
|---|---|---|
| PRAME | LYVDSLFFL | 21 |
| WT1 | RMFPNAPYL | 22 |
| Survivin | ELTLGEFLKL | 23 |
| AFP | GVALQTMKQ | 24 |
| ELF2M | ETVSEQSNV | 25 |
| proteinase 3 and its its peptide PR1 | VLQELNVTV | 26 |
| neutrophil elastase | VLQELNVTV | 27 |
| MAGE | EADPTGHSY | 28 |
| MART | AAGIGILTV | 29 |
| tyrosinase | RHRPLQEVYPEANAPIGHINRE | 30 |
| GP100 | WNRQLYPEWTEAQRLD | 31 |
| NY-Eso-1 | VLLKEFTVSG | 32 |
| Herceptin | KIFGSLAFL | 33 |
| carcino-embryonic antigen (CEA) | HLFGYSWYK | 34 |
| PSA | FLTPKKLQCV | 35 |

Specific non-limiting examples are angioimmunoblastic lymphoma or nodular lymphocyte predominant Hodgkin lymphoma. Angioimmunoblastic lymphoma (AIL) is an aggressive (rapidly progressing) type of T-cell non-Hodgkin lymphoma marked by enlarged lymph nodes and hypergammaglobulinemia (increased antibodies in the blood). Other symptoms may include a skin rash, fever, weight loss, positive Coomb's test or night sweats. This malignancy usually occurs in adults. Patients are usually aged 40-90 years (median around 65) and are more often male. As AIL progresses, hepatosplenomegaly, hemolytic anemia, and polyclonal hypergammaglobulinemia may develop. The skin is involved in approximately 40-50% of patients.

Nodular lymphocyte predominant Hodgkin lymphoma is a B cell neoplasm that appears to be derived from germinal center B cells with mutated, non-functional immunoglobulin genes. Similar to angioimmunoblastic lymphoma, neoplastic cells are associated with a meshwork of follicular dendritic cells. PD-1 expression is seen in T cells closely associated with neoplastic CD20+ cell in nodular lymphocyte predominant Hodgkin lymphoma, in a pattern similar to that seen for CD57+ T cells. CD57 has been identified as another marker of germinal center-associated T cells, along with CXCR5, findings which support the conclusion that the neoplastic cells in nodular lymphocyte predominant Hodgkin lymphoma have a close association with germinal center-associated T cells.

Expression of a tumor antigen of interest can be determined at the protein or nucleic acid level using any method known in the art. For example, Northern hybridization analysis using probes which specifically recognize one or more of these sequences can be used to determine gene expression. Alternatively, expression is measured using reverse-transcription-based PCR assays, such as using primers specific for the differentially expressed sequence of genes. Expression is also determined at the protein level, such as by measuring the levels of peptides encoded by the gene products described herein, or activities thereof. Such methods are well known in the art and include, for example immunoassays based on antibodies to proteins encoded by the genes. Any biological material can be used for the detection/quantification of the protein or the activity.

In one example, the subject has been previously diagnosed as having cancer. In additional examples, the subject has undergone prior treatment for the cancer. However, in some examples, the subject has not been previously diagnosed as having the cancer. Diagnosis of a solid tumor can be made through the identification of a mass on an examination, although it may also be through other means such as a radiological diagnosis, or ultrasound. Treatment of cancer can include surgery, or can include the use of chemotherapeutic agents such as docetaxel, vinorelbine gemcitabine, capecitabine or combinations of cyclophosphamide, methotrexate, and fluorouracil; cyclophosphamide, doxorubicin, and fluorouracil; doxorubicin and cyclophosphamide; doxorubicin and cyclophosphamide with paclitaxel; doxorubicin followed by CMF (Cyclophosphamide, epirubicin and fluorouracil). In addition, treatment can include the use of radiation.

In several examples, a therapeutically effective amount a PD-1 antagonist is administered to the subject. A therapeutically effective amount of a tumor antigen, or a nucleic acid encoding the antigen, is also administered to the subject. The administration can be concurrent or can be sequential.

For the treatment of a subject with a persistent infection (such as a chronic infection) or a tumor, a therapeutically effective amount of a PD-1 antagonist is administered to the subject of interest. In one example, a therapeutically effective amount of a PD-1 antagonist is a biologically active dose, such as a dose that will induce an increase in CD8+ T cell cytotoxic activity the increase in the immune response specific to the infectious agent. Desirably, the PD-1 antagonist has the ability to reduce the expression or activity of PD-1 in antigen specific immune cells (e.g., T cells such as CD8+ T cells) by at least 5%, 10%, 20%, 30%, 40%, 50%, 60%, 70%, 80%, 90%, or more than 100% below untreated control levels. The levels or activity of PD-1 in immune cells is measured by any method known in the art, including, for example, Western blot analysis, immunohistochemistry, ELISA, and Northern Blot analysis. Alternatively, the biological activity of PD-1 is measured by assessing binding of PD-1 to PD-L1, PD-L2, or both. The biological activity of PD-1 is determined according to its ability to increase CD8+ T cell cytotoxicity including, for example, cytokine production, clearance of the infectious agent, and proliferation of antigen specific CD8+ T cells. Preferably, the agent that reduces the expression or activity of PD-1 can increase the immune response specific to the infectious agent or the tumor by at least 5%, 10%, 20%, 30%, 40%, 50%, 60%, 70%, 80%, 90%, or more than 100% above untreated control levels. The agent of the present invention is therefore any agent having any one or more of these activities. Although the agent is preferably expressed in CD8+ T cells, it is understood that any cell that can influence the immune response to persistent infections is also amenable to the methods of the invention and include, for example, B cells.

Optionally, the subject is administered one or more additional therapeutic agents. Additional therapeutic agents include, for example, antiviral compounds (e.g., vidarabine, acyclovir, gancyclovir, valgancyclovir, nucleoside-analog reverse transcriptase inhibitor (NRTI) (e.g., AZT (Zidovudine), ddI (Didanosine), ddC (Zalcitabine), d4T (Stavudine), or 3TC (Lamivudine)), non-nucleoside reverse transcriptase inhibitor (NNRTI) (e.g., (nevirapine or delavirdine), protease inhibitor (saquinavir, ritonavir, indinavir, or nelfinavir), ribavirin, or interferon), antibacterial compounds, antifungal compounds, antiparasitic compounds, anti-inflammatory compounds, anti-neoplastic agent (chemotherapeutics) or analgesics.

The additional therapeutic agent is administered prior to, concomitantly, or subsequent to administration of the PD-1 antagonist. For example, the PD-1 antagonist and the additional agent are administered in separate formulations within at least 1, 2, 4, 6, 10, 12, 18, or more than 24 hours apart. Optionally, the additional agent is formulated together with the PD-1 antagonist. When the additional agent is present in a different composition, different routes of administration may be used. The agent is administered at doses known to be effective for such agent for treating, reducing, or preventing an infection.

Concentrations of the PD-1 antagonist and the additional agent depends upon different factors, including means of administration, target site, physiological state of the mammal, and other medication administered. Thus treatment dosages may be titrated to optimize safety and efficacy and is within the skill of an artisan. Determination of the proper dosage and administration regime for a particular situation is within the skill of the art.

Optionally, the subject is further administered a vaccine that elicits a protective immune response against the infectious agent that causes a persistent infection. For example, the subject receives a vaccine that elicits an immune response against human immunodeficiency virus (HIV), tuberculosis, influenza, XMRV, polyoma JC virus, or hepatitis C, amongst others. Exemplary vaccines are described, for example, in Berzofsky et al. (J. Clin. Invest. 114:456-462, 2004). If desired, the vaccine is administered with a prime-booster shot or with adjuvants. The vaccine can also be a tumor vaccine, such as a therapeutically effective amount of a tumor antigen. In several embodiments, a therapeutically effective amount of an antigenic polypeptide, such as a viral or a tumor antigen, is administered to the subject.

A therapeutically effective amount of the tumor antigen, or a nucleic acid encoding the tumor antigen can be administered to the subject. The polynucleotides include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides be ribonucleotides, deoxyribonucleotides, or modified forms of either nucleotide. The term includes single and double forms of DNA.

A number of viral vectors have been constructed, including polyoma, i.e., SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In one embodiment, the polynucleotide encoding a tumor antigen or a viral antigen is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

In several embodiments, PD-1 antagonists are administered in an amount sufficient to increase T cell, such as CD8+ T cell, cytotoxicity. An increase in T-cell cytotoxicity results in an increased immune response and a reduction in the persistent infection, or a reduction in a sign or a symptom of a tumor. An increased immune response can be measured, for example, by an increase in immune cell proliferation, such as T-cell or B cell proliferation, an increase in cytokine production, and an increase in the clearance of an infectious agent or a reduction in tumor burden. Thus, the method can result in alleviation of one or more of symptoms associated with the persistent infection or tumor. Thus, administration of the PD-1 antagonist reduces the persistent infection, inhibits the growth/size of a tumor, or alleviates one or more symptoms associated with the persistent infection or tumor by at least 10%, 20%, 30%, 40%, 50%, 60%, 70%, 80%, 90%, or 100% as compared to an untreated subject.

Treatment is efficacious if the treatment leads to clinical benefit such as, a reduction of the load of the infectious agent or a reduction of tumor burden in the subject. When treatment is applied prophylactically, "efficacious" means that the treatment retards or prevents an infection from forming, such as for a period of six months, one year, two years, three years or more. Efficacy may be determined using any known method for diagnosing or treating the particular infection or tumor.

Thus, the methods include administering to a subject a pharmaceutical composition that includes a therapeutically effective amount of a PD-1 antagonist. An effective amount of a therapeutic compound, such as an antibody, can be for example from about 0.1 mg/kg to about 150 mg/kg. Effective doses vary, as recognized by those skilled in the art, depending on route of administration, excipient usage, and coadministration with other therapeutic treatments including use of other anti-infection agents or therapeutic agents for treating, preventing or alleviating a symptom of a particular infection or cancer. A therapeutic regimen is utilized for a human patient suffering from (or at risk of developing) an infection or cancer, using standard methods.

The PD-1 antagonist is administered to such an individual using methods known in the art. Any PD-1 antagonist can be utilized, such as those disclosed herein. In addition, more than one PD-1 antagonist can be utilized. A PD-1 antagonist can be administered locally or systemically. For example, the PD-1 antagonist is administered orally, rectally, nasally, topically parenterally, subcutaneously, intraperitoneally, intramuscularly, and intravenously. The PD-1 antagonist can be administered prophylactically, or after the detection of an infection or tumor. The PD-1 antagonist is optionally formulated as a component of a cocktail of therapeutic drugs to treat infection. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, PD-1 antagonist is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The PD-1 antagonist can be administered in the form of a hard shell tablet or a capsule containing a binder, such as lactose or mannitol, a conventional filler, and a tableting agent. Other formulations include an ointment, suppository, paste, spray, patch, cream, gel, resorbable sponge, or foam. Such formulations are produced using methods well known in the art.

Additionally, PD-1 antagonists can be administered by implanting (either directly into an organ (e.g., intestine or liver) or subcutaneously) a solid or resorbable matrix which slowly releases the compound into adjacent and surrounding tissues of the subject. For example, for the treatment of gastrointestinal infection, the compound may be administered systemically (e.g., intravenously, rectally or orally) or locally (e.g., directly into gastric tissue). Alternatively, a PD-1 antagonist-impregnated wafer or resorbable sponge is placed in direct contact with gastric tissue. The PD-1 antagonist is slowly released in vivo by diffusion of the drug from the wafer and erosion of the polymer matrix. As another example, infection of the liver (i.e., hepatitis) is treated by infusing into the liver vasculature a solution containing the PD-1 antagonist.

Where the therapeutic compound is a nucleic acid encoding a PD-1 antagonist, the nucleic acid can be administered in vivo to promote expression of the encoded protein, by constructing it as part of an appropriate nucleic acid expression vector and administering it so that it becomes intracellular (such by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., Proc Natl Acad Sci USA 88:1864-1868, 1991), and the like. Alternatively, a nucleic acid therapeutic is introduced intracellularly and incorporated within host cell DNA for expression, by homologous recombination or remain episomal.

For local administration of DNA, standard gene therapy vectors can be used. Such vectors include viral vectors, including those derived from replication-defective hepatitis viruses (such as HBV and HCV), retroviruses (see, PCT Publication No. WO 89/07136; Rosenberg et al., N. Eng. J. Med. 323(9):570-578, 1990, adenovirus (see, Morsey et al., J. Cell Biochem., Supp. 17E, 1993), adeno-associated virus (Kotin et al., Proc. Natl. Acad. Sci. USA 87:2211-2215, 1990), replication defective herpes simplex viruses (HSV; Lu et al., Abstract, page 66, Abstracts of the Meeting on Gene Therapy, September. 22-26, Cold Spring Harbor Laboratory, Cold Spring Harbor, N.Y., 1992, and any modified versions of these vectors. Any other delivery system can be utilized that accomplishes in vivo transfer of nucleic acids into eukaryotic cells. For example, the nucleic acids may be packaged into liposomes, such as cationic liposomes (Lipofectin), receptor-mediated delivery systems, non-viral nucleic acid-based vectors, erythrocyte ghosts, or microspheres (such as microparticles; see, e.g., U.S. Pat. No. 4,789,734; U.S. Pat. No. 4,925,673; U.S. Pat. No. 3,625,214). Naked DNA may also be administered.

With regard to nucleic acid inhibitors, a therapeutically effective amount is an amount which is capable of producing a medically desirable result, e.g., a decrease of a PD-1 gene product in a treated animal. Such an amount can be determined by one of ordinary skill in the art. Dosage for any given patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately 106 to 1022 copies of the DNA molecule.

Typically, plasmids are administered to a mammal in an amount of about 1 nanogram to about 5000 micrograms of DNA. Desirably, compositions contain about 5 nanograms to 1000 micrograms of DNA, 10 nanograms to 800 micrograms of DNA, 0.1 micrograms to 500 micrograms of DNA, 1 microgram to 350 micrograms of DNA, 25 micrograms to 250 micrograms of DNA, or 100 micrograms to 200 micrograms of DNA. Alternatively, administration of recombinant adenoviral vectors encoding the PD-1 antagonist into a mammal may be administered at a concentration of at least 105, 106, 107, 108, 109, 1010, or 1011 plaque forming unit (pfu).

In some embodiments, for the treatment of neurological infections, the PD-1 antagonist can be administered intravenously or intrathecally (for example, by direct infusion into the cerebrospinal fluid). For local administration, a compound-impregnated wafer or resorbable sponge is placed in direct contact with central nervous system (CNS) tissue. The compound or mixture of compounds is slowly released in vivo by diffusion of the drug from the wafer and erosion of the polymer matrix. Alternatively, the compound is infused into the brain or cerebrospinal fluid using standard methods. For example, a burr hole ring with a catheter for use as an injection port is positioned to engage the skull at a burr hole drilled into the skull. A fluid reservoir connected to the catheter is accessed by a needle or stylet inserted through a septum positioned over the top of the burr hole ring. A catheter assembly (described, for example, in U.S. Pat. No. 5,954,687) provides a fluid flow path suitable for the transfer of fluids to or from selected location at, near or within the brain to allow administration of the drug over a period of time.

In additional embodiments, for cardiac infections, the PD-1 antagonist can be delivered, for example, to the cardiac tissue (such as the myocardium, pericardium, or endocardium) by direct intracoronary injection through the chest wall or using standard percutaneous catheter based methods under fluoroscopic guidance. Thus, the PD-1 antagonist may be directly injected into tissue or may be infused from a stent or catheter which is inserted into a bodily lumen. Any variety of coronary catheter or perfusion catheter may be used to administer the compound. Alternatively, the PD-1 antagonist is coated or impregnated on a stent that is placed in a coronary vessel.

Pulmonary infections can be treated, for example, by administering the PD-1 antagonist by inhalation. The compounds are delivered in the form of an aerosol spray from a pressured container or dispenser which contains a suitable propellant, such as a gas such as carbon dioxide or a nebulizer.

One in the art will understand that the patients treated can have been subjected to the same tests to diagnose a persistently infected subject or may have been identified, without examination, as one at high risk due to the presence of one or more risk factors (such as exposure to infectious agent, exposure to infected subject, genetic predisposition, or having a pathological condition predisposing to secondary infections). Reduction of persistent infection symptoms or damage may also include, but are not limited to, alleviation of symptoms, diminishment of extent of disease, stabilization (not worsening) state of disease, delay or slowing of disease progression, and amelioration or palliation of the disease state. Treatment can occur at home with close supervision by the health care provider, or can occur in a health care facility.

Methods for measuring the immune response following treatment using the methods disclosed herein are well known in the art. The activity of T cells may be assessed, for example, by assays that detect cytokine production, assays measuring T cell proliferation, assays that measure the clearance of the microbial agent, and assays that measure CD8+ T cell cytotoxicity. These assays are described, for example, in U.S. Pat. No. 6,808,710 and U.S. Patent Application Publication Nos. 20040137577, 20030232323, 20030166531, 20030064380, 20030044768, 20030039653, 20020164600, 20020160000, 20020110836, 20020107363, and 20020106730, all of which are hereby incorporated by reference. The measurement of a B cell response, such as a memory B cell response, is described below.

Optionally, the ability of a PD-1 antagonist to increase CD8+ T cell cytotoxicity is assessed by assays that measure the proliferation of CD8+ T cells (for example, thymidine incorporation, BrdU assays, and staining with cell cycle markers (for example, Ki67 and CFSE), described, for example, by Dong et al. (Nature 5:1365-1369, 1999). In one example, T-cell proliferation is monitored by culturing the purified T-cells expressing PD-1 with a PD-1 antagonist, a primary activation signal as described above, and $^3$H-thymidine. The level of T-cell proliferation is determined by measuring thymidine incorporation.

CD8+ T cell cytotoxicity also can be assessed by lysis assays (such as $^{51}$Cr release assays or assays detecting the release of perforin or granzyme), assays that detect caspase activation, or assays that measure the clearance of the microbial agent from the infected subject. For example, the viral load in a biological sample from the infected subject (e.g., serum, spleen, liver, lung, or the tissue to which the virus is tropic) may be measured before and after treatment.

The production of cytokines such as IFNγ, TNF-α, and IL-2 may also be measured. For example, purified T-cells are cultured in the presence of the PD-1 protein antagonist and a primary activation signal. The level of various cytokines in the supernatant can be determined by sandwich enzyme-linked immunosorbent assays or other conventional assays described, for example, in Dong et al. (Nature 5:1365-1369, 1999).

If desired, the efficacy of the PD-1 antagonist is assessed by its ability to induce co-stimulation of T cells. For example, a method for in vitro T-cell co-stimulation involves providing purified T-cells that express PD-1 with a first or primary activation signal by anti-CD3 monoclonal antibody or phorbol ester, or by antigen in association with class II MHC. The ability of a candidate compound agent to reduce PD-1 expression or activity and therefore provide the secondary or co-stimulatory signal necessary to modulate immune function, to these T-cells can then be assayed by any one of the several conventional assays well known in the art.

The B cell response to the PD-1 antagonist can be assessed by LCMV specific ELISA, plasma cell ELISPOT, memory B-cell assay, phenotyping of B cell, and analysis of germinal centers by immunohistochemistry.

Methods of Treatment

Adoptive Immunotherapy

Methods are disclosed herein for the treatment of a subject of interest, such as a subject with a persistent viral infection (such as a chronic infection) or a tumor. The methods include the administration of a therapeutically effective amount of cytoxic T cells specific for an antigen of interest, such as a viral antigen or a tumor antigen, and a therapeutically effective amount of a PD-1 antagonist. In some embodiments, the method can also include measuring memory B cell proliferation in a sample from the subject (see below). In additional embodiments, the methods include measuring naïve B cells in a sample from the subject. In further embodiments, the methods also include measuring T cells that express CD28. In some embodiments, the methods include measuring neutralizing antibodies. Thus, the disclosed methods include measuring at least one of neutralizing antibodies, memory B cell proliferation, naïve B cells, and T cells that express CD28. Two, three or all of these parameters can be measured using the methods disclosed herein.

Methods are disclosed herein for increasing the immune response, such as enhancing the immune system in a subject. Administration of the purified antigen-specific T cells and PD-1, as disclosed herein, will increase the ability of a subject to overcome pathological conditions, such as an infectious disease or a tumor, by targeting an immune response against a pathogen (such as a virus or fungus) or neoplasm. Therefore, by purifying and generating a purified population of selected antigen-specific T cells from a subject ex vivo and introducing a therapeutic amount of these cells, the immune response of the recipient subject is enhanced. The administration of a therapeutically effective amount of a PD-1 antagonist also enhances the immune response of the recipient.

Methods of inducing an immune response to an antigen of interest in a recipient are provided herein. The recipient can be any subject of interest, including a subject with a chronic infection, such as a viral or fungal infection, or a subject with a tumor. These infections are described above.

Infections in immune deficient people are a common problem in allograft stem cell recipients and in permanently immunosuppressed organ transplant recipients. The resulting T cell deficiency infections in these subjects are usually from reactivation of viruses already present in the recipient. For example, once acquired, most herpes group viruses (such as CMV, EBV, VZV, HSV) are dormant, and kept suppressed by T cells. However, when patients are immunosuppressed by conditioning regimens, dormant viruses can be reactivated. For example, CMV reactivation, Epstein Barr virus (EBV) reactivation which causes a tumor in B cells (EBV lymphoproliferative disease), and BK virus reactivation which causes hemorrhagic cystitis, can occur following immunosuppression. In addition, HIV infection and congenital immune deficiency are other examples of T cell immune deficiency. These viral infections and reactivations can be an issue in immunosuppressed subjects.

In several embodiments, an immune response against a tumor is provided to the recipient of a bone marrow transplant. Anti-tumor immunity can be provided to a subject by administration of antigen-specific T cells that recognize a tumor-antigen. Such administration to a recipient will enhance the recipient's immune response to the tumor by providing T cells that are targeted to, recognize, and immunoreact with a tumor antigen of interest.

In one example, the method includes isolating from the donor a population of donor cells including T cells (such as peripheral blood mononuclear cells) and contacting a population of donor cells comprising T cells with a population of antigen presenting cells (APCs) from the donor that are presenting an antigen of interest, optionally in the presence of PD-1, thereby producing a population of donor cells comprising activated donor CD4$^+$ and/or CD8$^+$ T cells depleted for alloreactive T cells that recognize an antigen of interest. A therapeutically effective amount of the population of donor activated CD4+ and/or CD8+ cells into the recipient, thereby producing an immune response to the antigen of interest in the recipient. Administration of the purified antigen-specific T cells can increase the ability of a subject to overcome pathological conditions, such as an infectious disease or a tumor, by targeting an immune response against a pathogen (such as a virus or fungus) or neoplasm. Thus, an immune response is produced in the recipient against the antigen of interest.

In several embodiments the method also includes administering a therapeutically effective amount of a PD-1 antagonist to the subject. The administration of PD-1 antagonists is described in detail above.

Any antigenic peptide (such as an immunogenic fragment) from an antigen of interest can be used to generate a population of T cells specific for that antigen of interest. Numerous such antigenic peptides are known in the art, such as viral and tumor antigens (see, for example, Tables 1-3). This disclosure is not limited to using specific antigen peptides. Particular examples of antigenic peptides from antigens of interest, include, but are not limited to, those antigens that are viral, fungal, and tumor antigens, such as those shown in Tables 1-3. Additional antigenic peptides are known in the art (for example see Novellino et al., *Cancer Immunol. Immunother.* 54(3):187-207, 2005, and Chen et al., Cytotherapy, 4:41-8, 2002, both herein incorporated by reference).

Although Tables 1 and 3 disclose particular fragments of full-length antigens of interest, one skilled in the art will recognize that other fragments or the full-length protein can also be used in the methods disclosed herein. In one example, an antigen of interest is an "immunogenic fragment" of a full-length antigen sequence. An "immunogenic fragment" refers to a portion of a protein which, when presented by a cell in the context of a molecule of the MHC, can in a T-cell activation assay, activate a T-cell against a cell expressing the protein. Typically, such fragments that bind to MHC class I molecules are 8 to 12 contiguous amino acids of a full length antigen, although longer fragments may of course also be used. In some examples, the immunogenic fragment is one that can specifically bind to an MHC molecule on the surface of an APC, without further processing of the epitope sequence. In particular examples, the immunogenic fragment is 8-50 contiguous amino acids from a full-length antigen sequence, such as 8-20 amino acids, 8-15 amino acids, 8-12 amino acids, 8-10 amino acids, or 8, 9, 10, 11, 12, 13, 14, 15 or 20 contiguous amino acids from a full-length antigen sequence. In some examples, APCs are incubated with the immunogenic fragment under conditions sufficient for the immunogenic fragment to specifically bind to MHC molecules on the APC surface, without the need for intracellular processing.

In one example, an antigen includes a peptide from the antigen of interest with an amino acid sequence bearing a binding motif for an HLA molecule of the subject. These motifs are well known in the art. For example, HLA-A2 is a common allele in the human population. The binding motif for this molecule includes peptides with 9 or 10 amino acids having leucine or methionine in the second position and valine or leucine in the last positions (see examples above). Peptides that include these motifs can be prepared by any method known in the art (such as recombinantly, chemically, etc.). With knowledge of an amino acid sequence of an antigen of interest, immunogenic fragment sequences predicted to bind to an MHC can be determined using publicly available programs. For example, an HLA binding motif program on the Internet (Bioinformatics and Molecular Analysis Section-BIMAS) can be used to predict epitopes of any tumor-, viral-, or fungal-associated antigen, using routine methods. Antigens of interest (either full-length proteins or an immunogenic fragment thereof) then can be produced and purified using standard techniques. For example, epitope or full-length antigens of interest can be produced recombinantly or chemically synthesized by standard methods. A substantially pure peptide preparation will yield a single major band on a non-reducing polyacrylamide gel. In other examples, the antigen of interest includes a crude viral lysate.

In one example, the antigen of interest is a tumor associated antigen and the amino acid sequences bearing HLA binding motifs are those that encode subdominant or cryptic epitopes. Those epitopes can be identified by a lower comparative binding affinity for the HLA molecule with respect to other epitopes in the molecule or compared with other molecules that bind to the HLA molecule.

Through the study of single amino acid substituted antigen analogs and the sequencing of endogenously bound, naturally processed peptides, critical residues that correspond to motifs required for specific binding to HLA antigen molecules have been identified (see, for example, Southwood et al., *J. Immunol.* 160:3363, 1998; Rammensee et al., *Immunogenetics* 41:178, 1995; Rammensee et al., *J. Curr. Opin. Immunol.* 10:478, 1998; Engelhard, *Curr. Opin. Immunol.* 6:13, 1994; Sette and Grey, *Curr. Opin. Immunol.* 4:79, 1992). Furthermore, x-ray crystallographic analysis of HLA-peptide complexes has revealed pockets within the peptide binding cleft of HLA molecules which accommodate, in an allele-specific mode, residues borne by peptide ligands; these residues in turn determine the HLA binding capacity of the peptides in which they are present. (See, for example, Madden, *Annu. Rev. Immunol.* 13:587, 1995; Smith et al., *Immunity* 4:203, 1996; Fremont et al., *Immunity* 8:305, 1998; Stern et al., *Structure* 2:245, 1994; Jones, *Curr. Opin. Immunol.* 9:75, 1997; Brown et al., *Nature* 364:33, 1993.)

The antigen of interest is selected based on the subject to be treated. For example, if the subject is in need of increased antiviral or antifungal immunity one or more target viral or fungal associated antigens are selected. Exemplary antigens of interest from viruses include antigens from Epstein bar virus (EBV), hepatitis C virus (HCV) cytomegalovirus (CMV), herpes simplex virus (HSV), BK virus, JC virus, and human immunodeficiency virus (HIV) amongst others. Exemplary antigens of interest from fungi include antigens from *Candida albicans, Cryptococcus, Blastomyces*, and *Histoplasma*, or other infectious agent. In another example, the subject is in need of increased anti-tumor immunity. Exemplary antigens of interest from tumors include WT1, PSA, PRAME. Exemplary antigens of interest for infectious agents are listed in Table 1. In some examples, the antigen of interest includes both a viral antigen and a tumor antigen, both a fungal antigen and a tumor antigen, or a viral antigen, a fungal antigen, and a tumor antigen.

For the treatment of a subject with a tumor, the tumor antigen of interest is chosen based on the expression of the protein by the recipient's tumor. For example, if the recipient has a breast tumor, a breast tumor antigen is selected, and if the recipient has a prostate tumor, a prostate tumor antigen is selected, and so forth. Table 2 lists exemplary tumors and respective tumor associated antigens that can be used to generate purified antigen-specific T cells that can be administered to a subject having that particular tumor. However, one skilled in the art will recognize that the same and other tumors can be treated using additional tumor antigens.

In one example, antigen-specific T cells that recognize a tumor antigen are administered in a therapeutically effective amount to a subject who has had, or will receive, a stem cell allograft or autograft, or who has been vaccinated with the tumor antigen. For example, a therapeutic amount of antigen-specific T cells can be administered that recognize one or more tumor-associated antigens, for example at least one of the antigens of interest listed in Tables 2-3.

In particular examples where the recipient has a tumor and has or will receive a stem cell allograft, donor tumor antigen-specific T cells and a therapeutically effective amount of a PD-1 antagonist are administered in a therapeutically effective amount after the stem cell allograft to prevent, decrease, or delay tumor recurrence, or to treat a malignant relapse. The purified antigen-specific T cells can be introduced back into the subject after debulking. In yet another example, the recipient is vaccinated with the tumor antigen of interest, purified antigen-specific T cells purified from the recipient and then re-introduced into the recipient with a therapeutically effective amount of a PD-1 antagonist to increase the recipient's immune system against the tumor.

Administration of a therapeutic amount of tumor antigen-specific T cells and a therapeutically effective amount of a PD-1 antagonist can be used prophylactically to prevent recurrence of the tumor in the recipient, or to treat a relapse of the tumor. Such antigen-specific T cells can kill cells containing the tumor-associated antigen or assist other immune cells.

In a specific example, a recipient has a tumor and has or will receive a stem cell allograft to reconstitute immunity. Following bone marrow irradiation or administration of a cytotoxic drug that has ablated or otherwise compromised bone marrow function, at least two types of donor antigen-specific T cells are administered in a therapeutically effective amount; antigen-specific T cells that specifically recognize a viral-associated antigen (or a fungal-associated antigen) and antigen-specific T cells that specifically recognize a tumor-associated antigen. In addition, a therapeutically effective amount of a PD-1 antagonist is administered to the subject. Such administration can be used to induce an anti-tumor effect and an anti-viral effect (such as an anti-viral effect).

In order to produce a population of antigen-specific T cells for administration to a subject of interest, a population of cells including T cells can be contacted with antigen presenting cells (APCs), such as dendritic cells or T-APCs, to present the antigen of interest. In some embodiments, the responder T cells (such as lymphocytes or PBMCs) are treated with an antagonist of PD-1 and are added to the APCs presenting one or more antigens of interest, and incubated under conditions sufficient to allow the interaction between the APCs presenting antigen and the T cells to produce antigen-specific T cells. The treatment of the responder T cells with the PD-1 antagonist can be simultaneously with the contact or the APCs. The treatment with the PD-1 antagonist can also be immediately prior to the contact with the APCs.

Thus, methods are provided herein for producing an enriched population of antigen-specific T cells. Generally, T-APCs present antigens to T cells and induce an MHC-restricted response in a class I (CD8+ T cells) and class II (CD4+ T cells) restricted fashion. The typical T cell response is activation and proliferation. Thus, a population is produced that includes T cells that specifically recognize an antigen of interest. Thus a therapeutically effective amount of this population of cells can be administered to a subject to produce an immune response, such as a subject with a chronic infection or a tumor.

Generally, the APCs and the T cells are autologous. In specific, non-limiting examples, the APCs and the responder T cells are from the same individual. However, the APCs and the responder T cells can be syngeneic. The APC can be used to present any antigen to a population of autologous T cells. One of skill in the art will appreciate that antigenic peptides that bind to MHC class I and II molecules can be generated ex vivo (for example instead of being processed from a full-length protein in a cell), and allowed to interact with (such as bind) MHC I and II molecules on a cell surface. Generally, APCs present antigen in the context of both MHC class I and II.

In one example, the antigen of interest incubated with the APCs is a fusion protein that includes an amino acid sequence from the antigen of interest (such as 8-50 contiguous amino acids, for example 8-15 or 8-12 contiguous amino acids from the antigen of interest). Thus, a series of MHC binding epitopes can be included in a single antigenic polypeptide, or a single chain trimer can be utilized, wherein each trimer has an MHC class I molecule, a b2 microglobulin, and an antigenic peptide of interest (see Nature 2005; vol. 436, page 578). In some examples, only a single antigen is used, but in other embodiments, more than one antigen is used, such as at least 2 different antigens, at least 3 different antigens, at least 4 different antigens, at least 5 different antigens, at least 10 different antigens, at least 15 different antigens, at least 20 different antigens, or even at least 50 different antigens.

In yet other examples, an antigen of interest is a full-length antigen amino acid sequence (such as a full-length fungal antigen, tumor antigen, or viral antigen, for example a viral lysate or full-length cathepsin G). In additional examples, one or more antigens from any infectious agent can be utilized. In some examples, the full-length antigen of interest is expressed by the APC.

APCs can be produced using methods known to one of skill in the art (see Melenhorst et al, Cytotherapy 7, supp. 1, 2005; Melenhorst et al., Blood 106: 671a, 2005; Gagliardi et al., Int. Immunol. 7: 1741-52, 1995, herein incorporated by reference). In one example, to produce T-APCs, donor peripheral blood monocytes are activated using IL-2 and an antibody that specifically binds CD3 (such as OKT3) for about three or more days, such as about one to two weeks, such as for about seven to ten days.

It has been observed that in the presence of presenting antigen, T cells that recognize the antigen bind to antigen presenting cells (APCs) presenting an antigen of interest more strongly than do T cells that are not specific for the antigen (and are thus not binding in an antigen-specific manner). In a particular example, antigen-specific T cells are selected by exposing APCs to a target peptide antigen (such as a target viral or tumor associated antigen) against which desired T cells are to be targeted in the presence of a PD-1 antagonist, such that the APC presents the antigen in association with a major histocompatibility complex (MHC) class I and/or class II. For example, APCs can be exposed to a sufficient amount of a antigen of interest to sufficiently occupy MHC molecules on the surface of the APC (for example, at least 1% of the MHC molecules are occupied, such at least 5%, at least 7.5% or at least 10%) and stimulate preferential binding of target T cells in the presence of a PD-1 antagonist to the APCs presenting the antigen of interest (as compared to APCs that do not present the antigen of interest). A population of T cells, such as population that has been primed for the antigen of interest, is then incubated with the APCs, optionally in the presences of a PD-1 antagonist, such as an antibody that specifically binds PD-1, to preferentially activate the cells, thereby producing a population of cells enriched with the desired T cells that recognize the antigen of interest.

T cells, such as those present in a population of PBMCs or lymphocytes, can be incubated with one or more antigens of interest, optionally in the presence of a PD-1 antagonist to generate a T cell population that is primed for the one or more antigens of interest. T cells can be primed using any method known in the art. In particular examples, PBMCs or lymphocytes are incubated in the presence of a purified target peptide antigen, optionally in the presence of a PD-1 antagonist. In some examples, the antigen of interest is an antigen of an infectious agent, or a tumor antigen, such as, but not limited to, one or more of the antigens of interest listed in the above tables. The antigen of interest can be in a purified form, such as a chemically synthesized peptide. In other examples, the antigen of interest is present in a non-purified form, such as in a crude lysate, for example a viral lysate.

The amount of antigen used to prime T cells can be readily determined using methods known in the art. Generally, if the antigen is used in a purified form, about 1-10 µg/ml of peptide is used. When a viral lysate is used, about 0.1-100 µl of lysate, such as about 75 can be used. When T-APCs are used, about 4-6 million T-APCs presenting the antigen of interest can be used for every 40-60 million T cells (or lymphocytes or PBMCs).

In a specific example, lymphocytes are primed in vitro by incubating them with soluble antigen or viral lysate for 5-7 days under conditions that permit priming of T cells. Viable T cells are recovered, for example by Ficoll-Hypaque centrifugation, thereby generating primed T cells. If desired, the viable primed T cells can be primed again one or more times, for example by incubation with the antigen for another 5-7 days under the same conditions as those used for the first priming, and viable T cells recovered.

In another example, lymphocytes are primed in vivo by inoculating a subject with the antigen, for example in the form of a vaccine. In this example, T cells obtained from the subject following immunization are already primed. For example, lymphocytes or PBMC obtained from a subject are then incubated with APCs in the presence of a PD-1 antagonist as described herein, without the need for additional priming.

The method can further include generating the APCs that present the antigen of interest. For example, APCs can be incubated with a sufficient amount of one or more different peptide antigens, under conditions sufficient for the target peptide(s) to be presented on the surface of the APCs. This generates a population of APCs that present the antigen of interest on MHC molecules on the surface of the APC. The disclosed methods are not limited to particular methods of presenting the antigen of interest on the surface of an APC.

Antigens can also be expressed by the APC either naturally or due to the insertion of a gene containing the DNA sequence encoding the target protein (antigen). A nucleic acid encoding the antigen of interest can be introduced into the T cells as messenger RNA, or using a vector, such as a mammalian expression vector, or a viral vector (for example, a adenovirus, poxvirus, or retrovirus vectors). The polynucleotides encoding an antigen of interest include a recombinant DNA which is an autonomously replicating plasmid or virus, or which is incorporated into the genomic DNA of a eukaryote, or which exists as a separate molecule independent of other sequences. A nucleic acid encoding an antigen of interest can also be introduced using electroporation, lipofection, or calcium phosphate-based transfection.

A number of viral vectors have been constructed, including polyoma, i.e., SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV, CMV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In one embodiment, the polynucleotide encoding an antigen of interest is included in a viral vector for transfer into APC. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which to nature are not contiguous with the flanking vaccinia regulatory DNA sequences that encode an antigen of interest. The recombinant virus containing such a chimeric gene is effective at expressing the antigen. In one example, the vaccine viral vector comprises (A) a segment comprised of (i) a first DNA sequence encoding an antigen and (ii) a poxvirus promoter, wherein the poxvirus promoter is adjacent to and exerts transcriptional control over the DNA sequence encoding an antigen polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

The population of APCs that present a sufficient density of the antigen(s) are incubated with T cells (such as lymphocytes or PBMCs), optionally in the presence of an effective amount of a PD-1 antagonist, under conditions sufficient to allow binding between the APCs presenting the antigen and the T cells that can specifically immunoreact with the antigen (antigen-specific T cells). A sufficient number of APCs expressing a sufficient density of antigen in combination with MHC to stimulate enhance binding of a target T cell to the APC are used. In particular examples, at least 20% of the APCs are presenting the desired antigen on MHC molecules on the APC surface, such as at least 30% of the APCs, at least 40% of the APCs, at least 50% of the APCs, or at least 60% of the APCs. The optimal amount of T cells added can vary depending on the amount of APCs used. In some examples, a T cell:APC ratio of at least 6:1 is used, such as at least 8:1, at least 10:1, at least 12:1, at least 15:1, at least 16:1, at least 20:1, or even at least 50:1.

To increase the number of antigen-specific T cells, proliferation of the cells can be stimulated, for example by incubation in the presence of a cytokine, such as IL-2, IL-7, IL-12 and IL-15. The amount of cytokine added is sufficient to stimulate production and proliferation of T cells, and can be determined using routine methods. In some examples, the amount of IL-2, IL-7, IL-12, or IL-15 added is about 0.1-100 IU/mL, such as at least 1 IU/mL, at least 10 IU/mL, or at least 20 IU/mL.

After a sufficient amount of binding of the antigen specific T cells to the APCs, T cells that specifically recognize the antigen of interest are produced. This generates a population of enriched (such as purified) antigen-specific T cells that are specific for the antigen of interest. In some examples, the resulting population of T cells that are specific for the antigen of interest is at least 30% pure, such as at least 40% pure, or even at least 50% pure. The purity of the population of antigen specific T cells can be assessed using methods known to one of skill in the art.

In one example, during stimulation of proliferation of antigen-specific T cells, the cells can be counted to determine the cell number. When the desired number of cells is achieved, purity is determined. Purity can be determined, for example, using markers present on the surface of antigen-specific T cells concomitant with the assessment of cytokine production upon antigen recognition, such as interferon (IFN)γ, tumor necrosis factor (TNF)α, interleukin (IL)-2, IL-10, transforming growth factor (TGF)β1, or IL-4. Generally, antigen-specific T cells are positive for the CD3 marker, along with the CD4 or CD8 marker, and IFN-γ (which is specific for activated T cells). For example, fluorescence activated cell sorting (FACS) can be used to identify (and sort if desired) populations of cells that are positive for CD3, CD4 or CD8, and IFN-γ by using differently colored anti-CD3, anti-CD4, anti-CD8 and anti-IFN-γ. Briefly, stimulated T antigen-specific cells are incubated in the presence of anti-CD3, anti-CD4, anti-CD8 and anti-IFN-γ (each having a different fluorophore attached), for a time sufficient for the antibody to bind to the cells. After removing unbound antibody, cells are analyzed by FACS using routine methods. Antigen-specific T cells are those that are INF-γ positive and CD8 positive or CD4 positive. In specific examples, the resulting population of antigenic T cells is at least 30% pure relative to the total population of CD4+ or CD8+ positive cells, such as at least 40% pure, at least 50% pure, at least 60% pure, or even at least 70% pure relative to the total population of CD4 positive or CD8 positive cells.

In another example, the method further includes determining the cytotoxicity of the antigen-specific T cells. Methods for determining cytotoxicity are known in the art, for example a $^{51}$Cr-release assay (for example see Walker et al. Nature 328:345-8, 1987; Qin et al. Acta Pharmacol. Sin. 23(6):534-8, 2002; all herein incorporated by reference).

The antigen-specific T cells can be subjected to one or more rounds of selection to increase the purity of the antigen-specific T cells. For example, the purified antigen-specific T cells generated above are again incubated with APCs presenting the antigen of interest in the presence of a PD-1 antagonist under conditions sufficient to allow binding between the APCs and the purified antigen-specific T cells. The resulting antigen-specific T cells can be stimulated to proliferate, for example with IL-2. Generally, the resulting antigen-specific T cells that specifically immunoreact with the antigen of interest are more pure after successive stimulations with APCs than with only one round of selection. In one example, the population of purified antigen-specific T cells produced is at least 90% pure relative to all CD3+ cells present, such as at least 95% pure or at least 98% pure. In a particular example, the population of purified antigen-specific T cells produced is at least 95% pure relative to all CD4+ cells present, such as at least 98% pure. In another example, the population of purified antigen-specific T cells produced is at least 90% pure relative to all CD3+ cells present, such as at least 93% pure.

The present disclosure also provides therapeutic compositions that include the enriched (such as purified) antigen-specific T cells and a PD-1 antagonist. In particular examples, the resulting enriched population of antigen-specific T cells (specific for the antigen of interest) are placed in a therapeutic dose form for administration to a subject in need of them. The PD-1 antagonist is also present in a therapeutic dose form for administration to a subject in need of treatment.

In one example, the population of purified antigen-specific T cells produced is at least 30% pure relative to all CD3+ cells present, such as at least 40% pure, at least 50% pure, at least 80% pure, or even at least 90% pure. In a particular example, the population of purified antigen-specific T cells produced is at least 30% pure relative to all CD3+ cells present, such as at least 40% pure, at least 50% pure, at least 80% pure, at least 90% pure, at least 95% pure, or even at least 98% pure. In another example, the population of purified antigen-specific T cells produced is at least 50% pure relative to all CD3+ cells present, such as at least 60% pure, at least 75% pure, at least 80% pure, at least 90% pure, or even at least 93% pure. Expanded and selected antigen-specific T cells can be tested for mycoplasma, sterility, endotoxin and quality controlled for function and purity prior cryopreservation or prior to infusion into the recipient.

A therapeutically effective amount of antigen-specific T cells is administered to the subject. Specific, non-limiting examples of a therapeutically effective amount of purified antigen-specific T cells include purified antigen-specific T cells administered at a dose of about $1 \times 10^5$ cells per kilogram of subject to about $1 \times 10^9$ cells per kilogram of subject, such as from about $1 \times 10^6$ cells per kilogram to about $1 \times 10^8$ cells per kilogram, such as from about $5 \times 10^6$ cells per kilogram to about $75 \times 10^6$ cells per kilogram, such as at about $25 \times 10^6$ cells per kilogram, or at about $50 \times 10^6$ cells per kilogram.

Purified antigen-specific T cells can be administered in single or multiple doses as determined by a clinician. For example, the cells can be administered at intervals of approximately two weeks depending on the response desired and the response obtained. In some examples, once the desired response is obtained, no further antigen-specific T cells are administered. However, if the recipient displays one or more symptoms associated with infection or the presence or growth of a tumor, a therapeutically effective amount of antigen-specific T cells can be administered at that time. The administration can be local or systemic.

The purified antigen-specific T cells disclosed herein can be administered with a pharmaceutically acceptable carrier, such as saline. The PD-1 antagonist can also be formulated in a pharmaceutically acceptable carrier, as described above. In some examples, other therapeutic agents are administered with the antigen-specific T cells and PD-1 antagonist. Other therapeutic agents can be administered before, during, or after administration of the antigen-specific T cells, depending on the desired effect. Exemplary therapeutic agents include, but are not limited to, anti-microbial agents, immune stimulants such as interferon-alpha, chemotherapeutic agents or peptide vaccines of the same antigen used to stimulate T cells in vitro. In a particular example, compositions containing purified antigen-specific T cells also include one or more therapeutic agents.

Methods of Treatment and Evaluation

It is disclosed herein that administration of a therapeutically effective amount of PD-1 antagonist affect B cells, such as by increasing the proliferation of memory B cells. Methods of treatment are provided herein that include the administration of a PD-1 antagonist to a subject, as described above. These methods include measuring B cells, such as but not limited to measuring the proliferation of memory B cells in the subject. In some examples, the methods include measuring naïve B cells in a sample from the subject. In some embodiments, the methods include measuring CD28 T cells and/or measuring neutralizing antibodies to an antigen of interest. Thus, the methods can include measuring one or more of memory B cell proliferation, naïve B cells, CD28 T cells, and neutralizing antibodies.

Methods are also provided herein to treat, and measure the efficacy of a PD-1 antagonist, in a variety of infections and cancers. The present disclosure encompasses methods to determine if treatment methods are effective in any subject of interest. In these methods, a subject of interest is selected, such as a subject with a persistent infection or cancer. This subject is administered a therapeutically effective amount of a PD-1 antagonist. In some examples, memory B cell proliferation is assessed to determine if the treatment method was effective, and/or to determine if the dose of the PD-1 antagonist should be altered. In additional examples, the methods include measuring naïve B cells. In further examples, the methods include measuring CD28 T cells and/or measuring neutralizing antibodies to an antigen of interest. Thus, the methods can include measuring one or more of memory B cell proliferation, naïve B cells, CD28 T cells, and neutralizing antibodies.

The subject can be any mammal such as human, a primate, mouse, rat, dog, cat, cow, horse, and pig. In several examples, the subject is a primate, such as a human. In additional examples, the subject is a murine subject, such as a mouse. In several embodiments, the subject is at risk of developing infection, as discussed above. A subject at risk of developing infection is a subject that does not yet have the infection, but can be infected by the infectious agent of interest. In additional examples, a subject is selected for treatment that has an infection, such as a persistent infection. In other embodiments, the subject is at risk of developing cancer or has cancer, as discussed above. These subjects can be identified by standard methods suitable by one of skill in the art, such as a physician. The disclosed methods include selecting a subject of interest, and administering a PD-1 antagonist, as described above. Memory B cell proliferation is then assessed. In some examples, the number of naïve B cells is also assessed.

In some embodiments, the subject has a persistent infection with a bacteria virus, fungus, or parasite, as described above. A therapeutically effective amount of a PD-1 antagonist is administered to treat the subject. Memory B cell proliferation is then assessed to determine if the treatment method was effective, and/or to determine if the dose of the PD-1 antagonist should be altered. Generally, persistent infections, in contrast to acute infections are not effectively cleared by the induction of a host immune response. The infectious agent and the immune response reach equilibrium such that the infected subject remains infectious over a long period of time without necessarily expressing symptoms. Persistent infections include for example, latent, chronic and slow infections. Persistent infection occurs with viruses such as human T-Cell leukemia viruses, XMRV, polyoma JC virus, Epstein-Barr virus, cytomegalovirus, herpesviruses, varicella-zoster virus, measles, papovaviruses, prions, hepatitis viruses, adenoviruses, parvoviruses and papillomaviruses. Additional persistent infections are described above. These methods can include measuring naïve B cells, CD28 T cells and/or neutralizing antibodies.

In further embodiments, the subject has a tumor. A therapeutically effective amount of a PD-1 antagonist is administered to the subject to treat the tumor, as described above. Memory B cell proliferation is then assessed to determine if the treatment method was effective, and/or to determine if the dose of the PD-1 antagonist should be altered. In several examples, a therapeutically effective amount of a tumor antigen, or a nucleotide encoding the tumor antigen, is also administered to the subject. The PD-1 antagonist and the tumor antigen, or nucleotide encoding the tumor antigen, can be administered simultaneously or sequentially. These methods can include measuring naïve B cells, CD28 T cells and/or neutralizing antibodies.

In additional embodiments, the subject is administered a therapeutically effective amount of cytoxic T cells specific for an antigen of interest, such as a viral antigen or a tumor antigen, and a therapeutically effective amount of a PD-1 antagonist. Administration of the purified antigen-specific T cells and PD-1, as disclosed herein, will increase the ability of a subject to overcome pathological conditions, such as an infectious disease or a tumor, by targeting an immune response against a pathogen (such as a virus or fungus) or neoplasm. Therefore, by purifying and generating a purified population of selected antigen-specific T cells from a subject ex vivo and introducing a therapeutic amount of these cells, the immune response of the recipient subject is enhanced. The administration of a therapeutically effective amount of a PD-1 antagonist also enhances the immune response of the recipient. Memory B cell proliferation is then assessed to determine if the treatment method was effective, and/or to determine if the dose of the PD-1 antagonist and/or cytotoxic T cells should be altered. These methods can include measuring naïve B cells, CD28 expressing (CD28+) T cells and/or neutralizing antibodies.

Thus, the methods disclosed herein for determining if a PD-1 antagonist is effective, or for determining the dose of a PD-1 antagonist is effective, can be used in combination with any of the therapeutic methods (and in any of the subjects) described above.

In some embodiments, memory B cells are measured. An increase in the proliferation of memory B cells from the a biological sample as compared to a control indicates that the dose of the PD-1 antagonist is of use treating the subject, and wherein an absence of a significant alteration in the proliferation of memory B cells as compared to the control indicates that the dose of the PD-1 antagonist is not of use to treat the subject.

In additional embodiments, the methods include detecting neutralizing antibodies in a biological sample from the subject, wherein an increase in neutralizing antibodies as compared to a control indicates that the dose of the PD-1 antagonist is of use treating the subject, and wherein an absence of a significant alteration in neutralizing antibodies as compared to the control indicates that the dose of the PD-1 antagonist is not of use to treat the subject. In further embodiments, the methods include detecting CD28 expressing (CD28+) T cells in a biological sample from the subject, wherein an increase in CD28+ T cells as compared to a control indicates that the that a dose of the PD-1 antagonist is of use treating the subject, and wherein an absence of a significant alteration in CD28+ T cells as compared to the control indicates that the dose of the PD-1 antagonist is not of use to treat the subject. These measurements can be performed in addition to measuring memory B cells, but can also be performed in the absence of measuring memory B cells.

Additional methods are disclosed herein to determine whether a particular PD-1 antagonist, or a particular dose of a PD-1 antagonist, is effective for treating a subject. These methods include measuring the proliferation of memory B cells, such as in a sample from the subject. These methods can also include measuring naïve B cells in a sample from the subject. For example, the expression of CD27, CD20 and CD21 can be evaluated (see below). In some examples, the measurement of memory B cells and/or naïve B cells occurs after a sufficient period of time for the PD-1 antagonist to decrease PD-1 activity in the subject.

The methods can also be used to evaluate the dose of a PD-1 antagonist that is therapeutically effective for a subject. For example, the methods disclosed herein can be used to determine if the dose administered to a subject of interest can be lowered and still be effective. The methods disclosed herein also can be used to determine if the dose administered to a subject is too low, and thus must be increased to be therapeutically effective.

In some embodiments, a first dose of a PD-1 antagonist is administered to the subject. An increase in proliferating memory B cells, as compared to a control, indicates that this dose is effective. In some cases, it can be advantageous to decrease the amount of an agent administered to a subject, such as to decrease side effects. Thus, if the first dose increases the proliferation of memory B cells, a second lower dose of the PD-1 antagonist can be administered to the subject, and a second sample including B cells can be obtained. An increase in the proliferation of memory B cells from the second sample as compared to a control indicates that the second dose of the PD-1 antagonist is of use treating the subject, and thus determines that the lower dose will be therapeutically effective for treating the subject. An absence of a significant alteration in the proliferation of memory B cells in the second sample as compared to the control indicates that the second dose of the PD-1 antagonist is not therapeutically effective to treat the subject. The method can be repeated to determine the lowest therapeutically effective dose for a subject of interest.

In additional embodiments, a first dose of a PD-1 antagonist is administered to the subject. A lack of an increase in the proliferation of memory B cells, as compared to a control, indicates that this dose is not therapeutically effective for treating the subject. If the first dose did not increase the proliferation of memory B cells, a second higher dose can be administered to the subject, and a second sample including B cells can be obtained. An increase in the proliferation of memory B cells from the second sample as compared to a control indicates that the second higher dose of the PD-1 antagonist is of use treating the subject, and thus determines that the higher dose will be therapeutically effective for treating the subject. An absence of a significant alteration in the proliferation of memory B cells in the second sample as compared to the control indicates that the second dose of the PD-1 antagonist is not therapeutically effective to treat the subject, and thus that a third higher dose is required. Thus, the method can be repeated to determine a therapeutically effective dose for a subject of interest.

The methods disclosed can also be used to determine if a particular PD-1 antagonist is therapeutically effective for treating a subject, and thus should be continued, or if the particular PD-1 antagonist is not effective for treating a subject, and thus that a different PD-1 antagonist should be utilized to treat the subject. These methods include administering a particular PD-1 antagonist to the subject, and assessing the proliferation of memory B cells in the sample from the subject. An increase in the proliferation of memory B cells in the sample as compared to a control indicates that the particular PD-1 antagonist is of use treating the subject. An absence of a significant alteration in the proliferation of memory B cells in the sample as compared to the control indicates that the particular PD-1 antagonist is not therapeutically effective to treat the subject, and that a different PD-1 antagonist or other therapeutic agent should be administered to the subject. Thus, the efficacy of a specific PD-1 antagonist can be monitored, or the effective dose of a PD-1 antagonist can be determined, using the methods disclosed herein. Generally, an increase in proliferation of memory B cells from a sample from a subject administered a PD-1 antagonist, as compared to a control, indicates that the PD-1 antagonist is therapeutically effective for a subject, and/or indicates that the dose is sufficient for treating the subject.

Generally, measuring the proliferation of memory B cells includes obtaining a sample that includes B cells from a subject, and determining the presence or number of proliferating memory B cells in the sample. In some examples, the sample is a biopsy sample, a blood sample, or a sample of peripheral blood mononuclear cells. The sample can be purified, for example to separate B cells, such as memory B cells and/or naïve B cells. In some embodiments, the methods include measuring the quantity of proliferating memory B cells and/or the quantity of naïve B cells in a sample from a subject administered a PD-1 antagonist of interest. In some examples, the quantity of proliferating memory B cells and/or the quantity of naïve B cells is compared to a control. With regard to proliferating memory B cells, the control can be a previously determined standard value, or the quantity of proliferating memory B cells from a subject not administered the PD-1 antagonist, or the quantity of proliferating memory B cells from a subject administered a control substance, such as vehicle alone. Similarly, with regard to naïve B cells, the control can be a previously determined standard value, or the quantity of naïve B cells from a subject not administered the PD-1 antagonist, or the quantity of naïve B cells from a subject administered a control substance, such as vehicle alone, or the quantity of naïve B cells in a subject, respectively.

In some examples, memory B cells are identified that express CD27, such as those cells that express CD20 and CD27, but do not express CD21 ($CD20^+CD27^+CD21^-$) compared to naïve B cells, which express CD20 and CD21, but do not express CD27 ($CD20^+CD27^-CD21^+$). Memory B cells and naïve B cells can be isolated and/or detected using antibodies that specifically bind CD20, CD21 and CD27. In some embodiments, memory B cells express CD27 ($CD27^+$). In some examples, memory B cells are identified as $CD27^+CD21^-$ B cells, such as $CD20^{hi}/CD21^-/CD27^+$ (activated memory).

Methods for isolating and detecting B cells are known in the art, and exemplary protocols are provided herein. Methods also are known in the art to measure the proliferation of memory B cells and/or to measure naïve B cells. These methods generally involve the use of molecular and/or biochemical techniques and not simple visual observation. In some examples, fluorescence activated cell sorting (FACS) is utilized. FACS can be used to sort (isolate) cells such as immature B cells or differentiated plasma cells or memory cells, by contacting the cells with an appropriately labeled antibody. In one embodiment, several antibodies (such as antibodies that bind CD27, CD20, CD21, CD45R, CD40, CD19, and/or IgM) and FACS sorting can be used to produce substantially purified populations of immature B cells, plasma cells and or memory B cells.

Methods are also known for measuring CD28 T cells in a sample from a subject. These methods generally involve the use of molecular and/or biochemical techniques and not simple visual observation. In some examples, fluorescence activated cell sorting (FACS) is utilized. FACS can be used to sort (isolate) cells such as immature B cells or differentiated plasma cells or memory cells, by contacting the cells with an appropriately labeled antibody. In one embodiment, several antibodies (such as antibodies that bind CD3, CD4, CD8 and CD28) and FACS sorting can be used to produce substantially purified populations of CD28+ T cells. Methods for the detection of neutralizing antibodies are also known in the art. These assays include obtaining a biological sample and detecting the binding of antibodies to an antigen of interest, as well as specific neutralization assays, such as for a virus, for example HIV.

FACS employs a plurality of color channels, low angle and obtuse light-scattering detection channels, and impedance channels, among other more sophisticated levels of detection, to separate or sort cells. Any FACS technique can be employed as long as it is not detrimental to the viability of the desired cells. (For exemplary methods of FACS see U.S. Pat. No. 5,061,620).

However, other techniques of differing efficacy can be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (e.g., CD45R or CD27) to bind to the solid-phase linked antibodies. The bound cells are then separated from the solid phase by any appropriate method, depending mainly upon the nature of the solid phase and the antibody employed.

Antibodies can be conjugated to biotin, which then can be removed with avidin or streptavidin bound to a support, or fluorochromes, which can be used with a fluorescence activated cell sorter (FACS), to enable cell separation.

For example, cells expressing CD45R and/or CD27 are initially separated from other cells by the cell-surface expression of CD45R or CD27. In one specific, non-limiting example, $CD45R^+$ or CD27+ cells are positively selected by magnetic bead separation, wherein magnetic beads are coated with CD45 or CD27 reactive monoclonal antibody. The $CD45R^+$ or $CD27^+$ cells are then removed from the magnetic beads.

Release of the $CD45R^+$ cells or $CD27^+$ cells from the magnetic beads can effected by culture release or other methods. Purity of the isolated $CD45R^+$ cells or $CD27^+$ cells is then checked, such as with a FACSCAN® flow cytometer (Becton Dickinson, San Jose, Calif.), if so desired. In one embodiment, further purification steps are performed, such as FACS sorting the population of cells released from the magnetic beads. In one example, this sorting can be performed to detect expression of MHC class II, IgM, CD19, and CD40, in order to detect or isolate immature B cells. In another example, mature B cells can be isolated and/or detected on the basis of expression of IgD and/or CD21, in addition to MHC class II, IgM, CD14, and CD40.

Methods for analyzing B cell proliferation, such as the assessment of the proliferation of memory B cells are known in the art. For example, membrane dye dilution approaches can be utilized which include ex vivo chemical labeling of cells of interest with fluorescent dyes. Labeling with tritiated nucleoside analogues (commonly $^3$H-thymidine deoxyribonucleoside, $^3$H-TdR) or bromodeoxyuridine (BrdU) can be utilized. FACS analysis is available for the measurement of BrdU incorporation. Surrogate markers of proliferation such as DNA content and cell cycle-associated proteins, can also be used.

In one example, measurement of Ki67 or PCNA can be utilized. Ki67 antigen is the prototypic cell cycle related nuclear protein that is expressed by proliferating cells in all phases of the active cell cycle (G1, S, G2 and M phase). It is absent in resting (G0) cells. Ki67 antibodies are useful in establishing proliferation. Ki67 antibodies can be used to quantify proliferating cells among and resting cells (Ki67 index). Ki67 is routinely used as a marker of cell cycling and proliferation; antibodies to Ki67 are commercially available, such as from ABCAM®, and methods are available to use these antibodies in immunohistochemical and FACS analyses.

Other methods can be used to detect those cells that are in the active cell cycle at the time of sampling. Proliferation of lymphocytes, such as memory B cells, can also be measured by using methods that utilize stable isotopes to label DNA in biological samples including cells. DNA is uniformly and highly labeled via the de novo synthesis pathway. The stable isotope labels used, e.g. $^2$H-glucose or heavy water ($^2$H$_2$O or H$_2$$^{18}$O), are non-toxic to animals and humans, and generally regarded as safe by the US Food and Drug Administration (FDA) (see U.S. Patent Application Publication No. 2009/0155179). The measurement of stable isotope label incorporation into lymphocyte DNA comprises the following steps: (i) extraction of DNA or its release from chromatin without further isolation, hydrolysis of DNA to deoxyribonucleotides, (ii) selective release of deoxyribose from purine deoxyribonucleotides, (iii) derivatization of purine deoxyribose to a volatile derivative (e.g., pentane tetraacetate, pentafluorobenzyl tetraacetyl derivative, or another suitable derivative) suitable for analysis by gas chromatography/mass spectrometry (GC/MS), (iv) GC/MS analysis of said derivative, (v) analysis of the pattern of mass isotopomer abundance of said derivative, and (vi) calculation from said pattern of an excess enrichment value that is a measure of stable isotope incorporation. Specific embodiments of each of these methods have been taught (see U.S. Pat. No. 5,910,40).

In Vitro Assay

Methods are disclosed herein for selecting a PD-1 antagonist. These methods include determining if an agent of interest is a PD-1 antagonist. Thus, the methods include screening a number of agent to determine if they function as PD-1 antagonists. This can be a library of compounds, small molecules or antibodies, and the assay can be conducted in a high-throughput format.

The methods also include determining if a specific PD-1 antagonist will be of use to treat a specific individual of interest. Thus, these disclosed methods can be used for "personalized medicine" wherein the population of cells is from a specific individual of interest, and a number of potential PD-1 antagonist are tested to determine the PD-1 antagonist most suited for treating that particular individual.

The methods include contacting an isolated population of cells comprising memory B cells with an agent in vitro. In some embodiments, the population of cells is peripheral blood mononuclear cells or purified memory B cells, such as activated or resting memory B cells. In one example, the population of cells is a memory B cell line.

The methods can include detecting the proliferation of memory B cells and/or detecting the differentiation of memory B cells into antibody secreting cells. In several embodiments, the methods include assays to detect IgM, IgG and antibody-producing B cells. The assay can be an ELISPOT assay. ELISPOT assays employ a technique very similar to the sandwich enzyme-linked immunosorbent assay (ELISA) technique. Either a monoclonal or polyclonal capture antibody is coated aseptically onto a PVDF (polyvinylidene fluoride)-backed microplate. These antibodies are chosen for their specificity for the analyte in question. The plate is blocked, usually with a serum protein that is non-reactive with any of the antibodies in the assay. After this, cells of interest are plated out at varying densities, along with antigen or mitogen, and then placed in a humidified 37° C. CO$_2$ incubator for a specified period of time.

Cytokine (or other cell product of interest, such as IgM or IgG antibodies) secreted by activated cells is captured locally by the coated antibody on the high surface area PVDF membrane. After washing the wells to remove cells, debris, and media components, a biotinylated polyclonal antibody specific for the chosen analyte is added to the wells. This antibody is reactive with a distinct epitope of the target and thus is employed to detect the captured producted of interest. Following a wash to remove any unbound biotinylated antibody, the detected product is then visualized, such as using an avidin-enzyme, and a precipitating substrate for the enzyme. The colored end product (a spot, usually colored) typically represents an individual product-producing cell. The spots can be counted manually (such as with a dissecting microscope) or using an automated reader to capture the microwell images and to analyze spot number and size.

The proliferation of memory B cells can also be assessed. Suitable assays are disclosed herein (see above). Methods for analyzing B cell proliferation, such as the assessment of the proliferation of memory B cells are known in the art. For example, membrane dye dilution approaches (commonly $^3$H-thymidine deoxyribonucleoside, $^3$H-TdR) or bromodeoxyuridine (BrdU) can be utilized. FACS analysis is available for the measurement of BrdU incorporation. Surrogate markers of proliferation such as DNA content and cell cycle-associated proteins, can also be used. In one example, measurement of Ki67 or PCNA can be utilized. Other methods can be used to detect those cells that are in the active cell cycle at the time of sampling. Proliferation of lymphocytes, such as memory B cells, can also be measured by using methods that utilize stable isotopes to label DNA in biological samples including cells. A exemplary, non-limited protocol for one assay of use is provided in the Examples section below.

Generally, an increase of the proliferation of memory B cells and/or an increase in the differentiation of memory B cells into antibody secreting cells and/or in increase in antibody production indicates that the agent is a PD-1 antagonist. The increase of the proliferation of memory B cells and/or an increase in the differentiation of memory B cells into antibody secreting cells and/or in increase in antibody production can indicate that a specific PD-1 antagonist will be of use in treating a subject.

The disclosure is illustrated by the following non-limiting Examples.

EXAMPLES

Example 1

Inhibition of the PD-1 Pathway in Chronically-Infected Mice Using Anti-PD-L1 Antibodies Mice infected with various strains of the lymphocytic choriomeningitis virus (LCMV) were used to study the effect of chronic viral infection on CD8+ T cell function. The LCMV Armstrong strain causes an acute infection that is cleared within 8 days, leaving behind a long-lived population of highly functional, resting memory CD8+ T cells. The LCMV Cl-13 strain, in contrast, establishes a persistent infection in the host, characterized by a viremia that lasts up to 3 months. The virus remains in some tissues indefinitely and antigen specific CD8+ T cells become functionally impaired. DbNP396-404 CD8+ T cells are physically deleted, while DbGP33-41 and DbGP276-286 CD8+ T cells persist but lose the ability to proliferate or secrete anti-viral cytokines, such as IFN-γ and TNF-α.

C57BL/6 mice were purchased from the National Cancer Institute (Frederick, Md.). Mice were infected intravenously (i.v.) with $2 \times 10^6$ pfu of LCMV-Cl-13. CD4 depletions were performed by injecting 500 μg of GK1.5 in PBS the day of infection and the day following the infection. LCMV immune mice are generated by infecting mice i.p. with $2 \times 10^5$ pfu LCMV Armstrong.

Gene array analysis was performed on FACS-purified naïve DbGP33-41 specific P14 transgenic CD8+ T cells, DbGP33-41 specific memory CD8+ T cells derived from LCMV Armstrong immune mice, and DbGP33-41 specific or DbGP276-286 specific CD8+ T cells derived from CD4+ depleted LCMV Cl-13 infected mice. RNA isolation and gene array analysis were performed as described in Kaech et al., (Cell 111:837-51, 2002). PD-1 mRNA was highly expressed in exhausted CD8+ T cells relative to memory CD8+ T cells (FIG. 1A). Furthermore, PD-1 was expressed on the surface of CD8+ T cells in LCMV Cl-13 infected mice, but was not present on the surface of CD8+ T cells after clearance of LCMV Armstrong (FIG. 1B). Chronically infected mice also expressed higher levels of one of the ligands of PD-1, PD-L1, on most lymphocytes and APC compared to uninfected mice. Thus, viral antigen persistence and CD8+ T cell exhaustion are concomitant with an induction in PD-1 expression.

Figure 2:
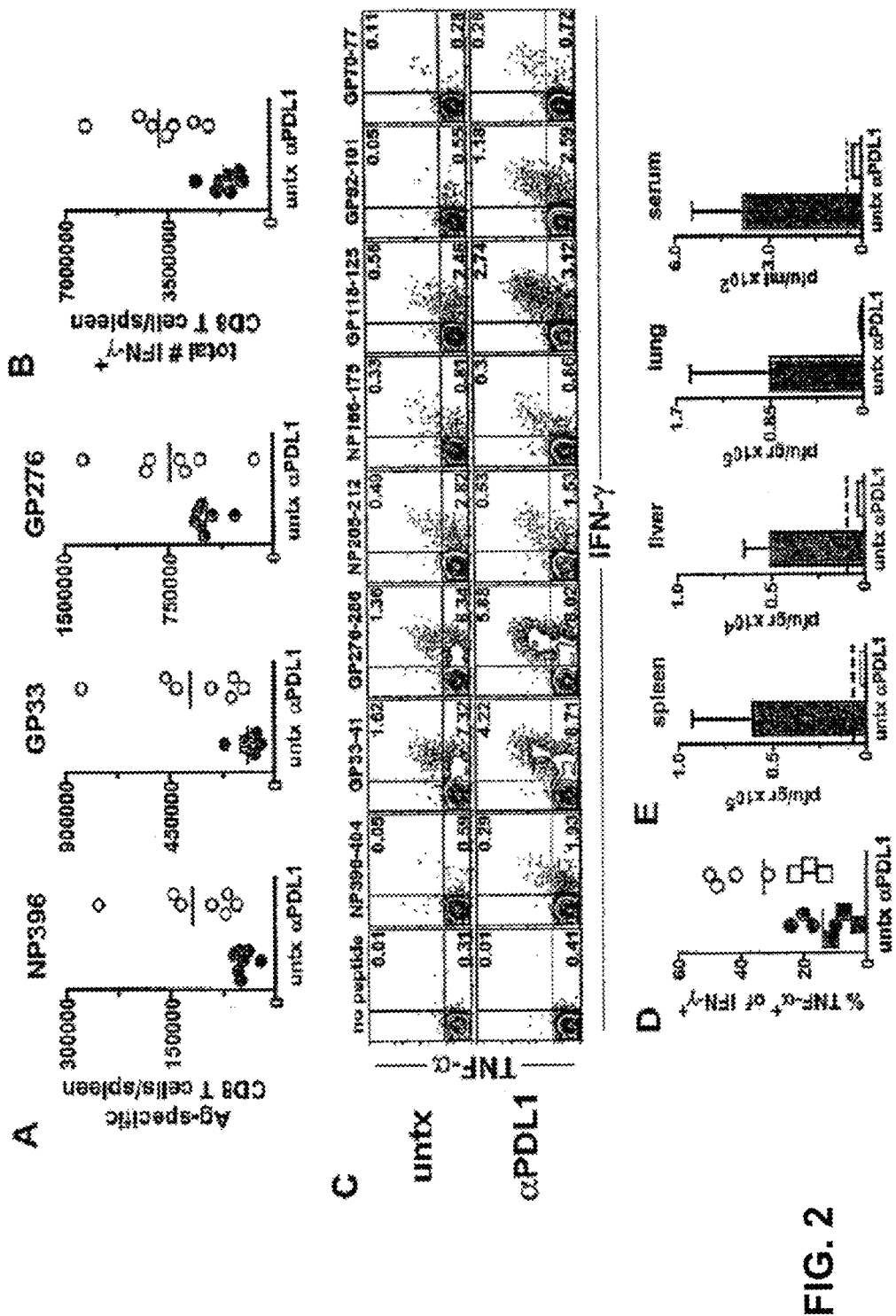
FIG. 2A is a series of scatter plots showing that when Cl-13 infected mice are treated from day 23 to 37 post-infection there was approximately a 3 fold increase in the number of DbNP396-404 specific and DbGP33-41 specific CD8+ T cells compared to the untreated controls. In order to determine any changes in function IFN-γ and TNF-α production was measured in response to 8 different LCMV epitopes.
FIG. 2B is a scatter plot showing that when all the known CD8+ T cell specificities are measured there is a 2.3 fold increase in total number of LCMV specific CD8+ T cells.
FIG. 2C is a series of flow cytometry graphs showing IFN-γ and TNF-α production in response to eight different LCMV epitopes.
FIG. 2D is a scatter plot showing that more virus specific CD8+ T cells in treated mice have the ability to produce TNF-α.
FIG. 2E is a series of bar charts showing that PD-L1 blockade also resulted in increased viral control in the spleen liver lung and serum.

To test the hypothesis that blocking the PD-1/PD-L1 pathway may restore T cell function and enhance viral control during chronic LCMV infection, the PD-1/PD-L1 co-inhibitory pathway was disrupted during chronic LCMV infection using αPD-L1 blocking antibodies. A blocking monoclonal antibody against PD-L1 was administered intraperitoneally (i.p.) every third day to mice infected with LCMV Cl-13 (200 μg of rat anti-mouse PD-L1 IgG2b monoclonal antibodies (clone 10F.5C5 or 10F.9G2)) from day 23 to day 37 post-infection. At day 37, there was approximately 2.5 fold more DbNP396-404 specific CD8+ T cells and 3 fold more DbGP33-41 specific CD8+ T cells in treated mice relative to the untreated controls (FIG. 2A). The induction in proliferation was specific to CD8+ T cells since the number of CD4+ T cells in the spleen were approximately the same in both treated mice and untreated mice (~$6 \times 10^4$ IAbGP61-80 of CD4+ T cells per spleen).

In addition to an increase in CD8+ T cell proliferation, the inhibition of PD-1 signaling also resulted in an increased production of anti-viral cytokines in virus-specific CD8+ T cells. The production of IFN-γ and TNF-α by CD8+ T cells to eight different CTL epitopes was determined. The combined response was 2.3 fold higher in treated mice as compared to untreated mice (FIGS. 2B and 2C). A 2-fold increase in the frequency of TNF-α producing cells was also observed following treatment (FIG. 2D). Viral clearance was also accelerated as the virus was cleared from the serum, spleen, and liver of treated mice. Reduced viral titers were observed in the lung and kidney (~10 fold) by day 37 post-infection (14 days following initiation of treatment) in treated mice. Untreated mice, however, displayed significant levels of virus in all these tissues (FIG. 2E). Viral titers in serum and tissue homogenates were determined using Vero cells, as described in Ahmed et al. (J. Virol. 51:34-41, 1984). The results showing that a PD-1 antagonist increases CD8+ T cell proliferation and viral clearance therefore indicate that the inhibition of PD-1 signaling restores CD8+ T cell function. Furthermore, inhibition of PD-1 signaling also enhanced B cell responses as the number of LCMV specific antibody secreting cells in the spleen was also increased (>10-fold) following treatment.

CD4+ T cells play a key role in the generation and maintenance of CD8+ T cell responses. In this regard, CD8+ T cells primed in the absence of CD4+ T cell (so-called "helpless" CD8+ T cells) are incapable of mounting normal immune responses. Furthermore, chronic LCMV infection is more severe in the absence of CD4+ T cells. Accordingly, helpless T cells generated during LCMV-Cl-13 infection display an even more profound functional impairment than T cells generated in the presence of CD4+ T cells. DbNP396-404 specific CD8+ T cells are deleted to undetectable levels, and DbGP33-41 and DbGP276-286 CD8+ T cells completely lose the ability to secrete IFN-γ and TNF-α.

Figure 3:
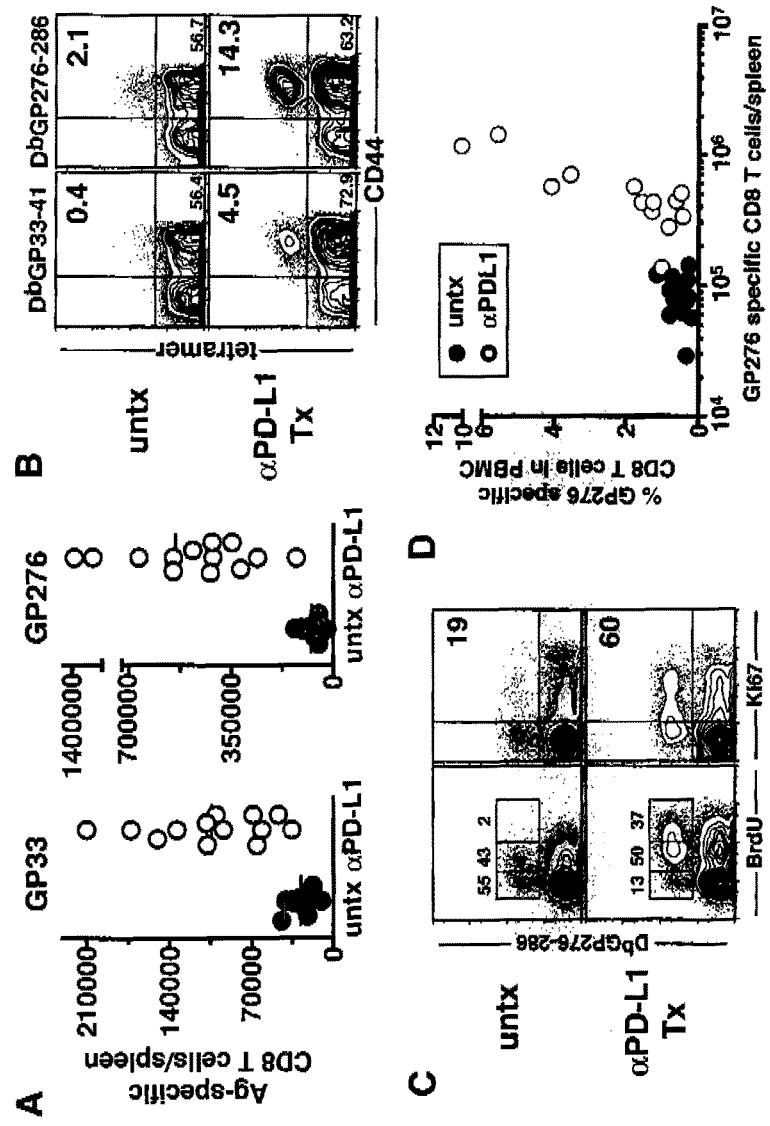
FIG. 3A is a graph demonstrating the increase in DbGP33-41 and DbGP276-286 specific CD8+ T cells (labeled "GP33" and "GP276") in CD4-depleted Cl-13 infected mice treated with anti-PD-L1 (labeled "αPD-L1") from day 46 to day 60 post-infection versus control (labeled "untx"), which demonstrates that mice treated with anti-PD-L1 contained approximately 7 fold more DbGP276-286 specific splenic CD8+ T cells and approximately 4 fold more DbGP33-41 specific splenic CD8+ T cells than untreated mice.
FIG. 3B is a series of images of a flow cytometry experiment demonstrating the increased frequency of DbGP33-41 and DbGP276-286 specific CD8+ T cells in the spleen of CD4-depleted Cl-13 infected mice treated with anti-PD-L1 (labeled "αPD-L1 Tx") from day 46 to day 60 post-infection versus control (labeled "untx").
FIG. 3C is a series of images of a flow cytometry experiment demonstrating increased proliferation of DbGP276-286 specific CD8+ T cells in anti-PD-L1-treated mice, as measured by BrdU incorporation and Ki67 expression.
FIG. 3D is a chart showing that mice having high levels of CD8+ T cell expansion demonstrate an appreciable response in peripheral blood mononuclear cells (PBMC), as shown by comparing DbGP276-286 specific CD8+ T cells in the PBMC as compared to DbGP276-286 specific CD8+ T cells in the spleen.

CD4+ T cells were depleted at the time of LCMV-Cl-13 infection and mice were treated with anti-PD-L1 antibodies treatment from day 46 to day 60 post-infection. LCMV-specific CD4+ T cells were not detectable by intracellular IFN-γ staining before or after treatment. Following treatment, treated mice had approximately 7 fold more DbGP276-286 CD8+ T cells and 4 fold more DbGP33-41 CD8+ T cells in their spleen than untreated control mice (FIG. 3A). The number of virus-specific CD8+ T cells in the spleen was also increased (FIG. 3B). This increase in virus-specific CD8+ T cells in treated mice was attributed to an increase in proliferation, as detected by BrdU incorporation. 43% of DbGP276-286 CD8+ T cells incorporated intermediate levels of BrdU and 2% incorporated high levels of BrdU in untreated mice, while 50% DbGP276-286 CD8+ T cells incorporated intermediate levels of BrdU and 37% incorporated high levels of BrdU in treated mice. BrdU analysis was performed by introducing 1 mg/ml BrdU in the drinking water during treatment and staining was performed according to the manufacturer's protocol (BD Biosciences, San Diego, Calif.). Moreover, treated mice contained a higher percentage of CD8+ T cells expressing the cell cycle-associated protein Ki67 (60% versus 19% in untreated mice, FIG. 3C). Response to treatment in CD8+ T cells in the PBMC was restricted to mice having high levels of CD8+ T cell expansion.

Figure 4:
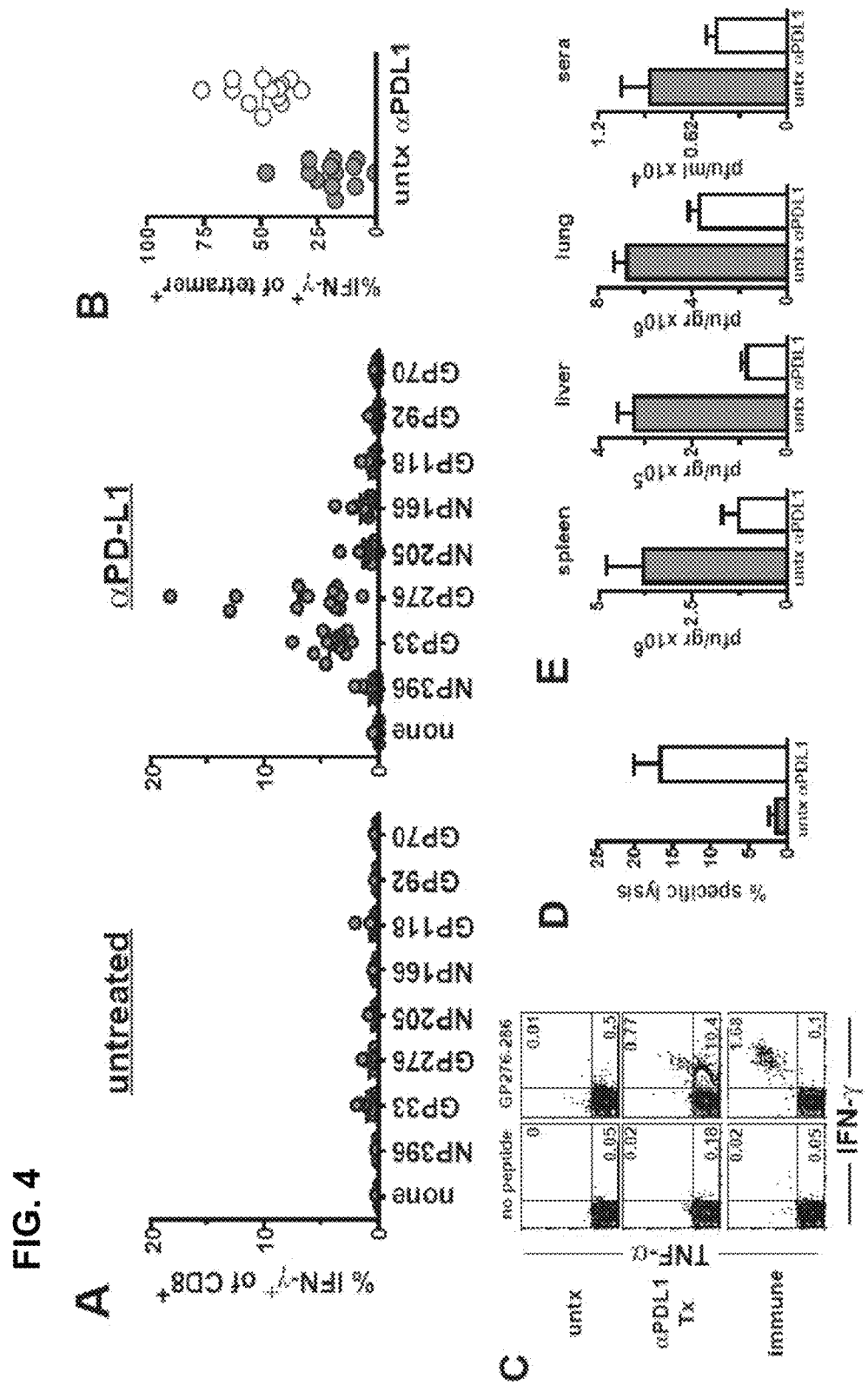
FIG. 4A is a series of charts demonstrating the increase in IFN-γ producing DbGP276-286 and DbGP33-41 specific CD8+ T cells in anti-PD-L1-treated mice, as compared to controls. Higher frequencies of DbNP396-404, KbNP205-212, DbNP166-175, and DbGP92-101 specific CD8+ T cells were also detected in anti-PD-L1-treated mice.
FIG. 4B is a chart demonstrating that in anti-PD-L1-treated mice, 50% of DbGP276-286 specific CD8+ T cells produce IFN-γ, as compared to 20% of DbGP276-286 specific CD8+ T cells in control mice.
FIG. 4C is a series of images of a flow cytometry experiment demonstrating that anti-PD-L1-treated chronically infected mice produce higher levels of TNF-α than untreated chronically infected mice, but still produce lower levels of TNF-α than immune mice infected with LCMV Armstrong virus.
FIG. 4D is a chart demonstrating that treatment of LCMV-Cl-13 infected mice with anti-PD-L1 renews ex vivo lytic activity of the virus-specific T cells, as compared to untreated infected mice, measured using a $^{51}$Cr release assay.
FIG. 4E is a series of charts demonstrating the reduction of viral titers in various organs following treatment of LCMV-Cl-13 infected mice with α-PD-L1. Viral titers decreased approximately 3 fold in the spleen, 4 fold in the liver, 2 fold in the lung, and 2 fold in serum after 2 weeks of anti-PD-L1 treatment, as compared to untreated mice.

PD-1 inhibition also increased anti-viral cytokine production in helpless, exhausted virus-specific CD8+ T cells. Following treatment, the number of DbGP33-41 and DbGP276-286 CD8+ T cells that produce IFN-γ was markedly increased (FIG. 4A), though higher numbers of DbNP396-404, KbNP205-212, DbNP166-175, and DbGP92-101 specific CD8+ T cells were also detected in treated mice (FIG. 4A). 50% of DbGP276-286 specific CD8+ T cells from treated mice can produce IFN-γ compared to the 20% of DbGP276-286 specific CD8+ T cells in control untreated mice. (FIG. 4B). Levels of IFN-γ and TNF-α produced by DbGP276-286 specific CD8+ T cells from treated mice, however, were lower than fully functional DbGP276-286 specific memory cells (FIG. 4C).

PD-1 inhibition also increased the lytic activity of helpless, exhausted virus-specific CD8+ T cells. Ex vivo lytic activity of virus-specific CD8+ T cells was detected following treatment, using a $^{51}$Cr release assay (Wherry et al., 2003. J. Virol. 77:4911-27). Viral titers were reduced by approximately 3 fold in the spleen, 4 fold in the liver, 2 fold in the lung, and 2 fold in serum after 2 weeks of treatment relative to untreated mice (FIG. 4E).

These results therefore demonstrate that blocking the PD-1 pathway breaks CTL peripheral tolerance to a chronic viral infection, and that exhausted CD8+ T cells deprived of CD4+ T cell help are not irreversibly inactivated.

Example 2

Administration of Anti-Viral Vaccine and PD-1 Antagonist

One approach for boosting T cell responses during a persistent infection is therapeutic vaccination. The rationale for this approach is that endogenous antigens may not be presented in an optimal or immunogenic manner during chronic viral infection and that providing antigen in the form of a vaccine may provide a more effective stimulus for virus-specific T and B cells. Using the chronic LCMV model, mice were administered a recombinant vaccinia virus expressing the LCMV GP33 epitope as a therapeutic vaccine (VVGP33), which resulted in a modest enhancement of CD8+ T cell responses in some chronically infected mice. Four out of the nine chronically infected mice that received the therapeutic vaccine showed a positive response while none of the control mice had a significant increase in the immune response against GP33. When this therapeutic vaccination was combined with a PD-L1 inhibitor, LCMV specific T cell responses were boosted to a greater level than compared to either treatment alone and the effect of combined treatment was more than additive.

Example 3

Inhibition of the PD-1 Pathway in Chronically-Infected Mice Using PD-1 RNAi

RNA interference (RNAi) is capable of silencing gene expression in mammalian cells. Long double stranded RNAS (dsRNAs) are introduced into cells and are next processed into smaller, silencing RNAs (siRNAs) that target specific mRNA molecules or a small group of mRNAs. This technology is particularly useful in situations where antibodies are not functional. For example, RNAi may be employed in a situation in which unique splice variants produce soluble forms of PD-1 and CTLA-4.

PD-1 silencer RNAs are inserted into a commercially available siRNA expression vector, such as pSilencer™ expression vectors or adenoviral vectors (Ambion, Austin, Tex.). These vectors are then contacted with target exhausted T cells in vivo or ex vivo (see Example 4 below).

Example 4

Ex Vivo Rejuvenation of Exhausted T Cells

Virus-specific exhausted CD8+ T cells are isolated from LCMV-Cl-13 chronically infected mice using magnetic beads or density centrifugation. Transfected CD8+ T cells are contacted with a monoclonal antibody that targets PD-L1, PD-L2 or PD-1. As described in Example 1, inhibition of the PD-1 pathway results in the rejuvenation of the CD8+ T cells. Accordingly, there is an increase in CD8+ T cell proliferation and cytokine production, for example. These rejuvenated CD8+ T cells are reintroduced into the infected mice and viral load is measured as described in Example 1.

Example 5

In Vitro Screening of Novel CD8+ T Cell Rejuvenator Compounds

Compounds that modulate the PD-1 pathway can be identified in in vivo and ex vivo screening assays based on their ability to reverse CD8+ T cell exhaustion resulting from chronic viral infection.

Exhausted CD8+ T cells are derived from mice chronically infected with LCMV-Cl-13 and next contacted with a test compound. The amount of anti-viral cytokines (for example, IFN-γ or TNF-α) released from the contacted T cell is measured, for example, by ELISA or other quantitative method, and compared to the amount, if any, of the anti-viral cytokine released from the exhausted T cell not contacted with the test compound. An increase in the amount of anti-viral cytokine released by treated cells relative to such amount in untreated cells identifies the compound as a PD-1 antagonist, useful to modulate T cell activity.

Example 6

In Vivo Screening of Novel CD8+ T Cell Rejuvenator Compounds

Exhausted CD8+ T cells are derived from mice chronically infected with LCMV-Cl-13. A test compound is administered intravenously to the infected mice. The amount of anti-viral cytokines (such as IFN-γ or TNF-α) that is released into the serum of treated and untreated mice is measured, for example, by ELISA or other quantitative method, and compared. An increase in the amount of anti-viral cytokine found in the serum in treated mice relative to such amount in untreated mice identifies the test compound as a PD-1 antagonist. Alternatively, the viral titer (e.g., serum viral titer) can be determined prior and subsequent to treatment of the test compound.

Example 7

Chimpanzees as a Model for Immunotherapy of Persistent HCV Infection

Chimpanzees provide a model of HCV persistence in humans. Defects in T cell immunity leading to life-long virus persistence both include a deficit in HCV-specific CD4+ T helper cells and impaired or altered CD8+ T effector cell activity. Persistently infected chimpanzees are treated with antibodies against CTLA-4, PD-1, or a combination of the two. The efficacy of blockade of the inhibitory pathways, combined with vaccination using recombinant structural and non-structural HCV proteins, and whether such strategies can enhance the frequency and longevity of virus-specific memory T cells are determined. The defect in T cell immunity is exclusively HCV-specific in persistently infected humans and chimpanzees. The blood and liver of infected chimpanzees are examined for expression of CTLA-4, PD-1, BTLA and their ligands and for the presence of Treg cells. Antiviral activity may then be restored by delivering to chimpanzees' humanized monoclonal antibodies that block signaling through these molecules.

Persistently infected chimpanzees are treated with humanized αCTLA-4 antibodies (MDX-010, Medarex) or αPD-1 antibodies. The initial dose of MDX-010 is 0.3 mg/kg followed 2 weeks later by 1.0 mg/kg and then 3, 10, 30 mg/kg at three week intervals. After treatment with antibodies to co-inhibitory molecules, the humoral and cellular immune responses as well as the HCV RNA load will be determined. Samples are collected at weeks 1, 2, 3, 5, and 8, and then at monthly intervals. Samples include: 1) serum for analysis of transaminases, autoantibodies, neutralizing antibodies to HCV, and cytokine responses, 2) plasma for viral load and genome evolution, 3) PBMC for in vitro measures of immunity, costimulatory/inhibitory receptor expression and function, 4) fresh (unfixed) liver for isolation of intrahepatic lymphocytes and RNA, and 5) fixed (formalin/paraffin embedded) liver for histology and immunohistochemical analysis. Regional lymph nodes are also collected at 2 or 3 time points to assess expression of co-inhibitory molecules and splice variants by immunohistochemistry and molecular techniques.

To determine if vaccination with HCV antigens potentiates the therapeutic effect of antibodies to PD-1, chimpanzees are treated as follows: 1) intramuscular immunization with recombinant envelope glycoproteins E1 and E2 (in MF59 adjuvant) and other proteins (core plus NS 3, 4, and 5 formulated with ISCOMS) at weeks 0, 4, and 24; 2) intramuscular immunization with the vaccine used in 1) but co-administered with αCTLA-4 antibodies (30 mg of each/Kg body weight, intravenously at weeks 0, 4, and 24 when vaccine is given); 3) identical to 2) except that αPD-1 (or BTLA) antibodies are substituted for the CTLA-4 antibodies; 4) identical to Groups 2 and 3 except that a combination of CTLA-4 and PD-1 (or BTLA) antibodies are used in addition to the vaccine. HCV-specific T and B cell responses are monitored at monthly intervals after immunization for a period of 1 year.

Markers examined on HCV-tetramer+ and total T cells in this analysis include markers of differentiation (e.g. CD45RA/RO, CD62L, CCR7, and CD27), activation (e.g. CD25, CD69, CD38, and HLA-DR), survival/proliferation (e.g. bcl-2 and Ki67), cytotoxic potential (e.g. granzymes and perforin), and cytokine receptors (CD122 and CD127). An interesting correlation exists between pre-therapy levels of the chemokine IP-10 and response to PEG IFN-γ/ribavirin. IP-10 levels are measured to investigate a potential correlation between negative regulatory pathways or HCV-specific T cell responses and IP-10 levels. Expression of inhibitory receptors and ligands on PBMC are performed by flow cytometry.

Example 8

PD-1 Immunostaining in Reactive Lymphoid Tissue

Case material was obtained from the Brigham & Women's Hospital, Boston, Mass., in accordance with institutional policies. All diagnoses were based on the histologic and immunophenotypic features described in the World Health Organization Lymphoma Classification system (Jaffe E S, et al. 2001) and in all cases diagnostic material was reviewed by a hematopathologist.

Immunostaining for PD-1 was performed on formalin-fixed paraffin embedded tissue sections following microwave antigen retrieval in 10 mM citrate buffer, pH 6.0 with a previously described anti-human PD-1 monoclonal antibody (2H7; 5), using a standard indirect avidin-biotin horseradish peroxidase method and diaminobenzidine color development, as previously described (Jones D, et al. 1999; Dorfman D M, et al. 2003). Cases were regarded as immunoreactive for PD-1 if at least 25% of neoplastic cells exhibited positive staining. PD-1 staining was compared with that of mouse IgG isotype control antibody diluted to identical protein concentration for all cases studied, to confirm staining specificity.

Monoclonal antibody 2H7 for PD-1 was used to stain formalin-fixed, paraffin-embedded specimens of reactive lymphoid tissue, thymus, and a range of cases of B cell and T cell lymphoproliferative disorders. In specimens of tonsil exhibiting reactive changes, including follicular hyperplasia, a subset of predominantly small lymphocytes in the germinal centers exhibited cytoplasmic staining for PD-1, with infrequent PD-1-positive cells seen in the interfollicular T cell zones. The PD-1 staining pattern in germinal centers was virtually identical to that seen with an antibody to CD3, a pan-T cell marker, whereas an antibody to CD20, a pan-B cell marker, stained the vast majority of germinal center B cells. Similar results were seen in histologic sections of reactive lymph node and spleen. No PD-1 staining was observed in adult thymus.

Example 9

PD-1 Immunostaining in Paraffin Embedded Tissue Sections of B Cell and T Cell Lymphoproliferative Disorders A range of B cell and T cell lymphoproliferative disorders for PD-1 expression were studied; the results are summarized in Table 4. Forty-two cases of B cell lymphoproliferative disorders were examined for PD-1 expression, including representative cases of precursor B lymphoblastic leukemia/lymphoblastic lymphoma, as well as a range of lymphoproliferative disorders of mature B cells, including a number of B cell non-Hodgkin lymphomas of follicular origin, including 6 cases of follicular lymphoma and 7 cases of Burkitt lymphoma. None of the B cell lymphoproliferative disorders showed staining for PD-1. In some cases, non-neoplastic reactive lymphoid tissue was present, and showed a PD-1 staining pattern as seen in tonsil and other reactive lymphoid tissue noted above.

Similarly, in 25 cases of Hodgkin lymphoma, including 11 cases of classical Hodgkin lymphoma and 14 case of lymphocyte predominant Hodgkin lymphoma, the neoplastic cells did not exhibit staining for PD-1. Interestingly, in all 14 cases of lymphocyte predominant Hodgkin lymphoma, the T cells surrounding neoplastic CD20-positive L&H cells were immunoreactive for PD-1, similar to the staining pattern noted for CD57+ T cells in lymphocyte predominant Hodgkin lymphoma. These PD-1-positive cells were a subset of the total CD3+ T cell population present.

A range of T cell lymphoproliferative disorders were studied for expression of PD-1; the results are summarized in Table 4. Cases of precursor T cell lymphoblastic leukemia/lymphoblastic lymphoma, a neoplasm of immature T cells of immature T cells, were negative for PD-1, as were neoplasms of peripheral, post-thymic T cells, including cases of T cell prolymphocytic leukemia, peripheral T cell lymphoma, unspecified, anaplastic large cell lymphoma, and adult T cell leukemia/lymphoma. In contrast, all 19 cases of angioimmunoblastic lymphoma contained foci of PD-1-positive cells that were also immunoreactive for pan-T cell markers such as CD3. PD-1-positive cells were consistently found at foci of expanded CD21+ follicular dendritic cells (FDC) networks, a characteristic feature of angioimmunoblastic lymphoma.

TABLE 4

PD-1 immunostaining in lymphoproliferative disorders

| | PD-1 immunostaining |
|---|---|
| B cell LPDs | 0/42* |
| B-LL/LL | 0/3 |
| CLL | 0/4 |
| MCL | 0/4 |
| FL | 0/6 |
| MZL | 0/3 |
| HCL | 0/3 |

TABLE 4-continued

PD-1 immunostaining in lymphoproliferative disorders

|  | PD-1 immunostaining |
| --- | --- |
| DLBCL | 0/6 |
| BL | 0/7 |
| LPL | 0/3 |
| MM | 0/3 |
| Hodgkin lymphoma | 0/25 |
| Classical | 0/11 |
| Nodular lymphocyte predominant | 0/14** |
| T cell LPDs | 18/55 |
| T-LL/LL | 0/5 |
| T-PLL | 0/3 |
| AIL | 19/19 |
| PTCL, unspecified | 0/14 |
| ALCL | 0/12 |
| ATLL | 0/3 |

Abbreviations:
B-LL/LL - precursor B cell lymphoblastic lymphoma/lymphoblastic leukemia;
CLL - chronic lymphocytic leukemia;
MCL - mantle cell lymphoma;
FL - follicular lymphoma;
MZL - marginal zone lymphoma;
HCL - hairy cell leukemia;
DLBCL - diffuse large B cell lymphoma;
BL - Burkitt lymphoma;
LPL - lymphoplasmacytic lymphoma;
MM - multiple myeloma;
T-LL/L - precursor T lymphoblastic leukemia/lymphoblastic lymphoma;
T-PLL - T cell prolymphocytic leukemia;
AIL - angioimmunoblastic lymphoma;
PTCL - peripheral T cell lymphoma, unspecified;
ALCL - anaplastic large cell lymphoma;
ATLL - adult T cell leukemia/lymphoma.
*number of immunoreactive cases/total number of cases
**PD-1-positive cells form rosettes around neoplastic L&H cells in 14/14 cases Example 10

General Methods for Studying PD-1 Expression on HIV-Specific Human CD8+ T Cells

The following methods were used to perform the experiments detailed in Examples 11-14.

Subjects: Study participants with chronic clade C HIV-1 infection were recruited from outpatient clinics at McCord Hospital, Durban, South Africa, and St. Mary's Hospital, Mariannhill, South Africa. Peripheral blood was obtained from 65 subjects in this cohort, all of whom were antiretroviral therapy naïve at the time of analysis. Subjects were selected for inclusion based on their expressed HLA alleles matching the ten class I tetramers that were constructed (see below). The median viral load of the cohort was 42,800 HIV-1 RNA copies/ml plasma (range 163-750,000), and the median absolute CD4 count was 362 (range 129-1179). Information regarding duration of infection was not available. All subjects gave written informed consent for the study, which was approved by local institutional review boards.

Construction of PD-1 and PD-L1 antibodies: Monoclonal antibodies to human PD-L1 (29E.2A3, mouse IgG2b) and PD-1 (EH12, mouse IgG1) were prepared as previously described and have been shown to block the PD-1:PD-L1 interaction.

MHC class I tetramers: Ten HIV MHC Class I tetramers, synthesized as previously described (Altman J D, et al. 1996), were used for this study: A*0205 GL9 (p24, GAFDLSFFL; SEQ ID NO:1), A*3002 KIY9 (Integrase, KIQNFRVYY; SEQ ID NO:2), B*0801 DI8 (p24, DIYKRWII; SEQ ID NO:3), B*0801 FL8 (Nef, FLKEKGGL; SEQ ID NO:4), B*4201 RM9 (Nef, RPQVPLRPM; SEQ ID NO:5), B*4201 TL9 (p24, TPQDLNTML; SEQ ID NO:6), B*4201 TL10 (Nef, TPGPGVRYPL; SEQ ID NO:7), B*4201 YL9 (RT, YPGIKVKQL; SEQ ID NO:8), B*8101 TL9 (p24, TPQDLNTML; SEQ ID NO:9), and Cw0304 YL9 (p24, YVDRFFKTL; SEQ ID NO:10).

HLA class I tetramer staining and phenotypic analysis: Freshly isolated peripheral blood mononuclear cells (PBMC, 0.5 million) were stained with tetramer for 20 minutes at 37° C. The cells were then washed once with phosphate buffered saline (PBS), pelleted, and stained directly with fluorescein isothiosyanate (FITC)-conjugated anti-CD8 (Becton Dickinson), phycoerythrin-conjugated anti-PD-1 (clone EH12), and ViaProbe (Becton Dickinson). Cells were incubated for 20 minutes at room temperature, washed once in PBS, and resuspended in 200 µl PBS with 1% paraformaldehyde and acquired on a fluorescence-activated cell sorter (FACSCalibur™, Becton Dickinson). A minimum of 100,000 events were acquired on the FACSCalibur™

CFSE proliferation assays: One million freshly isolated PBMC were washed twice in PBS, pelleted, and resuspended in 1 ml of 0.5 µM carboxy-fluorescein diacetate, succinimidyl ester (CFSE, Molecular Probes) for 7 minutes at 37° C. The cells were washed twice in PBS, resuspended in 1 ml R10 medium (RPMI 1640 supplemented with glutathione, penicillin, streptomycin, and 10% fetal calf serum [FCS]), and plated into one well of a 24-well plate. Initial studies revealed that a final concentration of 0.2 µg/ml peptide yielded optimal proliferative responses, therefore this was the final peptide concentration in the well used for each assay. Negative control wells consisted of PBMC in medium alone, or PBMC in medium with purified anti-PD-L1 (10 µg/ml), and positive control wells were stimulated with 10 µg/ml of phytohemagluttinin (PHA). Following 6-day incubation in a 37° C. incubator, the cells were washed with 2 ml PBS and stained with PE-conjugated MHC Class I tetramers, ViaProbe (Becton Dickinson), and anti-CD8-APC antibodies. Cells were acquired on a FACSCalibur and analyzed by CellQuest® software (Becton Dickinson). Cells were gated on ViaProbe-CD8+ lymphocytes. The fold increase in tetramer+ cells was calculated by dividing the percentage of CD8+ tetramer+ cells in the presence of peptide by the percentage of CD8+ tetramer+ cells in the absence of peptide stimulation.

Statistical Analysis: Spearman correlation, Mann-Whitney test, and paired t-test analyses were performed using GraphPad Prism Version 4.0a. All tests were 2-tailed and p values of p<0.05 were considered significant.

Example 11

PD-1 Expression on HIV-Specific CD8+ T Cells

Figure 5:
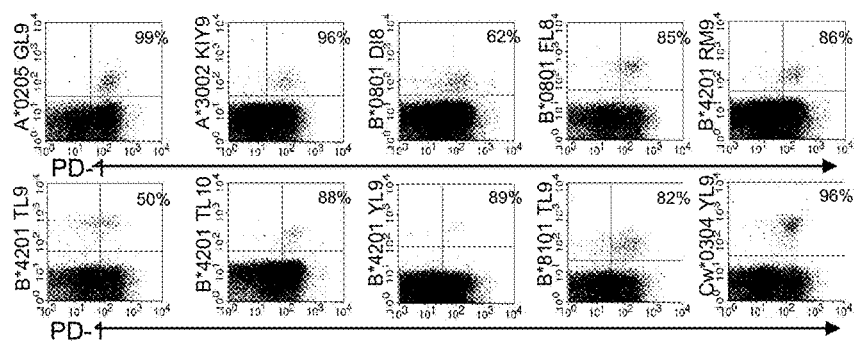
FIG. 5A is a series of images of a flow cytometry experiment showing PD-1 surface expression using 10 HIV tetramers specific for dominant epitopes targeted in chronic Glade C HIV infection. The percentages indicate the percentage of tetramer+ cells that are PD-1+.
FIG. 5B is a series of charts demonstrating that the percentage and MFI of PD-1 is significantly upregulated on HIV-specific CD8+ T cells compared to the total CD8+ T cell population (p<0.0001) in antiretroviral therapy naïve individuals, and PD-1 is increased on the total CD8+ T cell population in HIV-infected versus HIV-seronegative controls (p=0.0033 and p<0.0001, respectively). 120 HIV tetramer stains from 65 HIV-infected individuals and 11 HIV seronegative controls were included in the analysis.
FIG. 5C is a series of charts showing the median percentage and MFI of PD-1 expression on tetramer+ cells by epitope specificity.
FIG. 5D is a chart depicting the variation in the percentage of PD-1+ cells on different epitope-specific populations within individuals with multiple detectable responses. Horizontal bars indicate the median percentage of PD-1+ HIV tetramer+ cells in each individual.
Figure 5:
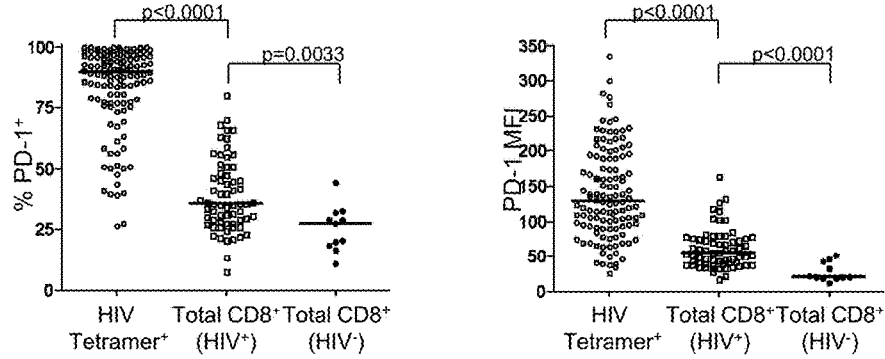
Figure 5:
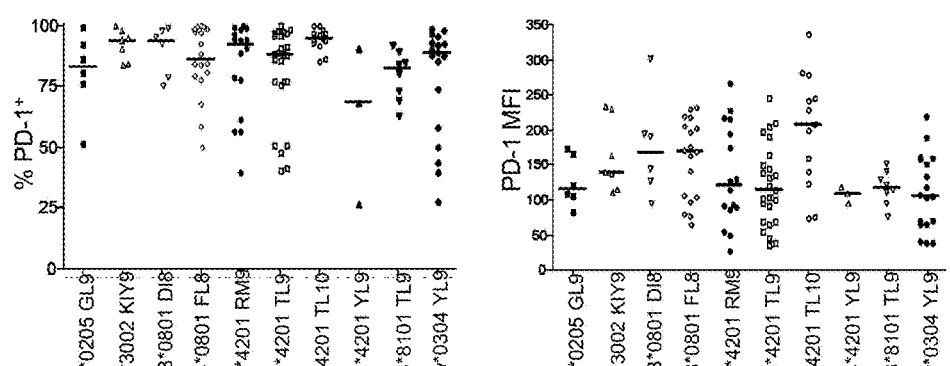
Figure 5:
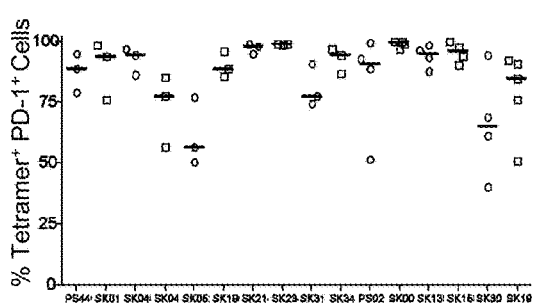

A panel of 10 MHC Class I tetramers specific for dominant HIV-1 clade C virus CD8+ T cell epitopes was synthesized, based on prevalent HLA alleles and frequently targeted epitopes in Gag, Nef, Integrase, and RT allowing direct visualization of surface PD-1 expression on these cells. High resolution HLA typing was performed on the entire cohort, and a subset of 65 antiretroviral therapy naïve persons was selected for study based on expression of relevant HLA alleles. A total of 120 individual epitopes were examined, and representative ex vivo staining of PD-1 on HIV tetramer+ cells is shown in FIG. 5A. PD-1 expression was readily apparent on these tetramer+ cells, and was significantly higher than in the total CD8 T cell population from the same individuals (p<0.0001); in turn, PD-1 expression on both tetramer+ CD8+ T cells and the total CD8+ T cell population was significantly higher than in HIV-seronegative controls (FIG. 5B). For eight of the ten tetramers tested at least one person was identified in whom the level of expression on antigen-specific CD8+ cells was 100% (FIG. 5C). PBMC from 3 to 25 individuals were stained for each HIV tetramer response, with median PD-1 expression levels ranging from 68% to 94% of tetramer+ cells (FIG. 5C). These findings were further confirmed by analysis of the mean fluorescence intensity (MFI) of PD-1 on both tetramer+ cells and the total CD8+ T cell population (FIG. 5B, C).

It was next determined whether there was evidence for epitope-specific differences in terms of PD-1 expression levels in persons with multiple detectable responses. Of the 65 persons examined, 16 individuals had between 3 and 5 tetramer positive responses each. PD-1 expression was nearly identical and approaching 100% for each response analyzed for three of the sixteen subjects; however, the other 13 individuals displayed different patterns of PD-1 expression depending on the epitope (FIG. 5D). These data indicate that PD-1 expression may be differentially expressed on contemporaneous epitope-specific CD8+ T cells from a single person, perhaps consistent with recent data indicating epitope-specific differences in antiviral efficacy (Tsomides T J, et al. 1994; Yang O, et al. 1996; Loffredo J T, et al. 2005).

Example 12

The Relationship Between PD-1 Expression and HIV Disease Progression

Figure 6:
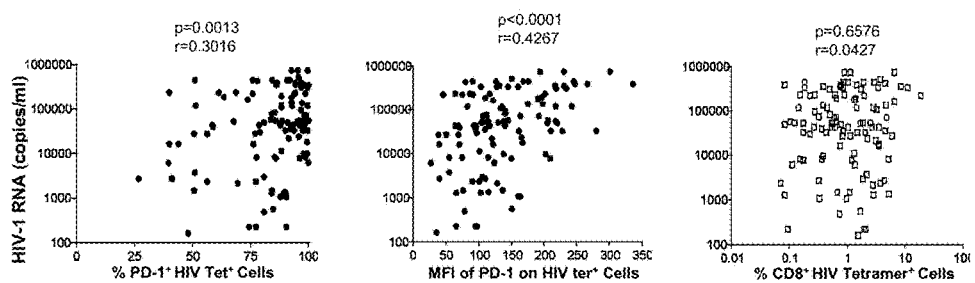
FIG. 6A is a series of charts demonstrating that there is no correlation between the number of HIV-specific CD8+ T cells, as measured by tetramer staining, and plasma viral load, whereas there is a positive correlation between both the percentage and MFI of PD-1 on tetramer+ cells and plasma viral load (p=0.0013 and p<0.0001, respectively).
FIG. 6B is a series of charts showing that there is no correlation between the number of HIV tetramer+ cells and CD4 count, whereas there is an inverse correlation between the percentage and MFI of PD-1 on HIV tetramer+ cells and CD4 count (p=0.0046 and p=0.0150, respectively).
FIG. 6C is a series of charts demonstrating that the percentage and MFI of PD-1 on the total CD8+ T cell population positively correlate with plasma viral load (p=0.0021 and p<0.0001, respectively).
FIG. 6D is a series of charts depicting the percentage and MFI of PD-1 expression on the total CD8+ T cell population is inversely correlated with CD4 count (p=0.0049 and p=0.0006, respectively).
Figure 6:
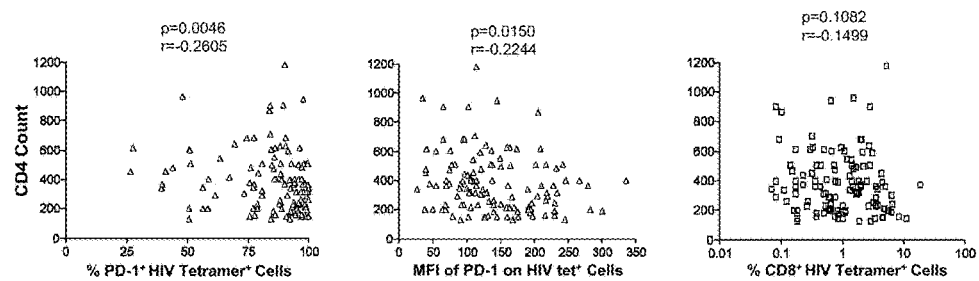
Figure 6:
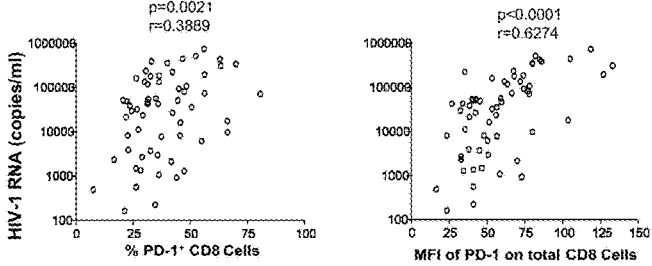
Figure 6:
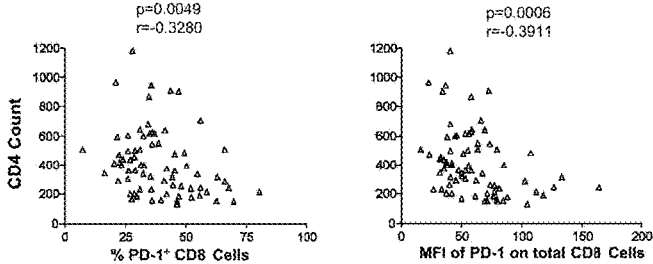

The relationship was determined between PD-1 expression on HIV-specific CD8+ T cells and plasma viral load and CD4+ cell counts, both of which are predictors of HIV disease progression. Consistent with previous studies, the relationship between the number of tetramer positive cells and viral load or CD4+ cell count failed to show any significant correlation (FIG. 6A, B). In contrast, there were significant positive correlations with viral load and both the percentage and MFI of PD-1 expression on HIV tetramer positive cells (p=0.0013 and p<0.0001, respectively; FIG. 6A). There were also inverse correlations between CD4 count and both the percentage and MFI of PD-1 on HIV tetramer positive cells (p=0.0046 and p=0.0150, respectively; FIG. 6B). Since the tetramers tested likely represent only a fraction of the HIV-specific CD8+ T cell population in these subjects, the relationship between PD-1 expression on all CD8+ cells and these parameters was also examined. There were significant positive correlations between viral load and both the percentage and MFI of PD-1 expression on the total CD8+ T cell population (p=0.0021 and p<0.0001, respectively; FIG. 6C), and inverse correlations were also observed between CD4+ cell count and both the percentage and MFI of PD-1 expression on the total CD8+ T cell population (p=0.0049 and p=0.0006, respectively; FIG. 6D). In this same group, PD-1 expression on CMV-specific CD8+ T cells was tested in 5 subjects, and significantly less PD-1 was expressed on these cells compared to HIV-specific CD8 T cells (median 23% CMV tetramer+PD-1+, p=0.0036), and was not different than bulk CD8+ T cells in these same individuals, indicating that high PD-1 expression is not a uniform feature of all virus-specific CD8+ T cells. These data suggest increasing amounts of antigen in chronic HIV infection result in increased expression of PD-1 on CD8+ T cells, and are consistent with murine data in chronic LCMV infection, in which PD-1 expression is associated with functional exhaustion of CD8+ T cells (Barber D L, et al. 2005). Moreover, they provide the first clear association, in a large study including analysis of multiple epitopes, between HIV-specific CD8+ T cells and either viral load or CD4 count.

Example 13

Figure 7:
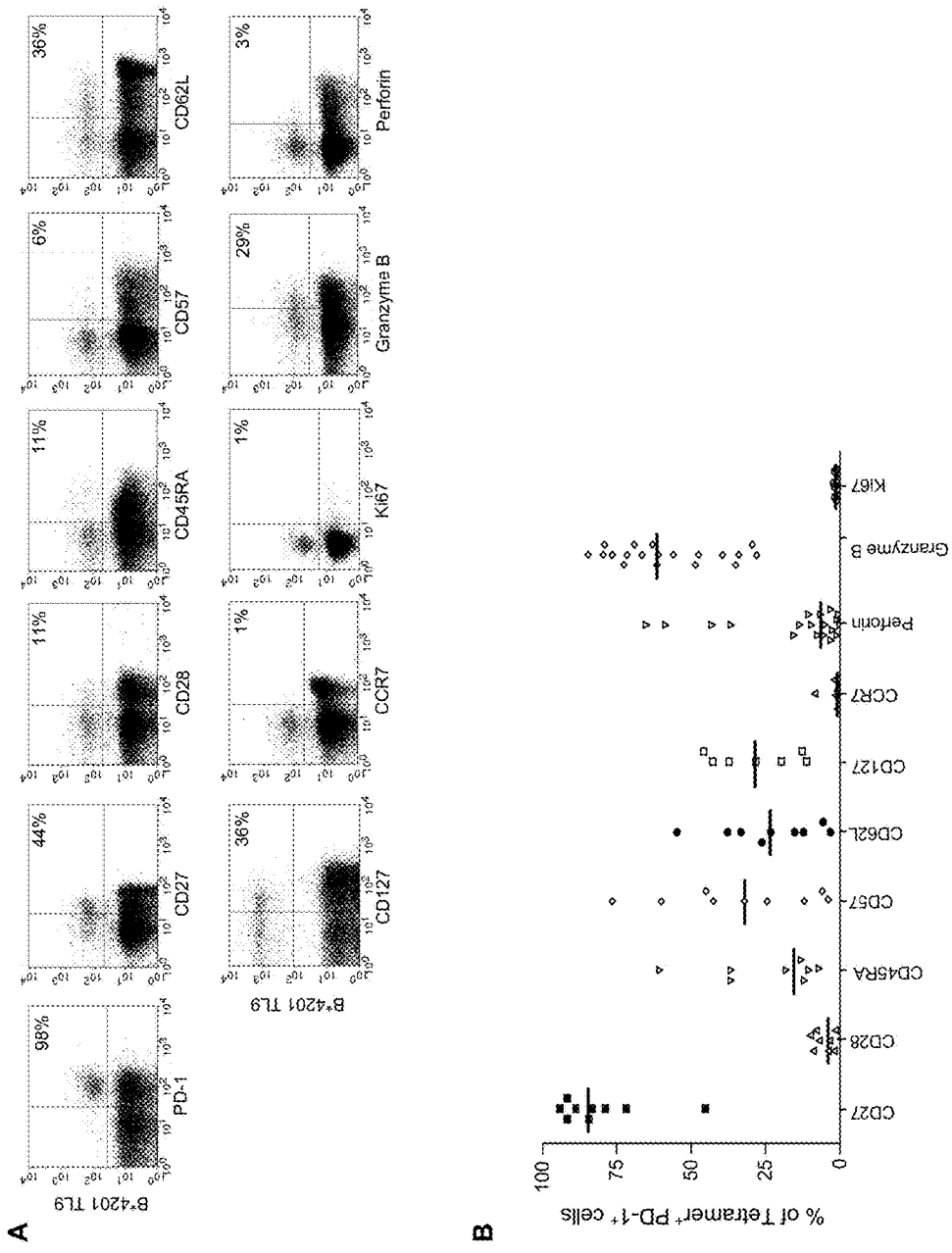
FIG. 7A is a series of images of a flow cytometry experiment showing representative phenotypic staining of B*4201 TL9-specific CD8+ T cells from subject SK222 in whom 98% of B*4201 TL9-specific CD8+ T cells are PD-1$^+$.
FIG. 7B is a chart illustrating a summary of phenotypic data from persons in whom >95% of HIV-specific CD8+ T cells are PD-1$^+$. Seven to 19 samples were analyzed for each of the indicated phenotypic markers. The horizontal bar indicates median percentage of tetramer PD-1$^+$ cells that were positive for the indicated marker.

The Relationship Between PD-1 Expression and CD8 T Cell Memory Status and Function PD-1 expression was next analyzed in the context of a number of additional phenotypic markers associated with CD8+ T cell memory status and function, including CD27, CD28, CD45RA, CD57, CD62L, CD127, CCR7, perforin, granzyme B, and Ki67 (FIG. 7). Representative stainings for these markers on B*4201 TL9 tetramer+ cells from one individual are shown in FIG. 7A, and aggregate data for 13 subjects are shown in FIG. 7B. These studies were limited to those tetramer responses that were greater than 95% PD-1 positive, as multiparameter flow cytometry of greater than 4 colors was not available in KwaZulu Natal. The HIV tetramer+PD-1+ cells express high levels of CD27 and granzyme B, very low levels of CD28, CCR7, and intracellular Ki67, low levels of CD45RA and perforin, and intermediate levels of CD57 and CD62L (FIG. 7B). These data indicate that HIV-specific PD-1+ T cells display an effector/effector memory phenotype, and are consistent with previous reports of skewed maturation of HIV-specific CD8+ T cells. In addition, virus sequencing was performed to determine whether these cells were driving immune escape. Of 45 of these tetramer-positive responses evaluated, the viral epitopes in only 5 were different from the South African clade C consensus sequence, indicating these cells exert little selection pressure in vivo.

Previous experiments in mice using the LCMV model showed that in vivo blockade of PD-1/PD-L1 interaction by infusion of anti-PD-L1 blocking antibody results in enhanced functionality of LCMV-specific CD8+ T cells as measured by cytokine production, killing capacity, proliferative capacity, and, most strikingly, reduction in viral load. Short-term (12-hour) in vitro antigen-specific stimulation of freshly isolated PBMC from 15 HIV+ subjects, in the presence or absence of 1 µg/ml purified anti-PD-L1 antibody, failed to increase IFN-γ, TNF-α, or IL-2 production.

Example 14

Figure 8:
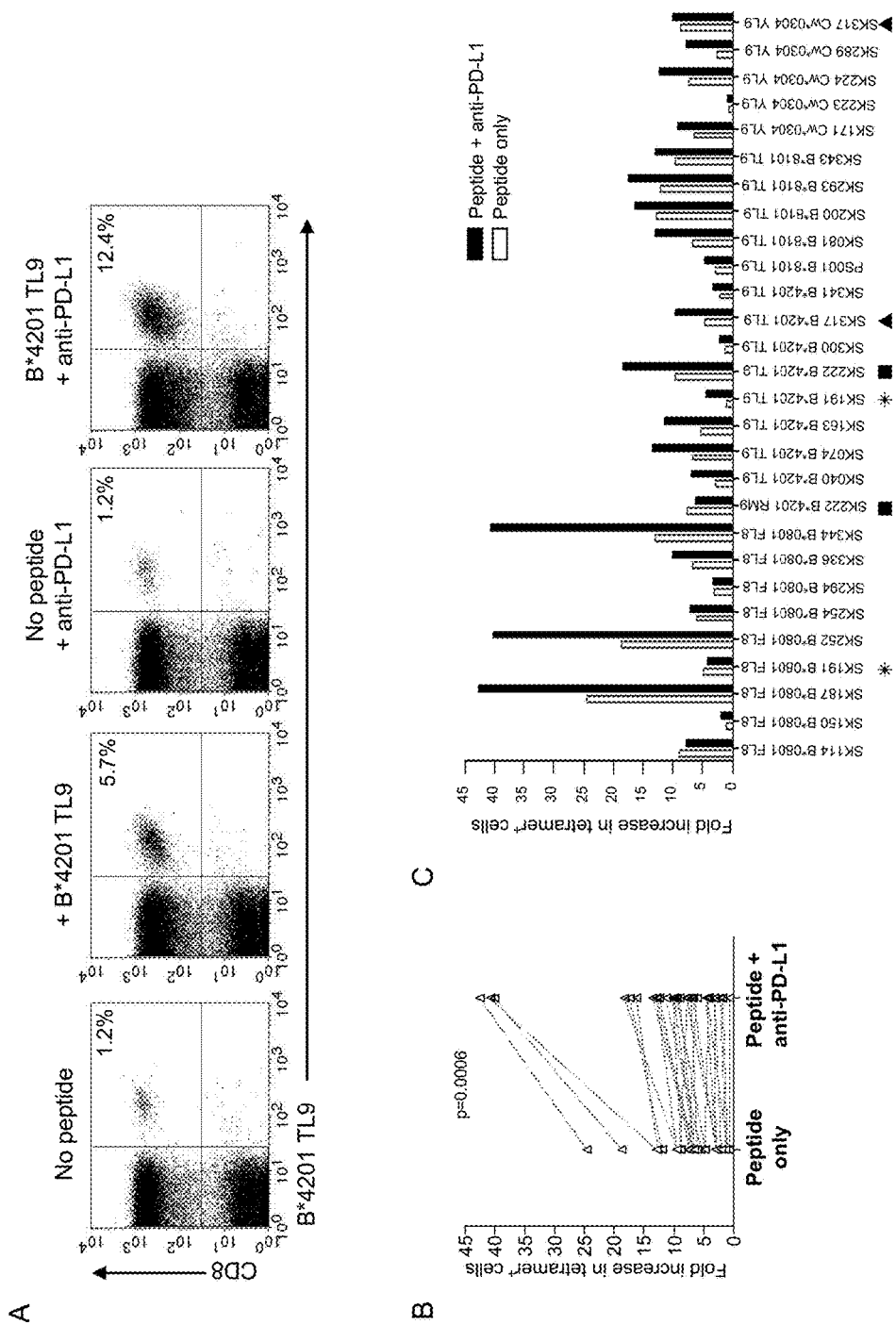
FIG. 8A is a series of images of a flow cytometry experiment showing the representative proliferation assay data from a B*4201 positive subject. After a 6-day stimulation with peptide, the percentage of B*4201 TL9-specific CD8+ T cells increased from 5.7% to 12.4% in the presence of anti-PD-L1 blocking antibody.
FIG. 8B is a line graph depicting the summary proliferation assay data indicating a significant increase in proliferation of HIV-specific CD8+ T cells in the presence of anti-PD-L1 blocking antibody (n=28, p=0.0006, paired t-test).
FIG. 8C is a bar graph showing the differential effects of PD-1/PD-L1 blockade on proliferation of HIV-specific CD8+ T cells on an individual patient basis. White bars indicate fold increase of tetramer$^+$ cells in the presence of peptide alone, black bars indicate the fold increase of tetramer$^+$ cells in the presence of peptide plus anti-PD-L1 blocking antibody. Individuals in whom CFSE assays were performed for more than one epitope are indicated by asterisk, square, or triangle symbols.

Effect of Blockading the PD-1/PD-L1 Pathway on Proliferation of HIV-Specific CD8+ T Cells Because HIV-specific CD8+ T cells also exhibit impaired proliferative capacity (2004), it was determined whether blockade of the PD-1/PD-L1 could enhance this function in vitro. Representative data from a B*4201-positive individual are shown in FIG. 8A. Incubation of freshly isolated CFSE-labeled PBMC with medium alone, or medium with anti-PD-L1 antibody, resulted in maintenance of a population of B*4201-TL9-specific CD8+ T cells (1.2% of CD8+ T cells) that remained CFSEhi after six days in culture. Simulation of CFSE-labeled PBMC for 6 days with TL9 peptide alone resulted in a 4.8-fold expansion of CFSElo B*4201 TL9 tetramer+ cells, whereas stimulation of CFSE-labeled PBMC with TL9 peptide in the presence of anti-PD-L1 blocking antibody further enhanced proliferation of TL9-specific cells, resulting in a 10.3-fold increase in tetramer+ cells. CFSE proliferation assays were performed on 28 samples in the presence and absence of purified anti-human PD-L1 blocking antibody. A significant increase in the proliferation of HIV-specific CD8+ T cells was observed in the presence of peptide plus anti-PD-L1 blocking antibody as compared to the amount of proliferation following stimulation with peptide alone (FIG. 8B; p=0.0006, paired t-test). The fold increase of tetramer+ cells in the presence of anti-PD-L1 blocking antibody varied by individual and by epitope within a given individual (FIG. 8C), again suggesting epitope-specific differences in the degree of functional exhaustion of these responses.

Example 15

Therapeutic Vaccination in Conjunction with Blocking PD-1 Inhibitory Pathway Synergistically Improves the Immune Control of Chronic Viral Infection: A Concept Study of Combinatorial Therapeutic Vaccine The functional impairment of T cells including cytokine proliferation, cytolysis, and proliferation of antigen-specific T cells, is a defining characteristic of many chronic infections. Inactivated T cell immune response is observed during a variety of different persistent pathogen infections, including HIV, HBV, HCV, and TB in humans. T cell inactivation during chronic infection might correlate with the magnitude and persistence of the antigen burden and originate from disrupted proximal T cell receptor signals, upregulation of inhibitory proteins or down regulation of costimulatory proteins, and defects in accessory and cytokine signals. The defect in exhausted T cells is a primary reason for the inability of the host to eliminate the persisting pathogen. During chronic infection, exhausted virus specific CD8 T cells upregulate two key inhibitory proteins: PD-1 and CTLA-4. An in vivo blockade of PD-1 increases the number and function of virus-specific CD8 T cells and results in decreased viral load.

There are several drawbacks of current vaccination strategies for chronic viral infections. Specifically, effective boosting of antiviral CD8 T-cell responses is not observed after therapeutic vaccination. In addition, a high viral load and the low proliferative potential of responding T cells during chronic infection are likely to limit the effectiveness of therapeutic vaccination. Thus, it is important to develop therapeutic vaccine strategy to boost effectively the host's endogenous T cell responses to control chronic infection.

A well-known chronic infection model induced by LCMV Clone-13 infection was used to determine the effectiveness of using a PD-1 antagonist in combination with a therapeutic vaccine. A vaccinia virus expressing GP33 epitope of LCMV was used as a therapeutic vaccine to monitor an epitope-specific CD8 T cell immune response. A therapeutic vaccine was combined with anti-PD-L1 antibody for blocking an inhibitory pathway in order to investigate the synergist effect regarding a proliferation of antigen-specific CD8 T cells and a resolution of persisting virus.

The following methods were used in these experiments:

Mice and infections: C57BL/6 mice (4- to 6-week-old females) were from The Jackson Laboratory (Bar Harbor, Me.). Mice were maintained in a pathogen-free vivarium according to NIH Animal Care guidelines. For the initiation of chronic infections, mice were infected with $2\times10^6$ PFU of LCMV clone-13 (CL-13) as described previously. Viral growth and plaque assays to determine viral titers have been described previously.

In vivo antibody blockade and therapeutic vaccination: Two hundred micrograms of rat anti-mouse PD-L1 (10F:9G2) were administered intraperitoneally every third day from 4 weeks post-infection with CL-13. At the time point of first treatment of anti-PD-L1, $2\times10^6$ PFU of recombinant vaccinia virus expressing the GP33-41 epitope (VV/GP33) as therapeutic vaccine or wild-type vaccinia virus (VV/WT) as control vaccine were given intraperitoneally.

Lymphocyte isolation: Lymphocytes were isolated from tissues and blood as previously described. Liver and lung were perfused with ice-cold PBS prior to removal for lymphocyte isolation.

Flow cytometry: MHC class I peptide tetramers were generated and used as previously described. All antibodies were obtained from BD Pharmingen except for granzyme B (Caltag), Bcl-2 (R&D Systems), and CD127 (eBioscience). All surface and intracellular cytokine staining was performed as described (Barber et al., Nature 439:682, 2006). To detect degranulation, splenocytes were stimulated for 5 h in the presence of brefeldin, monensin, anti-CD107a-FITC, and anti-CD107b-FITC.

Confocal microscopy: Spleens were removed from mice and frozen in OCT (TissueTek). From these blocks, 10-20 mm cryostat sections were cut and fixed in ice-cold acetone for 10 minutes. For immunofluorescence, sections were stained with the following antibodies: ER-TR7 to detect reticular cells (Biogenesis, Kingston, N.H.) and polyclonal anti-LCMV guinea-pig serum. Stains were visualized with Alexa Fluor-488 goat anti-rat and Alexa Fluor-568 goat anti-guinea-pig Ig (Molecular Probes) and analyzed by confocal microscopy (Leica Microsystems AG, Germany). Images were prepared using ImageJ (National Institutes of Health) and Photoshop (Adobe Systems Inc.).

Figure 9:
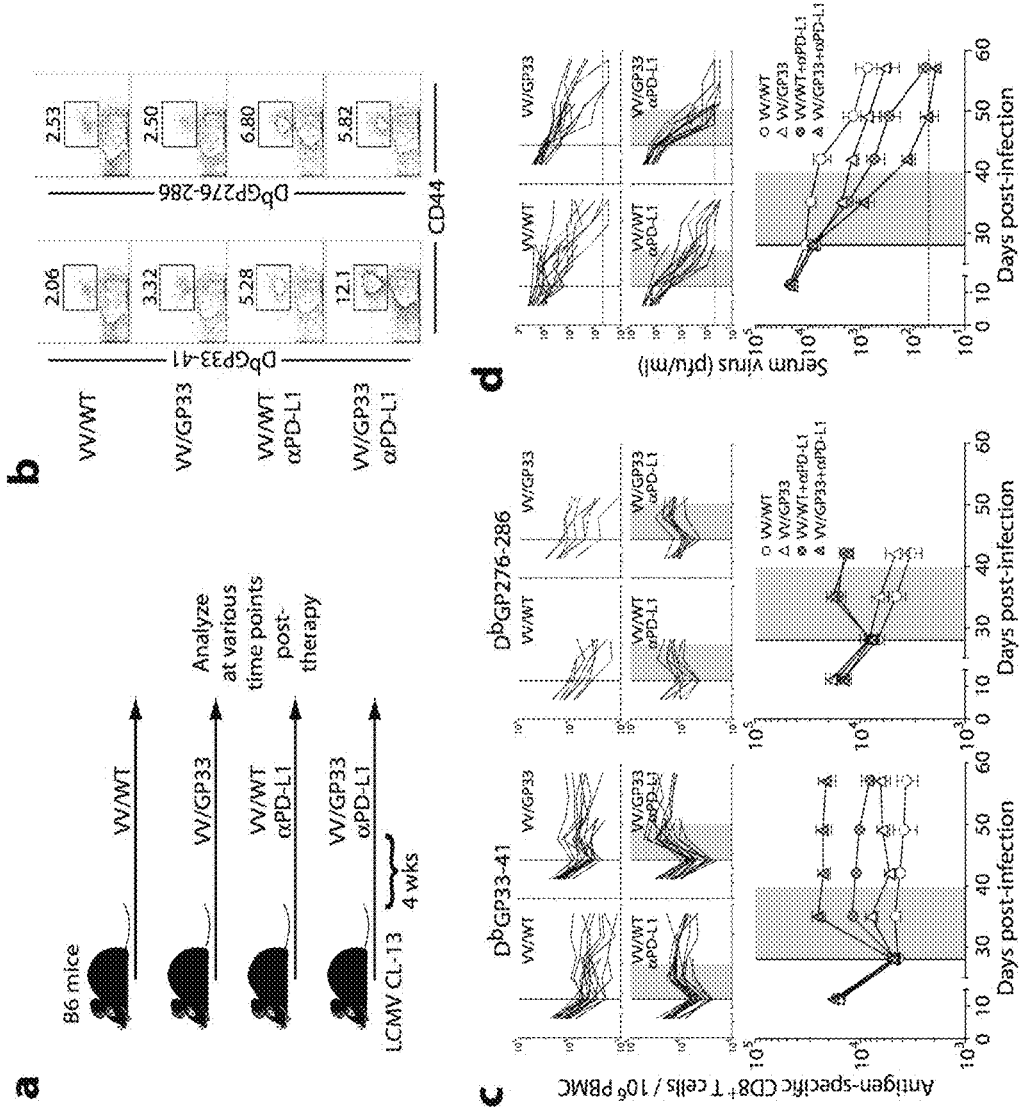
FIGS. 9A-9D are a diagram and a set of graphs showing the synergistic effect of therapeutic vaccine combined with PD-L1 blockade on antigen-specific CD8-T cell frequency and viral titer in chronically infected mice.
Figure 10:
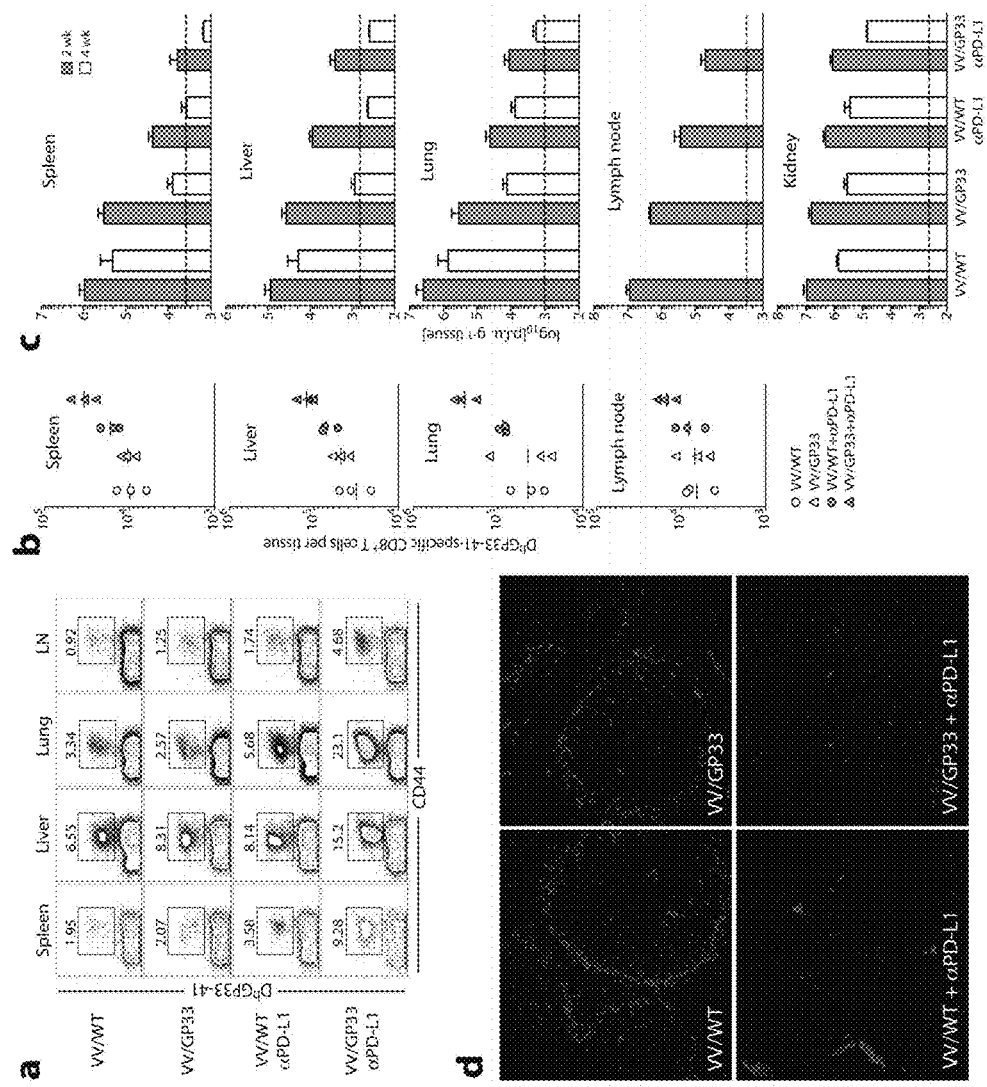
FIGS. 10A-10D are graphs and digital images showing increased antigen-specific CD8-T cells and enhanced viral control in different tissues of the mice given therapeutic vaccine combined with PD-L1 blockade.
Figure 11:
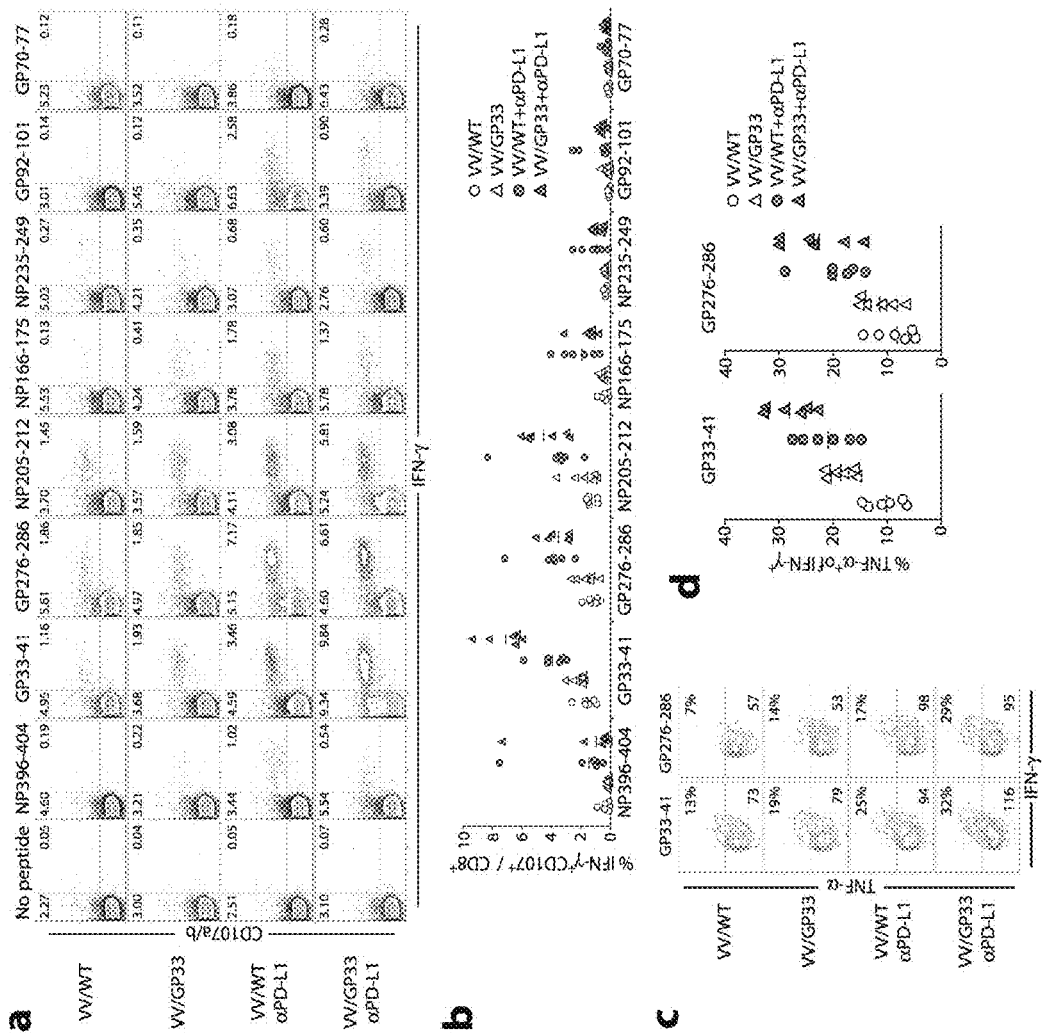
FIG. 11A-11D are plots and graphs showing enhanced restoration of function in exhausted CD8-T cells by therapeutic vaccine combined with PD-L1 blockade.
Figure 12:
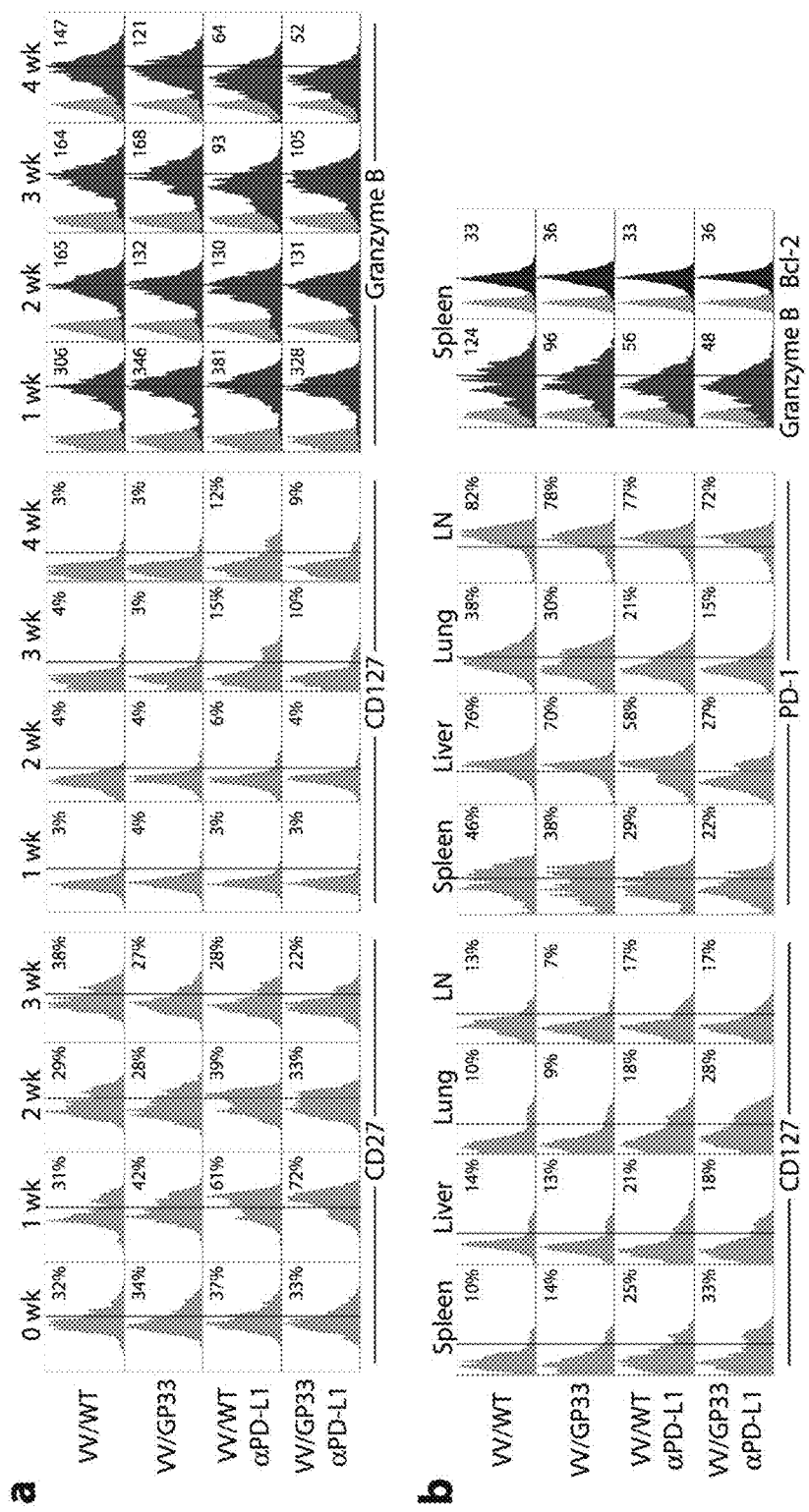
FIG. 12A-12B are a set of plots showing the effect of a therapeutic vaccine combined with PD-L1 blockade changes phenotype of antigen-specific CD8-T cells of chronically infected mice.

The results demonstrated that a combination of therapeutic vaccine and anti-PD-L1 antibody displays a synergistic effect on proliferation of antigen-specific CD8 T cells and resolution of persisting virus. Therapeutic vaccine could boost effectively a functionally restored CD8 T cell population by blockade of PD-1/PD-L1 inhibitory pathway. Enhanced proliferation of antigen-specific CD8 T cells and accelerated viral control were systematically achieved by combinatorial therapeutic vaccination (FIGS. 9A-9D and FIG. 10A-10D). Combinatorial therapeutic vaccine guides to a dramatic increase of functionally active CD8 T cells (FIG. 11A-D). In addition, therapeutic vaccine using vector expressing specific epitope during blockade of PD-1/PD-L1 pathway enhances a proliferation of CD8 T cell specific to epitope encoded in vector (FIGS. 9 and 11). The increased expression level of CD127 seen on antigen-specific CD8 T cells in the group treated with the combinatorial vaccine reflects the generation of a long-term memory T cell responses, while decreased expression levels of PD-1 and Granzyme B correlate to resolution of persisting virus (FIGS. 12A-12B).

Figure 13:
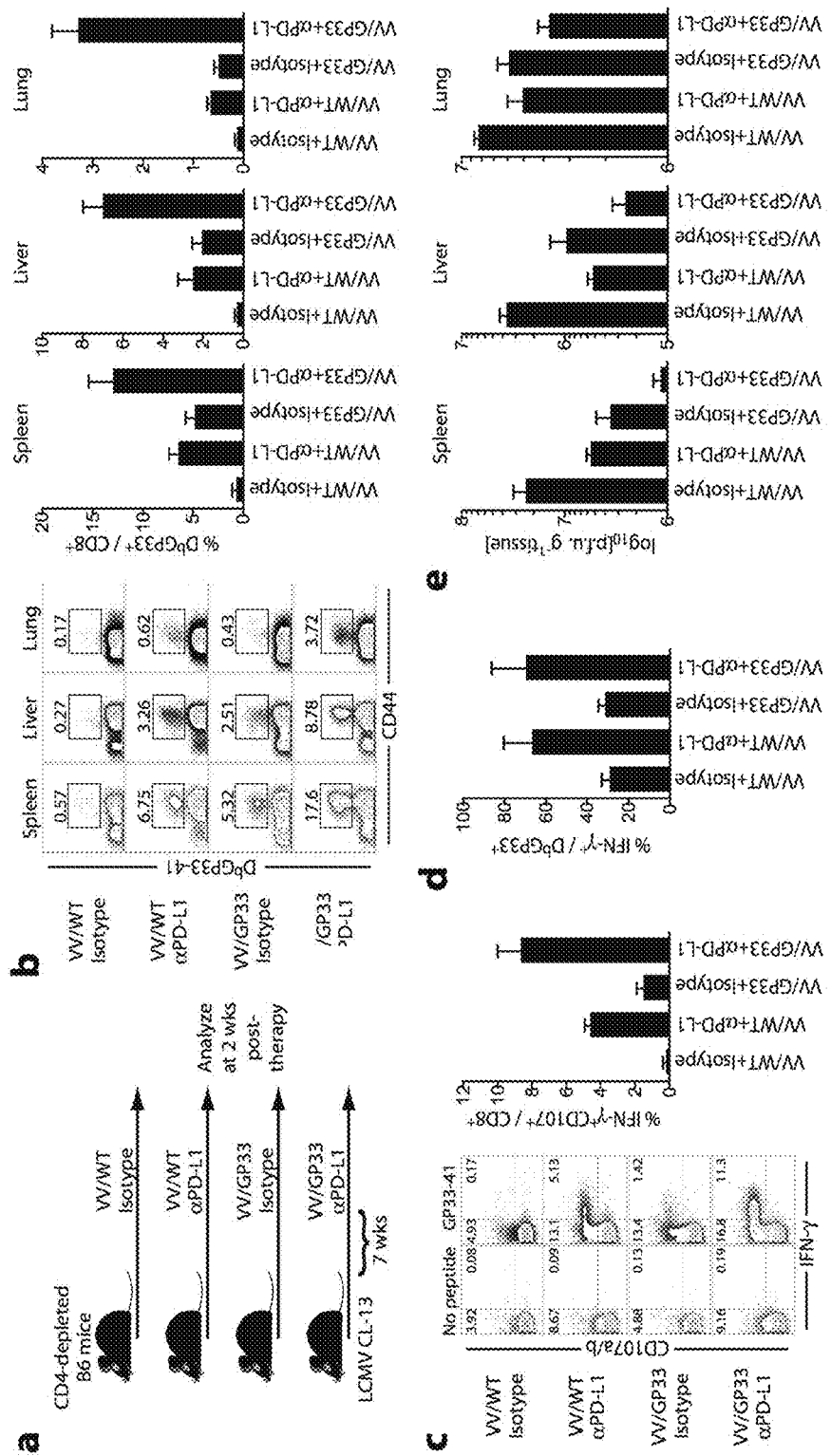
FIGS. 13A-13E are a schematic diagram, plots and graphs showing the synergistic effect of therapeutic vaccine combined with PD-L1 blockade on restoration of function in 'helpless' exhausted CD8 T cells.

There was a synergistic effect of therapeutic vaccine combined with PD-L1 blockade on restoration of function in 'helpless' exhausted CD8 T cells (see (FIG. 13A-13E). Mice were depleted of CD4 T cells and then infected with LCMV clone-13. Some mice were vaccinated with wild-type vaccinia virus (VV/WT) or LCMV GP33-41 epitope-expressing vaccinia virus (VV/GP33) at 7-wk post-infection. At the same time, the mice were treated 5 times every three days with αPD-L1 or its isotype. Two weeks after initial treatment of antibodies, mice were sacrificed for analysis. The results are shown in FIG. 13A. The frequency of GP33 specific CD8 T cells was also examined (FIG. 13B). Splenocytes were stimulated with GP33 peptide in the presence of αCD107a/b antibodies and then co-stained for IFN-γ. The shown plots are gated on CD8-T cells (FIG. 13C). The percentage of IFN-γ+ cells after stimulation with GP33 peptide per cells positive for Db-restricted GP33-41 tetramer was also determined (FIG. 13D), as was the viral titer ((FIG. 13E). The results demonstrate the synergistic effect of a vaccine combined with PD-1 blockade.

These results show that combinations of blocking negative regulatory pathway and boosting CD8 T cells during chronic infection can be used in the development of therapeutic vaccines to improve T cell responses in patients with chronic infections or malignancies. Therapeutic interventions, such as the use of an antagonist of PD-1, that boost T-cell responses and lower the viral load could increase disease-free survival and decrease transmission of the virus. Effective therapeutic vaccination could be used for chronic viral infections and persisting bacterial, parasitic infections. This strategy is also of use for the treatment of malignancies.

Example 16

Enhancement of T Cell Immunotherapy Through Blockade of the PD1/PDL1 Pathway

It is important to develop strategies to treat and eliminate chronic viral infections such as the Human Immunodeficiency virus and Hepatitis C. The CDC has recently reported that over one million American's are living with HIV, exemplifying the need for more effective therapies. It is important to determine how inhibitory signaling to lymphocytes can contribute to a pathogen's ability to persistently evade the host immune response.

The inhibitory immunoreceptor PD-1 (a member of the B7/CD28 family of costimulatory receptors) and its ligand (PD-L1) have been shown to be dramatically upregulated during states of chronic infection with lymphocytic choriomeningitis virus (LCMV). Additional studies using the LCMV model have demonstrated that blocking of the PD1/PDL1 pathway significantly augments the endogenous antiviral CD8 T cell response during the late phases of chronic infection when CD8 T cells are exhausted. Exhausted T cells are functionally compromised and do not mount effective immune responses upon antigen encounter. However, blockade of the PD1/PD-L1 pathway appears to reverse exhaustion and restore their functional capacity. Data suggests that these effects persist well beyond the immediate period of anti-PDL1 treatment.

The following experiments were performed in order to (1) assess the ability of anti-PDL1 to enhance the proliferation and survival anti-viral CD8 T cells upon adoptive transfer of immune (memory) splenocytes into congenitally infected (carrier) mice, (2) to evaluate the functionality of virus-specific, memory CD8 T cells that have expanded in the presence of PD1/PDL1 blockade, and (3) to determine the expression of various markers of differentiation in virus-specific CD8 T cells that have expanded in the presence of PD1/PDL1 blockade.

The role of the PD-1 pathway was assessed in a well-developed model of cyto-immune therapy for chronic viral infection. The model described herein parallels that of T cell cyto-immune therapy for tumors in regard to the immunological barriers the limit the applicability of these therapies (such as corrupted or suppressed T cell/anti-tumor responses). Mice infected neonatally or in utero with LCMV do not mount endogenous LCMV-specific immune responses and go on to have high levels of infectious LCMV in blood and all tissues throughout their lives. These animals are congenital carriers and are essentially tolerant to the pathogen. When splenocytes from an LCMV immune mouse are adoptively transferred into a congenital carrier the transferred immune memory cells rapidly undergo expansion and establish a vigorous immune response against the virus. Approximately ⅔ of the animals receiving adoptive cyto-immune therapy go on to completely clear the infection when high doses of splenocytes are transferred.

The following materials and methods were used in these experiments:

Mice and infections. 4-6 week old female B57BL/6 mice were purchased from the Jackson Laboratory (Bar Harbor, Me.). Acute infection was initiated by intraperitoneal injection of $2 \times 10^5$ PFU LCMV Armstrong. Congenital carrier mice were bred at Emory University (Atlanta, Ga.) from colonies derived from neonatally infected mice ($10^4$ PFU LCMV clone-13, intracerebral).

Adoptive immunotherapy and in vivo antibody blockade. $40 \times 10^6$ whole splenocytes from LCMV immune mice (day 30-90 post-infection) were isolated and transferred intravenously into 6-12 week old LCMV carrier mice. 200 micrograms of rat-anti-mouse PD-L1 (10F.9G2) were administered every $3^{rd}$ day for 15 days following adoptive immunotherapy.

Flow cytometry and tetramer staining. MHC class I tetramers of H-2 Db complexed with LCMV $GP_{33-41}$ were generated as previously described. All antibodies were purchased from BD/Pharmingen (San Diego, Calif.). Peripheral blood mononuclear cells and splenocytes were isolated and stained as previously described. Data was acquired using a FACSCalibur™ flow cytometer (BD) and analyzed using FlowJoe software (Tree Star Inc. Ashland, Oreg.)

Intracellular cytokine staining. For intracellular cytokine staining $10^6$ splenocytes were cultured in the presence or absence of the indicated peptide (0.2 µg/ml) and brefeldin A for 5-6 hours at 37° C. Following staining for surface markers, cells were permeabilized and stained for intracellular cytokines using the Cytofix/Cytoperm preparation (BD/Pharmigen).

Figure 14:
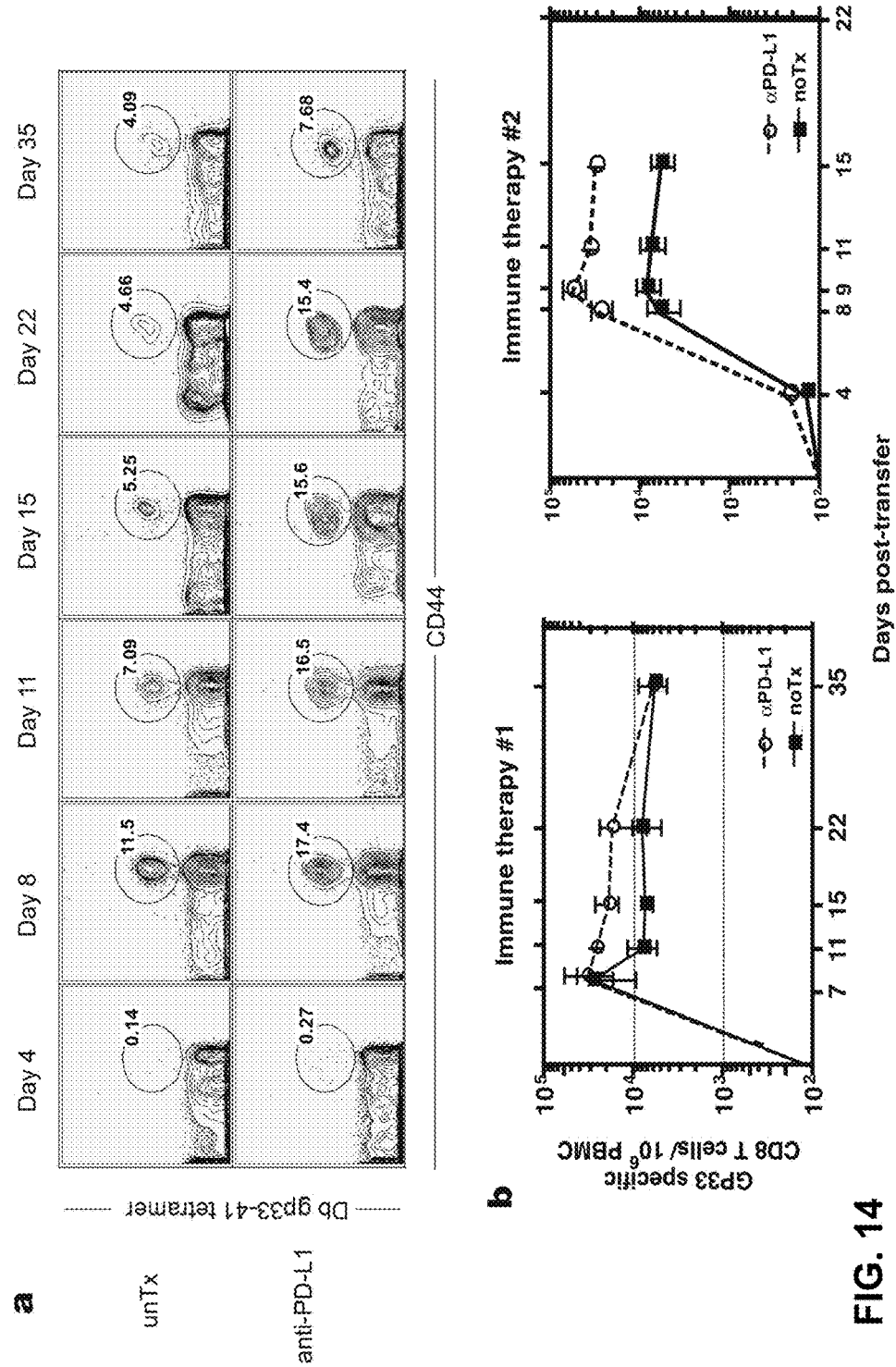
FIGS. 14A-14B are a set of plots and graphs showing that blockade of the PD1/PD-L1 signaling pathway increases the total number of antigen-specific T cells following adoptive transfer into congenital carrier mice. Whole splenocytes were adoptively transferred into congenital carrier mice with or without therapy with anti-PD-L1.

The following results were obtained:

Anti-PD-L1 therapy increases the number of virus specific CD8 T cells: Peripheral blood mononuclear cells (PBMCs) were isolated from treated or untreated animals on days 7, 11, 15, 22, and 35. Cells specific for the $D^b$ GP33 epitope were assessed by tetramer staining. In two independent experiments it was found that animals treated with anti-PD-L1 therapy during the first 15 days following adoptive transfer developed significantly larger numbers of LCMV specific CD8 T cells when normalized to the number of $D^b$ GP33 positive cells per million PBMC's (FIG. 14). These data support the role of the PD-1/PD-L1 pathway in conferring some degree of proliferative suppression in normal memory T cells. Moreover these results suggest that therapeutic inhibition of this pathway could augment the development and maintenance of the secondary immune response generated following adoptive transfer into a setting of chronic infection with high antigen load.

Figure 15:
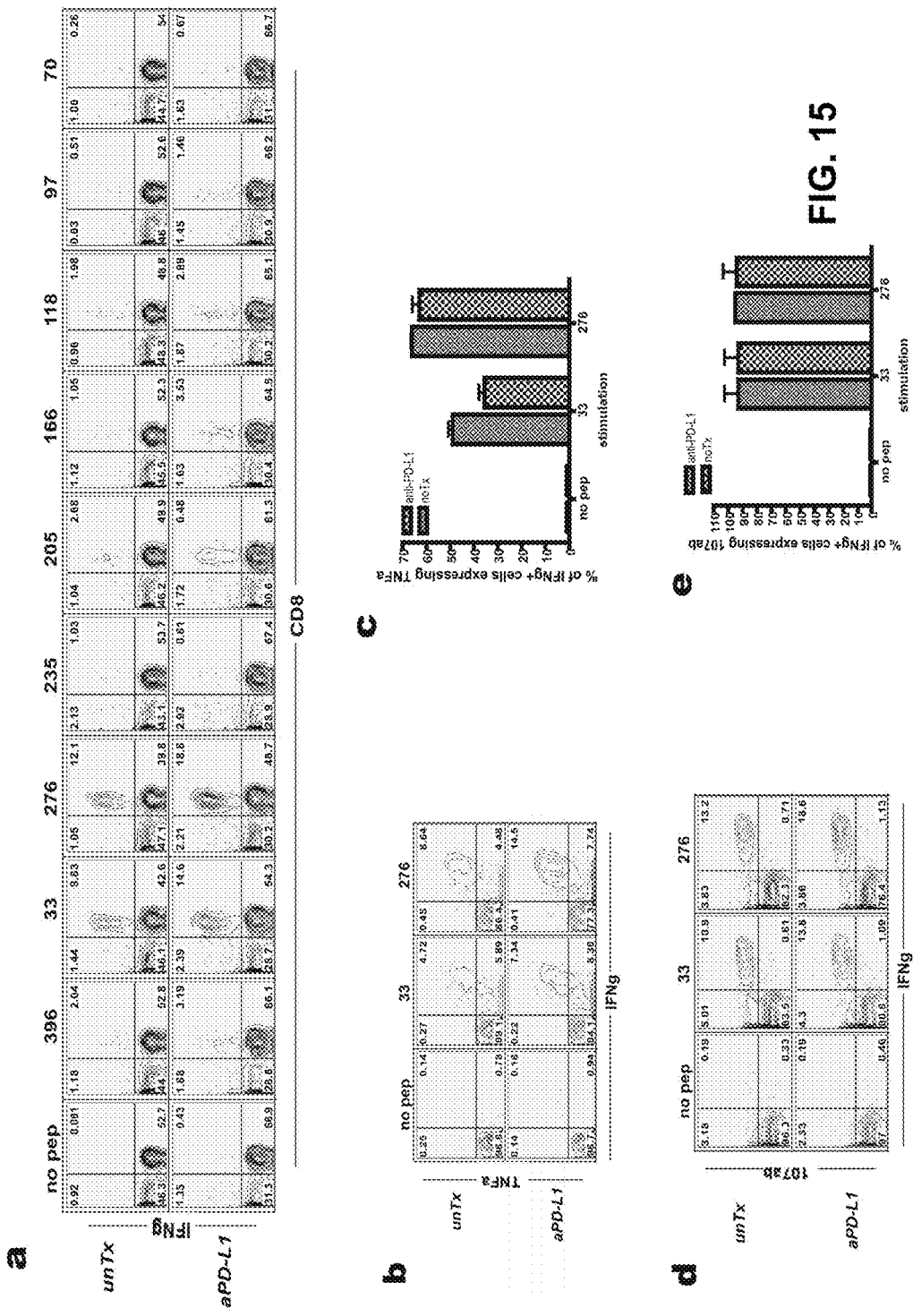
FIGS. 15A-15E are plots and graphs showing that blockade of the PD-1/PDL1 pathway following adoptive T cell immunotherapy enhances cytokine production in antigen specific CD8 T cells. Splenocytes were isolated at day 17 post-transfer and analyzed for cytokine expression upon stimulation with antigenic peptide.

PD-1/PD-L1 blockade enhances the functionality of antigen specific CD8 T cells: Spenocytes were isolated from treated and untreated animals on day 17 post-adoptive transfer and analyzed for the expression of inflammatory cytokines (IFN-gamma and TNF alpha) or CD107ab (lysomal associated membrane protein, LAMP). Across all defined CD8 epitopes, IFN gamma expression was found to be enhanced in animals receiving anti-PD-L1 blockade compared to untreated animals (FIG. 15a). Additionally, coexpression of IFN gamma and TNF alpha and CD107ab was also increased following anti-PD-L1 therapy (FIGS. 15B-15E). These findings indicate that adoptively transferred memory splenocytes expanding in the presence of PD-L1 blockade are functionally superior, in terms of inflammatory cytokine production and release of cytolytic granules, as compared to splenocytes from untreated animals.

Example 17

Murine B Cell Responses During PD-1 Blockade

The following experiments were performed in order to determine whether PD-1 blockade enhances B cell responses during chronic LCMV infection. Both B cell and T cell responses are critical in controlling chronic LCMV infection, thus improving B cell responses in chronic LCMV infected mice may help lower viral load and enhance T cell function.

The following material and methods were used in these experiments:

Mice and virus: Four- to six-week-old female C57Bl/6 mice were purchased from Jackson Laboratory (Bar Harbor, Me.). Prior to infection, chronic LCMV mice were depleted of CD4 T cells by administration of gk1.5 antibody. Previous data demonstrates that administration of 500 ug of gk1.5 days −2 and 0 prior to viral challenge results in 95-99% decrease in the number of CD4 T cells in the spleen and lymph node with the CD4 T cell numbers slowly recovering over 2 to 4 weeks. Mice received $2 \times 10^6$ PFU of the Clone-13 strain of LCMV intravenously on day 0 initiate chronic infection. Titers of virus were determined by a 6 day plaque assay on Vero cells.

Detection of ASC by ELISPOT: Spleen and bone marrow single cell suspensions were depleted of red blood cells by 0.84% $NH_4CL$ treatment and resuspended in RPMI supplemented with 5% FCS. Antibody secreting cells were detected by plating cells onto nitrocellulose-bottom 96-well Multiscreen HA filtration plates (Millipore). Plates were previously coated with 100 ul of 5 ug/ml of goat anti-mouse IgG+IgM+IgA (Caltag/Invitrogen) overnight at 4° C. Plates were then washed 3× with PBS/0.2% tween followed by 1× with PBS and blocked for 2 hours with RPMI+10% FCS to prevent non-specific binding. Blocking medium was replaced with 100 ul of RPMI 5% FCS and 50 ul of $1 \times 10^7$ cells/ml was plated in serial three-fold dilutions across the plate. Plates were incubated for 6 hours at 37° C. and 5% $CO_2$. Cells were removed and plates were washed 3× with PBS and 3× with PBS/0.2% tween. Wells were then coated with biotinylated goat anti-mouse IgG (Caltag/Invitrogen) diluted 1/1000 in PBS/0.2% tween/1% FCS and incubated overnight at 4° C. The secondary antibody was removed and plates were washed 3× with PBS/0.2% tween. Avidin-D HRP (Vector) diluted 1/1000 in PBS/0.2% tween/1% FCS was incubated for one hour at RT. Plates were washed 3× with PBS/0.2% tween and 3× with PBS and detection was carried out by adding 100 ml of horseradish peroxidase-$H_2O_2$ chromogen substrate. The substrate was prepared by adding 150 ul of a freshly made AEC solution (10 mg of 3-amino-9-ethylcarbazole (ICN) per ml dissolved in dimethylformamide (Sigma)) to 10 ml of 0.1 M sodium acetate buffer pH 4.8), filtering it through a 0.2-mm-pore-size membrane, and immediately before use adding 150 ml of 3% $H_2O_2$. Granular red spots appeared in 3 to 5 minutes, and the reaction was terminated by thorough rinsing with tap water. Spots were enumerated with a stereomicroscope equipped with a vertical white light.

Determination of total bone marrow cells: For calculation of the total ASC response in bone marrow, the response was multiplied by the marrow cells of two femurs by a coefficient of 7.9, since $^{59}Fe$ distribution studies have shown that 12.6% of total mouse bone marrow is located in both femurs combined. No differences have been detected among the ASC activities of bone marrow cells from the femur, tibia, humorous, rib, or sternum. Typically, two adult femurs yield $2.0 \times 10^7$ to $2.5 \times 10^7$ total bone marrow cells.

Flow Cytometry: Directly conjugated antibodies were purchased from Pharmingen (anti-B220, anti-CD4, anti-CD138 anti-CD95, anti-Ki67, anti-IgD biotinylated), or Vector labs (PNA). Strepavidin-APC was purchased from Molecular Probes. All staining was carried out at 4° C. in PBS supplemented with 1% FCS and 0.1% sodium azide. Cells were then fixed in 2% formaldehyde (in PBS) and analyzed on a FACS Calibur using CellQuest software (BD Biosciences).

Statistical analysis: Tests were performed using Prism 4.0 (GraphPad, San Diego, Calif.). Statistics were done using two-tailed, unpaired T test with 95% confidence bounds.

Figure 16A:
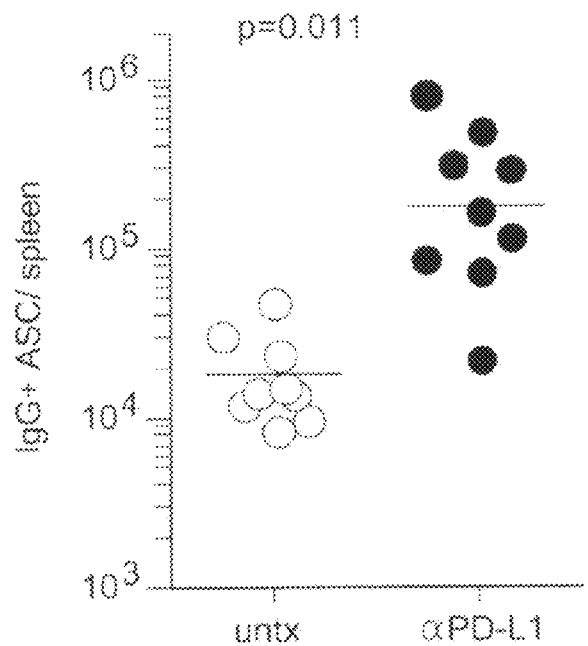
FIGS. 16A-16B are a graph and plots showing increased levels of Antibody Secreting cells in LCMV Clone-13 infected mice. Total ASC levels were measured in chronic LCMV infected mice following αPD-L1 treatment by ELISPOT and CD138 staining.
Figure 16B:
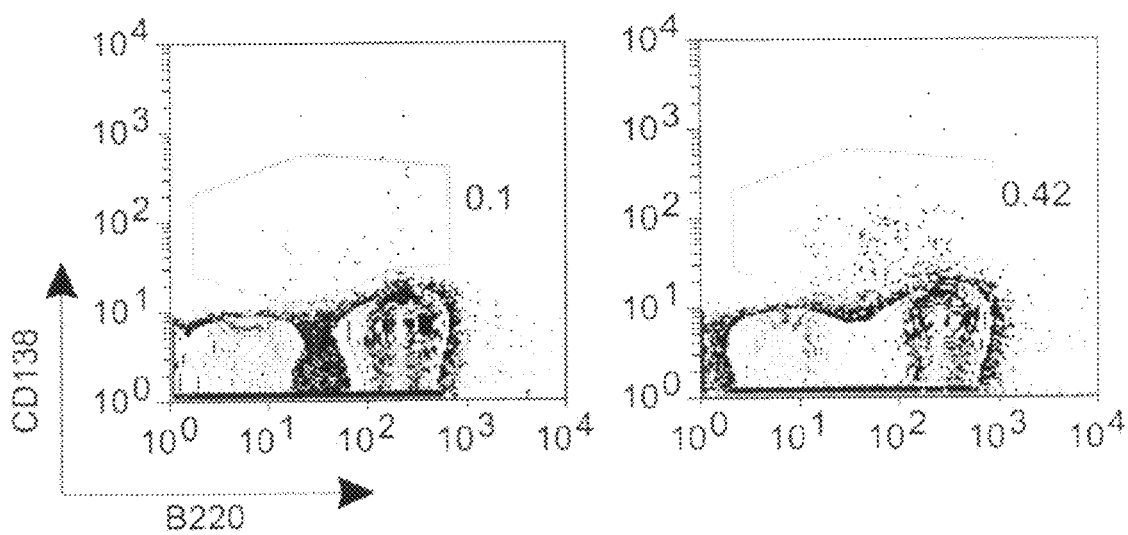

Total numbers of antibody secreting cells in the spleen is enhanced following in-vivo PD-1 blockade: Mice infected with LCMV Clone-13 were treated with anti (α)PD-L1 approximately 60 days post infection. Mice were administered 200 ug αPD-L1 every third day for two weeks. At day 14 of αPD-L1 treatment, the mice were sacrificed and the number of antibody secreting cells in the spleen was measured by ELISPOT and flow cytometric staining. In three separate experiments, mice treated with αPD-L1 showed significantly increased levels of antibody-secreting cells (ASC) in the spleen (p=0.011) as compared to untreated mice (FIG. 16a). ASC can be differentiated from B cells in the spleen by their down-regulation of the B cell marker B220 and by expression of CD138 (syndecam-1). In agreement with the ELISPOT results, increased numbers of $B220^{low/int}$ CD138+ cells were seen in infected mice treated with αPD-L1 (FIG. 16b).

Figure 17:
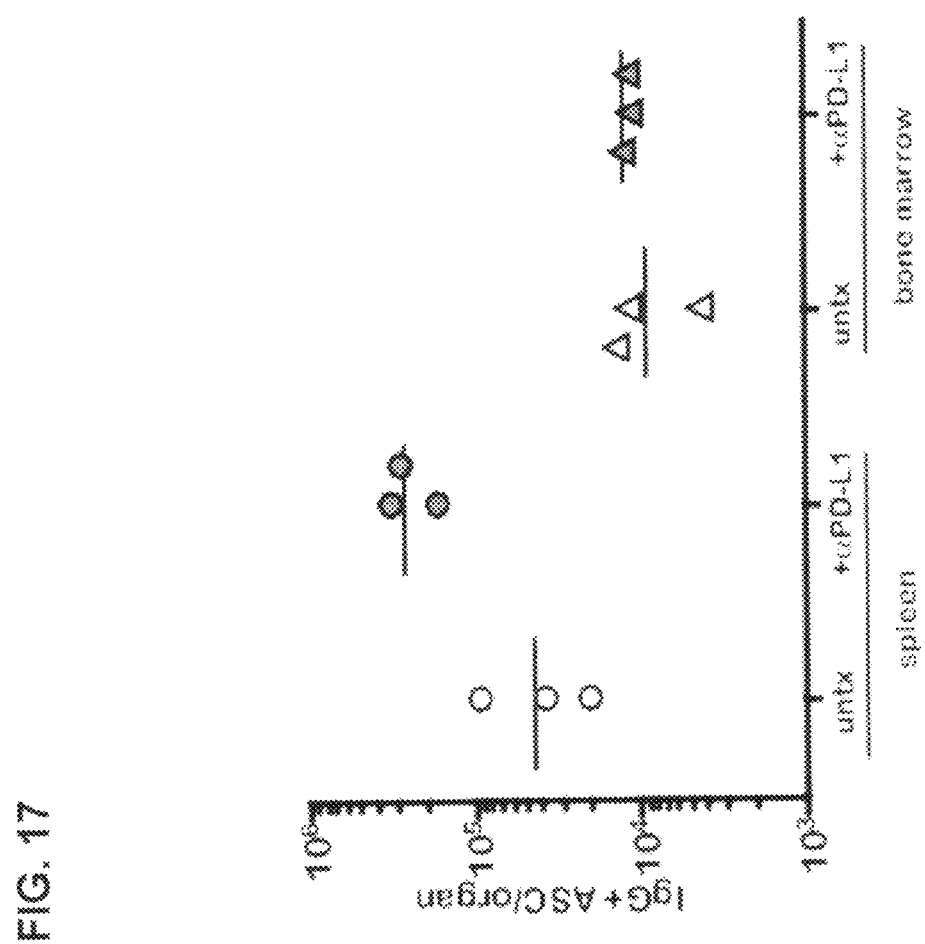
FIG. 17 is a graph showing treatment of chronic LCMV infected mice with anti-PD-L1 does not lead to elevated levels of bone marrow ASC. Total numbers of ASC were enumerated from the spleen and bone marrow of chronic LCMV infected mice 14 days post anti (α)PD-L1 treatment by ELISPOT. Line represents geometric mean within the group.

Treatment of chronic LCMV infected mice with αPD-L1 does not lead to elevated levels of bone marrow ASC. It was determined whether antibody secreting cells within the bone marrow were also enhanced during αPD-L1 treatment. The majority of long-lived plasma cells reside within the bone marrow, and these plasma cells are critical to long-term maintenance of serum antibody levels. Chronic LCMV infected mice were treated with αPD-L1 approximately 60 days post infection. Day 14 of αPD-L1 treatment, spleen and bone marrow ASC levels were measured by ELISPOT. Although there were elevated numbers of ASC in the spleen two weeks post-treatment, there was no change in the numbers of ASC in the bone marrow at this time-point (FIG. 17).

Figure 18:
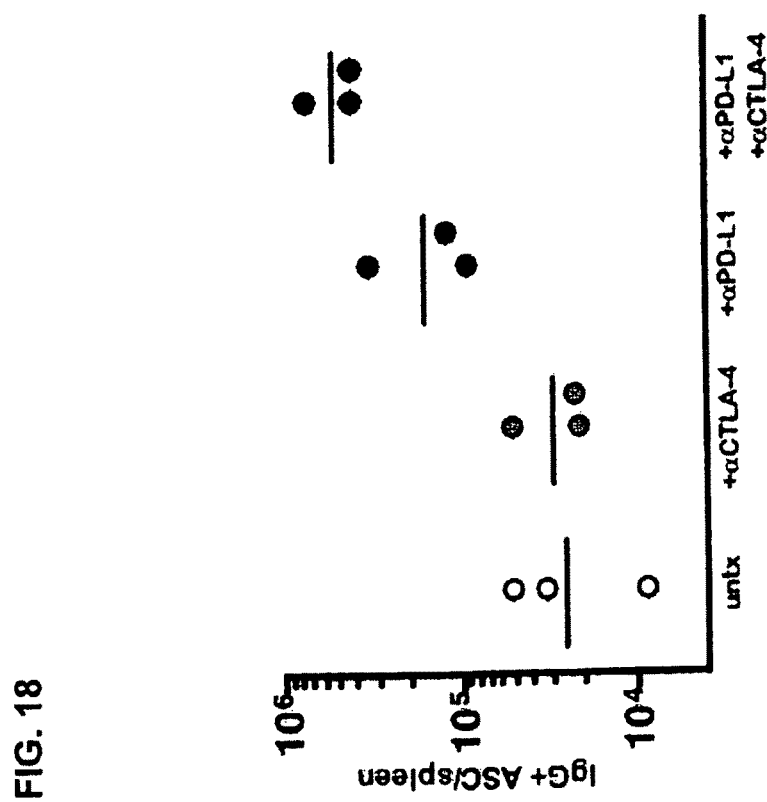
FIG. 18 is a graph showing that co-administration of αPD-L1 and αCTLA-4 leads to synergistic increases in splenic ASC. Chronic LCMV infected mice were administered αPD-L1, αCTLA-4, or both for 14 days and ASC in the spleen was enumerated by ELISPOT. Line represents geometric mean within treatment group.

Co-treatment of chronic LCMV infected mice with αPD-L1 and [130] αCTLA-4 results in synergistic increases in splenic ASC levels: It was further investigated whether blocking signaling with of another negative regulatory molecule, CTLA-4, would enhance the effect seen during the PD-1 blockade. CTLA-4 binding to B7 is thought to both compete with the positive co-stimulatory molecule CD28 and/or provide directly antagonizing TCR signals. Mice infected with LCMV Clone-13 were treated with either treated with αPD-L1, αCTLA-4, both or left untreated, and two weeks post-treatment the levels of antibody secreting cells were measured by ELISPOT. Although treatment with αCTLA-4 showed no impact on ASC levels, co-treatment of αPD-L1 with αCTL-4 led to a synergistic increase in ASC above that seen with αPD-L1 treatment alone (FIG. 18).

Figure 19B:
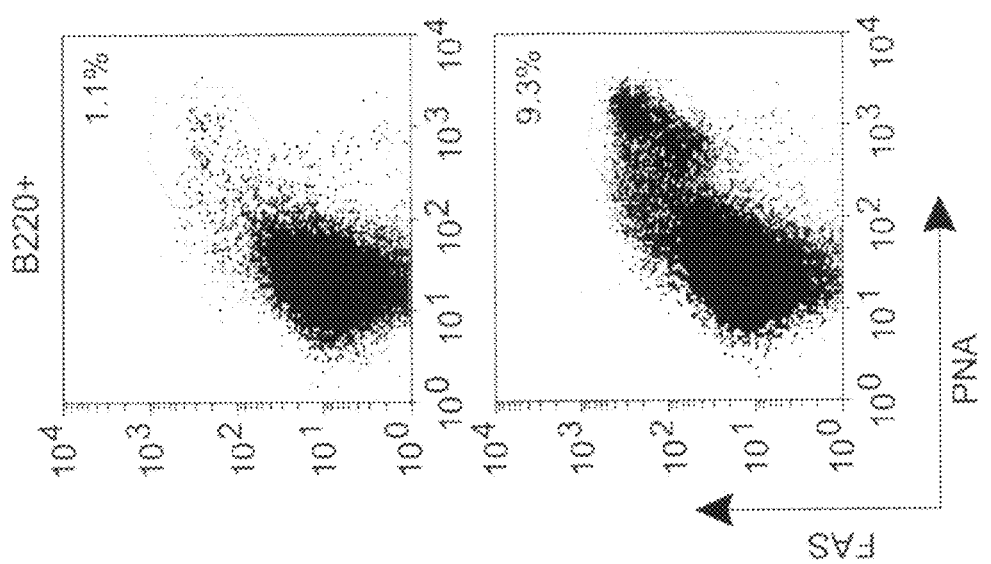
FIGS. 19A-19B are plots showing enhanced B cell and CD4 T cell proliferation and germinal center activity in αPD-L1 treated mice.
Figure 19A:
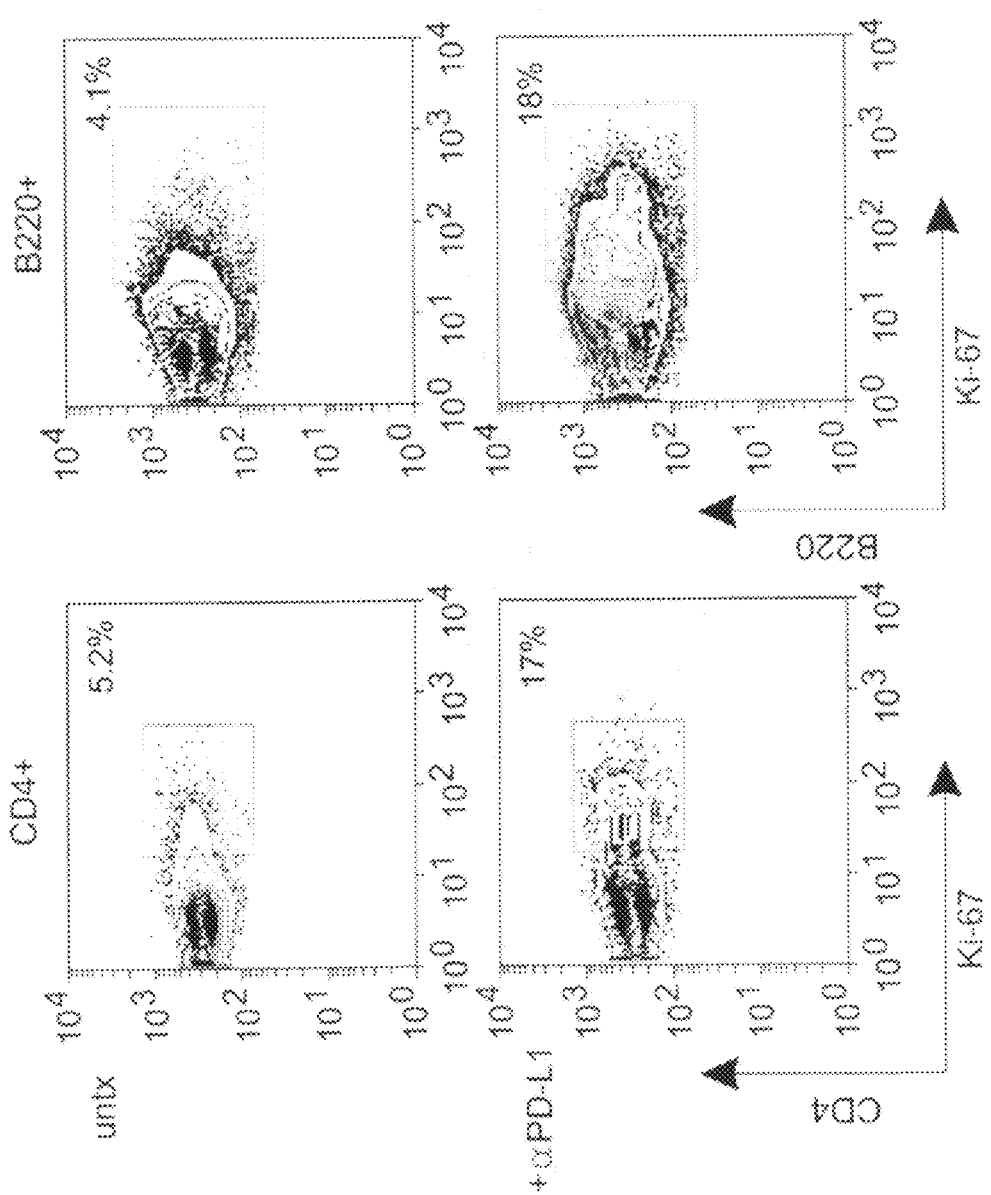

Enhanced B cell and CD4 T cell proliferation and germinal center activity in αPD-L1 treated mice: Flow cytometric analysis of spleen populations in chronic mice treated with αPD-L1 showed enhanced levels of proliferation by increased Ki-67 staining in both CD4 T cells and B cells. B cells within the germinal center reaction can be identified in the spleen by high levels of PNA and FAS staining. Following αPD-L1 treatment, there was a large increase in the frequency of PNA+FAS+ B cells compared to untreated controls (FIG. 19a-19b).

Example 17

PD-1 Expression on Human T Cells

CD8 T cells are essential for the control of many chronic infections. As disclosed herein, these CD8 T cells become exhausted following chronic antigenic stimulation, which is characterized by the induction of a hypoproliferative state and loss of the ability to produce anti-viral cytokines. Exhausted T cells have high expression of programmed death-1 (PD-1) and, also PD-1 is upregulated by T cell activation and can be triggered by the PD-1 ligands, PD-L1 and PD-L2. It is disclosed herein that the PD-1 inhibitory pathway is an important mediator of CD8 T cell exhaustion during a chronic viral infection in mice. Virus specific CD8 T cells maintained high levels of PD-1 expression in response to a chronic infection, but not in response to an infection that is successfully eliminated. Blocking the interaction of PD-1/PD-L1 interaction resulted in enhanced CD8 T cell proliferation, production of anti-viral cytokines, and a reduction in viral load.

It was evaluated whether CD8 T cells specific for chronic infections in humans express PD-1, and whether PD-1 blockade enhances CD8 T cells responses. This study (1) determined the expression pattern of PD-1 on subsets of human peripheral blood mononuclear cells (PBMC): CD4, CD8, B cell, NK, monocytes, DC; (2) Determined the phenotype of CD4 and CD8 T cells that express PD-1; (3) determined PD-1 expression on chronic persistent antigen [(Epstein-Barr virus (EBV) and cytomegalovirus (CMV)] and acute resolved antigen (influenza and vaccinia)-specific cells; and (4) determined the effect of blocking PD-1/PD-L1 interaction on the proliferation of antigen-specific cells.

The following materials and methods were used in these studies:

Blood samples: Peripheral blood samples were obtained from 36 healthy individuals who were seropositive for EBV, CMV, influenza or vaccinia viruses. These subjects were selected based on their HLA allele expression matching HLA class I tetramers specific for EBV, CMV, influenza or vaccinia virus proteins. PBMC were isolated from the blood samples over lymphocyte-separation medium (Cellgro, Herndon, Va.).

Antibodies, peptides and tetramers: Phycoerythrin-conjugated anti-human PD-1 (EH12, mouse IgG1) and unconjugated human PD-L1 (29E.2A3, mouse IgG2b) were obtained. Directly conjugated antibodies were obtained from Beckman Coulter, San Diego, Calif. (anti-CD3, CD11a, CD27, CD28, CD38, CD45RA, CD57, CD62L and granzyme-B), BD Pharmingen, San Diego, Calif. (CD8, CD95, CD195, HLA-DR, Ki-67 and perforin), and R&D systems, Minneapolis, Mass. (CCR7). Peptides were made at the peptide synthesis lab at Emory University, Atlanta, Ga. The plasmid constructs expressing HLA-A2, -B7 and -B8 were kindly provided by the NIH Tetramer Core Facility, Atlanta, Ga. and APC-labeled MHC class I/peptide tetramers carrying CTL epitopes of EBV (HLA-A2-GLCTLVAML (SEQ ID NO: 36), HLA-B8-RAKFKQLL (SEQ ID NO: 37) and FLRGRAYGL (SEQ ID NO: 38)), CMV (HLA-A2-NLVPMVATV (SEQ ID NO: 39), HLA-B7-TPRVTGGGAM (SEQ ID NO: 40)), influenza (HLA-A2-GILGFVFTL (SEQ ID NO: 41)) and vaccinia (HLA-A2-CLTEYILWV (SEQ ID NO: 42) and KVDDTFYYV (SEQ ID NO: 43)).

Immunophenotyping and CFSE proliferation: Heparinised human whole blood samples (200 ul) were stained with antibodies or tetramers and then analyzed (Ibegbu et al., *J Immunol.* 174: 6088-6094, 2005) on a FACS Calibur using CellQuest software or on a LSRII flow cytometer using FACSDiva software (BD Immunocytometry Systems). For CFSE assays, PBMC ($2\times10^6$/ml) were washed thoroughly and labeled with 3 μM carboxy-fluorescein diacetate, succinimidyl ester (CFSE, Molecular Probes) at room temperature in dark for 5 min (see, for example, Weston and Parish, *J Immunol Methods* 133:87-97, 1990). The CFSE labeled PBMC were stimulated with either peptide alone (1 μg/ml) or peptide with anti-PD-L1 antibody (10 μg/ml). Control cultures consisted of either PBMC alone, PBMC with anti-PD-L1 antibody or PBMC with an isotype control antibody (IgG2b; 10 μg/ml). Following a 6-day incubation at 37° C., the cells were washed and stained with tetramer along with anti-CD3 and -CD8 antibodies extracellularly.

The following results were obtained:

Expression pattern of PD-1 on PBMC subsets: PD-1 expression was examined on PBMC subsets in healthy individuals. It was observed that CD8+ T cells, CD4+ T cells and monocytes (CD14+) express high levels of PD-1, B cells (CD20+) express low levels of PD-1 and NK cells (CD56+) and DC (CD11c+) do not express PD-1.

Figure 20A:
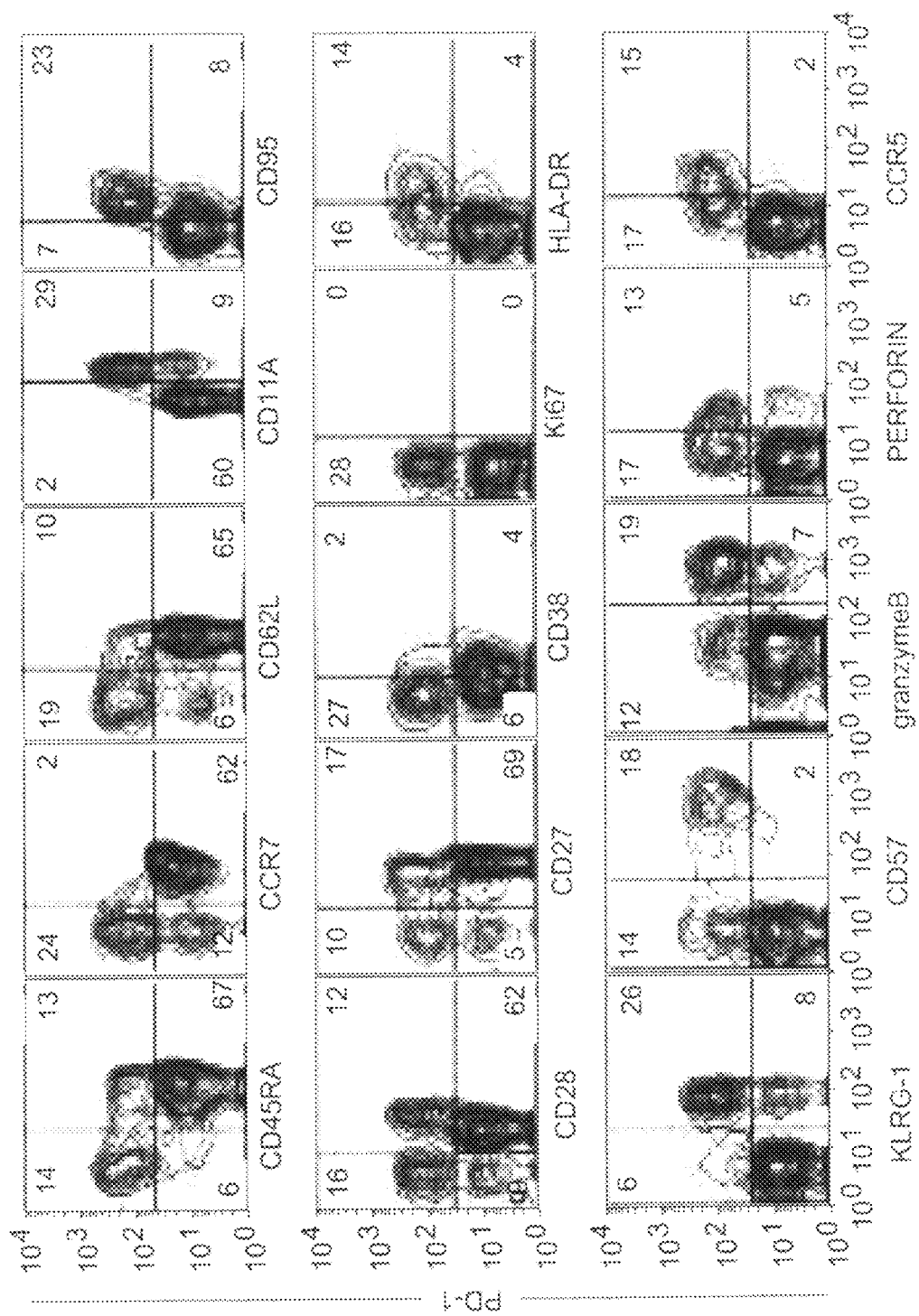
FIGS. 20A-20C are plots and graphs showing PD-1 expression on CD8 and CD4 T cell subsets.
Figure 20B:
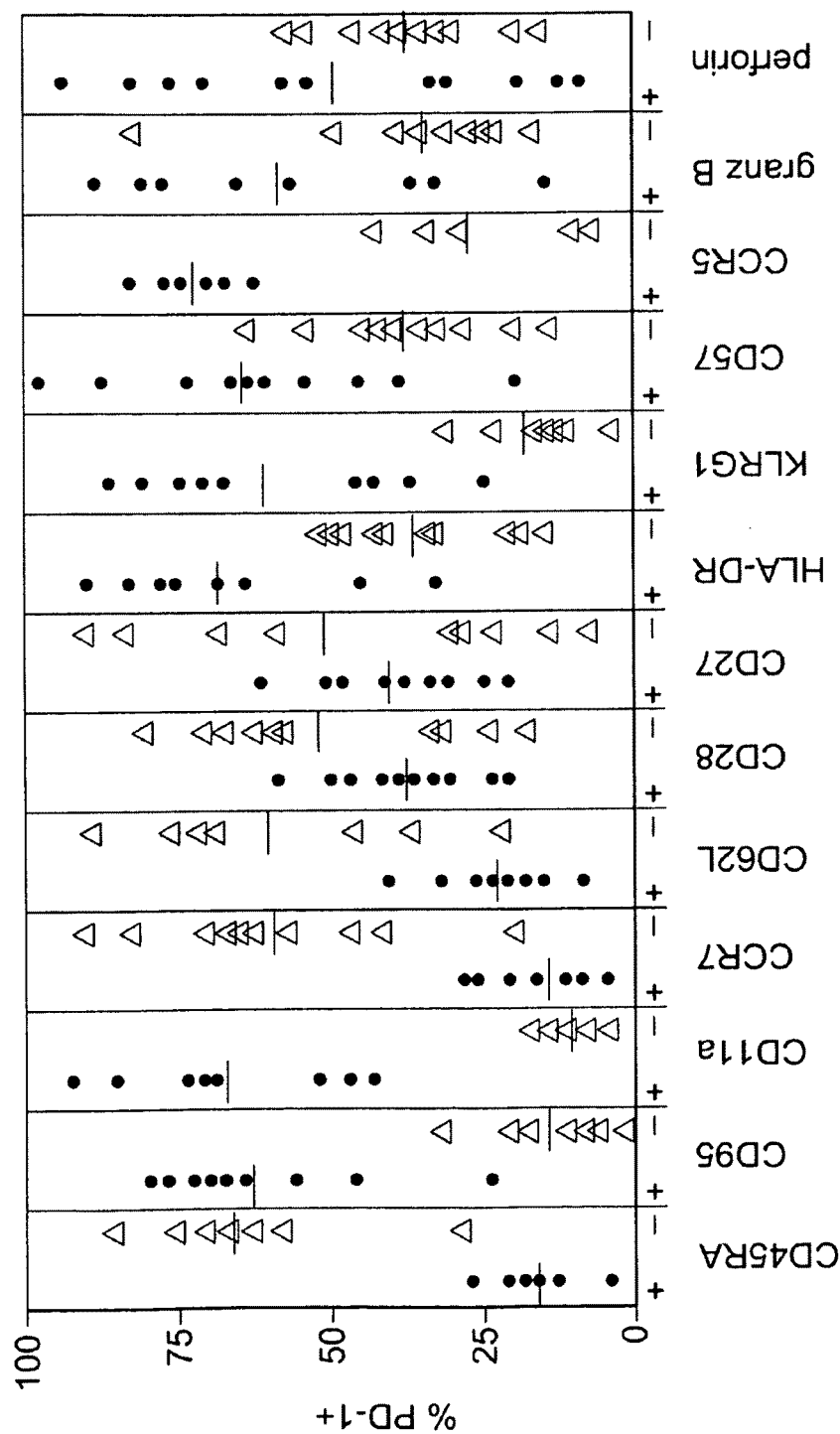
Figure 20C:
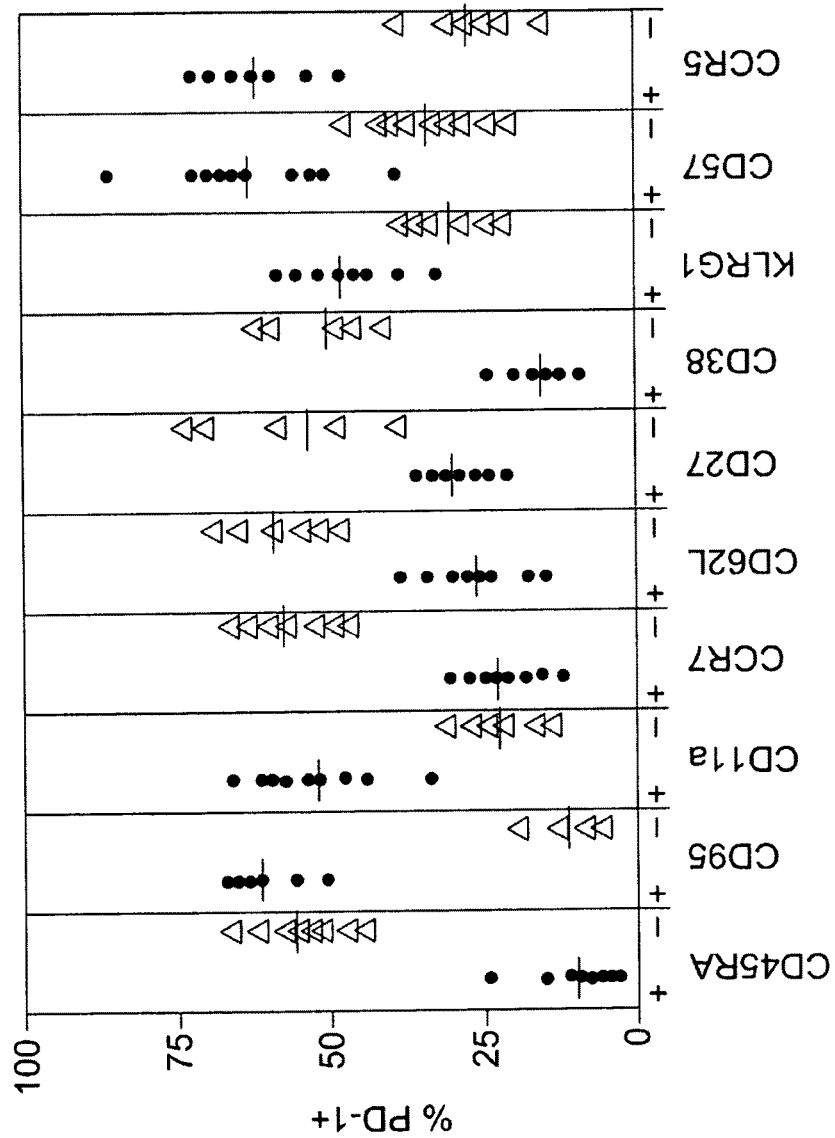

PD-1 is preferentially expressed among effector memory CD8 and CD4 T cells: CD8 T cells from normal healthy individuals were examined for co-expression of PD-1 with various phenotypic markers associated with differentiation state and function (FIG. 20A). In summary, naïve and central memory phenotype CD8 T cells only expressed low levels of PD-1, whereas CD8 T cells that expressed various markers associated with effector/effector memory/or exhausted phenotype also expressed high levels of PD-1 (FIG. 20B). These data suggested that PD-1 was preferentially expressed among effector memory CD8 T cells. When the CD4 T cells were examined we found similar trend (FIG. 20C).

PD-1 is upregulated on persistent antigen-specific memory CD8 T cells: To evaluate whether CD8 T cells specific for chronic infections in humans show increased expression of PD-1, PD-1 expression on memory CD8 T cells specific for chronic persistent viruses (EBV and CMV) was compared with acute virus specific T cells (influenza and vaccinia) in 36 healthy individuals by staining with EBV-, CMV-, influenza- and vaccinia virus-specific tetramers (FIGS. 21A-21B). FIG. 21A shows representative PD-1 GMFI of EBV, CMV, influenza and vaccinia virus-specific CD8 T cells. PD-1 expression was found to be increased on EBV-specific CD8 T cells than influenza (p=0.0335) and vaccinia (p=0.0036) virus-specific CD8 T cells (FIGS. 21A-21B). Similarly, CMV-specific CD8 T cells more frequently expressed PD-1 than influenza (p=0.0431) and vaccinia (p=0.019) (FIGS. 21A-21B). These results suggest a correlation between PD-1 expression and antigen experience.

Figure 22A:
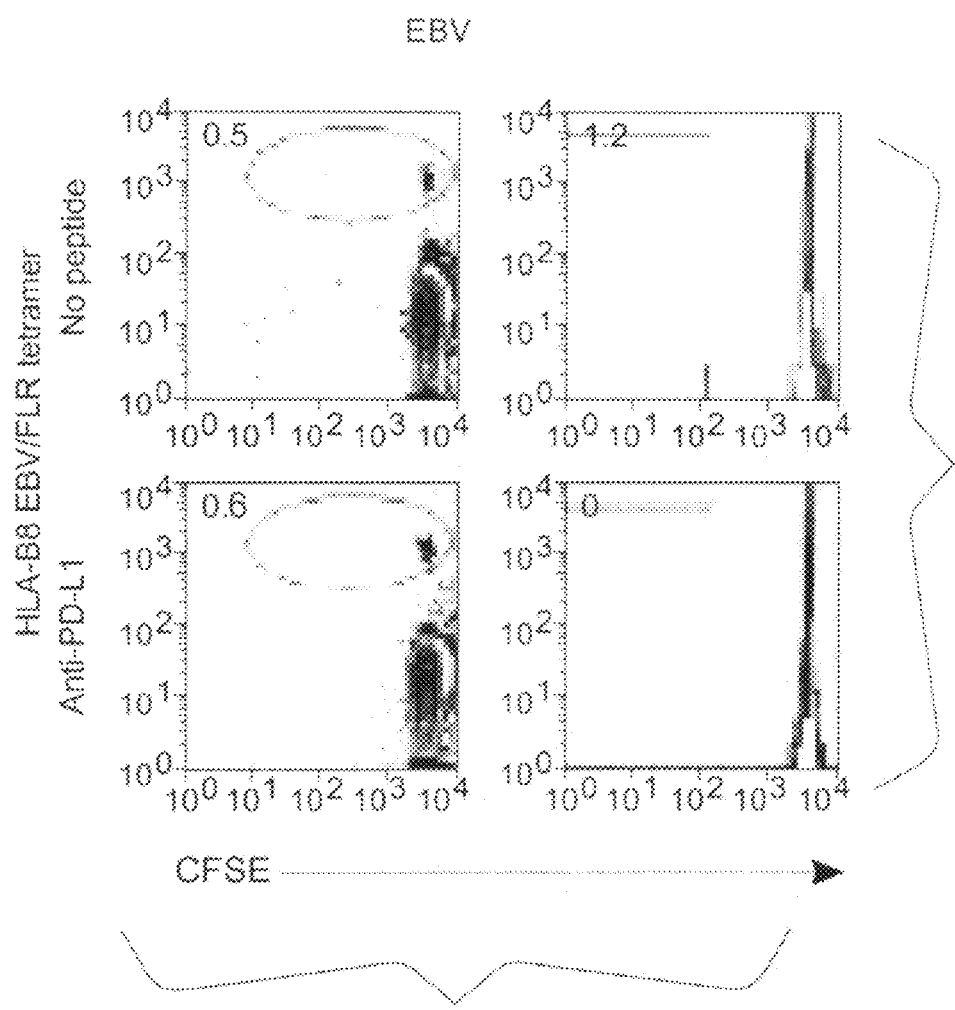
Figure 22A:
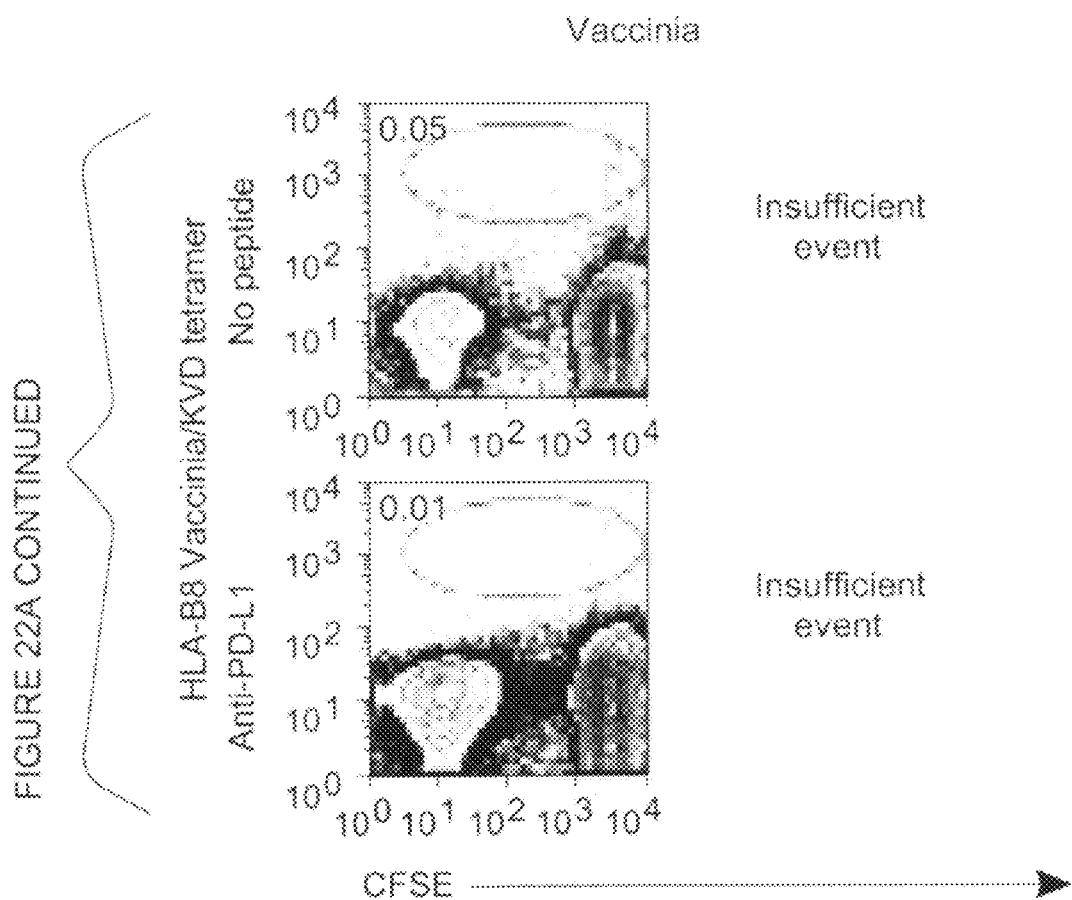
Figure 22A:
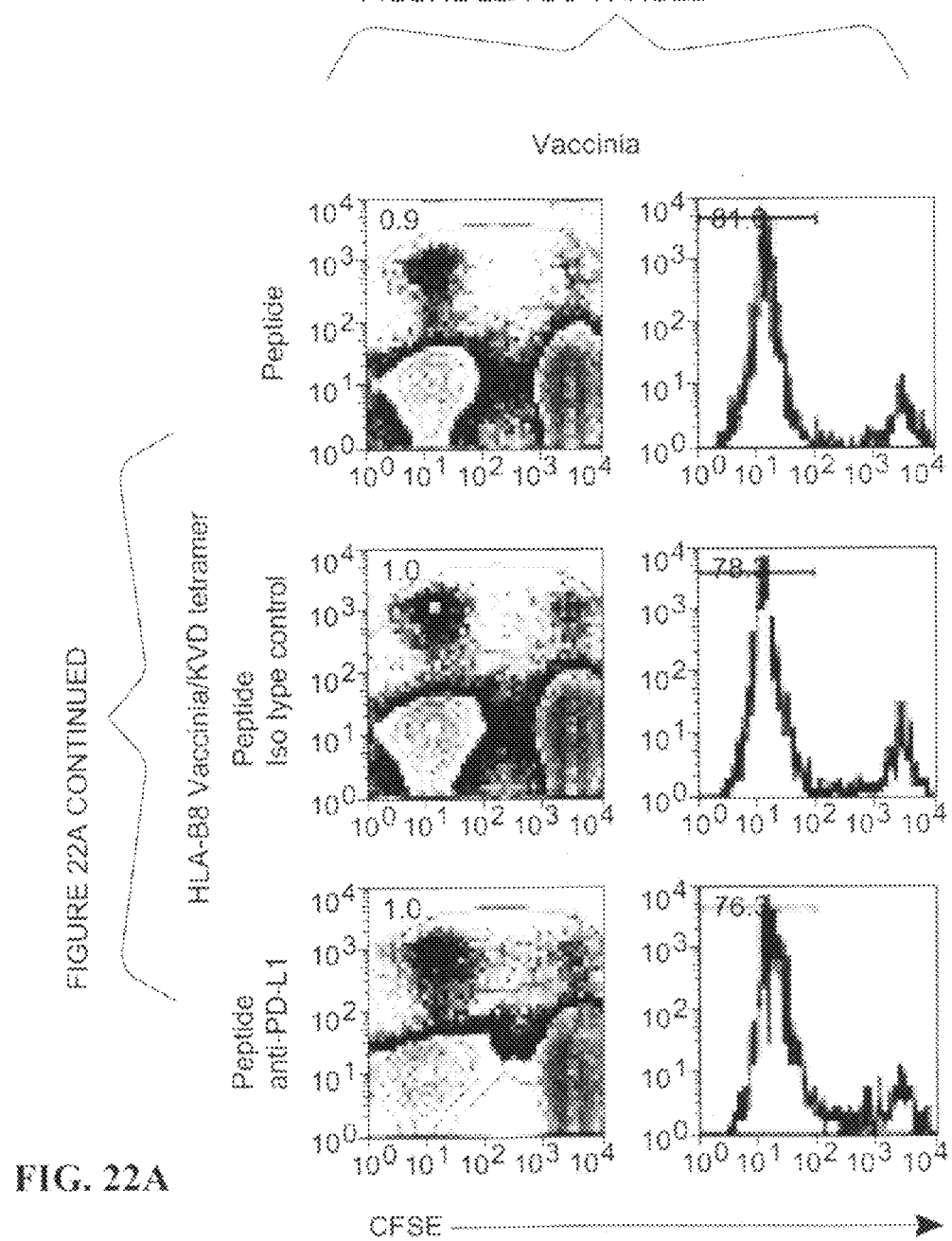
Figure 22C:
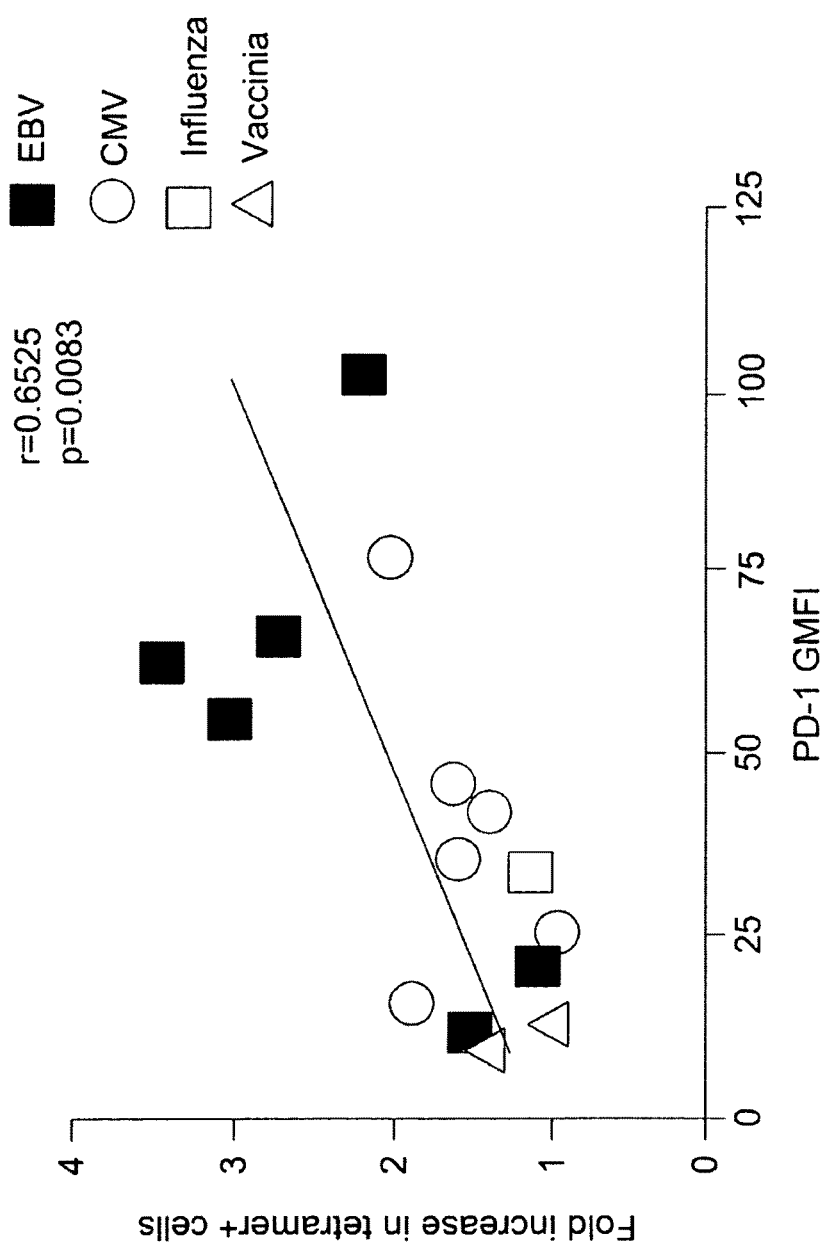

Anti-PD-L1 blockade increases proliferation of chronic persistent virus-specific CD8 T cells: It was assessed whether PD-1 blockade enhances persistent antigen-specific CD8 T cell responses similar to the results observed in mice. CFSE labeled cells were stimulated with either EBV, CMV, influenza or vaccinia virus-specific peptides in the presence or absence of anti-PD-L1 antibodies. After 6 days, the percentage of tetramer+ CFSE$^{lo}$ cells and CD8+ CFSE$^{lo}$ cells was compared between cultures that were stimulated with peptide alone and cultures that were stimulated with peptide and subsequently blocked with anti-PD-L1. Representative flow cytometry plots with proliferation of CMV and EBV-specific CD8 T cells are shown in FIG. 22A. Aggregated data from CMV (n=5), EBV (n=6), influenza (n=2) and vaccinia (n=2) seropositive individuals are shown in FIG. 22B. Blocking PD-1/PD-L1 interaction with anti-PD-L1 antibody resulted in increased proliferation of EBV and CMV-specific CD8 T cells whereas influenza and vaccinia virus-specific CD8 T cells did not show proliferation following blocking with anti-PD-L1. These results show that in the presence of peptide plus anti-PD-L1 blocking antibody, there is up to 3.5-fold increase in the frequency of EBV or CMV-specific CD8 T cells compared to stimulation with the peptide alone. It was assessed whether the proliferation of antigen-specific CD8 T cells following anti-PD-L1 antibody blockade is related to the PD-1 expression by these cells. The data indicate a positive correlation between PD-1 expression and proliferation of antigen-specific CD8 T cells (p=0.0083) (FIG. 22C).

Example 18

Liver Infiltrating Lymphocytes in Chronic Human HCV Infection Display an Exhausted Phenotype with High PD-1 and Low CD127 Expression The experiments described below document that chronic HCV infection, peripheral HCV-specific T cells express high levels of PD-1 and that blockade of the PD-1/PD-L1 interaction led to an enhanced proliferative capacity. Importantly, intrahepatic HCV-specific T cells not only express high levels of PD-1 but also decreased IL-7 receptor alpha (CD127), an exhausted phenotype that was HCV antigen specific and compartmentalized to the liver, the site of viral replication.

Currently, no vaccine exists to prevent HCV infection and the only licensed therapy, alpha interferon (IFNα), either alone or in combination with the nucleoside analog ribavirin is expensive, associated with, at best, only a 50% clearance rate for the most prevalent genotype (genotype 1) and complicated by significant side effects. The paucity of efficacious anti-HCV therapeutic options highlights the need for effective interventions aimed at augmenting or supplementing the natural immune response that, alone or in concert with antiviral drug therapy, can prevent the detrimental consequences of HCV infection.

Currently, little is known about the expression of PD-1 and its role in T cell exhaustion in chronic HCV infection, particularly at the site of active infection, the liver. The present study was undertaken to better understand the T cell phenotype in HCV infection by measuring expression of PD-1 on antigen-specific CD8+ T cells in both the liver and peripheral blood of patients with chronic HCV infection.

The following materials and method were used in these studies:

Subjects: Seventeen patients with chronic HCV infection (HCV antibody and HCV PCR positive) and negative for HIV by antibody screening were enrolled in the study. All patients were naïve to HCV anti-viral therapies prior to enrollment. Seven of the fifteen patients were positive for HLA-A2 by FACS analysis. The patient characteristics are summarized in Table 5.

TABLE 5

Patient cohort demographic and clinical data

| Patient Identification | Gender | Age | HLA-A2 | HCV Genotype | Baseline Viral Load (IU/ml) | ALT |
|---|---|---|---|---|---|---|
| 153 HCV* | M | 43 | + | 2b | 7,340,000 | 25 |
| 178 HCV* | F | 48 | + | 2 | 18,330,000 | 62 |
| 179 HCV | M | 54 | − | 1a | 197,000 | 197 |
| 183 HCV | F | 56 | + | 1a | 1,170,000 | 45 |
| 190 HCV | M | 52 | − | 1a | 5,990,000 | 27 |
| 193 HCV | M | 66 | + | 1a | 16,120,000 | 30 |
| 601 HCV | M | 60 | − | 1b | 4,690,000 | 25 |
| 602 HCV | M | 48 | − | 1a | 586,000 | 80 |
| 603 HCV | M | 58 | + | 1a | 1,820,000 | 36 |
| 604 HCV | M | 58 | − | 1a | 2,850,000 | 57 |
| 605 HCV | F | 30 | − | 1 | 819,000 | 57 |
| 606 HCV | M | 50 | − | 1b | 591,000 | 18 |
| 607 HCV | M | 59 | + | 3a | 343,000 | 31 |
| 608 HCV | M | 57 | − | 1b | 395,000 | 16 |
| 609 HCV | M | 55 | + | 1a | 833,000 | 67 |
| 611 HCV | M | 53 | − | 1a | 1,220,000 | 88 |
| 613 HCV | M | 59 | − | 1b | 6,160,000 | 40 |

HCV antibody testing, viral load determination and genotyping: HCV antibody testing by ELISA was performed using a kit per the manufacturer's instructions (Abbott Diagnostics, Abbott Park, Ill.; Bio-Rad Laboratories, Hercules, Calif.). HCV viral load quantification was performed using a real-time RT-PCR assay (Roche Molecular Systems, Alameda Calif.). HCV genotyping was performed using a real-time RT-PCR assay (Abbott Diagnostics, Abbott Park, Ill.) and using a line probe assay (LIPA) (Bayer Diagnostics, Research Triangle Park, N.C.).

Peripheral blood mononuclear cells: EDTA and heparin anticoagulated blood (50-70 ml) was collected from each patient and either used directly for FACS staining or for PBMC isolation. PBMCs were isolated using Ficoll-Paque PLUS density gradient (Amersham, Oslo, Norway), washed twice in PBS, and either analyzed immediately or cryopreserved in media containing 90% fetal calf serum (Hyclone) and 10% dimethyl sulfoxide (Sigma-Aldrich, St. Louis, Mo.).

Liver biopsy: Liver tissue was obtained by either ultrasound-guided needle biopsy or via transjugular fluoroscopic technique and immediately put into RPMI-1640 medium (Gibco) containing 10% fetal calf serum (Hyclone, Logan, Utah) for immunological assays. Another fragment was fixed in formalin for histological examination.

Intrahepatic T cell isolation: The liver biopsy sample obtained in RPMI-1640 medium (Gibco, Carlsbad, Calif.) containing 10% fetal calf serum (Hyclone, Logan, Utah) was washed three times with the same media to remove cell debris and RBCs. Isolation of liver infiltrating lymphocytes was performed using an automated, mechanical disaggregation system (Medimachine, Becton Dickinson, San Jose Calif.). The sample was inserted into a 50 µm Medicon and inserted into the Medimachine and run for 15 seconds. Dissagregated cells were removed using a syringe in the syringe port. The Medicon was rinsed twice with RPMI medium (Gibco, Carlsbad, Calif.) containing 10% fetal calf serum (Hyclone, Logan, Utah) to ensure maximum cell recovery. Cells were used immediately for FACS staining.

Antibodies, HLA-A2 tetramers and flow cytometry: Cells were stained with FITC, PE, PerCP and APC labeled monoclonal antibodies or tetramers according to the manufacturers' instructions and flow cytometry performed using FACS Calibur (Becton Dickinson, San Jose, Calif.). FACS data were analyzed with FlowJo software (Treestar). The following monoclonal antibodies from BD Pharmingen (BD Biosciences, San Jose, Calif.) were used: Anti-CD8 PerCP and anti-CD45RA APC. Anti-CD62L FITC, CD3 FITC and CD127 PE were obtained from Beckman Coulter (Fullerton, Calif.). Anti-PD-1 PE conjugated antibody (clone EH12) was generated as described (Dorfman et al., Am. J. Surg. Pathol. 30:802-810, 2006). HLA-A2 tetramers were specific for the following CD8+ T cell epitopes: HCV 1073: CINGVCWTV (SEQ ID NO: 44); HCV-1406: KLVALGI-NAV (SEQ ID NO: 45). Flow cytometric collection was performed on a FACSCaliber™ (BD Biosciences, San Jose, Calif.) and analysis performed using FlowJo software (v8.1.1).

CFSE labeling and antibody blockade: $10 \times 0^6$ PBMCs were washed with PBS and labeled with 3 μM CFSE (Molecular Probes). Cells were adjusted to $1 \times 10^6$ cells/ml and cultured in the presence of 2 μg/ml of A2-HCV 1073 (CINGVCWTV, SEQ ID NO: 44) peptide. 10 U/ml of IL-2 were added on day 3 post stimulation. An unstimulated control was included in each assay. Specific blocking antibodies (anti-PD-L1; clone #29E and anti-PD-1; clone #EH12 (Dofman et al., supra) were added to cell cultures at a concentration of 10 ng/ml at the time of stimulation. Cells were incubated for 6 days, harvested and stained with surface antibodies and tetramers and analyzed by flow cytometry.

Statistical analysis: Results were graphed and analyzed using GraphPad Prism (v4). Comparisons made within the same patient were performed using paired t tests. Comparisons made between patients were made using unpaired t tests.

Figure 23:
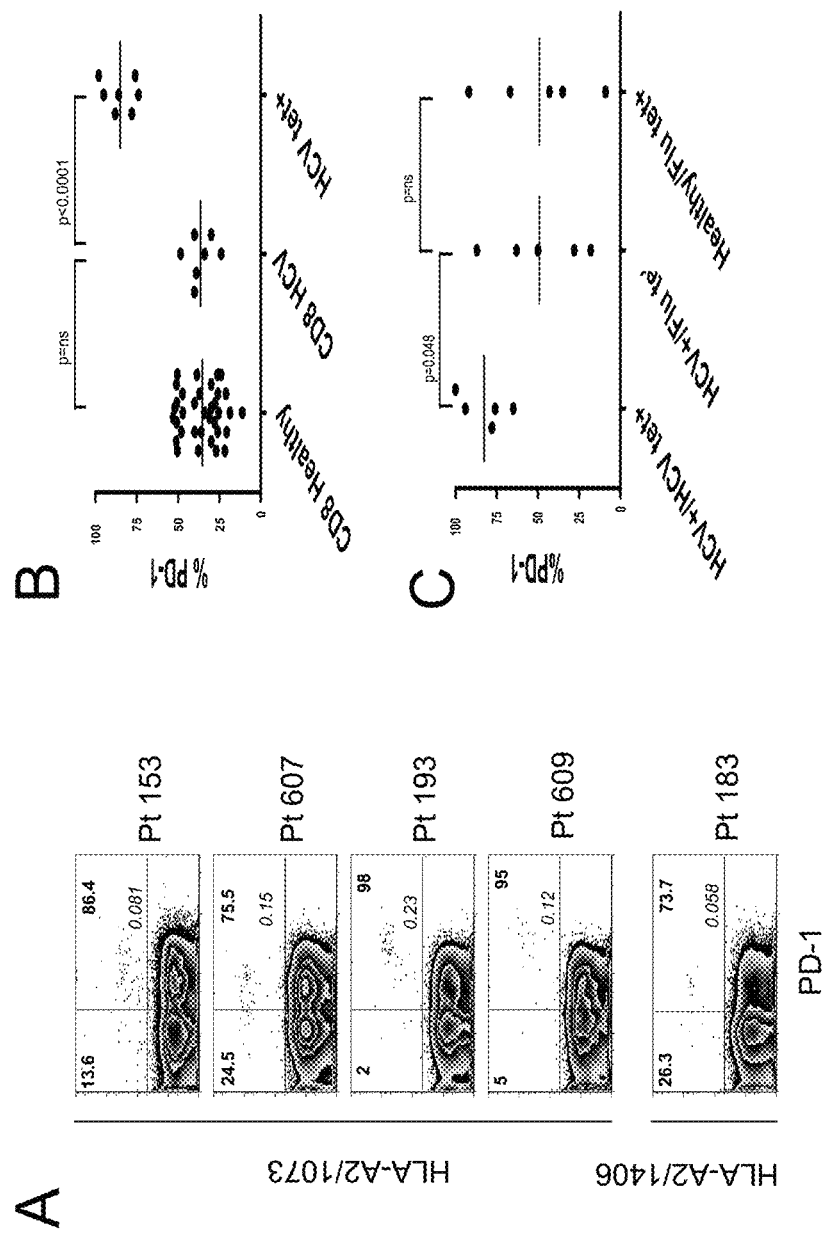
FIGS. 23B-23C are plots and graphs showing hepatitis C virus (HCV) specific CD8+ T cells express PD-1 in human chronic HCV infection.
FIG. 23A are representative plots from five patients with chronic HCV infection showing the expression of PD-1 on HCV specific CD8+ T cells. Numbers in bold identify the frequency of PD-1 expression (x-axis) on HCV specific CD8+ T cells (y-axis). Numbers in italics within the plots identify the frequency of tetramer positive cells among total CD8+ T cells. On the y-axis, 1073 and 1406, identify the HCV epitope specificity of the tetramer. Patients are identified by "Pt" followed by the patient number. Cells were gated on CD8+ lymphocytes. Plots are on a logarithmic scale.

The following results were obtained:

PD-1 expression on HCV antigen specific CD8+ T cells: Seventeen patients with HCV infection (all HIV negative) were studied (Table 1). Fifteen patients underwent both blood and liver sampling for phenotyping by flow cytometric analysis, and all were untreated with pharmacologic antiviral therapy prior to study enrollment. Seven patients in the cohort were HLA-A2 positive and demonstrated a population of HCV specific CD8+ T cells in the periphery by HLA tetramer staining (Table 1). These HCV specific CD8+ T cells were evaluated for PD-1 expression (FIG. 23A). The level of PD-1 expression on total CD8+ T cells in the peripheral blood from healthy donors was not significantly different from that of the total pool of peripheral CD8+ T cells from HCV infected patients (FIG. 23B). In contrast, the majority of HCV-specific tetramer positive CD8+ T cells sampled from the peripheral blood were PD-1 positive (mean 85%, SEM 3.6) (FIG. 23A) with significantly higher expression than that of the total CD8+ T cell population (p<0.0001) (FIG. 23B). Expression of differentiation, co-stimulatory, trafficking and effector function molecules on antigen specific CD8+ T cells was also investigated. The HCV-specific tetramer positive cells exhibit a memory phenotype (high CD11a, low CD45RA), early differentiation markers (high CD27, high CD28, intermediate expression of CCR7 and CD62L) and low levels of mediators of effector function granzyme B and perforin. Interestingly, these HCV tetramer positive T cells in the peripheral blood expressed high levels of CD127 (IL-7 receptor a chain), a phenotypic marker that when expressed at low levels identifies impaired memory T cell differentiation.

To determine whether the phenotype of CD8+ T cells was different in the setting of non-chronic infection, Flu-specific T cells were examined in five healthy HLA-A2+ donors who were not infected with HCV. The percentage of peripheral Flu tetramer+ CD8+ T cells that expressed PD-1 was 49% (SEM 14.1) (FIG. 23C). Five of the seven HLA-A2 positive chronic HCV patients were also identified by tetramer analysis to have Flu specific CD8+ T cells. The percentage of Flu-specific T cells expressing PD-1 in these chronically infected HCV patients was not significantly different from the same population in healthy donors (FIG. 23C). Importantly, because five of the seven HLA-A2+ HCV patients also had detectable Flu specific CD8+ T cells, a comparison could be made, within each patient, of PD-1 for T cells specific for a non-chronic (Flu) and chronic (HCV) infection. The difference between Flu-specific and HCV-specific T cell expression of PD-1 expression was significant (FIG. 23C). The percentage of HCV specific CD8+ T cells expressing PD-1 (mean 83%, SEM 6.4) was greater than the percentage of PD-1+ Flu specific CD8+ T cells (49%, SEM 12.3) (p=0.048) (FIG. 23C).

Figure 24:
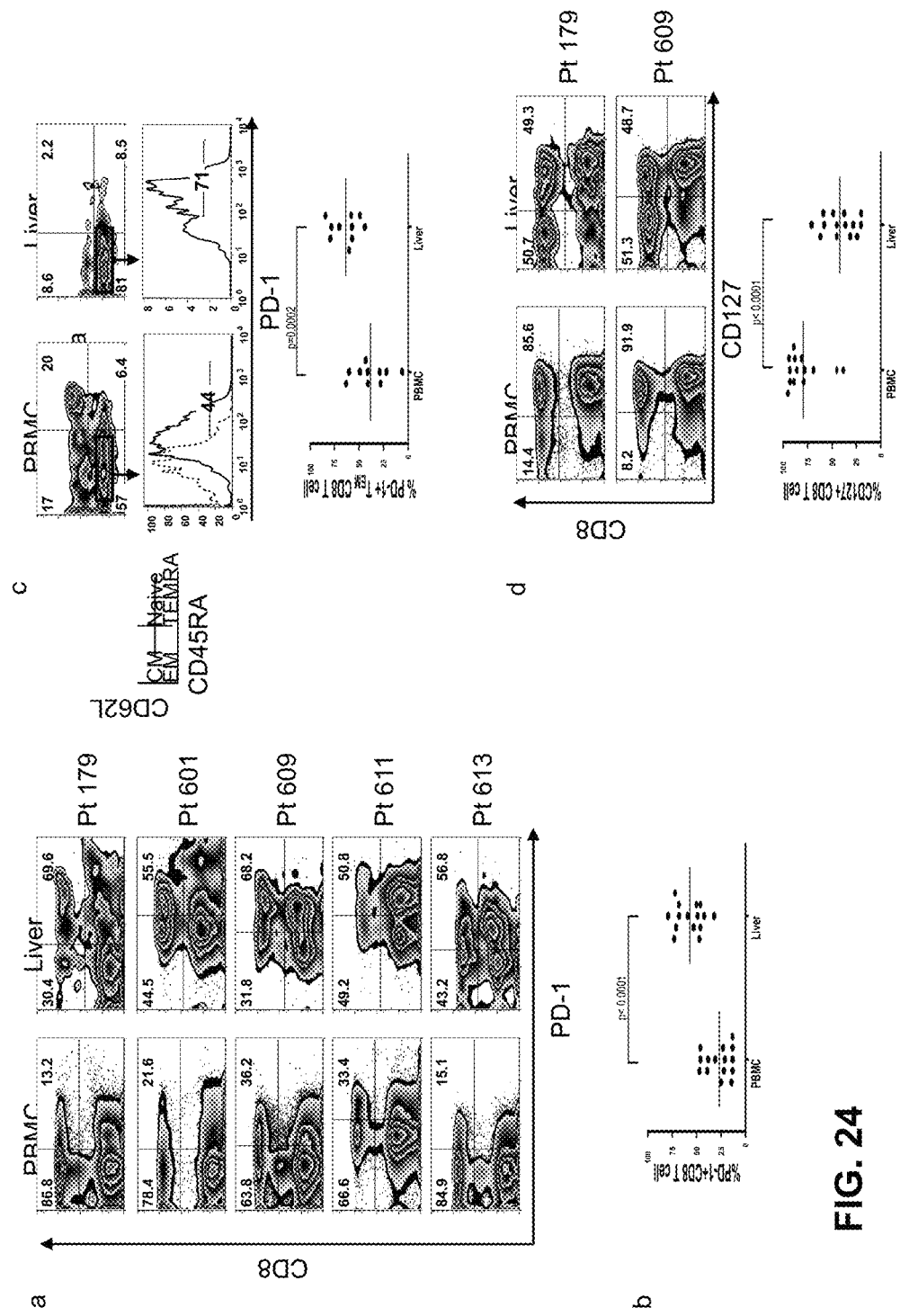
FIGS. 24A-24D are plots and graphs showing the frequency of PD-1 expressing CD8+ T cells from the liver is greater than in the peripheral blood.

PD-1 expression on human peripheral blood and liver infiltrating lymphocytes: Peripheral blood and liver biopsies were analyzed for the expression of PD-1 from fifteen patients chronically infected with HCV. Representative flow cytometric analysis from five patients is shown in FIG. 24A. Whereas in the peripheral blood, 27% (SEM 3.4) of CD8+ T cells were PD-1+, the frequency of such cells was increased two fold (57%, SEM 3.6) in the liver (FIG. 24B). Hence, the liver is enriched in cells expressing high levels of PD-1. While naïve cells should express high levels of both CD62L and CD45RA, in the liver the majority of CD8+ T cells were CD62L low/CD45RA low consistent with a memory phenotype (FIG. 24C). Analysis specifically of this memory population in both the liver and the periphery showed that PD-1 expression was elevated in the liver compared with the periphery (FIG. 24C). These data suggest that the increase in the percentage of cells expressing PD-1 on the intrahepatic T cells is not merely due to the absence of the naïve population in this compartment. Rather, there is a preferential enrichment of PD-1+CD8+ T effector memory (CD62L low/CD45RA low) cells within the liver compared to the peripheral blood (FIG. 23C).

CD127 expression on human peripheral blood and liver infiltrating lymphocytes: IL-7 is required for maintenance of memory CD8+ T cells (Kaech et al., Nat Immunol 4:1191-8, 2003), and the alpha chain of its receptor, CD127, is downregulated on antigen specific T cells in persistent LCMV and gammaherpesvirus infections (see, for example, Fuller et al., J Immunol 174:5926-30, 2005). This loss of CD127 during chronic infection correlates with impaired cytokine production, increased susceptibility to apoptosis, and a reduction in the ability of memory virus-specific CD8+ T cells to persist in the host. Accordingly, resolution of acute hepatitis B virus (HBV) infection correlates with upregulation of CD127 expression and concomitant loss of PD-1 expression (Boettler et al., J Virol 80:3532-40, 2006). Interestingly, in the chronic HCV patients, only 20% (SEM 4.8) of total peripheral CD8+ T cells were CD127 negative, but in the hepatic CD8+ T cell infiltrates, this percentage increased significantly to 58% (SEM 4.4) (FIG. 24D). Hence, the liver is enriched in cells expressing an exhausted phenotype with high PD-1 and low CD127 cells predominating. These data suggest that liver infiltrating CD8+ T cells in chronic HCV patients do not phenotypically mirror the peripheral CD8+ T cell population. In the setting of HIV infection where the virus infects T cells and monocytes in the peripheral blood, low levels of CD127 are associated with functional or memory T cell defects (Boutboul et al., Aids 19:1981-6, 2005). In this study, the hepatic compartmentalization of the cells showing this exhausted phenotype suggests that the phenotype is intimately tied to the site of persistent viral replication.

Figure 25:
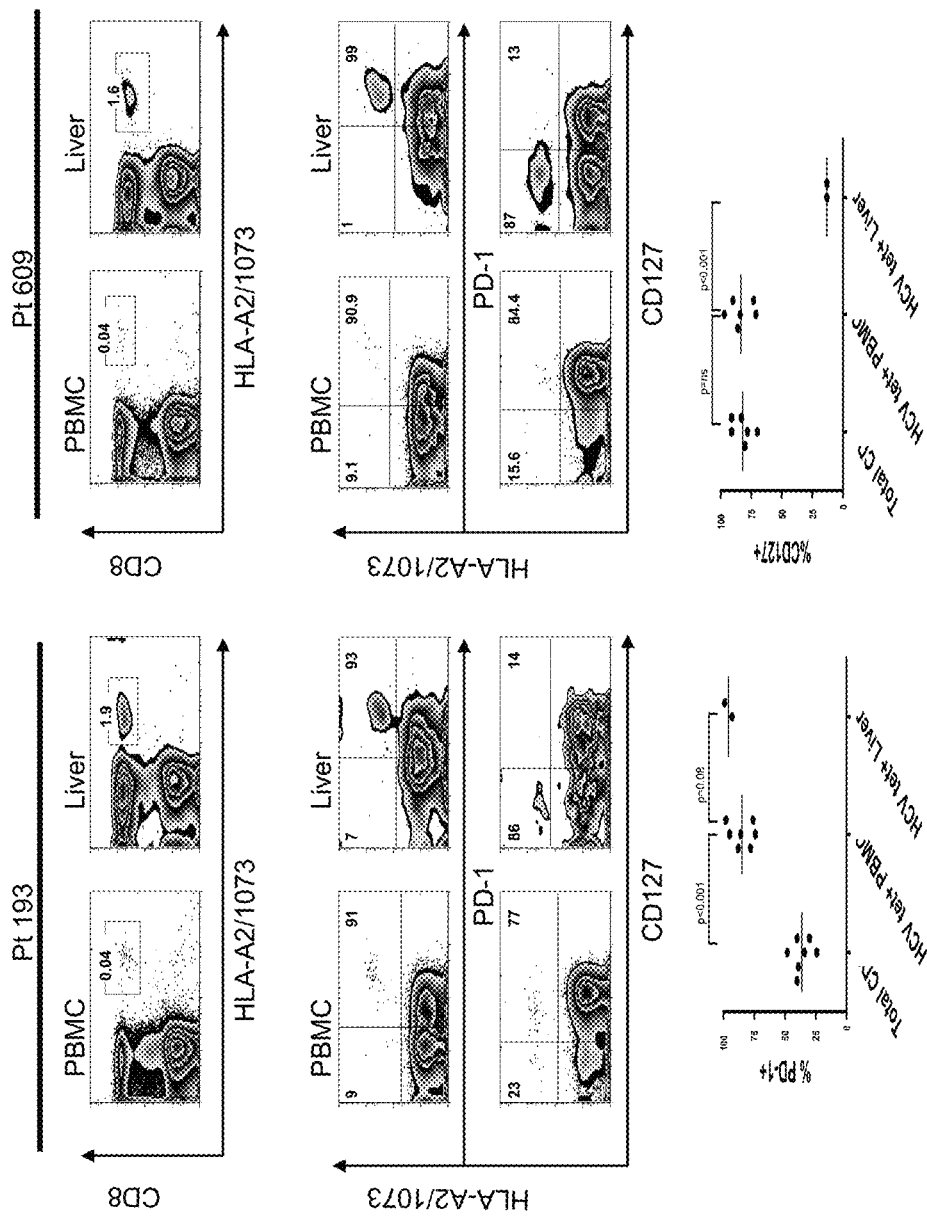
FIG. 25 is sets of graphs and plots showing HCV specific CD8+ T cells in the liver express an exhausted phenotype. Representative plots of PD-1 and CD127 expression on HCV specific CD8+ T cells from the peripheral blood and the liver of two patients with chronic HCV infection. The first row of plots identifies the HCV tetramer positive population (boxes). The numbers above the boxes represent the frequency of tetramer positive cells among CD3+ lymphocytes. The epitope specificity of the HCV tetramer is identified on the y-axis (1073). The second and third row of plots shows PD-1 and CD127 expression on HCV specific CD8+ T cells from the peripheral blood and liver of two patients with chronic HCV infection. Numbers in bold represent the frequency of PD-1 or CD127 expression on HCV specific CD8+ T cells. Plots are on a logarithmic scale and gated on CD3+CD8+ lymphocytes. Below the FACS plots, a summary of the comparison of PD-1 expression (left) and CD127 expression (right) on total CD8+ T cells versus CD8+ HCV specific T cells from the periphery (HCV tet+ PBMC) versus HCV specific CD8+ T cells from the liver (HCV tet+ Liver) is shown. Paired t tests were used to compare expression within the same patient.

PD-1 and CD127 expression on HCV antigen specific CD8+ T cells in the liver: Two of our HLA-A2 patients in the cohort also had an identifiable HCV specific population by tetramer staining in the liver (FIG. 25). Expression of PD-1 and CD127 was directly compared on HCV specific tetramer positive CD8+ T cells in the liver versus the periphery of these individuals. HCV specific CD8+ T cells from the periphery were mostly PD-1 positive (mean 85%, SEM 3.6) and CD127 positive (mean 84%, SEM 4.0), while the hepatic HCV specific CD8+ T cells were mostly PD-1 positive (mean 92%) but only rarely CD127 positive (mean 13%) (FIG. 25). At the site of viral replication, there appeared to be an expansion of CD127 negative cells expressing high levels of PD-1. That peripheral antigen specific CD8+ T cells differentially express CD127 compared with the intrahepatic compartment could be related to the level or timing of antigen exposure needed to cause downregulation of CD127. In LCMV infection of mice, exposure to persistent antigen load with chronic infection, CD127 was persistently downregulated whereas short-lived exposure to LCMV antigen using GP33 only temporarily suppressed CD127 expression and failed to induce T cell exhaustion (Lang et al., Eur J Immunol 35:738-45, 2005). Dependence on availability of antigen and time of exposure was also observed to affect the expression of CD62L and CD127, whereas persistent antigen led to persistent downregulation of both CD62L and CD127 (Bachmann et al., J Immunol 175:4686-96, 2005). Without being bound by theory, in chronic HCV infection, the few HCV specific CD8+ T cells detected in the periphery may not be continuously exposed to sufficient antigen to maintain low levels of CD127. Thus, the T cells may "believe" that the virus has been cleared.

Figure 26:
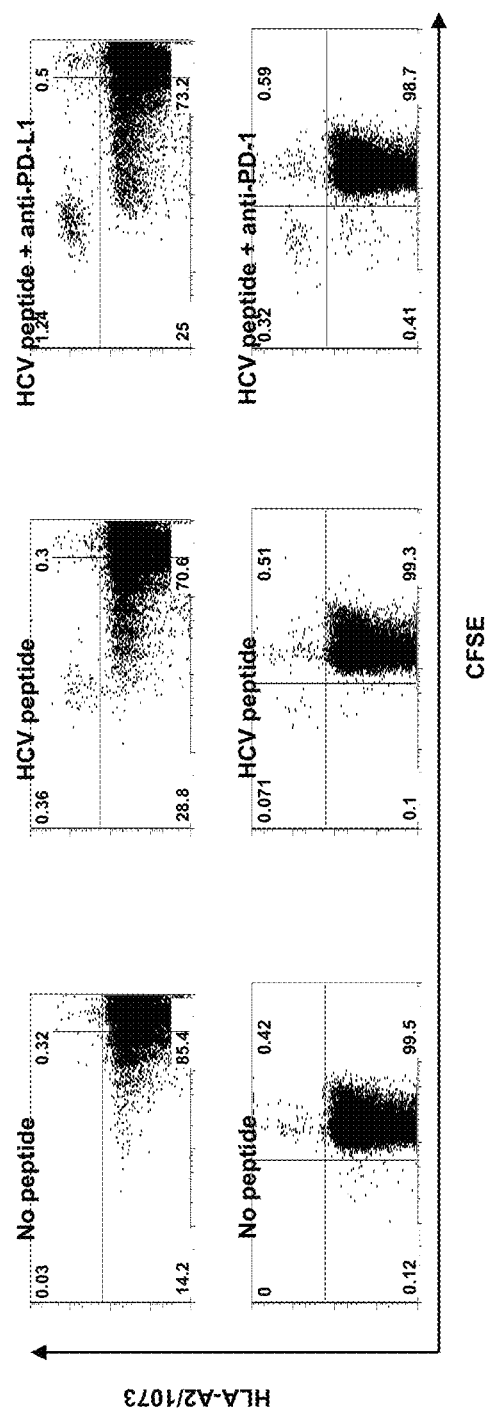
FIG. 26 is a set of plots showing blockade of the PD-1/PD-L1 pathway increases the expansion of antigen stimulated HCV-specific T cells. CFSE labeled PBMCs from two separate HLA-A2 patients were stimulated using the cognate peptide antigen for 6 days in the presence of IL-2 and anti-PD-L1 antibody (top panel) or anti-PD-1 antibody (lower panel). An unstimulated control is also shown. The percentage of proliferating CFSE low- and CFSE high-HCV-specific HLA-A2+CD8+ T cells are shown in each quadrant.

Blockade of PD-1/PD-L1 leads to increased expansion of HCV specific tetramer positive CD8+ T cells: Evidence from the patient population suggests that blockade of the PD-1/PD-L1 interaction with anti-PD-L1 or anti-PD-1 antibody increases the proliferative capacity of HCV-specific T cells (FIG. 26). Addition of blocking antibodies in the presence of IL-2 and HCV-specific peptide resulted in a four-fold increase in expansion of the HCV-specific T cells as demonstrated by monitoring the frequency of carboxyfluorescein succinimidyl ester (CFSE)$^{low}$ tetramer labeled CD8+ T cells after stimulation with cognate peptide for 6 days.

The results show that at the site of infection, the liver, the frequency of HCV specific CD8+ T cells expressing PD-1 is high. Second, the majority of HCV specific CD8+ T cells from the peripheral blood of patients with chronic HCV infection express high levels of CD127. The phenotype of T cells in chronic HCV infection was characterized by studying the expression of the PD-1 molecule linked to impaired effector function and T cell exhaustion. The results show that the majority of HCV specific T cells in the intrahepatic compartment express PD-1 but lack CD127, a phenotype consistent with T cell exhaustion. Thus, PD-1 antagonists are of use as therapeutic agents for the treatment of HCV infection.

Example 19

PD1 Blockade Induces Expansion of SIV-Specific CD8 Cells In Vitro

Anti-viral CD8 T cells play a critical role in the control of HIV/SIV infections. A central role for CD8 T cells has been shown by viral re-emergence during transient in vivo depletions in SW-infected macaques. Consistent with this, contemporary vaccine strategies designed to elicit high frequencies of anti-viral CD8 T cells have contained pathogenic SHIV and SW challenges in macaques (see, for example Barouch et al., Science 290, 486-92 (2000); Casimiro et al., J Virol 79, 15547-55 (2005).

Both the function and the frequency of anti-viral CD8 T cells are crucial for the control of chronic viral infections such as HIV (Migueles et al. Nat Immunol 3, 1061-8, 2002) and Lymphocytic choriomeningitis virus (LCMV). Effective anti-viral CD8 T cells possess a number of functional properties including the ability to produce different cytokines, cytotoxic potential, and high proliferative potential and low apoptosis. In chronic viral infections virus-specific CD8 T cells undergo exhaustion that is associated with the loss of many of these functions (Zajac et al., J Exp Med 188, 2205-13, 1998). Similarly, HIV-specific CD8 T cells from individuals with progressive disease have been shown to be impaired for their function. These CD8 T cells can produce cytokines such as IFN-γ but are impaired for the production of IL-2, a cytokine that is critical for the T cell proliferation and survival; expression of perforin (Appay et al., J Exp Med 192, 63-75, 2000, a molecule that is critical for cytolytic function; and proliferative capacity, a property that has been implicated to be critical for the control of HIV (see, for example, Harari et al., Blood 103, 966-72, 2004) and SW. HIV-specific T cells express high levels of PD-1 and this expression is directly proportional to the level of viremia. A transient blockade of interaction between PD-1 and PD-L1 in vitro restores HIV-specific T cell function.

Figure 27:
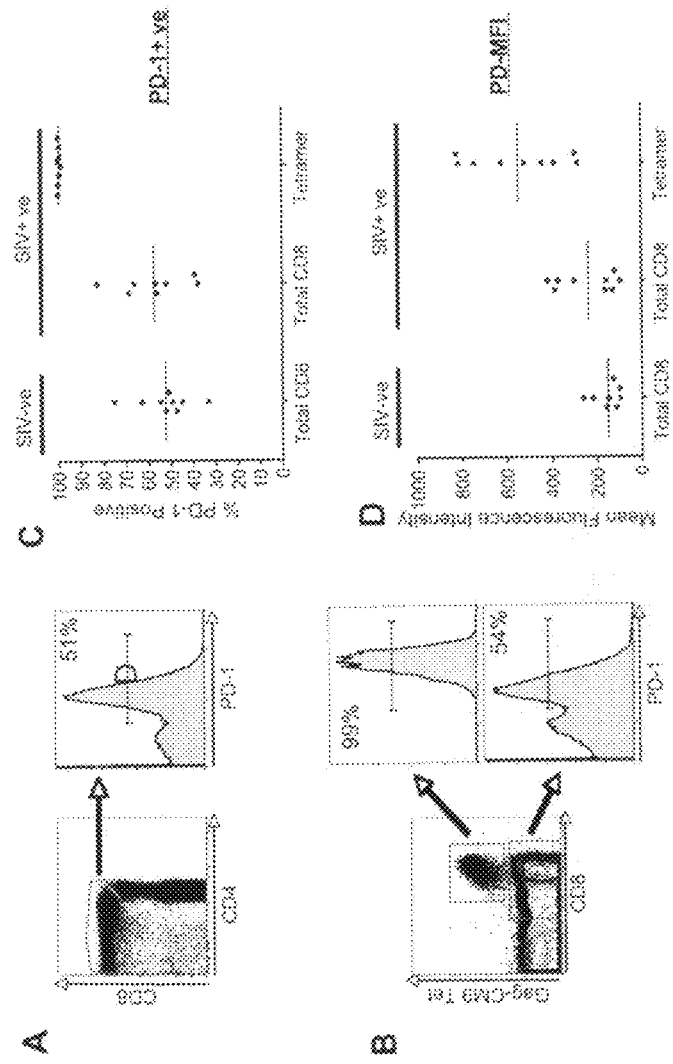
FIGS. 27A-27D are plots and graphs showing elevated PD-1 expression on simian immunodeficiency virus (SIV) specific CD8 T cells following SIV239 infection.

The expression of PD-1 on SW-specific CD8 T cells following infection with a pathogenic SIV239 in macaques was investigated. The results demonstrate that SW-specific CD8 T cells express high levels of PD-1 and blockade of PD-1:PDL-1 pathway in vitro results in enhanced expansion of these cells. The following results were obtained:

Elevated PD-1 expression on SIV-specific CD8 T cells following SIV239 infection: The level of PD-1 expression on CD8 T cells from normal healthy and SW-infected macaques was investigated to understand the role of PD-1 expression and its relationship with the control of SW-infection. A significant proportion (40-50%) of total CD8 T cells from normal healthy macaques expressed PD-1 (FIG. 27A). The PD-1 expression was predominantly restricted to memory cells and was absent on naïve CD8 T cells. A similar PD-1 expression pattern was also observed for total CD8 T cells from SIVmac239-infected macaques (FIGS. 27B and C). However, the majority (>95%) of SW Gag CM9-specific CD8 T cells were positive for PD-1 expression and a significant proportion of these cells further up regulated PD-1 expression (MFI of 580) compared to total CD8 T cells (MFI of 220) (FIG. 27D). Collectively, these results demonstrate that a significant proportion of memory CD8 T cells from normal and SW-infected macaques express PD-1 and the level of PD-1 expression is further elevated on the SW-specific CD8 T cells.

Figure 28:
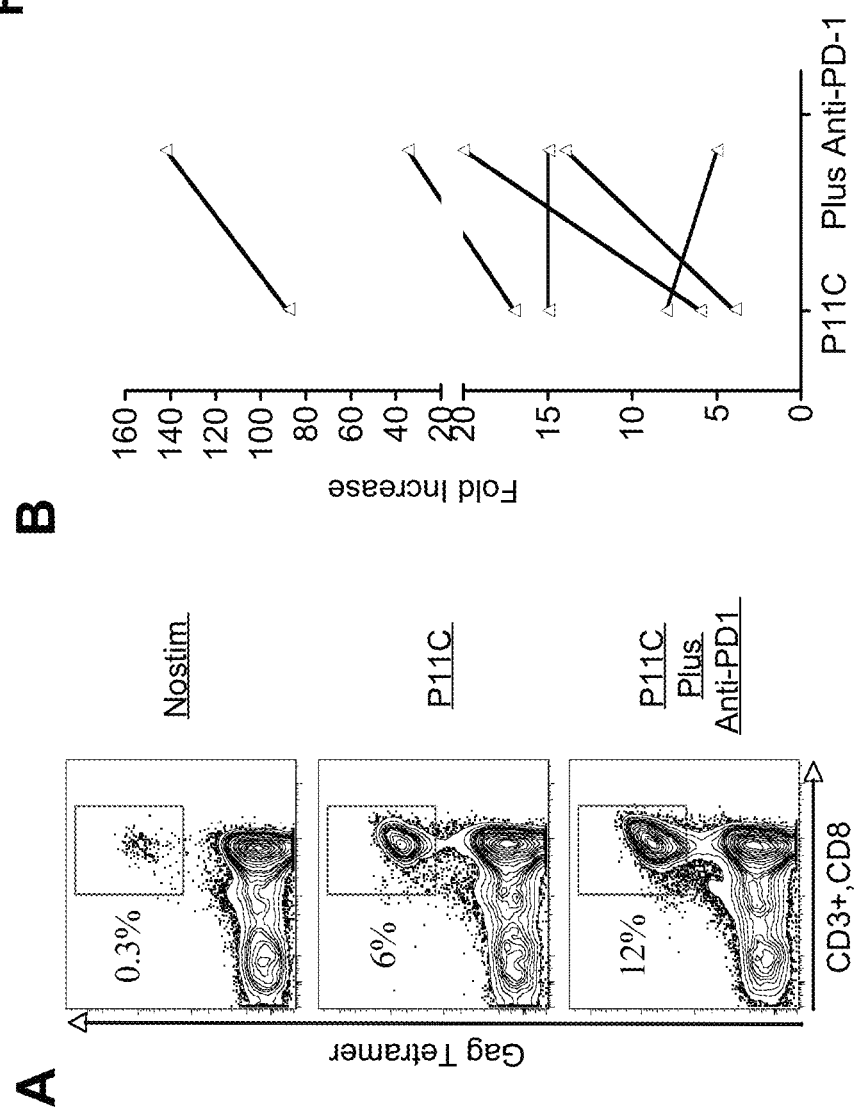
FIGS. 28A-28B are a plot and a graph, respectively, showing in vitro blockade of PD-1 results in enhanced expansion of SIV-specific CD8 T cells. PBMC from Mamu A*01 positive macaques that were infected with SHIV89.6P were stimulated with P11C peptide (0.1 µg/ml) in the absence and presence of anti-PD-1 blocking Ab (10 µg/ml) for six days. After three days of stimulation, IL-2 (50 units/ml) was added. At the end of stimulation cells were stained on the surface for CD3, CD8 and Gag-CM9 tetramer. Unstimulated cells (nostim) served as negative controls. Cells were gated on lymphocytes based on scatter then on CD3 and analyzed for the expression of CD8 and tetramer.

In vitro blockade of PD-1 results in enhanced expansion of SIV-specific CD8 T cells: To study the effect of PD-1 blockade on the function of SW-specific CD8 T cells, proliferation assays were conducted in the presence and absence of a blocking antibody to human PD-1 molecule that is cross reactive to macaque PD-1. PBMC from Mamu A*01 positive rhesus macaques that were infected with a pathogenic simian and human immunodeficiency virus 89.6P (SHIV 89.6P) were stimulated with P11C peptide (Gag-CM9 epitope) in the absence and presence of anti-PD-1 blocking Ab for six days. The frequency of Gag CM-9 tetramer positive cells was evaluated at the end of stimulation. Unstimulated cells served as negative controls. As can be seen in FIG. 28A-28B, stimulation with P11C peptide resulted in an about 4-80 fold increase in the frequency of tetramer positive cells. In addition, in four out of six macaques tested, stimulations with P11C peptide in the presence of anti-PD-1 blocking Ab resulted in about 2-4 fold further enhancement in the frequency of tetramer positive cells over stimulations with P11C peptide in the absence of blocking antibody.

These results demonstrate that PD-1 blockade enhances the proliferative capacity of SW-specific CD8 T cells in SW-infected macaques.

Example 20

Role of PD-L2

Figure 29:
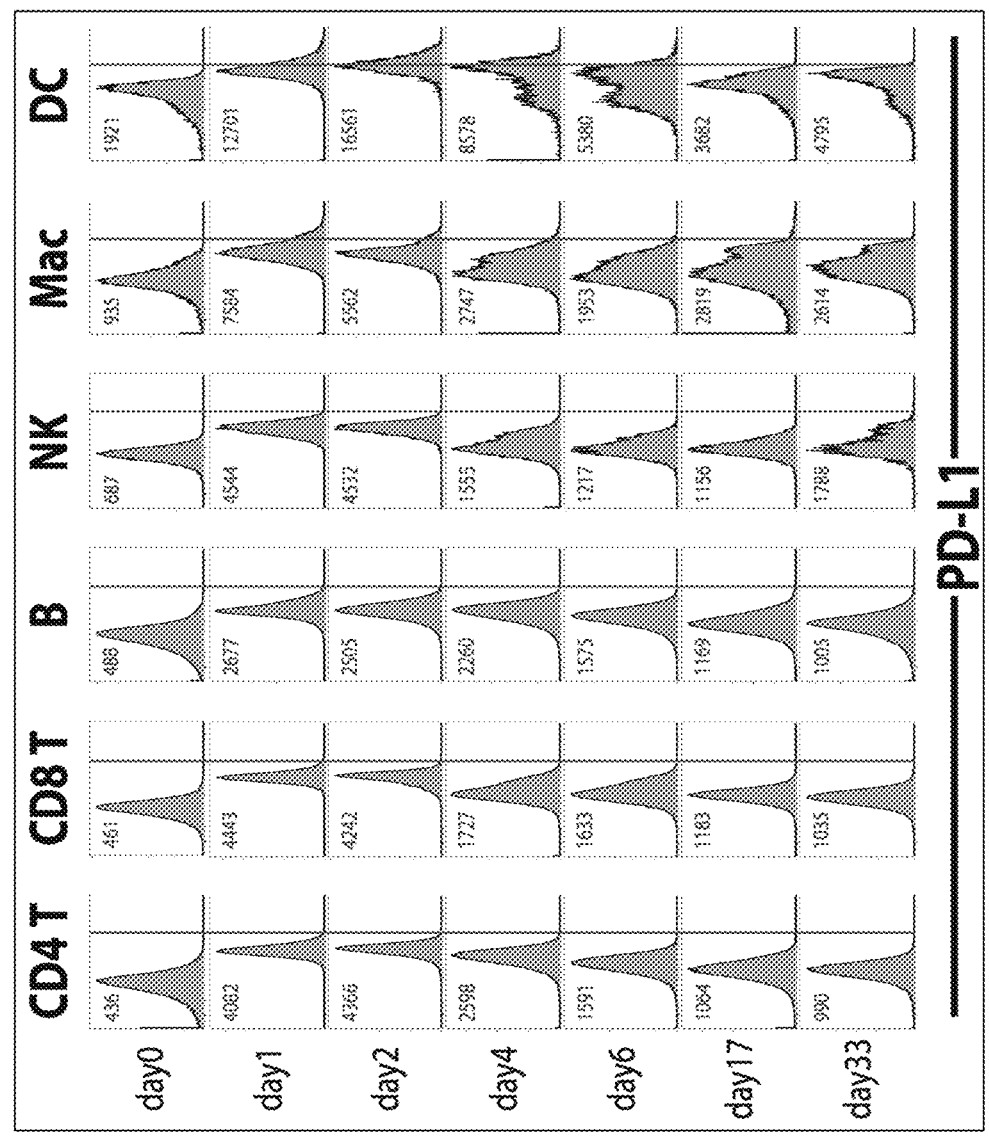
FIG. 29 is a set of plots showing the kinetics of PD-L1, PD-L2, and PD-1 expression on different cell types after LCMV infection. Mice were infected with $2 \times 10^6$ pfu of clone-13 (CL-13). PD-L1, PD-L2, and PD-1 expression on different type of cells was shown as a histogram at the indicated time points post-infection. Mean fluorescence intensity (MFI) of PD-1 expression on the indicated type of cells is shown.

Two PD-1 ligands differ in their expression patterns: PD-L1 is constitutively expressed and upregulated to higher amounts on both hematopoietic and nonhematopoeitic cells, whereas PD-L2 is only inducibly expressed on dendritic cells (DCs) and macrophages. Although some studies for evaluating the role that PD-L2 plays in T cell activation have demonstrated inhibitory function for PD-L2, other studies reported that PD-L2 stimulate T cell proliferation and cytokine production. To delineate the role of PD-L2 on T cell immune response, the kinetics of PD-L2 expression on different cell types ex vivo was examined after LCMV Armstrong infection (FIG. 29). In contrast to PD-L1 expression, PD-L2 expression was expressed limitedly on DC during a very short time (day 1-4 post-infection). This result suggests that PD-L2 expression is closely related to DC regulation and results in regulation of T cell activation.

Example 21

PD-1 is Expressed by the Majority of Effector Memory CD8 T Cells in the Blood of Healthy Humans PD-1 expression on CD3+/CD8+ T cells from the blood of healthy human adults was investigated. In human blood 20-60% of CD8 T cells expressed PD-1. The relationship between T cell differentiation state and PD-1 expression was examined. CD3+/CD8+ T cells were delineated into naïve, central memory ($T_{CM}$), effector memory ($T_{EM}$), and terminally differentiated effector ($T_{EMRA}$) subsets based on patterns of CD45RA and CCR7 expression. PD-1 was not expressed by naïve T cells, and by approximately one third of $T_{CM}$ and $T_{EMRA}$. In contrast, 60% of $T_{EM}$ expressed PD-1. These data demonstrate that the majority of $T_{EM}$ isolated from the blood of healthy human adults express PD-1.

Based on these analyses, T cells were subdivided into multiple populations based on CD45RA and CCR7 expression. An additional relationship was found between CD45RA expression and PD-1 expression. Specifically, CCR7−/CD8+ T cells with the lowest CD45RA expression contained the highest proportion of PD-1+ cells. In conclusion, PD-1 was predominantly expressed by $T_{EM}$, to a lesser extent by $T_{EMRA}$ and $T_{CM}$, and was not expressed among naïve CD8 T cells. These data illustrate that a large proportion of $T_{EM}$ CD8 T cells express PD-1 among healthy human adults.

To characterize the properties of PD-1+CD8 T cells further, the co-expression of PD-1 and several T cell differentiation markers was examined. The majority of PD-1+ CD8 T cells bore markers associated with antigen experience and effector/effector memory differentiation. For instance, CD11a+/CCR7−/CD62L−/CD45RA−/KLRG1+/granzyme B+/perforin+ CD8 T cells were enriched in PD-1 expression. In contrast, naïve phenotype (CD11a−/CCR7+/CD62L+/CD45RA+/KLRG1−) CD8 T cells expressed low levels of PD-1. Thus, PD-1 was preferentially expressed on antigen-experienced CD8 T cells with effector/effector memory qualities.

Example 22

PD-1 is Expressed by the Majority of Effector Memory CD4 T Cells in Blood of Healthy Humans PD-1 expression among CD3+CD4+ T cells was then investigated. Thirty percent of CD4 T cells expressed PD-1 in the blood of healthy adults. Similar to CD8 T cells, naïve CD4 T cells expressed little PD-1. While a minority of $T_{CM}$ CD4 T cells expressed PD-1, PD-1 expression was preferentially enriched among $T_{EM}$ CD4 T cells (50%).

To further characterize the properties of CD4 T cells that expressed PD, CD4+/CD3+ T cells were assayed from the blood of healthy individuals for the co-expression of PD-1 and several T cell differentiation markers. Similar to CD8 T cells, PD-1 expression was enriched on CD4 T cells with an effector/effector memory phenotype, including CD62L−, CD95+, CD45RA−, CCR7−, and CCR5+ cells.

Example 23

PD-1 is More Highly Expressed on CD8 T Cells Specific for EBV and CMV Infections in Humans To test whether PD-1 expression is correlated with viral antigen persistence, PD-1 expression was compared on EBV, CMV, influenza, and vaccinia virus specific CD8 T cells. EBV and CMV-specific CD8 T cells expressed high levels of PD-1. In contrast, influenza virus specific memory CD8 T cells expressed intermediate levels of PD-1 and vaccinia virus specific CD8 T cells express low levels of PD-1. Hence memory CD8 T cells specific for chronic infections (EBV and CMV) expressed higher levels of PD-1 than acute (influenza and vaccinia) infections. These results show that CD8 T cells specific for chronic infections (EBV and CMV) expressed higher levels of PD-1 than acute infections (influenza and vaccinia viruses). CD8 T cells specific for very common chronic infections can express high levels of PD-1.

Example 24

Anti-PD-L1 Blockade Increases Proliferation of CD8 T Cells Specific for EBV and CMV Infections in Humans Blockade of the PD-1 inhibitory pathway results in enhanced clonal expansion of HIV-specific CD8 T cells upon in vitro stimulation. As CD8 T cells specific for common chronic infections also express PD-1, it was tested whether blockade of the PD-1/PD-L1 pathway could enhance the proliferation of CD8 T cells specific for EBV, CMV, and also vaccinia virus (an acute infection resulting in PD-1 memory CD8 T cells). Lymphocytes were isolated from the blood of individuals containing CD8 T cells specific for CMV, EBV, or VV were labeled with CFSE and cultured for 6 days under various conditions. As expected, incubation of freshly isolated peripheral blood mononuclear cells (PBMC) with medium alone, or medium with anti-PD-L1 antibody, did not induce proliferation of virus-specific CD8 T cells. Stimulation of PBMC for 6 days with virus-derived peptides resulted in division of tetramer+ CD8 T cells. However, peptide stimulation of PBMC in the presence of anti-PD-L1 blocking antibody further enhanced division of EBV and CMV-specific CD8 T cells, resulting in a greater fold-expansion than peptide alone The enhanced division induced by anti-PD-L1 blocking antibody varied among individuals and even among different epitopes within a given individual. Moreover, PD-1 blockade did not result in enhanced expansion of vaccinia or influenza specific CD8 T cells. The degree of enhanced division induced by blocking PD-L1 in culture could be related to the amount of PD-1 expressed by antigen specific CD8 T cells prior to stimulation. These data suggest that PD-1 expression on CD8 T cells specific for chronic infections inhibits their proliferative capacity upon antigenic stimulation.

Example 25

Sustained PD-L1 Blockade Further Increases Proliferation of CD8 T Cells Specific for Chronic Infections Upon in vitro stimulation, the addition of PD-L1 blocking antibody led to increased division among CD8 T cells specific for EBV and CMV. Anti-PD-L1 mAb was added once (day 0), and proliferation was assessed at the end of the six-day culture period. In vivo anti-PD-L1 treatment in mice involved multiple injections of blocking antibody. Furthermore, in these murine studies, in vivo PD-L1 blockade resulted in a rapid upregulation of PD-1 expression among CD8 T cells specific for chronic viral antigen. For these reasons, it was tested whether repeated additions of anti-PD-L1 to stimulated T cell cultures would further enhance proliferation. The addition of a-PD-L1 mAb on days 0, 2, and 4 of culture resulted in an even greater accumulation of EBV specific CD8 T cells than a single addition of mAb at day 0, Similar data was observed for CMV specific CD8 T cells. These data suggest that continued blocking of PD-1 signaling can optimize the ability to increase the numbers of CD8 T cells specific for chronic antigens.

Example 26

Additional Methods for Studies Described in Example 27

Study group: Fourteen Indian rhesus macaques (*Macaca mulatta*) infected with SW were studied. Eight macaques were used for the early chronic phase and were infected intravenously with 200 TCID50 of SIV251. Six macaques were used for the late chronic phase, three were infected with SIV251 intrarectally and three were infected with SIV239 intravenously. All macaques, except RDb11, were negative for Mamu B08 and Mamu B17 alleles. RDb11 was positive for Mamu B17 allele.

In vivo antibody treatment: Macaques were infused with either partially humanized mouse anti-human PD-1 antibody (clone EH12-1540) (Doforman et al., *Am J Surg Pathol* 30, 802-810 (2006)) or a control antibody (SYNAGIS). The anti-PD-1 antibody has mouse variable heavy chain domain linked to human IgG1 (mutated to reduce FcR and complement binding) (Xu et al., *Cell Immunol* 200, 16-26 (2000)) and mouse variable light chain domain linked to human K. The clone EH12 binds to macaque PD-1 and blocks interactions between PD-1 and its ligands in vitro (Velu et al., *J Virol* 81, 5819-5828 (2007). SYNAGIS is a humanized mouse monoclonal antibody (IgG1κ) specific to F protein of respiratory syncytial virus (Medimmune). Antibodies were administered intravenously at 3 mg kg$^{-1}$ of body weight on days 0, 3, 7 and 10.

Immune responses: Peripheral blood mononuclear cells from blood and lymphocytes from rectal pinch biopsies were isolated as described previously (Velu et al., *J Virol* 81, 5819-5828 (2007). Tetramer staining (Amara et al., *Science* 292, 69-74 (2001)), intracellular cytokine production (Kannanganat et al., *J Virol* 81, 8468-8476 (2007)) and measurements of anti-SW Env binding antibody (Lai et al., *Virology* 369, 153-167 (2007)) were performed as described previously.

B cell responses: A total of 100 µl of blood was surface stained with antibodies to CD3 (clone SP34-2, BD Biosciences), CD20 (2H7, e-Biosciences), CD21 (B-ly4, Becton Dickson) CD27 (M-T2712, Becton Dickson) and PD-1 (clone EH-12), each conjugated to a different fluorochrome. Cells were lysed and fixed with FACS lysing solution, and permeabilized using FACS perm (BD Biosciences) according to the manufacturer's instructions. Cells were then stained for intracellular Ki67 using an anti-Ki67 antibody conjugated to phycoerythrin (PE) (clone B56, Becton Dickson). After staining, cells were washed and acquired using LSRII (BD Biosciences), and analysed using FLOWJO™ software.

Titres of anti-PD-1 antibody and monkey antibody response against anti-PD-1 antibody in serum: To measure the levels of anti-PD-1 antibody, plates were coated with goat anti-mouse immunoglobulin (pre-absorbed to human immunoglobulin, Southern Biotech), blocked and incubated with different dilutions of serum to capture the blocking antibody. Bound antibody was detected using anti-mouse IgG conjugated to HRP (pre-absorbed to human immunoglobulin, Southern Biotech). Known amounts of blocking antibody captured in the same manner were used to generate a standard curve. To measure the levels of monkey antibody response against the anti-PD-1 antibody, plates were coated with anti-PD-1 antibody (5 µg ml$^{-1}$), blocked and incubated with different dilutions of serum to capture the anti-blocking antibody. Bound antibody was detected using anti-human λ-chain-specific antibody conjugated to HRP (Southern Biotech). This detection antibody does not bind to the blocking antibody because only the constant regions of the heavy and light chains were humanized and the constant region of light chain is K. The amount of captured monkey immunoglobulin was estimated using a standard curve that consisted of known amounts of purified macaque immunoglobulin that had been captured using anti-macaque immunoglobulin.

Quantification of SIV copy number: SW copy number was determined using a quantitative real-time PCR as previously described (Amara et al., *Science* 292, 69-74 (2001)). All specimens were extracted and amplified in duplicates, with the mean result reported.

Amplification and sequencing of the Tat TL8 epitope: A 350-nucleotide fragment including Tat TL8 epitope was amplified by limiting dilution RT-PCR. Viral RNA was extracted using the QIAAMP™ Viral RNA mini kit (Qiagen) from plasma. vRNA was reverse transcribed with the SIV-mac239-specific primer Tat-RT3 (5'-TGGGGATAATTTTA-CACAAGGC-3') and Superscript III (Invitrogen) using the manufacturer's protocol. The resultant cDNA was diluted and copy number was determined empirically in our nested PCR protocol. Limiting dilution, nested PCR was performed at ~0.2 copies per reaction using the Expand HiFi PCR kit (Roche Applied Sciences) with the following primers:

```
outer primers:
                                          (SEQ ID NO: 53)
Tat-F1 (5'-GATGAATGGGTAGTGGAGGTTCTGG-3')

(SEQ ID NO: 54)
Tat-R2 (5'-CCCAAGTATCCCTATTCTTGGTTGCAC-3')

inner primers:
                                          (SEQ ID NO: 55)
Tat-F3 (5'-TGATCCTCGCTTGCTAACTG-3')

(SEQ ID NO: 56)
Tat-R3 (5'-AGCAAGATGGCGATAAGCAG-3').
```

The first round reactions were cycled using the following program: 94° C. for 1 min, followed by 10 cycles of 94° C. for 30 s, 55° C. for 30 s, and 68° C. for 1 min, followed by 25 more cycles identical to the first ten but for the addition of 5 s to the extension time at every cycle, followed by a final extension at 68° C. for 7 min. The second round reactions were cycled using the following programme: 94° C. for 1 min, followed by 35 cycles of 94° C. for 30 s, 53° C. for 30 s, and 68° C. for 1 min, followed by a final extension at 68° C. for 7 min. After clean-up with ExoSap-IT (USB Corporation), PCR products were sequenced directly using the inner primers on an automated sequencer. Contigs were assembled using Sequencher 4.8 (Gene Codes Corporation). Amplicons containing nucleotides with double chromatogram peaks were excluded.

Statistical Analyses: Linear mixed effects models were used to determine differences in blood chemistry and complete blood count values between anti-PD-1-antibody-treated and control-antibody-treated animals. The Bonferroni method was used to adjust P values for multiple tests. A paired t-test was used for comparison of immune responses before and after PD-1 blockade. Log-transformed data were used when the data were not normal, but log-normal. A Wilcoxon rank-sum test was used to compare the fold reductions in viral loads between the groups. A Mantel Haenszel log rank test was used to compare the survival curves between the groups. Statistical analyses were performed using S-PLUS 8.0. A two-sided P<0.05 was considered statistically significant.

Example 27

Proliferation of Memory B Cells Induced by PD-1 Blockade

Chronic immunodeficiency virus infections are characterized by dysfunctional cellular and humoral antiviral immune responses. As such, immune modulatory therapies that enhance and/or restore the function of virus-specific immunity may protect from disease progression. The safety and immune restoration potential of blockade of the co-inhibitory receptor programmed cell death 1 (PD-1) during chronic simian immunodeficiency virus (SW) infection was investigated in macaques. It was demonstrated that PD-1 blockade using an antibody to PD-1 is well tolerated and results in rapid expansion of virus-specific CD8 T cells with improved functional quality. This enhanced T-cell immunity was seen in the blood and also in the gut, a major reservoir of SIV infection. PD-1 blockade also resulted in proliferation of memory B cells and increases in SW envelope-specific antibody. These improved immune responses were associated with significant reductions in plasma viral load and also prolonged the survival of SW-infected macaques. Blockade was effective during the early (week 10) as well as late (week 90) phases of chronic infection even under conditions of severe lymphopenia. These results demonstrate enhancement of both cellular and humoral immune responses during a pathogenic immunodeficiency virus infection by blocking a single inhibitory pathway and identify a novel therapeutic approach for human immunodeficiency virus/acquired immunodeficiency syndrome, and demonstrate that monitoring B cell response can be used to assess the efficacy of therapy.

Virus-specific T cells show varying degrees of functional impairment during chronic infections (Wherry et al., *Immunity* 27, 670-684 (2007); Klenerman et al., *Nat Immunol* 6, 873-879 (2005)). Although these T cells retain some antiviral functions, they are less polyfunctional compared with antiviral T cells seen in acute infections. This defect in T-cell function greatly contributes to the inability of the host to eliminate the persisting pathogen. It is disclosed herein that the exhaustion of virus-specific T cells is present during persistent LCMV infection of mice Zajac et al., *J Exp Med* 188, 2205-2213 (1998); Galimore et al., *J Exp Med* 187, 1383-1393 (1998)) and in other viral infections, including human immunodeficiency virus (HIV), hepatitis B virus (HBV) and hepatitis C virus (HCV) infections in humans (Letvin et al., *Nat Med* 9, 861-866 (2003); Pantaleo et al., *Nat Med* 10, 806-810 (2004); Rehermann et al., *Nat Rev Immunol* 5, 215-229 (2005)). The co-inhibitory receptor PD-1 was highly expressed by the exhausted virus-specific CD8 T cells (Barber et al., *Nature* 439, 682-687 (2006); Sharpe et al., *Nat Immunol* 8, 239-245 (2007)). PD-1 is also upregulated on HIV-1-specific (Petrovas et al., *J Exp Med* 203, 2281-2292 (2006); Day et al., *Nature* 443, 350-354 (2006)) and SW-specific (Velu et al., *J Virol* 81, 5819-5828 (2007)). CD8 T cells and in vitro blockade of PD-1 enhanced cytokine production and proliferative capacity of these cells. An SIV/macaque model was used to evaluate the effects of in vivo blockade of PD-1 on the safety and restoration of virus-specific cellular and humoral immunity during chronic immunodeficiency virus infections.

PD-1 blockade was performed using an antibody specific to human PD-1 that blocks the interaction between macaque PD-1 and its ligands (PDLs) in vitro (Velu et al., *J Virol* 81, 5819-5828 (2007). Blockade was performed during the early (10 weeks) as well as late (~90 weeks) phases of chronic SW infection. Nine macaques (five during the early phase and four during the late phase) received the anti-PD-1 antibody and five macaques (three during the early phase and two during the late phase) received an isotype control antibody (Synagis, anti-Rous sarcoma virus (RSV)-specific) (Malley et al., *J Infect Dis* 178, 1555-1561 (1998)).

Figure 30:
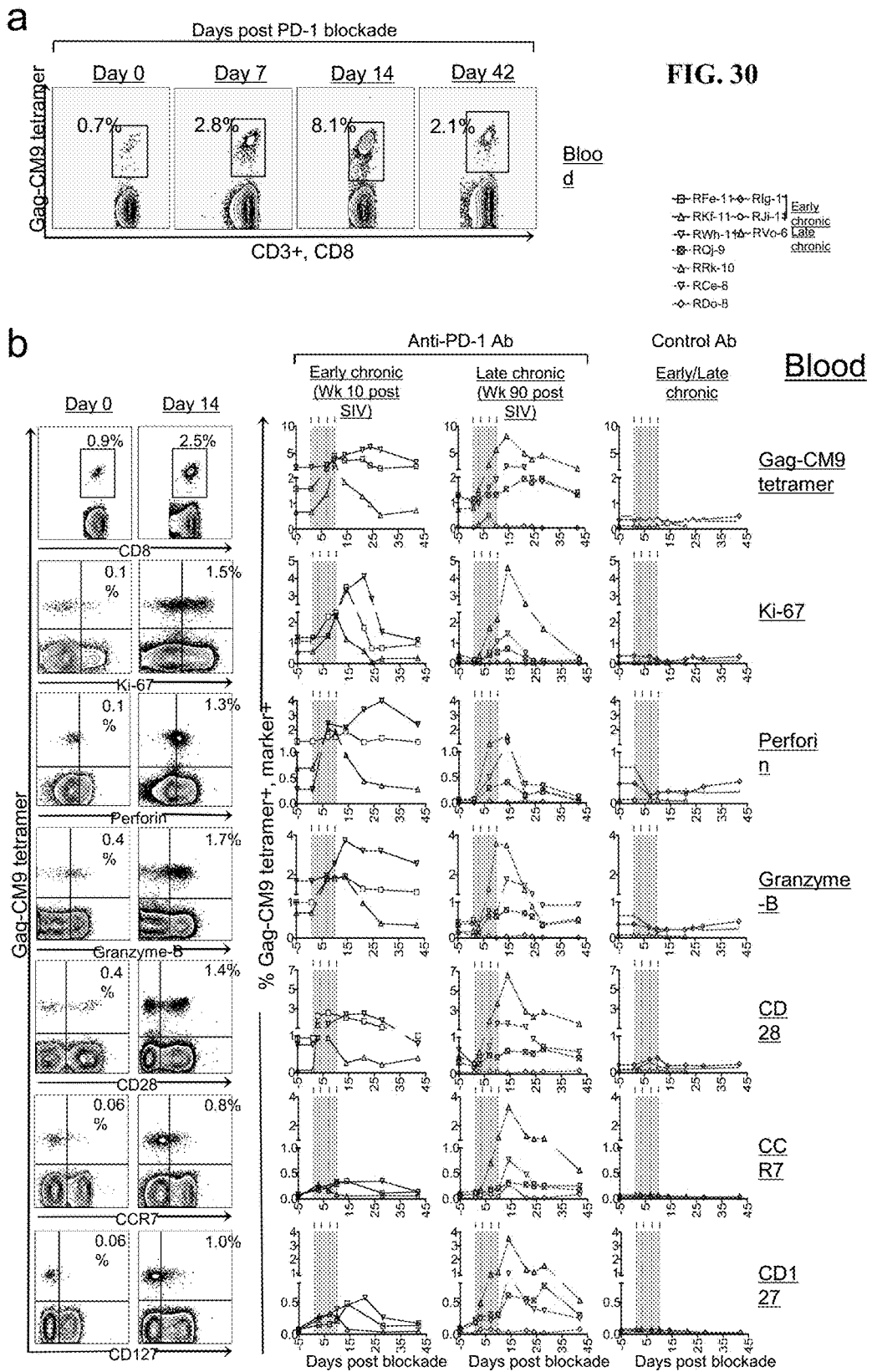
FIGS. 30a-30c are FACS plots showing in vivo PD-1 blockade during chronic SIV infection increases the Gag-CM9-specific CD8 T cells with improved functional quality in both blood and gut.
Figure 30:
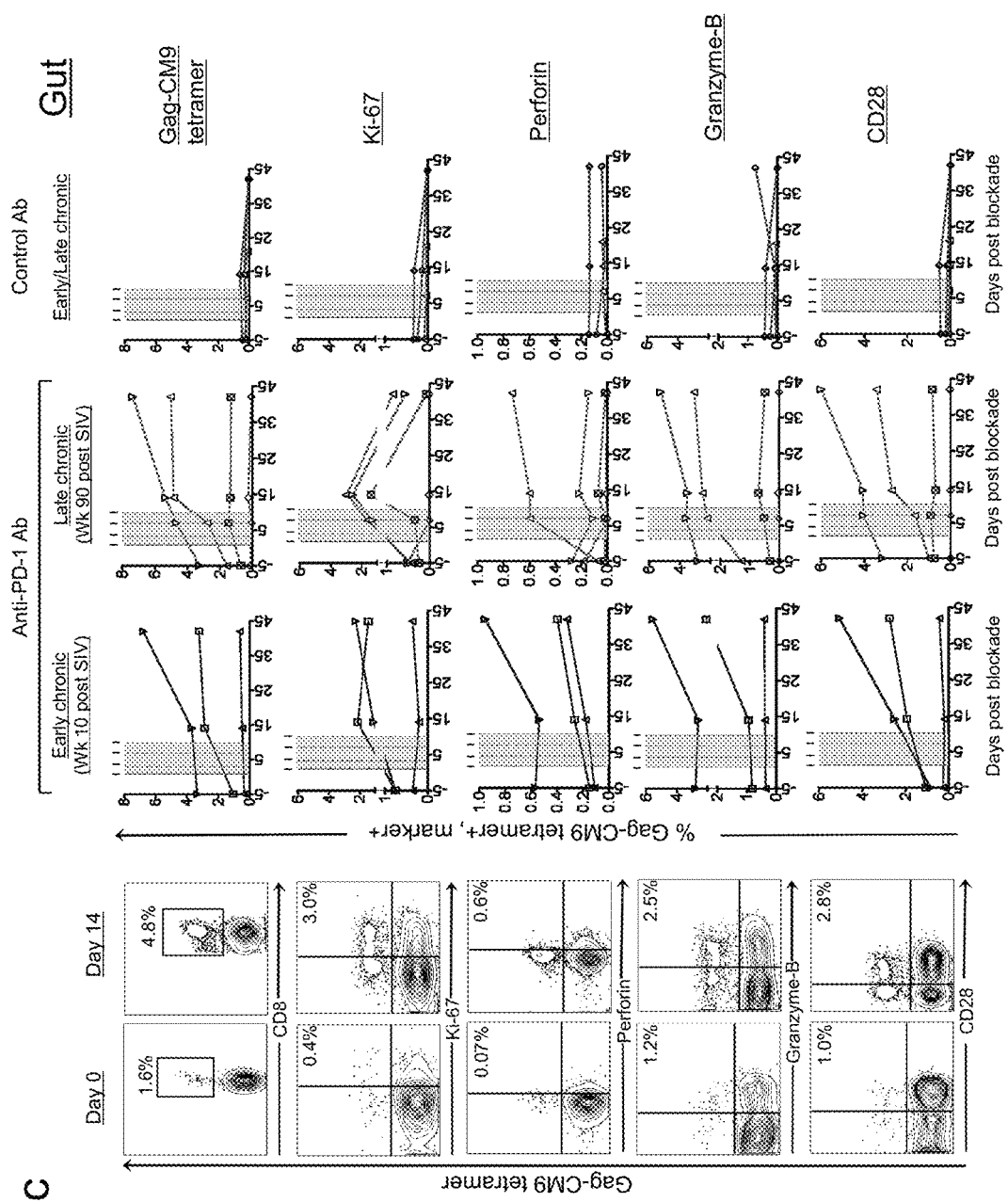

PD-1 blockade during chronic SW infection resulted in a rapid expansion of SW-specific CD8 T cells in the blood of all macaques (FIG. 30a, b). The CD8 T-cell responses to two immunodominant epitopes, Gag CM9 and Tat SL8/TL8 (Allen et al., *Nature* 407, 386-390. (2000)), was studied using major histocompatibility complex (MHC) I tetrameric complexes in seven of the anti-PD-1-antibody-treated and three of the control-antibody-treated macaques that expressed the Mamu A*01 histocompatibility molecule. Most (>98%) of the Gag-CM9 tetramer-specific CD8 T cells expressed PD-1 before blockade. After PD-1 blockade, the Gag-CM9 tetramer-specific CD8 T cells expanded rapidly and peaked by 7-21 days. At the peak response, these levels were about 2.5-11-fold higher than their respective levels on day 0 (P=0.007) and remained elevated until 28-45 days (FIG. 30b). Similar results were observed with blockade during the early as well as late phases of chronic SW infection. A 3-4-fold increase in the frequency of Gag-specific interferon (IFN)-γ-positive CD8 T cells was also observed by day 14 after blockade in the two Mamu A*01-negative animals (RTd11 and RDb11), demonstrating that PD-1 blockade can enhance the frequency of virus-specific CD8 T cells that are restricted by non-Mamu A*01 alleles. As expected, expansion of SW-specific CD8 T cells was not observed in the control-antibody-treated macaques (FIG. 30).

PD-1 blockade was also associated with a significant increase in the frequency of virus-specific CD8 T cells that were undergoing active cell division in vivo with improved functional quality (FIG. 30b). Consistent with the rapid expansion of SW-specific CD8 T cells, the frequency of Gag-CM9 tetramer-specific CD8 cells that co-expressed Ki67 (marker for proliferating cells) also increased as early as by day 7 after blockade (P=0.01). Similarly, an increase in the frequencies of Gag-CM9 tetramer-specific CD8 T cells co-expressing perforin and granzyme B (cytolytic potential; P=0.001 and P=0.03, respectively), CD28 (co-stimulation potential; P=0.001), CD127 (proliferative potential; P=0.0003) (Kaech et al., Nat Immunol 4, 1191-1198 (2003)) and CCR7 (lymph-node homing potential; P=0.001) was observed (Salusto et al, Nature 401, 708-712. (1999)). A transient 1.5-2-fold increase in the frequency of tetramer-negative and Ki67-positive CD8 T cells after blockade was also observed. This could be due to expansion of CD8 T cells specific to other epitopes in Gag as well as other proteins of SW, and other chronic viral infections in these animals. No significant enhancement was observed for these markers in the three control-antibody-treated macaques.

Notably, no expansion was observed for Tat-TL8-specific CD8 T cells after blockade. This could be due to viral escape from recognition by Tat-TL8-specific CD8 T cells, as PD-1 blockade is known to result in expansion of T cells only when they simultaneously receive signals through T-cell receptor. To test this possibility, the viral genomes present in the plasma just before the initiation of blockade from all three Mamu A*01-positive macaques that were infected with SIV251 and received the blocking antibody during the early phase of infection were sequenced. Indeed, mutations in the viral genome were found corresponding to the Tat TL8 epitope region. All these mutations either have been shown or predicted to reduce the binding of Tat SL8/TL8 peptide to Mamu A*01 MHC molecule and result in escape from recognition by the Tat-SL8/TL8-specific CD8 T cells (Allen et al., Journal of Immunology 160, 6062-6071 (1998); Allen et al., Nature 407, 386-390. (2000)). These results suggest that in vivo blockade of PD-1 may not result in expansion of T cells that are specific to escape mutants of viral epitopes.

PD-1 blockade also resulted in expansion of Gag-CM9-specific CD8 T cells at the colorectal mucosal tissue (gut), a preferential site of SIV/HIV replication (Pierson et al., Annu Rev Immunol 18, 665-708 (2000)) (FIG. 30c). Expansion was not observed for two of the seven macaques, although expansion was evident for one of them in blood. In contrast to blood, the expansion in gut peaked much later by day 42 and ranged from 2- to 3-fold compared with their respective day 0 levels (P=0.003). Similar to blood, the Gag-CM9 tetramer-specific cells that co-expressed Ki67 (P=0.01), perforin (P=0.03), granzyme B (P=0.01) and CD28 (P=0.01) also increased in the gut after blockade.

Figure 31:
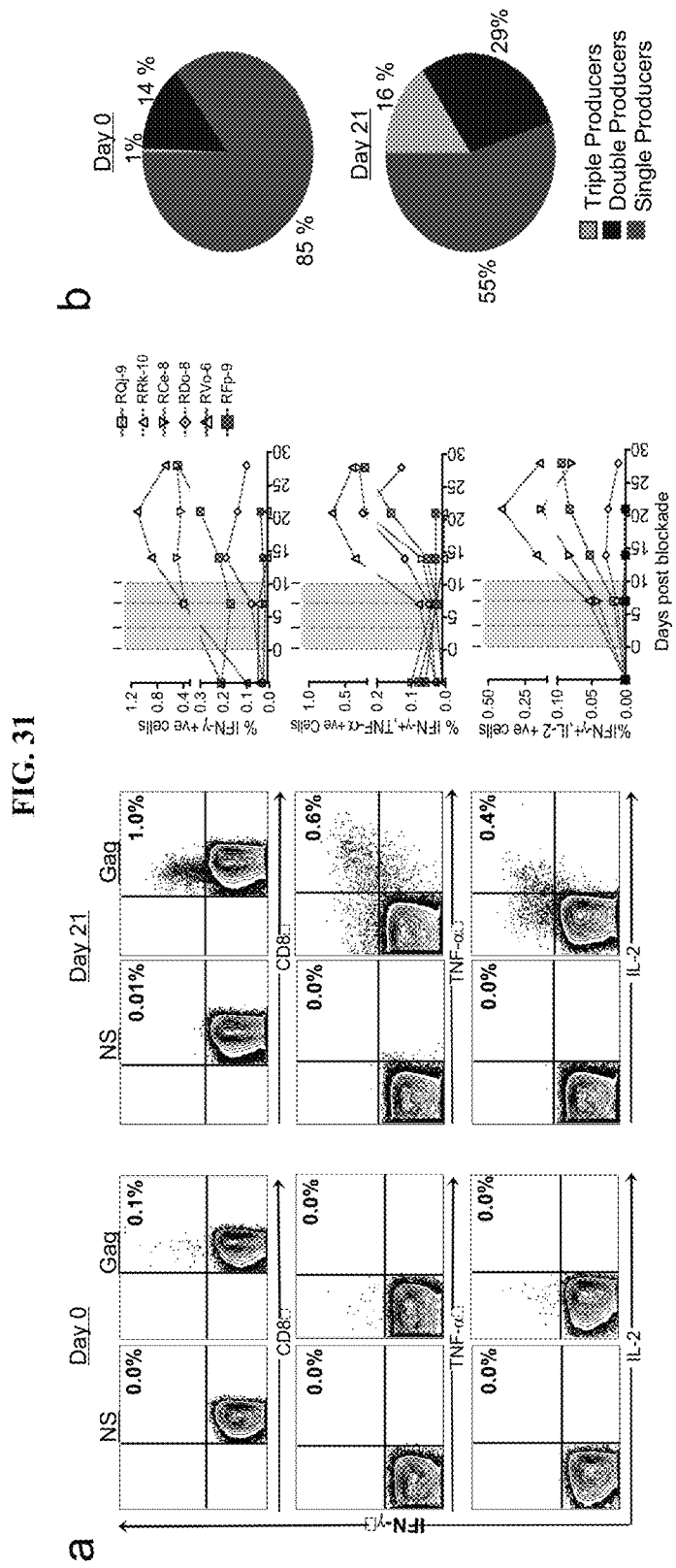
FIGS. 31a-31b show that in vivo PD-1 blockade during chronic SW infection increases the polyfunctional virus-specific CD8 T cells.

PD-1 blockade also enhanced the functional quality of anti-viral CD8 T cells and resulted in the generation of polyfunctional cells capable of co-producing the cytokines IFN-γ, tumour-necrosis factor (TNF)-α and interleukin (IL)-2 (FIG. 31). On the day of initiation of PD-1 blockade during the late chronic phase of infection, the frequency of Gag-specific IFN-γ-positive cells was low and they failed to co-express TNF-α and IL-2 (FIG. 31a). However, after the blockade, the frequency of IFN-γ-positive cells increased in all four PD-1 antibody-treated macaques (P=0.03) and they acquired the ability to co-express TNF-α and IL-2. The expansion of IFN-γ-positive cells peaked by 14-21 days and the peak levels were 2-10-fold higher than the respective day 0 levels. On day 21, about 16% of the total Gag-specific cells co-expressed all three cytokines, and about 30% co-expressed IFN-γ and TNF-α (FIG. 31b). This is in contrast to <1% of the total Gag-specific cells co-expressing all three cytokines (P=0.01), and about 14% co-expressing IFN-γ and TNF-α on day 0 (P=0.04). Similar results were also observed after blockade during the early chronic phase of infection.

Figure 32:
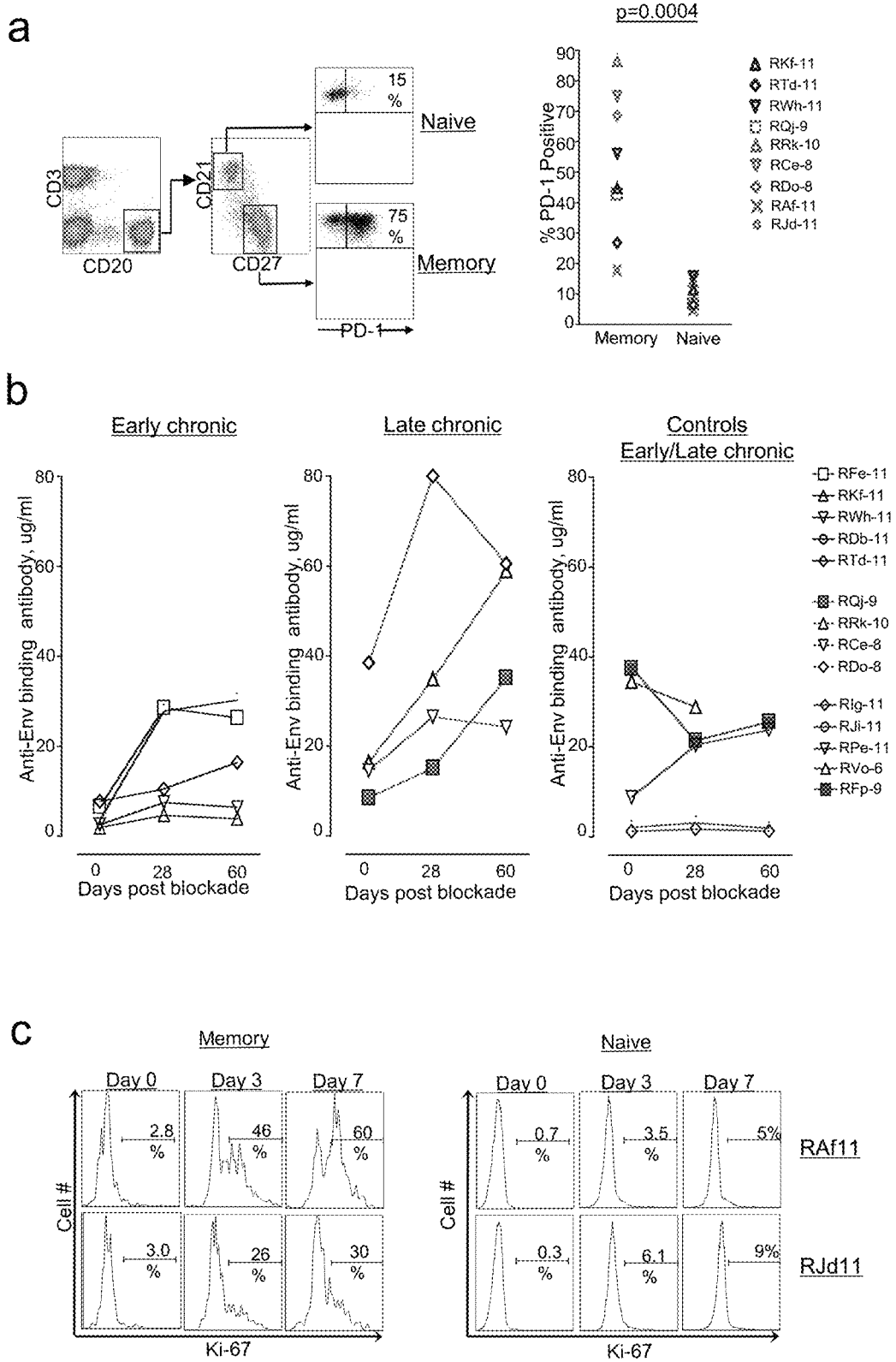
FIGS. 32a-32b show that in vivo PD-1 blockade during chronic SW infection enhances SW-specific humoral immunity.
FIG. 32c shows Ki67 expression (marker for proliferation) on memory and naïve B cells after blockade. Numbers on the FACS plots represent Ki67-positive cells as a percentage of respective total cells. Macaques RAf11 and RJd11 were treated simultaneously with anti-PD-1 antibody and anti-retroviral therapy at 22 weeks after SW infection.

Chronic immunodeficiency virus infections are associated with B-cell dysfunction (De Milito, Current HIV Research 2, 11-21 (2004); Moir and Faucci, J Allergy Clin Immunol 122, 12-19; quiz 20-11 (2008)) but very little is known about the role of PD-1 in regulating B-cell function/exhaustion. The B-cell responses after PD-1 blockade in SW-infected macaques (FIG. 32) was characterized. Analysis of PD-1 expression on different B-cell subsets before PD-1 blockade revealed preferential expression of PD-1 by memory B cells (CD20$^+$CD27$^+$CD21$^-$) compared to naïve B cells (CD20$^+$CD27$^-$CD21$^+$; FIG. 32a, P<0.001). In vivo blockade of PD-1 resulted in a 2-8-fold increase in the titre of SW-specific binding antibody by day 28 after blockade (P<0.001; FIG. 32b).

The proliferation of memory B cells was studied in SW-infected macaques that were treated simultaneously with anti-PD-1 antibody and anti-retroviral therapy and observed a significant increase in Ki67$^+$ (proliferating) memory, but not naïve, B cells as early as day 3 (FIG. 32c). These results demonstrate the PD-1-PDL pathway's role in regulating B-cell dysfunction during chronic SW infection. Neutralization assays revealed a twofold increase in titres against the easily neutralizable laboratory-adapted SIV251 and no increase in titres against hard-to-neutralize wild-type SIV251 or SW239. In two of the nine animals treated with anti-PD-1 antibody, only a minimal (<2-fold) expansion of SW-specific antibody was observed after blockade. Notably, the frequency of total memory B cells in these two animals was lower (~40% of total B cells) compared with the remaining seven animals (60-90% of total B cells) before blockade, indicating that the level of SW-specific memory B cells before blockade can determine the level of expansion of SW-specific antibody after blockade.

Figure 33:
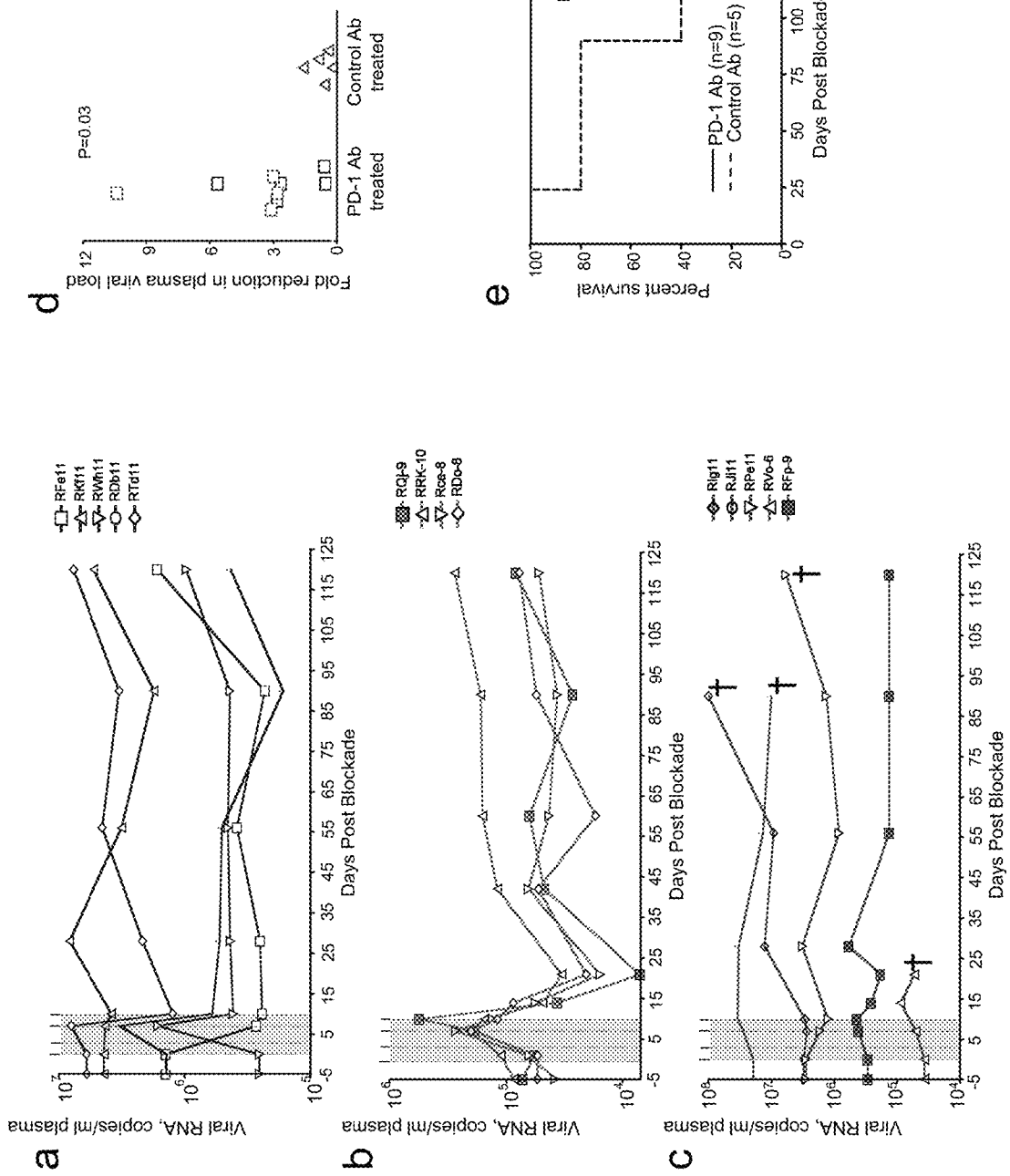
FIGS. 33a-33e show that in vivo PD-1 blockade reduces plasma viraemia and prolongs survival of SW-infected macaques. Plasma viral load in macaques treated with anti-PD-1 antibody during the early chronic phase of infection (FIG. 33a), macaques treated with anti-PD-1 antibody during the late chronic phase of infection (FIG. 33b), and macaques treated with control antibody during the early/late chronic phase of SW infection (FIG. 33c). An asterisk indicates death of animal.

PD-1 blockade resulted in significant reductions in plasma viraemia (P=0.03) and also prolonged the survival of SW-infected macaques (P=0.001; FIG. 33). In two of the five macaques treated with anti-PD-1 antibody during the early chronic phase, viral load declined by day 10 and persisted at or below this level until day 90 (FIG. 33a). In one macaque viral load declined transiently and in the remaining two macaques increased transiently and returned to pre-blockade levels. In contrast to the early chronic phase, all four macaques treated with the anti-PD-1 antibody during the late chronic phase showed a transient increase in viraemia by day 7, but rapidly reduced the virus load by day 21 to levels that were below their respective day 0 levels (FIG. 33b). However, the viral RNA levels returned to pre-blockade levels by day 43. As expected, no significant reductions in the plasma viral loads were observed in any of the five macaques treated with the control antibody (FIG. 33c). By 21-28 days after blockade, the viral RNA levels in the anti-PD-1-antibody-treated animals were 2-10-fold lower than their respective day 0 levels (P=0.03; FIG. 33d). By day 150 after the blockade, four of the five macaques in the control group were killed owing to AIDS-related symptoms (for example loss of appetite, diarrhoea, weight loss), whereas all nine animals in the anti-PD-1-antibody-treated group had survived (P=0.001; FIG. 33e).

The observed initial rise in plasma viraemia levels in all of the late-phase-treated and some of the early-phase-treated animals could be due to an increase in the frequency of activated CD4 T cells. The percentage of Ki67-positive total CD4 T cells was measured, as well as the frequency of SIV Gag-specific IFN-γ-producing CD4 T cells (preferential targets for virus replication (Douek et al., Nature 417, 95-98 (2002)) after blockade. These analyses revealed a transient increase in the percentage of Ki67-positive CD4 T cells by day 7-14 after blockade (P=0.002) and this increase was higher in animals treated during the late phase than early phase of infection (P=0.015). Similarly, an increase in the frequency of Gag-specific CD4 T cells was also observed, but only in animals treated during the late phase of infection. No significant increases were observed for these activated CD4 T cells in the control-antibody-treated macaques. These results suggest that the activated CD4 T cells could have contributed to the observed initial rise in plasma viraemia levels after blockade.

Before initiation of PD-1 blockade, the set point viral load in plasma and total CD4 T cells in blood and gut were similar between the anti-PD-1-antibody-treated and control-antibody-treated groups. However, the frequencies of Gag CM9$^+$ cells and Gag CM9$^+$ cells co-expressing perforin, granzyme B or CD28 were not similar between the two treatment groups before in vivo blockade (FIG. 30b). This raises the possibility that these differences could have contributed to the expansion of Gag CM9$^+$ cells after PD-1 blockade. To study the influence of the frequency of Gag CM9$^+$ cells before blockade on their expansion after blockade, the anti-PD-1-antibody-treated group were divided into two subgroups based on the frequency of Gag CM9$^+$ cells before initiation of blockade such that one group has similar levels and the other group has higher levels of Gag CM9$^+$ cells compared with the control-antibody-treated group. These subgroups were then analysed for expansion of CM9$^+$ cells after blockade. Expansion of CM9$^+$ cells was evident in both subgroups of animals after blockade of PD-1, irrespective of whether they were at low or high levels before blockade. Similar results were also observed with subgroup analyses based on the frequency of CM9$^+$ cells co-expressing molecules associated with better T-cell function such as perforin, granzyme B, CCR7, CD127 or CD28. However, there was a trend towards better expansion of CM9$^+$CD28$^+$ cells in animals with higher levels of CM9$^+$CD28$^+$ cells before blockade, suggesting that CD28 expression serves as a biomarker for predicting the outcome of in vivo PD-1 blockade.

To evaluate the safety of PD-1 blockade, an extensive analysis of serum proteins, ions, lipids, liver and kidney enzymes, and complete blood count after blockade. These analyses revealed no significant changes for all parameters tested between the anti-PD-1-antibody-treated and control-antibody-treated macaques. Similarly, the levels of anti-nuclear antibodies (ANA) in serum (measure of autoimmunity) also did not change significantly after treatment with anti-PD-1 antibody.

TABLE 6

Biochemical parameters of blood after the anti-PD-1 antibody treatment

| Markers | Pre-infection* | Post SIV infection, Days after PD-1 blockade* (n = 5) | | |
|---|---|---|---|---|
| Biochemical profile | (n = 8) | Day 0 | Day 14 | Day 56 |
| ALT (U/L) | 16.8 ± 5.0 | 27 ± 11.6 | 24.8 ± 7.7 | 27 ± 7.9 |
| AST (U/L) | 33.1 ± 8.2 | 35.0 ± 8.3 | 29.8 ± 3.6 | 49.0 ± 18.5 |
| Alkaline Phosphatase (U/L) | 466 ± 135 | 410 ± 367 | 367 ± 78 | 451 ± 89 |
| Bilirubin (g/L) | 0.2 ± 0.1 | 0.16 ± 0.1 | 0.12 ± 0.0 | 0.2 ± 0.2 |
| Creatinine (mg/dL) | 0.9 ± 0.1 | 0.7 ± 0.1 | 0.66 ± 0.1 | 0.6 ± 0.1 |
| Total protein (g/dL) | 7.3 ± 0.3 | 7.0 ± 0.3 | 7.14 ± 0.4 | 6.9 ± 0.4 |
| Albumin g/L | 4.5 ± 0.3 | 4.28 ± 0.2 | 4.1 ± 0.2 | 4.1 ± 0.2 |
| Globulin (g/dL) | 2.7 ± 0.2 | 2.72 ± 0.3 | 3.14 ± 0.3 | 2.8 ± 0.2 |
| Albumin/Globulin (ratio) | 1.7 ± 0.2 | 1.62 ± 0.2 | 1.32 ± 0.1 | 1.4 ± 0.1 |
| Glucose (mg/dL) | 82 ± 16 | 69 ± 8 | 66 ± 9 | 64 ± 8.0 |
| Cholesterol (mg/dL) | 161 ± 32 | 149 ± 32 | 145 ± 20 | 140 ± 18 |
| Triglyceriods (mg/dL) | 58 ± 19 | 64 ± 12 | 60 ± 7 | 73 ± 34 |
| Blood Urea Nitrogen (mg/dL) | 18 ± 3 | 17 ± 3 | 17 ± 3 | 16 ± 3 |
| Blood urea nitrogen-creatinine (ratio) | 21 ± 3 | 24 ± 5 | 26 ± 5 | 26 ± 5 |
| Lipase (U/L) | 21 ± 17 | 20 ± 7 | 21 ± 9 | 23 ± 10 |
| Creatinine Phosphokinase (U/L) | 428 ± 272 | 537 ± 303 | 486 ± 129 | 462 ± 312** |
| Gamma glutamil transpeptidase (U/L) | 74 ± 23 | 66 ± 16 | 58 ± 18 | 71 ± 15 |
| Calcium (mg/dl) | 10 ± 0.5 | 10 ± 0.2 | 10 ± 0.5 | 10 ± 03 |
| Chloride (mEq/L) | 110 ± 3 | 107 ± 3 | 108 ± 1 | 107 ± 2 |
| Potassium (mEq/L) | 4 ± 0.3 | 4 ± 0.2 | 4 ± 0.1 | 4 ± 0.6 |
| Sodium (mEq/L) | 150 ± 5 | 149 ± 3 | 149 ± 1 | 147 ± 2 |
| Phosphorus (mg/dL) | 5 ± 0.9 | 5 ± 0.6 | 5 ± 0.8 | 6 ± 0.4 |

*Values represent mean ± standard deviation
**Day 91 values were used because of RBC lysis on day 56

TABLE 7

Complete blood count after the anti-PD-1 antibody treatment

| Cell type | Pre-infection* (n = 8) | Post SIV infection, Days after PD-1 blockade* (n = 5) | | |
|---|---|---|---|---|
| | | Day 0 | Day 14 | Day 56 |
| Red blood cells (Millions/mm$^3$) | 5.7 ± 0.3 | 5.9 ± 0.3 | 5.4 ± 0.4 | 5.9 ± 0.3 |
| Hematocrit (%) | 41 ± 1 | 42 ± 1 | 38 ± 2 | 41 ± 2 |
| White blood cells (per µL) | 8500 ± 2171 | 9260 ± 3685 | 7500 ± 2068 | 7800 ± 1972 |
| Neutrophils (counts/µL) | 3685 ± 1883 | 3274 ± 2124 | 2573 ± 865 | 2028 ± 1585 |
| Lymphocytes (counts/µL) | 4477 ± 1583 | 4700 ± 1791 | 4235 ± 1880 | 5041 ± 1705 |
| Monocytes (counts/µL) | 166 ± 116 | 635 ± 374 | 336 ± 123 | 350 ± 206 |
| Eosinophils (counts/µL) | 161 ± 155 | 591 ± 580 | 277 ± 275 | 342 ± 175 |
| Basophils (counts/µL) | 10 ± 29 | 29 ± 65 | 78 ± 78 | 37 ± 53 |
| Platelets (counts/µL) | 341 ± 64 | 275 ± 45 | 364 ± 79 | 241 ± 74 |

*Values represent mean ± standard deviation

In one macaque, the levels of ANA increased about 3-fold by day 10 after blockade, but returned to day 0 levels by day 56. These results demonstrate that anti-PD-1 antibody treatment during chronic SIV infection results in no observable toxicity. This is consistent with a recent study that demonstrated the safety of PD-1 blockade in patients with advanced haematological malignancies (Berger et al., *Clin Cancer Res* 14, 3044-3051 (2008)).

The pharmacokinetics of the partially humanized anti-PD-1 antibody in serum after in vivo blockade was studied. The titre of anti-PD-1 antibody rapidly declined between days 14 and 28 after blockade and coincided with macaques generating antibody response against the mouse immunoglobulin variable domains of anti-PD-1 antibody. Hence completely humanized anti-PD-1 antibody may allow longer periods of treatment that may further enhance the efficacy of in vivo blockade.

The results demonstrate that in vivo blockade of PD-1 during chronic SW infection is safe and results in rapid expansion and restoration of SW-specific polyfunctional CD8 T cells and enhanced B-cell responses. Expansion was observed with blockade performed during the early as well as late phases of chronic infection even under conditions of high levels of persisting viraemia and AIDS. Expansion was also observed at the colorectal mucosal tissue, a preferential site of SIV/HIV replication (Pierson et al., *Annu Rev Immunol* 18, 665-708 (2000)). Importantly, PD-1 blockade resulted in a significant reduction of plasma viral load and also prolonged the survival of SW-infected macaques. These results are highly significant considering the failure of blockade of a related co-inhibitory molecule CTLA-4 to expand virus-specific CD8 T cells and to reduce plasma viral load in SW-infected macaques (Cecchinato et al. *J Immunol* 180, 5439-5447 (2008)). The therapeutic benefits of PD-1 blockade could be improved further by using combination therapy with anti-retrovirals and/or therapeutic vaccination.

Example 28

Materials and Methods for Example 29

Animals, SIy inoculation and infection stages: Indian rhesus monkeys (*Macaca mulatta*) and sooty mangabeys were utilized. SW infection was performed by intravenous inoculation, and the animals were grouped by stage of infection into: -acute (2 weeks post infection, p.i.), early chronic (10-12 weeks p.i) and late chronic (1.5 years p.i.).

Viral load measurements: Plasma viral load was determined by quantitative real-time PCR as previously described (Amara et al., *Science* 292:69-74, 2001). All viral RNA specimens were extracted and assayed in duplicate, with mean results reported and used in the analyses.

Phenotypic analysis by flow cytometry: Surface lymphocyte stainings were performed using 100 µl A whole blood samples using multi-parameter, multi-color analysis. Lymphocytes were obtained from necropsy tissue. The following antibodies were used: mouse anti-human antibodies against CD3 (clone SP34-2), CD21 (clone B-Ly4), CD27 (clone M-T2712), CD80 (clone L307.4), CD11c (clone S-HCL-3), all from BD BIODSCIENCES®; CD20 (clone 2H7, eBIOSCIENCES®), CD40 (clone MAB89, BECKMAN COULTER®), CD95 (clone DX2, CALTAG®) and PD-1 (clone EH-12). Cells were analyzed on a LSRII flow cytometer and data analyzed with FLOWJO® software version 8.8.2.

Concanavalin A ELISA to measure SIV env-specific antibody titers and avidity: Titers of anti-env IgG Ab were measured using envelope proteins produced in transient transfections of 293T cells with DNA/89.6 VLP (51). Briefly, 96-well ELISA plates (Costar, Corning Life Sciences) were coated with 25 µg/ml concanavalin A (Con A) in 10 mM Hepes buffer and incubated overnight at 4° C. Plates were washed six times with PBS containing 0.05% Tween-20 (PBS-T), 100 µl of VLP added to each well followed by 1 hour incubation at room temperature, another wash and blocking for 1 hour at room temperature with 100 µl blocking buffer (PBS-T with 4% whey and 5% dry milk) per well. Plates were washed and test sera serially diluted in PBS-T/4% whey added to duplicate wells and incubated for 1 hour at room temperature. For ELISA assays, the plates were washed 6 times with PBS-T, and bound Ab detected using horseradish peroxidase-conjugated anti-monkey IgG (Rockland Immunochemicals) and tetramethyl benzene (TMB) substrate (KPL), and reactions stopped with 100 µl A of 2N $H_2SO_4$. Each plate included a standard curve generated using goat anti-monkey IgG (Rockland Immunochemicals) and rhesus IgG (Accurate chemicals). Standard curves were fitted and sample concentrations interpolated as µg of Ab per ml of serum using SOFTMAX® 2.3 software.

Avidity of Ab to viral envelope proteins was determined by measuring resistance of antibody-envelope complexes to elution by the chaotropic agent NaSCN in a modification of the env Ab ELISA. Test sera were added to the plates in quadruplicates, in 3-fold dilutions starting from 1:100. Following binding of test sera in the ConA env eLISA, one set of duplicates was treated with PBS and the other set with 1.5M NaSCN for 10 minutes before washing and detection with horseradish peroxidase-conjugated anti-monkey IgG and TMB substrate. Reactions were stopped with 100 µl of 2N $H_2SO_4$. The avidity index was calculated by dividing the dilution of the serum that gave an O.D. of 0.5 with NaSCN treatment by the dilution of serum that gave and O.D. of 0.5 with PBS, multiplied by 100.

Neutralization assay: Neutralization was measured as a function of a reduction in luciferase (luc) reporter gene expression after single rounds of infection in 5.25.EGFP-.Luc.M7 cells (TCLA SIVmac25) and TZM-bl cells (293T pseudovirus) as previously reported (51, 52). Values reported represent the serum dilution at which relative luminescence units (RLUs) were reduced 50% compared to virus control wells.

Apoptosis assays: PBMC form 7 SW-infected macaques were plated in 96-well round-bottomed tissue culture plates at $2.5 \times 10^5$ cells/well under four different culture conditions: complete RPMI-1640 medium only (spontaneous apoptosis), complete RPMI-1640 medium+10 ng/ml soluble His-tagged rhFasL (R&D Systems) (Fas-mediated apoptosis) & complete RPMI-1640 medium+10 ng/ml soluble His-tagged rhFasL+10 ng/ml anti-PD-1 blocking Ab. Plates were incubated for 24 h at 37° C. after which the cells were stained for CD20, CD27, CD21 and Annexin-V and immediately analyzed on an LSRII flow cytometer.

Huh-7.5 cells (53) were transfected with a plasmid expressing HLA-A2 under the CMV promoter with a Neomycin resistance gene. Clones were selected and propagated, and then subsequently transfected with a second plasmid (cCNA3.1-Zeo) expressing the full-length INCYTE® human cDNA PD-L1 (OPEN BIOSYSTEMS®, Huntsville, Ala.). A second round of selection and propagation of clones resistant to both Neomycin and Zeocin was performed. Verification of expression of HLA-A2 and PD-L1 was performed by flow cytometry. The Huh-7.5.A2.PD-L1 cells were used to assess PD-L1-mediated apoptosis of activated memory B cells, with Huh-7.5 cells as control. Both cell lines were seeded onto separate 24-well plates and incubated at 37° C. a day before the experiment. B cells were isolated from PBMC using NHP-specific CD20 microbeads (Miltenyi Biotec) and isolated B cells were added to the cell lines and plates incubated for 24 h at 37° C. after which the cells were stained for CD20, CD27, CD21 and Annexin-V and immediately analyzed on an LSRII flow cytometer.

In vitro PBMC stimulation and memory B cell ELISpot assays: PBMC were stimulated and used in memory B cell ELISpot assays using modifications of the method described by Crotty et al (23). Briefly, PBMC were plated in sterile 24-well tissue culture plates (Costar) at $0.5 \times 10^6$ cells/well in complete RPMI-1640 medium containing β-2 mercaptoethanol under 3 different culture conditions-medium only (control); mitogen cocktail-pokeweed mitogen diluted 1:1000, fixed Staphylococcus aureus Cowan strain, SAC (SIGMA®) diluted 1:10,000 and 6 µg/ml CpG ODN-2006 (Qiagen-Operon); mitogen cocktail+10 ng/ml anti-PD-1 blocking Ab (clone 1540-29C9, provided by GF) in triplicates. Cells were cultured at 37° C. with 5% $CO_2$ for 6 days.

On Day 5 of culture, 96-well filter ELISpot plates were coated with affinity-purified goat anti-monkey IgM and IgG (Rockland Immunochemicals) at 10 µg/ml, and SIVmac239 gp130 at 1 µg/ml, and incubated overnight at 4° C.

On Day 6, plates were washed once with PBS-T and three times with PBS and blocked with RPMI-1640 for 2 h at 37° C. Cultured PBMC were washed twice, added to the prepared ELISpot plates and incubated at 37° C. for 6 hours. Plates were then washed 3× with PBS and 3× with PBS-T and incubated overnight at 4° C. with 1 µg/ml biotin-conjugated anti-monkey IgM (for detection of total IgM ASC) or 1 µg/ml anti-monkey IgG (for detection of total IgG and anti-gp130 ASC) diluted in PBS-T/1% FCS. Plates were then washed 4× with PBS-T and incubated at for 1 hour at room temperature with 5 µg/ml HRP-conjugated Avidin D (Vector laboratories) diluted in PBS-T/1% FCS. Plates were washed 4× with and developed using 3-Amino-9-Ethylcarbazole (AEC). Spots on developed plates were counted using an ELISpot plate reader. Data are represented as number of spots (ASC) per $10^6$ PBMC.

Statistical analyses: Statistical analyses were performed using GRAPHPAD PRISM®.

Example 29

Memory B Cells and PD-1 in Progression of a Chronic Infection

Four distinct B cell subsets can be identified in rhesus macaque peripheral blood: The rhesus macaque B cell compartment was characterized. Four distinct B cell subsets in peripheral blood of healthy RM: $CD20^{int}/CD21^+/CD27^-$ (naïve), $CD20^{int}/CD21^+/CD27^+$ (resting memory), $CD20^{hi}/CD21^-/CD27^+$ (activated memory) and $CD20^{hi}/CD21^-/CD27^-$ (unconventional or tissue memory), all with significantly different mean fluorescence intensity (MFI) of CD20 (P<0.0001). Naïve and activated memory B cells were the majority subsets, making up 37% and 36% of total B cells respectively, followed by tissue (18%) and resting (9%) memory B cells. Cells were stained for surface IgM and IgD and it was found that unlike in humans there were virtually no IgM-only cells. The naïve B cells were evenly split between IgD-only and $IgD^+IgM^+$. All three memory subsets were made up of ~20% IgD-only cells; the remaining resting memory B cells were $IgD^+IgM^+$ (~50%) and $IgD^-IgM^-$ (~30%). The activated memory B cells were the most class-switched subset, with ~60% of them $IgD^-IgM^-$ and ~20% $IgD^+IgM^+$. The tissue-like memory B cells on the other hand were mostly IgD+IgM+ (~70%) with only ~10% $IgD^-IgM^-$). Thus, a novel B cell subset was identified for rhesus macaques (RM), which unlike the activated memory B cell subset lacked CD27 expression, but was also $CD21^-$. These B cells could be similar to the unique tissue-like memory B cell subset of cells, whose defining surface marker is the immuno-regulatory molecule FCRL4 in humans.

To further characterize the subsets, the expression of the activation and differentiation markers CD40, CD80, CD95 and CD11c was assessed. Virtually all naïve and resting memory B cells and >70% of resting memory B cells were $CD40^{hi}$, while the majority (>70%) of activated memory B cells were $CD40^{int}$. Activated memory B cells expressed the most CD80, CD95 and CD11c, closely followed by resting memory B cells. CD11c was only expressed on activated and unconventional memory B cells, with naïve B cells expressing negligible amounts of CD80, CD95 and CD11c.

SIV infection leads to depletion of activated memory B cells: The intravenous route of SIV infection, which we used in this study, has been associated with a more rapid course of disease progression in non-human primates, with up to 30% of animals inoculated via this route progressing to AIDS within six months of infection. Animals that developed AIDS-like symptoms or full-blown AIDS and died by week 24 of infection were classified as rapid progressors and all the other animals were classified as typical progressors. One of the first observable changes occurring in the B cell compartment following HIV and SW infections is a marked decrease in numbers of total B cells but it is not clear which specific B cell subsets are deleted. It was found that as early as two weeks following SW infection, peripheral blood total B cells were severely depleted, regardless of rate of disease progression. A rebound in numbers of B cells occurred by the twelfth week of infection in both rapid and typical progressors, but the B cell numbers remained significantly different from pre-infection levels (P<0.0001). The memory B cells in general were depleted following SIV infection with a significant decrease in percentage and numbers of activated memory B cells. By 12 weeks post infection, the rapid progressors had lost 82% of their activated memory B cells, while the typical progressors had lost only 23%. In contrast to the rapid progressors, the activated memory B cell proportions returned to pre-infection levels by week 12 of infection in the typical progressors. This striking contrast in degree of activated memory depletion between rapid and typical progressors prompted the investigation of whether the depletion of activated memory B cells has any significance for disease progression and SW pathogenesis.

Depletion of activated memory B cells is an early predictor of rapid disease progression: Set-point viral load (12 weeks post infection) was shown to be a good predictor of clinical outcome of SIV infection. The association between rapid disease progression and viral load and interestingly was analyzed, both rapid and typical progressors had similar peak (week 2 post infection) viral loads (P=0.8); set-point viral load in the rapid progressors was however a log greater than in the typical progressors (P<0.0001). Given that differences were observed in activated memory B cell proportions as early as 2 weeks post infection, it was hypothesized that depletion of activated memory B cells could be a much earlier predictor of rapid disease progression. Blood central memory ($CD28^+CD95^+$, $T_{CM}$) and gut $CD4^+$ T cells have also been suggested as markers of disease progression in SIV infection so comparisons were preformed of all these markers to evaluate the predictive value of each one. Two weeks post SW infection, the rapid progressors had significantly lower proportions of activated memory B cells compared to the typical progressors and activated memory B cells were the only cell subset whose distribution was significantly different (P<0.001) between rapid and typical progressors. By 12 weeks post infection, the activated memory B cells were even further depleted in the rapid progressors (P<0.0001), and significant differences between rapid and typical progressors also emerged with respect to proportions of $T_{CM}$ and gut $CD4^+$ T cells (P<0.01) (FIG. 3B, bottom panel). To further confirm the usefulness of 2-week depletion of activated memory B cells as an early marker of disease progression, correlation analyses were performed of the set point (week 12 post SW infection) viral load versus week 2 and week 12 percentages of activated memory B cells, gut $CD4^+$ T cells and $T_{CM}$ cells. Whereas both week 2 and week 12 activated memory B cells were inversely correlated with set-point viral loads, only week 12 gut $CD4^+$ percentages correlated with set-point viremia, and $T_{CM}$ showed no correlation with set-point viremia at all. The loss of activated memory B cells is therefore an early predictor of rapid disease progression in rhesus macaques (RM), with better early predictive value than peak viral load, $T_{CM}$ and gut $CD4^+$ T cells.

Depletion of activated memory B cells in rapidly progressing SIV infection impairs SIV-specific humoral immune response and resistance to other non-SIV infections: RM with rapidly progressing SW infection were shown to have low antibody responses as a consequence of the acute destruction of the B cell compartment. Opportunistic infections and non-SW related Ags are a significant cause of mortality in SW-infected animals. The loss of activated memory B cells could have important consequences for the humoral immune response of rapidly progressing animals to SW and non-SW Ags. Thus, the serum titers of SW env-binding Abs were measured in both rapid and typical progressors; it was found that of the 9 rapid progressors assayed, only 2 mounted a modest env Ab response by week 12 and only 1 of the animals had sustained Ab titers by week 20. The remaining 7 rapid progressors had undetectable SIV env Ab titers through week 20 of infection. The typical progressors on the other hand developed strong env Ab responses by 12 weeks post infection, with even higher titers by week 20.

Bacterial opportunistic infections are a significant cause of morbidity in SW-infected animals and the causative agents of these infections are usually flagellated. Serum Ab titers to flagellin (FliC isolated from *Salmonella typhimurium*) were measured as a means to assess the effect of loss of activated memory B cells on pre-existing humoral immunity. Despite starting off with comparable anti-FliC Ab titers, the rapid progressors had significantly lower (P=0.001) titers by week 20 post infection compared to the typical progressors in which titers were unchanged (P=0.9) (FIG. 5C). Clinical infection data was analyzed for both groups over a 6-month period following initial SW infection and it was found that a wide variety of other infections occurred in the animals following SW infection. These included bacterial (*Campylobacter, Shigella*, enteropathogenic *E. coli*), parasitic (*Trichomonas*, whip worms, *Giardia*) and yeast (*Candida*) infections. Rapid progressors succumbed to these infections as early as 1 month p.i. and by 3 months p.i. >50% of the rapid progressors were infected compared to <10% of the typical progressors. This rate of infection in rapid progressors was sustained throughout the 6-month period.

In vitro PD-1 blockade decreases Fas-mediated apoptosis, and ligation of PD-1 induces apoptosis of activated memory B cells: PD-1 is mainly expressed on memory B cells of rhesus macaques. Expression of PD-1 was assessed on all B cell subsets in more detail before and after SW infection, and it was found that a higher proportion of all 3 memory B cell subsets expressed higher amounts (mean fluorescence intensity, MFI) of PD-1 compared to naïve B cells (P<0.001). The activated memory cells not only expressed the highest amounts of PD-1, but also had the highest proportion of PD-$1^+$ cells compared to the other subsets (P<0.001). Following SW infection, irrespective of disease progression status, there was a preferential depletion of PD-$1^+$ memory B cells. This raised the possibility that PD-1 may play a role in depletion of activated memory B cells.

Memory B cells in HIV-infected humans are primed to undergo both spontaneous and death receptor-induced apoptosis notably through the Fas-FasL pathway, but there is little information on what role the Fas-FasL pathway plays in B cell apoptosis during SW infection. In order to determine susceptibility of activated memory B cells to Fas-mediated apoptosis and to identify a possible role for PD-1 in activated memory B cell depletion, PBMC from 7 SW-infected animals were cultured with and without sFasL in combination with PD-1 blockade and analyzed Annexin-V expression on activated memory B cells was assessed after 24 hours of culture. In all 6 animals a significant increase in apoptosis was seen with the addition of sFasL to the cultures, and in 4 animals a decrease in FasL-mediated apoptosis was observed following PD-1 blockade, indicating that PD-1 could contribute to apoptosis of activated memory B cells.

To further demonstrate the role of PD-1 on apoptosis of activated memory B cells, the human hepatoma cell line, Huh-7.5 transfected with PD-L1 (Huh-7.5.A2.PD-L1) was used as a source of ligand for the PD-1-expressing activated memory B cells. Expression of PD-L1 as verified by flow cytometry showed no PD-L1 expression in the non-transfected Huh-7.5 cells (control) compared to >90% PD-L1 expression on the Huh-7.5.A2.PD-L1 cells. There was an increased rate of apoptosis in the activated memory B cells cultured in the presence of PD-L1 compared to the control wells, in 5 out of 7 animals tested. In one animal (4) a similar rate of apoptosis was observed with or without PD-L1, and in the other animal (3), the rate of spontaneous apoptosis was >30% and addition of PD-L1 did not significantly alter the apoptosis. Thus PD-1 signaling during SIV infection plays a role in activated memory B cell apoptosis.

Blocking PD-1-PD-L1 interaction was shown to increase the capacity of HIV-specific $CD8^+$ T cells to proliferate and survive. Thus, the effect of in vitro PD-1 blockade on spontaneous and Fas-mediated activated memory B cell apoptosis. The effect of in vitro blockade was assessed on the ability of memory B cells from SW-infected animals to survive, proliferate in response to polyclonal stimulation, and differentiate into antibody-secreting cells (ASC) in a memory B cell ELISPot assay. Blockade resulted in slightly decreased Fas-mediated apoptosis of activated memory B cells, but did not have an effect on spontaneous apoptosis. Cells stimulated in the presence of PD-1 blocking Ab proliferated better and produced higher numbers of ASC against total IgM and IgG, but also env-specific spots.

RM Activated memory B cells have lower expression of BAFF-R, which is decreased further by SIV infection: B cell activating factor belonging to the TNF family, BAFF (also known as B-lys) is an important regulator of B cell homeostasis (21), and $CD21^-$ B cells in cynomolgus macaques were shown to express lower expression of one of its receptors, BAFF-R. $CD21^{low}$ B cells of HIV viremic patients were also shown to express lower levels of BAFF-R. It was found that activated and tissue memory B cells expressed the lowest levels of BAFF-R compared to naïve and resting memory B cells. Expression was further decreased 2 weeks post infection but interestingly was restored by week 12. Thus low expression of BAFF-R may be a contributing factor in the depletion of activated memory B cells.

In vitro PD-1 blockade increases memory B cell proliferation and antibody production: It was investigated whether the presence of PD-1 on memory B cells would affect their ability to proliferate and differentiate into antibody secreting cells (ASC). An in vitro elispot assay was designed to track IgM, IgG and SW gp130-producing memory B cells based on assays that have been described. Following polyclonal stimulation, there was a significant increase in IgM ($P<0.05$) and IgG ($P<0.01$) ASC in both early (12 weeks, n=3) and late chronic (>1 year, n=2) infection. Cells stimulated in the presence of α-PD-1 blocking Ab generally proliferated better and produced a higher number of spots than cells stimulated without blocking Ab. gp130-specific ASC were however detectable only in the late chronic monkeys and as with the IgM and IgG ASCs, polyclonal stimulation resulted in a significantly higher number of gp130 specific ASCs, and blockade of PD-1 further increased the numbers of ASCs.

In vivo PD-1 blockade results in increased SIV env binding antibody titers with higher avidity, and increased neutralizing Ab titers: In vivo blockade of PD-1 in rhesus macaques with chronic SIV infection resulted in increased titers of SW env binding Abs. The avidity of env Abs following in vivo PD-1 blockade was measured. It was found that not only were the titers of the env Abs increased, but the avidity of the binding Abs were also increased in the treated animals. This was not the case in the control Ab-treated animal in which avidity was decreased following treatment.

Neutralizing activity was also assessed in the PD-1 treated animals, and it was found that though neutralization against a primary SW isolate was not significantly different, neutralization against a TCLA SW strain was significantly different in the treated animals, with 2 of the animals showing 3-6 fold increase in neutralizing Ab titers.

Distribution of B cell subsets in sooty mangabeys: Sooty mangabeys, one of the natural hosts of SW, do not develop AIDS despite persistent high viral titers comparable to those of rhesus macaques. This makes SM an interesting 'control' model for studies of pathogenic SW infection in RM. A cohort of uninfected (n=8) and SW-infected (n=10) sooty mangabeys (SM) was studied. Healthy SM had far fewer circulating total B cells than healthy RM and unlike in RM, we did not see a decrease in percentage of circulating total B cells following SW infection in SM. Identical B cell subsets were identified in SM, but the distribution of subsets in SM was very different from that in RM. Naïve B cells constituted the major peripheral blood B cell subset (>40%), and the majority memory B cell subset was the tissue-like memory B cells and not activated memory B cells as in RM. Like RM, <10% of circulating memory B cells in the SM were resting memory B cells but compared to RM, the percentage of activated memory B cells was significantly lower in SM. Following SW infection, there was no depletion of activated memory B cells; in fact there was a slight increase in percentage of both resting and activated memory B cells, although these changes did not reach statistical significance. PD-1 expression on B cell subsets of SM, as in the RM, was highest on the activated memory B cells and unlike in RM, PD-1 expression was equally high on tissue memory B cells. Another significant difference between RM and SM was that unlike in RM, the proportions of PD-1 expressing cells went up following SIV infection in SM.

Example 30

Method of Determining the Efficacy of a PD-1 Antagonist

The efficacy of a PD-1 antagonist for treating a subject can be determined by measuring B cells, such as by measuring the presence of neutralizing antibodies, the proliferation of memory B cells, naïve B cells, and/or by measuring CD28+ T cells. Generally, a statistically significant increase in neutralizing antibodies, the proliferation of memory B cells, naïve B cells, and/or by measuring CD28+ T cells indicates that the PD-1 antagonist is effective for treating the subject. B cells can be measured, for example, as described in U.S. Pat. No. 7,378,276 and/or U.S. Pat. No. 6,376,459, both of which are incorporated herein by reference. PD-1 antagonists include antibodies that specifically bind PD-L1 and PD-L2, see for example, U.S. Pat. No. 7,432,059.

Determining the efficacy of a PD-1 antagonist involves obtaining a biological sample from the subject. A biological sample, such as a blood sample or a sample of peripheral blood mononuclear cells is taken from a human subject, such as a subject with a persistent infection. The presence of proliferating memory B cells, naïve B cells and/or CD28+ T cells is measured using a FACS analysis. The presence of neutralizing antibodies can be measured, such as by using an ELISA. The proliferating memory B cells, naïve B cells and/or CD28+ cells, and/or the presence of neutralizing antibodies can be compared to a control, such as the in a sample from the subject obtained prior to treatment with the PD-1 antagonist. A statistical test is performed. A statistically significant increase in proliferating memory B cells, and/or neutralizing antibodies and/or CD28+ T cells in the blood sample from the subject following administration to the subject in comparison to the control demonstrates that the PD-1 antagonist is effective for treating the subject. However, naïve B cells are not affected by the administration of the PD-1 antagonist.

A number of types of subject are treated and tested. These subjects include a subject with an HIV infection, a subject with an xenotropic murine leukemia virus-related virus (XMRV) infection, and a subject with an polyomavirus JC infection. The PD-1 antagonist can be administered with anti-retroviral therapy, such as for treating HIV and XMRV. Suitable subject also include those with tumors, such as a solid tumor or a lymphoma or a leukemia. These subject can also be administered a chemotherapeutic agent and/or a tumor antigen.

It will be apparent that the precise details of the methods or compositions described may be varied or modified without departing from the spirit of the described invention. We claim all such modifications and variations that fall within the scope and spirit of the claims below.

The invention claimed is:

1. A method for diagnosing and treating a human subject having a persistent viral infection or cancer, said method comprising:
   a) administering to the human subject a first dose of a PD-1 antagonist;
   b) obtaining a first sample comprising peripheral blood mononuclear cells from the human subject;
   c) quantifying both $CD20^+CD27^+CD21^-$ memory B cell proliferation and $CD20^+CD21^+CD27^-$ naïve B cell proliferation in the first sample
   d) diagnosing the human subject as having effective treatment when an increased proliferation of $CD20^+CD27^+CD21^-$ memory B cells and no significant increase in proliferation of $CD20^+CD21^+CD27^-$ naïve B cells is detected from the first sample; and
   e) administering second dose of the PD-1 antagonist to treat the persistent viral infection or the cancer in the human subject subsequently to step (d).

2. The method of claim 1, wherein the subject has the persistent viral infection, and wherein the persistent viral infection is an HIV infection.

3. The method of claim 1, wherein quantifying $CD20^+CD27^+CD21^-$ memory B cell proliferation and/or $CD20^+CD21^+CD27^-$ naïve B cell proliferation comprises a) measuring the expression of Ki67 using an antibody that specifically binds Ki67, b) measuring incorporation of bromodeoxyuridine into the $CD20^+CD27^+CD21^-$ memory B cells, and/or c) using fluorescence activated cell sorting (FACS).

4. The method of claim 1, wherein the subject has the cancer.

5. A method of inducing an immune response in a mammalian subject with a persistent infection with a virus or cancer, comprising:
   a) administering to the subject a first dose of a PD-1 antagonist;
   b) obtaining a first sample comprising peripheral blood mononuclear cells from the human subject;
   c) quantifying $CD20^+CD27^+CD21^-$ memory B cell proliferation and $CD20^+CD21^+CD27^-$ naïve B cell proliferation in the first sample;
   d) diagnosing the human subject as not having effective treatment when no significant increase in proliferation $CD20^+CD27^+CD21^-$ memory B cells and no significant increase in proliferation of $CD20^+CD21^+CD27^-$ naïve B cells is detected from the first sample; and
   e) administering an increased second dose of the PD-1 antagonist to treat the persistent viral infection or the cancer in the human subject subsequently to step (d).

6. The method of claim 1, further comprising quantifying $CD20^+CD27^+CD21^-$ memory B cell proliferation and $CD20^+CD21^+CD27^-$ naïve B cell proliferation in a second sample from the subject following the administration of the second dose.

7. The method of claim 2, wherein quantifying $CD20^+CD27^+CD21^-$ memory B cell proliferation comprises measuring the expression of Ki67 using an antibody that specifically binds Ki67.

8. The method of claim 2, wherein quantifying $CD20^+CD27^+CD21^-$ memory B cell proliferation comprises measuring the incorporation of bromodeoxyuridine.

9. The method of claim 2, wherein quantifying $CD20^+CD27^+CD21^-$ memory B cell proliferation comprises the use of fluorescence activated cell sorting (FACS).

10. The method of claim 1, wherein the subject has the persistent viral infection.

11. The method of claim 10, wherein the subject is administered a viral antigen.

12. The method of claim 10, wherein the viral infection is an infection with a hepatitis virus, a human immunodeficiency virus (HIV), a human T-lymphotrophic virus (HTLV), a herpes virus, an Epstein-Barr virus, or a human papilloma virus.

13. The method of claim 1, wherein the PD-1 antagonist is an antibody that specifically binds PD-1, an antibody that specifically binds PD-L1, an antibody that specifically binds PD-L2, a small inhibitory anti-PD-1 RNAi, a small inhibitory anti-PD-L1 RNA, a small inhibitory anti-PD-L2 RNAi, an anti-PD-1 antisense RNA, an anti-PD-L1 antisense RNA, an anti-PD-L2 antisense RNA, a dominant negative PD-1 protein, a dominant negative PD-L1 protein, a dominant negative PD-L2 protein, a small molecule inhibitor of PD-1, or combinations thereof.

14. The method of claim 13, wherein the PD-1 antagonist is an antibody that specifically binds PD-1, and wherein the antibody that specifically binds PD-1 is (1) a monoclonal antibody or a functional fragment thereof, (2) a humanized antibody or a functional fragment thereof, or (3) an immunoglobulin fusion protein.

15. The method of claim 13, wherein the PD-1 antagonist is an antibody that specifically binds PD-L1, and wherein the antibody that specifically binds PD-L1 is (1) a monoclonal antibody or a functional fragment thereof, (2) a humanized antibody or a functional fragment thereof, or (3) an immunoglobulin fusion protein.

16. The method of claim 13, wherein the PD1 antagonist is an antibody that specifically binds PD-L2, and wherein the antibody that specifically binds PD-L2 is (1) a monoclonal antibody or a functional fragment thereof, (2) a humanized antibody or a functional fragment thereof, or (3) an immunoglobulin fusion protein.

17. The method of claim 1, wherein the subject is immunosuppressed.

18. The method of claim 1, wherein the subject is assymptomatic.

19. The method of claim 1, wherein the subject is human.

20. The method of claim 19, wherein the subject has a human immunodeficiency virus (HIV) infection and wherein the PD-1 antagonist is an antibody that specifically binds PD-1.

21. The method of claim 1, wherein the subject has a human immunodeficiency virus (HIV) infection, and wherein the PD-1 antagonist is an antibody that specifically binds PD-1.

22. The method of claim 1, wherein the method further comprises measuring differentiation of the $CD20^+CD27^+CD21^-$ memory B cells into antibody secreting cells.

23. The method of claim 1, wherein the subject has a human immunodeficiency virus infection and wherein the method further comprises administering to the subject a therapeutically effective amount of an anti-retroviral agent.

24. The method of claim 1, wherein the subject has a human immunodeficiency virus infection and wherein the method further comprises administering to the subject a therapeutically effective amount of a vaccine comprising a human immunodeficiency virus gp41, gp120 or polymerase.

25. The method of claim 5, wherein the subject has the cancer.

26. The method of claim 5, wherein the-virus is a hepatitis virus, a human immunodeficiency virus (HIV), a human T-lymphotrophic virus (HTLV), a herpes virus, an Epstein-Barr virus, or a human papilloma virus.

27. The method of claim 5, wherein the infection with the virus is a hepatitis viral infection.

28. The method of claim 5, wherein the infection with the virus is a human immunodeficiency viral (HIV) infection.

29. The method of claim 5, wherein the PD-1 antagonist is an antibody that specifically binds PD-1, an antibody that specifically binds PD-L1, an antibody that specifically binds PD-L2, a small inhibitory anti-PD-1 RNAi, a small inhibitory anti-PD-L1 RNA, a small inhibitory anti-PD-L2 RNAi, an anti-PD-1 antisense RNA, an anti-PD-L1 antisense RNA, an anti-PD-L2 antisense RNA, a dominant negative PD-1 protein, a dominant negative PD-L1 protein, a dominant negative PD-L2 protein, a small molecule inhibitor of PD-1, or combinations thereof.

30. The method of claim 29, wherein the PD1 antagonist is an antibody that specifically binds PD-1, and wherein the antibody that specifically binds PD-1 is (1) a monoclonal antibody or a functional fragment thereof, (2) a humanized antibody or a functional fragment thereof, or (3) an immunoglobulin fusion protein.

31. The method of claim 29, wherein the PD1 antagonist is an antibody that specifically binds PD-L1, and wherein the antibody that binds PD-L1 is (1) a monoclonal antibody or a functional fragment thereof, (2) a humanized antibody or a functional fragment thereof, or (3) an immunoglobulin fusion protein.

32. The method of claim 29, wherein the PD1 antagonist is an antibody that specifically binds PD-L2, and wherein the antibody that binds PD-L2 is (1) a monoclonal antibody or a functional fragment thereof, (2) a humanized antibody or a functional fragment thereof, or (3) an immunoglobulin fusion protein.

33. The method of claim 5, wherein quantifying proliferation of the memory B cells comprises measuring expression of Ki67 using an antibody that specifically binds Ki67.

34. The method claim 5, wherein quantifying proliferation of the memory B cells comprises measuring the incorporation of bromodeoxyuridine.

35. The method of claim 5, wherein quantifying proliferation of the memory B cells comprises the use of fluorescence activated cell sorting (FACS).

36. The method of claim 1, further comprising administering to the subject a therapeutically effective amount of an additional compound.

37. The method of claim 36, wherein the additional compound is an antiviral compound, an antibacterial compound, an antifungal compound, an antiparasitic compound, an anti-inflammatory compound, or an analgesic.

38. The method of claim 5, wherein the subject has a human immunodeficiency virus (HIV) infection, and wherein the PD-1 antagonist is an antibody that specifically binds PD-1.

39. The method of claim 5, wherein isolating the $CD20^+CD27^+CD21^-$ memory B cells comprises the use of fluorescence actived cell sorting.

40. The method of claim 5, wherein the method further comprises measuring differentiation of the $CD20^+CD27^+CD21^-$ memory B cells into antibody secreting cells.

* * * * *

SEQUENCE LISTING

```
<160> NUMBER OF SEQ ID NOS: 52

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Phe Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270
```

```
Ser Ala Gln Pro Leu Arg Pro Glu Asp Gly His Cys Ser Trp Pro Leu
        275                 280                 285

<210> SEQ ID NO 2
<211> LENGTH: 288
<212> TYPE: PRT
<213> ORGANISM: Mus musculus

<400> SEQUENCE: 2

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285

<210> SEQ ID NO 3
<211> LENGTH: 290
<212> TYPE: PRT
<213> ORGANISM: Homo sapiens

<400> SEQUENCE: 3

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30
```

-continued

```
Gly Ser Asn Met Thr Ile Glu Cys Lys Phe Pro Val Glu Lys Gln Leu
            35                  40                  45
Asp Leu Ala Ala Leu Ile Val Tyr Trp Glu Met Glu Asp Lys Asn Ile
 50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                85                  90                  95
Ala Ala Leu Gln Ile Thr Asp Val Lys Leu Gln Asp Ala Gly Val Tyr
            100                 105                 110
Arg Cys Met Ile Ser Tyr Gly Gly Ala Asp Tyr Lys Arg Ile Thr Val
            115                 120                 125
Lys Val Asn Ala Pro Tyr Asn Lys Ile Asn Gln Arg Ile Leu Val Val
130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
            195                 200                 205
Cys Thr Phe Arg Arg Leu Asp Pro Glu Glu Asn His Thr Ala Glu Leu
210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
            275                 280                 285
Glu Thr
    290

<210> SEQ ID NO 4
<211> LENGTH: 273
<212> TYPE: PRT
<213> ORGANISM: Homo sapiens

<400> SEQUENCE: 4

Met Ile Phe Leu Leu Leu Met Leu Ser Leu Glu Leu Gln Leu His Gln
 1               5                  10                  15
Ile Ala Ala Leu Phe Thr Val Thr Val Pro Lys Glu Leu Tyr Ile Ile
            20                  25                  30
Glu His Gly Ser Asn Val Thr Leu Glu Cys Asn Phe Asp Thr Gly Ser
            35                  40                  45
His Val Asn Leu Gly Ala Ile Thr Ala Ser Leu Gln Lys Val Glu Asn
 50                  55                  60
Asp Thr Ser Pro His Arg Glu Arg Ala Thr Leu Leu Glu Glu Gln Leu
 65                  70                  75                  80
Pro Leu Gly Lys Ala Ser Phe His Ile Pro Gln Val Gln Val Arg Asp
                85                  90                  95
Glu Gly Gln Tyr Gln Cys Ile Ile Ile Tyr Gly Val Ala Trp Asp Tyr
```

```
            100                 105                 110
Lys Tyr Leu Thr Leu Lys Val Lys Ala Ser Tyr Arg Lys Ile Asn Thr
        115                 120                 125
His Ile Leu Lys Val Pro Glu Thr Asp Glu Val Glu Leu Thr Cys Gln
        130                 135                 140
Ala Thr Gly Tyr Pro Leu Ala Glu Val Ser Trp Pro Asn Val Ser Val
145                 150                 155                 160
Pro Ala Asn Thr Ser His Ser Arg Thr Pro Glu Gly Leu Tyr Gln Val
                165                 170                 175
Thr Ser Val Leu Arg Leu Lys Pro Pro Gly Arg Asn Phe Ser Cys
        180                 185                 190
Val Phe Trp Asn Thr His Val Arg Glu Leu Thr Leu Ala Ser Ile Asp
        195                 200                 205
Leu Gln Ser Gln Met Glu Pro Arg Thr His Pro Thr Trp Leu Leu His
        210                 215                 220
Ile Phe Ile Pro Ser Cys Ile Ile Ala Phe Ile Phe Ile Ala Thr Val
225                 230                 235                 240
Ile Ala Leu Arg Lys Gln Leu Cys Gln Lys Leu Tyr Ser Ser Lys Asp
                245                 250                 255
Thr Thr Lys Arg Pro Val Thr Thr Thr Lys Arg Glu Val Asn Ser Ala
                260                 265                 270
Ile

<210> SEQ ID NO 5
<211> LENGTH: 23
<212> TYPE: PRT
<213> ORGANISM: Homo sapiens

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 6
<211> LENGTH: 14
<212> TYPE: PRT
<213> ORGANISM: Homo sapiens

<400> SEQUENCE: 6

Trp Tyr Gln Gln Lys Pro Gly Gln Pro Pro Leu Leu Ile Tyr
1               5                   10

<210> SEQ ID NO 7
<211> LENGTH: 32
<212> TYPE: PRT
<213> ORGANISM: Homo sapiens

<400> SEQUENCE: 7

Gly Val Pro Asp Arg Pro Phe Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 8
<211> LENGTH: 11
<212> TYPE: PRT
<213> ORGANISM: Homo sapiens
```

```
<400> SEQUENCE: 8

Phe Gly Gln Gly Gln Thr Lys Leu Glu Ile Lys
1               5                   10

<210> SEQ ID NO 9
<211> LENGTH: 30
<212> TYPE: PRT
<213> ORGANISM: Homo sapiens

<400> SEQUENCE: 9

Gln Val Gln Leu Val Gln Ser Gly Ala Glu Val Lys Lys Pro Gln Ala
1               5                   10                  15

Ser Val Lys Val Ser Cys Lys Ala Ser Gln Tyr Thr Phe Thr
            20                  25                  30

<210> SEQ ID NO 10
<211> LENGTH: 14
<212> TYPE: PRT
<213> ORGANISM: Homo sapiens

<400> SEQUENCE: 10

Trp Val Arg Gln Ala Pro Gly Gln Arg Leu Glu Trp Met Gly
1               5                   10

<210> SEQ ID NO 11
<211> LENGTH: 32
<212> TYPE: PRT
<213> ORGANISM: Homo sapiens

<400> SEQUENCE: 11

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 12
<211> LENGTH: 11
<212> TYPE: PRT
<213> ORGANISM: Homo sapiens

<400> SEQUENCE: 12

Trp Gly Gln Gly Thr Leu Val Thr Val Ser Ser
1               5                   10

<210> SEQ ID NO 13
<211> LENGTH: 15
<212> TYPE: PRT
<213> ORGANISM: Artificial sequence
<220> FEATURE:
<223> OTHER INFORMATION: Exemplary antigenic peptide

<400> SEQUENCE: 13

Thr Leu Tyr Lys Lys Met Glu Gln Asp Val Lys Val Ala His Gln
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Exemplary antigenic peptide

<400> SEQUENCE: 14

Gly Asn Leu Pro Leu Met Arg Lys Ala Tyr Leu Arg Lys Cys Lys
```

```
<210> SEQ ID NO 15
<211> LENGTH: 15
<212> TYPE: PRT
<213> ORGANISM: Artificial sequence
<220> FEATURE:
<223> OTHER INFORMATION: Exemplary antigenic peptide

<400> SEQUENCE: 15

Thr Phe Ser Arg Met Lys Tyr Asn Ile Cys Met Gly Lys Cys Ile
1               5                   10                  15

<210> SEQ ID NO 16
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 16

Ser Ile Thr Glu Val Glu Cys Phe Leu
1               5

<210> SEQ ID NO 17
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 17

Gln Pro Arg Ala Pro Ile Arg Pro Ile
1               5

<210> SEQ ID NO 18
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 18

Asn Leu Val Pro Met Val Ala Thr Val
1               5

<210> SEQ ID NO 19
<211> LENGTH: 10
<212> TYPE: PRT
<213> ORGANISM: Artificial sequence
<220> FEATURE:
<223> OTHER INFORMATION: Exemplary antigenic peptide

<400> SEQUENCE: 19

Tyr Met Leu Asp Leu Gln Pro Glu Thr Thr
1               5                   10

<210> SEQ ID NO 20
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 20

Gly Ile Leu Gly Phe Val Phe Thr Leu
1               5
```

```
<210> SEQ ID NO 21
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 21

Leu Tyr Val Asp Ser Leu Phe Phe Leu
1               5

<210> SEQ ID NO 22
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 22

Arg Met Phe Pro Asn Ala Pro Tyr Leu
1               5

<210> SEQ ID NO 23
<211> LENGTH: 10
<212> TYPE: PRT
<213> ORGANISM: Artificial sequence
<220> FEATURE:
<223> OTHER INFORMATION: Exemplary antigenic peptide

<400> SEQUENCE: 23

Glu Leu Thr Leu Gly Glu Phe Leu Lys Leu
1               5                   10

<210> SEQ ID NO 24
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 24

Gly Val Ala Leu Gln Thr Met Lys Gln
1               5

<210> SEQ ID NO 25
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 25

Glu Thr Val Ser Glu Gln Ser Asn Val
1               5

<210> SEQ ID NO 26
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 26

Val Leu Gln Glu Leu Asn Val Thr Val
1               5
```

```
<210> SEQ ID NO 27
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 27

Val Leu Gln Glu Leu Asn Val Thr Val
1               5

<210> SEQ ID NO 28
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 28

Glu Ala Asp Pro Thr Gly His Ser Tyr
1               5

<210> SEQ ID NO 29
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 29

Ala Ala Gly Ile Gly Ile Leu Thr Val
1               5

<210> SEQ ID NO 30
<211> LENGTH: 21
<212> TYPE: PRT
<213> ORGANISM: Artificial sequence
<220> FEATURE:
<223> OTHER INFORMATION: Exemplary antigenic peptide

<400> SEQUENCE: 30

Arg His Arg Pro Leu Gln Glu Val Tyr Pro Glu Ala Asn Ala Pro Ile
1               5                   10                  15

Gly His Asn Arg Glu
            20

<210> SEQ ID NO 31
<211> LENGTH: 16
<212> TYPE: PRT
<213> ORGANISM: Artificial sequence
<220> FEATURE:
<223> OTHER INFORMATION: Exemplary antigenic peptide

<400> SEQUENCE: 31

Trp Asn Arg Gln Leu Tyr Pro Glu Trp Thr Glu Ala Gln Arg Leu Asp
1               5                   10                  15

<210> SEQ ID NO 32
<211> LENGTH: 10
<212> TYPE: PRT
<213> ORGANISM: Artificial sequence
<220> FEATURE:
<223> OTHER INFORMATION: Exemplary antigenic peptide

<400> SEQUENCE: 32

Val Leu Leu Lys Glu Phe Thr Val Ser Gly
```

```
<210> SEQ ID NO 33
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 33

Lys Ile Phe Gly Ser Leu Ala Phe Leu
1               5

<210> SEQ ID NO 34
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 34

His Leu Phe Gly Tyr Ser Trp Tyr Lys
1               5

<210> SEQ ID NO 35
<211> LENGTH: 10
<212> TYPE: PRT
<213> ORGANISM: Artificial sequence
<220> FEATURE:
<223> OTHER INFORMATION: Exemplary antigenic peptide

<400> SEQUENCE: 35

Phe Leu Thr Pro Lys Lys Leu Gln Cys Val
1               5                   10

<210> SEQ ID NO 36
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 36

Gly Leu Cys Thr Leu Val Ala Met Leu
1               5

<210> SEQ ID NO 37
<211> LENGTH: 8
<212> TYPE: PRT
<213> ORGANISM: Artificial sequence
<220> FEATURE:
<223> OTHER INFORMATION: Exemplary antigenic peptide

<400> SEQUENCE: 37

Arg Ala Lys Phe Lys Gln Leu Leu
1               5

<210> SEQ ID NO 38
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 38

Phe Leu Arg Gly Arg Ala Tyr Gly Leu
1               5
```

```
<210> SEQ ID NO 39
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 39

Asn Leu Val Pro Met Val Ala Thr Val
1               5

<210> SEQ ID NO 40
<211> LENGTH: 10
<212> TYPE: PRT
<213> ORGANISM: Artificial sequence
<220> FEATURE:
<223> OTHER INFORMATION: Exemplary antigenic peptide

<400> SEQUENCE: 40

Thr Pro Arg Val Thr Gly Gly Gly Ala Met
1               5                   10

<210> SEQ ID NO 41
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 41

Gly Ile Leu Gly Phe Val Phe Thr Leu
1               5

<210> SEQ ID NO 42
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 42

Cys Leu Thr Glu Tyr Ile Leu Trp Val
1               5

<210> SEQ ID NO 43
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 43

Lys Val Asp Asp Thr Phe Tyr Tyr Val
1               5

<210> SEQ ID NO 44
<211> LENGTH: 9
<212> TYPE: PRT
<213> ORGANISM: Artificial sequence
<220> FEATURE:
<223> OTHER INFORMATION: Exemplary antigenic peptide

<400> SEQUENCE: 44

Cys Ile Asn Gly Val Cys Trp Thr Val
1               5
```

<210> SEQ ID NO 45
<211> LENGTH: 10
<212> TYPE: PRT
<213> ORGANISM: Artificial sequence
<220> FEATURE:
<223> OTHER INFORMATION: Exemplary antigenic peptide

<400> SEQUENCE: 45

Lys Leu Val Ala Leu Gly Ile Asn Ala Val
1               5                   10

<210> SEQ ID NO 46
<211> LENGTH: 273
<212> TYPE: PRT
<213> ORGANISM: Homo sapiens

<400> SEQUENCE: 46

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile

<210> SEQ ID NO 47
<211> LENGTH: 24
<212> TYPE: PRT
<213> ORGANISM: Artificial sequence

```
<220> FEATURE:
<223> OTHER INFORMATION: Exemplary antigenic peptide

<400> SEQUENCE: 47

Cys Glu Leu Asp Asn Ser His Glu Asp Tyr Asn Trp Asn Leu Trp Phe
1               5                   10                  15

Lys Trp Cys Ser Gly His Gly Arg
            20

<210> SEQ ID NO 48
<211> LENGTH: 24
<212> TYPE: PRT
<213> ORGANISM: Artificial sequence
<220> FEATURE:
<223> OTHER INFORMATION: Exemplary antigenic peptide

<400> SEQUENCE: 48

Thr Gly His Gly Lys His Phe Tyr Asp Cys Asp Trp Asp Pro Ser His
1               5                   10                  15

Gly Asp Tyr Ser Trp Tyr Leu Trp
            20

<210> SEQ ID NO 49
<211> LENGTH: 24
<212> TYPE: PRT
<213> ORGANISM: Artificial sequence
<220> FEATURE:
<223> OTHER INFORMATION: Exemplary antigenic peptide

<400> SEQUENCE: 49

Asp Pro Ser His Gly Asp Tyr Ser Trp Tyr Leu Trp Asp Tyr Leu Cys
1               5                   10                  15

Gly Asn Gly His His Pro Tyr Asp
            20

<210> SEQ ID NO 50
<211> LENGTH: 24
<212> TYPE: PRT
<213> ORGANISM: Artificial sequence
<220> FEATURE:
<223> OTHER INFORMATION: Exemplary antigenic peptide

<400> SEQUENCE: 50

Asp Tyr Leu Cys Gly Asn Gly His His Pro Tyr Asp Cys Glu Leu Asp
1               5                   10                  15

Asn Ser His Glu Asp Tyr Ser Trp
            20

<210> SEQ ID NO 51
<211> LENGTH: 24
<212> TYPE: PRT
<213> ORGANISM: Artificial sequence
<220> FEATURE:
<223> OTHER INFORMATION: Exemplary antigenic peptide

<400> SEQUENCE: 51

Asp Pro Tyr Asn Cys Asp Trp Asp Pro Tyr His Glu Lys Tyr Asp Trp
1               5                   10                  15

Asp Leu Trp Asn Lys Trp Cys Asn
            20

<210> SEQ ID NO 52
<211> LENGTH: 24
<212> TYPE: PRT
```

```
<213> ORGANISM: Artificial sequence
<220> FEATURE:
<223> OTHER INFORMATION: Exemplary antigenic peptide

<400> SEQUENCE: 52

Lys Tyr Asp Trp Asp Leu Trp Asn Lys Trp Cys Asn Lys Asp Pro Tyr
1               5                   10                  15

Asn Cys Asp Trp Asp Pro Tyr His
            20
```